(12) United States Patent
Roy et al.

(10) Patent No.: US 11,701,436 B2
(45) Date of Patent: *Jul. 18, 2023

(54) GENE EDITING-BASED METHOD OF ATTENUATING THE BETA-AMYLOID PATHWAY

(71) Applicant: Wisconsin Alumni Research Foundation, Madison, WI (US)

(72) Inventors: Subhojit Roy, Madison, WI (US); Jichao Sun, Madison, WI (US)

(73) Assignee: WISCONSIN ALUMNI RESEARCH FOUNDATION, Madison, WI (US)

(*) Notice: Subject to any disclaimer, the term of this patent is extended or adjusted under 35 U.S.C. 154(b) by 0 days.

This patent is subject to a terminal disclaimer.

(21) Appl. No.: 17/494,457

(22) Filed: Oct. 5, 2021

(65) Prior Publication Data

US 2022/0023444 A1 Jan. 27, 2022

Related U.S. Application Data

(62) Division of application No. 16/251,970, filed on Jan. 18, 2019, now Pat. No. 11,173,216.

(60) Provisional application No. 62/618,694, filed on Jan. 18, 2018.

(51) Int. Cl.
| | |
|---|---|
| *A61P 25/28* | (2006.01) |
| *A61K 48/00* | (2006.01) |
| *A61K 9/00* | (2006.01) |
| *C12N 15/90* | (2006.01) |
| *C07K 14/47* | (2006.01) |
| *C12N 9/22* | (2006.01) |
| *C12N 15/10* | (2006.01) |

(52) U.S. Cl.
CPC ........ *A61K 48/0066* (2013.01); *A61K 9/0019* (2013.01); *A61K 48/0008* (2013.01); *A61K 48/0058* (2013.01); *A61K 48/0075* (2013.01); *A61P 25/28* (2018.01); *C07K 14/4711* (2013.01); *C12N 9/22* (2013.01); *C12N 15/102* (2013.01); *C12N 15/907* (2013.01); *C12N 2310/20* (2017.05); *C12N 2740/16043* (2013.01); *C12N 2750/14143* (2013.01)

(58) Field of Classification Search
CPC ............ A61K 48/0066; A61K 48/0008; A61K 48/0058; A61K 48/0075; A61K 9/0019; A61P 25/28; C07K 14/4711; C12N 9/22; C12N 15/102; C12N 15/907; C12N 2310/20; C12N 2740/16043; C12N 2740/4143
See application file for complete search history.

(56) References Cited

U.S. PATENT DOCUMENTS 11,173,216 B2 * 11/2021 Roy .................. A61P 25/28
2019/0216950 A1 7/2019 Roy et al.

FOREIGN PATENT DOCUMENTS

WO 0173002 A2 10/2001

OTHER PUBLICATIONS

Aime, P. et al.; Trib3 Is Elevated in Parkinson's Disease and Mediates Death in Parkinson's Disease Models: Journal of Neuroscience, vol. 35; 2015; pp. 10731-10749, doi:10.1523/JNEUROSCI. 0614-15.2015.

Banks, W.; "From blood-brain barrier to blood-brain interface: new opportunities for CNS drug delivery"; Nature Reviews, vol. 15; 2016; pp. 275-292.

Beckett, C., et al.; Nuclear signalling by membrane protein intracellular domains: the AICD enigma; Cell Signal, vol. 24; 2012; pp. 402-409; doi:10.1016/j.cellsig.2011.10.007.

Brinkman, E. K. et al.; "Easy quantitative assessment of genome editing by sequence trace decomposition"; Nucleic Acids Research vol. 42, e168; 2014; doi:10.1093/nar/gku936.

Carlson-Stevermer, J. et al. "Assembly of CRISPR ribonucleoproteins with biotinylated oligonucleotides via an RNA aptamer for precise gene editing"; Nat Commun, vol. 8, 1711; 2017; doi:10.1038/s41467-017-01875-9.

Chakrabarty, P. et al.; "Capsid serotype and timing of injection determines AAV transduction in the neonatal mice brain"; PLoS One, vol. 8, e67680; 2013; doi:10.1371/journal.pone.0067680.

Chow, V. W., et al.; "An overview of APP processing enzymes and products" Neuromolecular Med, vol. 12; 2010; pp. 1-12; doi:10. 1007/s12017-009-8104-z.

Citron, M. et al.; "Generation of amyloid beta protein from its precursor is sequence specific"; Neuron, vol. 14; 1995; pp. 661-670; doi:0896-6273(95)90323-2.

Das, U. et al.; "Activity-induced convergence of APP and BACE-1 in acidic microdomains via an endocytosis-dependent pathway"; Neuron, vol. 79; 2013; pp. 447-460, doi:10.1016/j.neuron.2013.05. 035.

De Strooper, B. et al.; "The Cellular Phase of Alzheimer's Disease"; Cell, vol. 164; 2016; pp. 603-615.

Deverman, B. et al.; "Cre-dependent selection yields AAV variants for widespread gene transfer to the adult brain"; Nature Biotechnology, vol. 34, Issue No. 2; 2016; pp. 204-209.

(Continued)

*Primary Examiner* — Antonio Galisteo Gonzalez
*Assistant Examiner* — Khaleda B Hasan
(74) *Attorney, Agent, or Firm* — Cantor Colburn LLP

(57) ABSTRACT

Described herein is a method for treating Alzheimer's disease (AD) by selective silencing of the amyloid precursor protein (APP) using Cas9 nuclease gene editing. Methods of making and using genetic constructs comprising a Cas9 nuclease and a sequence encoding guide RNA (gRNA) specific to APP capable of truncating the C-terminus of APP, as well as compositions comprising these constructs, are provided.

12 Claims, 53 Drawing Sheets
(37 of 53 Drawing Sheet(s) Filed in Color)

Specification includes a Sequence Listing.

(56) References Cited

OTHER PUBLICATIONS

Deyts, C. et al.; "APP Receptor? To Be or Not To Be"; Trends in Pharmacological Sciences, vol. 37; 2016; pp. 390-411, doi:10.1016/j.tips.2016.01.005.

Doench, J. et al.; "Optimized sgRNA design to maximize activity and minimize off-target effects of CRISPR-Cas9"; Nature Biotechnology, vol. 34, Issue No. 2; 2016; pp. 184-191 doi:10.1037/nbt3437.

Fellmann, C. et al.; "Cornerstones of CRISPR-Cas in drug discovery and therapy"; Nat Rev Drug Discov, vol. 16; 2017; pp. 89-100; doi:10.1038/nrd.2016.238.

Fol, R. et al. "Viral gene transfer of APPsalpha rescues synaptic failure in an Alzheimer's disease mouse model"; Acta Neuropathol, vol. 131; 2016; pp. 247-266; doi:10.1007/S00401-015-1498-9.

Fu, Y. et al.; "Improving CRISPR-Cas nuclease specificity using truncated guide RNAs"; Nature Biotechnology, vol. 32, Issue No. 3; 2014; pp. 279-284.

Guo, W. et al.; "Fragile X Proteins FMRP and FXR2P Control Synaptic GluA1 Expression and Neuronal Maturation via Distinct Mechanisms"; Cell Rep, vol. 11; 2015; pp. 1651-1666; doi:10.1016/j.celrep.2015.05.013.

Gyorgy, B. et al.; "CRISPR/Cas9 Mediated Disruption of the Swedish APP Allele as a Therapeutic Approach for Early-Onset Alzheimer's Disease"; Mol Ther Nucleic Acids, vol. 11; 2018; pp. 429-440, doi:10.1016/j.omtn.2018.03.007.

Haass, C. et al.; "Soluble protein oligomers in neurodegeneration: lessons from the Alzheimer's amyloid ß-peptide"; Molecular Cell Biology, vol. 8; 2007; pp. 101-112.

Haass, C. et al.; "Trafficking and Proteolytic Processing of APP"; Cold Spring Harbor Perspectives in Medicine, vol. 2, Issue No. 5; 2012; pp. 1-25.

Hampel, H. et al.; "The future of Alzheimer's disease: The next 10 years"; Progress in Neurobiology, vol. 95; 2011; pp. 718-728.

Hardy, J. et al.; "The Amyloid Hypothesis of Alzheimer's Disease: Progress and Problems on the Road to Therapeutics"; Science, vol. 297; 2002; pp. 353-355.

Hendriks, L. et al.; "Presenile dementia and cerebral haemorrhage linked to a mutation at codon 692 of the ß-amyloid precursor protein gene"; Nature Genetics, vol. 1; 1992; pp. 218-221.

Hocquemiller, M. et al.; "Adeno-Associated Virus-Based Gene Therapy for CNS Diseases"; Human Gene Therapy, vol. 27, Issue No. 7; 2016; pp. 478-496.

International Search Report and Written Opinion for International Application PCT/US2019/014249; International Filing Date: Jan. 18, 2019; dated May 21, 2019; 16 pages.

Joung, J. et al.; "Genome-scale CRISPR-Cas9 knockout and transcriptional activation screening"; Nat Protoc, vol. 12; 2017; pp. 828-863; doi:10.1038/nprot.2017.016.

Kim, J. Y.; "Widespread Neuronal Transduction of the Rodent CNS via Neonatal Viral Injection"; Methods Mol Biol, vol. 1382; 2016; pp. 239-250; doi:10.1007/978-1-4939-3271-9_17.

Komor, A. et al.; "CRISPR-Based Technologies for the Manipulation of Eukaryotic Genomes"; Cell, vol. 168; 2017; pp. 20-36.

Koo, E. H. et al.; "Evidence that production and release of amyloid beta-protein involves the endocytic pathway"; J Biol Chem, vol. 269; 1994; pp. 17386-17389.

Kuscu, C. et al.; "Genome-wide analysis reveals characteristics of off-target sites bound by the Cas9 endonuclease"; Nature Biotechnology, vol. 32, Issue No. 7; 2014; pp. 677-683.

Lai, A., et al.; "Characterization of sorting signals in the beta-amyloid precursor protein cytoplasmic domain"; J Biol Chem, vol. 270; 1995; pp. 3565-3573.

Lee, M. S. et al.; "APP processing is regulated by cytoplasmic phosphorylation"; J Cell Biol, vol. 163; 2003; pp. 83-95; doi:10.1083/jcb.200301115.

Liu, Y. et al.; "Brain-targeting gene delivery and cellular internalization mechanisms for modified rabies virus glycoprotein RVG29 nanoparticles"; Biomaterials, vol. 30; 2009; pp. 4195-4202.

Luo, S. et al.; "Water Soluble Poly(histamine acrylamide) with Superior Buffer Capacity Mediates Efficient and Nontoxic In Vitro Gene Transfection"; Journal of Polymer Science Part A: Polymer Chemistry, vol. 49; 2011; pp. 3366-3373.

McMahon, M. A. et al.; "Gene therapy: Gene-editing therapy for neurological disease"; Nat Rev Neurol, vol. 13; 2017; pp. 7-9; doi:10.1038/nrneurol.2016.190.

Mendell, J. et al.; "Single-Dose Gene-Replacement Therapy for Spinal Muscular Atrophy"; The New England Journal of Medicine, vol. 377, Issue No. 18; 2017; pp. 1713-1722.

Mockett, B. G. et al.; "Therapeutic Potential of Secreted Amyloid Precursor Protein APPsalpha"; Front Mol Neurosci, vol. 10; 2017; pp. 30; doi:10.3389/fnmol.2017.00030.

Morel, E. et al.; "Phosphatidylinositol-3-phosphate regulates sorting and processing of amyloid precursor protein through the endosomal system"; Nat Commun, vol. 4, Issue No. 2250; 2013; doi:10.1038/ncomms3250.

Muller, U. C. et al.; "Physiological functions of APP family proteins"; Cold Spring Harb Perspect Med, vol. 2, a006288; 2012; doi:10.1101/cshperspect.a006288.

Muller, U. C., et al.; "Not just amyloid: physiological functions of the amyloid precursor protein family"; Nat Rev Neurosci, vol. 18; 2017; pp. 281-298, doi:10.1038/nrn.2017.29.

Musiek, E. et al.; "Three dimensions of the amyloid hypothesis: time, space and 'wingmen'"; Nature Neuroscience, vol. 18; 2015; pp. 800-806.

Nitsch, et al.; "Release of Alzheimer amyloid precursor derivatives stimulated by activation of muscarinic acetylcholine receptors"; Science, vol. 258; 1992; pp. 304-307.

O'Brien, R. J. et al.; "Amyloid precursor protein processing and Alzheimer's disease"; Annu Rev Neurosci, vol. 34; 2011; 185-204, doi:10.1146/annurev-neuro-061010-113613.

Paquet, D. et al.; "Efficient introduction of specific homozygous and heterozygous mutations using CRISPR/Cas9"; Nature, vol. 533, 125-129; 2016; doi:10.1038/nature17664.

Das, U. et al.; "Visualizing APP and BACE-1 approximation in neurons yields insight into the amyloidogenic pathway" Nat Neurosci, vol. 19; 2016; pp. 55-64; doi:10.1038/nn.4188.

Pardossi, et al.; "The physiology of the beta-amyloid precursor protein intracellular domain AICD"; J Neurochem, vol. 120, Suppl 1; 2012; pp. 109-124; doi:10.1111/j.1471-4159.2011.07475.x.

Park, C. Y. et al.; "Reversion of FMR1 Methylation and Silencing by Editing the Triplet Repeats in Fragile X iPSC-Derived Neurons"; Cell Rep, vol. 13; 2015; pp. 234-241; doi:10.1016/j.celrep.2015.08.084.

Passini, M. A. et al.; "Widespread gene delivery and structure-specific patterns of expression in the brain after intraventricular injections of neonatal mice with an adeno-associated virus vector"; J Virol, vol. 75; 2001; pp. 12382-12392; doi:10.1128/JVI.75.24.12382-12392.2001.

Perez, R. G. et al.; "Mutagenesis identifies new signals for beta-amyloid precursor protein endocytosis, turnover, and the generation of secreted fragments, including Abeta42 "; J Biol Chem, vol. 274; 1999; pp. 18851-18856.

Perrin, et al.; "Multimodal techniques for diagnosis and prognosis of Alzheimer's disease"; Nature, vol. 461, Issue No. 7266; pp. 916-922.

Putnam, D. et al.; "Polymer-based gene delivery with low cytotoxicity by a unique balance of side-chain termini"; PNAS, vol. 98, Issue No. 3; 2001; pp. 1200-1205.

Ran, F. et al.; "Genome engineering using the CRISPR-Cas9 system"; Nature Protocols, vol. 8, Issue No. 11; 2013; pp. 2281-2308.

Richter, M. C. et al.; "Distinct in vivo roles of secreted APP ectodomain variants APPsalpha and APPsbeta in regulation of spine density, synaptic plasticity, and cognition"; EMBO J, vol. 37; 2018; doi:10.15252/embj.201798335.

Ring, S. et al.; "The secreted beta-amyloid precursor protein ectodomain APPs alpha is sufficient to rescue the anatomical, behavioral, and electrophysiological abnormalities of APP-deficient mice"; J Neurosci, vol. 27; 2007; pp. 7817-7826; doi:10.1523/JNEUROSCI.1026-07.2007.

(56) References Cited

OTHER PUBLICATIONS

Rohn, T. et al.; "The Potential of CRISPR/Cas9 Gene Editing as a Treatment Strategy for Alzheimer's Disease"; Journal of Alzheimer's Disease and Parkinsonism, vol. 8, Issue No. 3; 2018; 12 pages; doi:10.4172/2161-0460.1000439.
Sander, J. D. et al.; "CRISPR-Cas systems for editing, regulating and targeting genomes"; Nat Biotechnol, vol. 32; 2014; pp. 347-355; doi:10.1038/nbt.2842.
Sanjana, N. E., et al.; "Improved vectors and genome-wide libraries for CRISPR screening"; Nat Methods, vol. 11; 2014; pp. 783-784; doi:10.1038/nmeth.3047.
Schwartz, M. et al.; "Human pluripotent stem cell-derived neural constructs for predicting neural toxicity"; PNAS, vol. 112, Issue No. 40; 2015; pp. 12516-12521.
Scott, D. et al.; "A Pathologic Cascade Leading to Synaptic Dysfunction in a-Synuclein-Induced Neurodegeneration"; The Journal of Neuroscience, vol. 30, Issue No. 24; 2010; pp. 8083-8095.
Scott, D. et al.; "Mechanistic Logic Underlying the Axonal Transport of Cytosolic Proteins"; Neuron, vol. 70, Issue No. 3; 2011; pp. 441-454.
Shrestha, R. et al.; "Endosomal escape and siRNA delivery with cationic shell crosslinked knedel-like nanoparticles with tunable buffering capcities"; Biomaterials, vol. 33, Issue No. 33; 2012; pp. 8557-8568.
Sisodia, S. S.; "Beta-amyloid precursor protein cleavage by a membrane-bound protease"; Proc Natl Acad Sci U S A, vol. 89; 1992; pp. 6075-6079.
Sun, J. et al.; "CRISPR/Cas9 editing of APP C-terminus attenuates ß-cleavage and promotes α-cleavage"; Nature Communications, vol. 10, Issue No. 1; 2019; 11 pages; doi:10.1038/s41467-018-07971-B.
Sun, J. et al.; "The physical approximation of APP and BACE-1: A key event in alzheimer's disease pathogenesis"; Dev Neurobiol, vol. 78; 2018; pp. 340-347, doi:10.1002/dneu.22556.
Swiech, L. et al.; "In vivo interrogation of gene function in the mammalian brain using CRISPR-Cas9"; Nat Biotechnol, vol. 33; 2015; pp. 102-106; doi:10.1038/nbt.3055.
Tang, Y. et al.; "Early and selective impairments in axonal transport kinetics of synaptic cargoes induced by soluble amyloid beta-protein oligomers"; Traffic, vol. 13; 2012; pp. 681-693; doi:101111/j.1600-0854.2012.01340.x.
Thinakaran, G. et al.; "Amyloid precursor protein trafficking, processing, and function"; J Biol Chem, vol. 283; 2008; pp. 29615-29619; doi:10.1074/jbc.R800019200.
Topol, A., et al.; "A guide to generating and using hiPSC derived NPCs for the study of neurological diseases"; J Vis Exp, e52495; 2015; doi:10.3791/52495.
Ubelmann, F. et al.; "Bin1 and CD2AP polarise the endocytic generation of beta-amyloid"; EMBO Rep, vol. 18; 2017; pp. 102-122, doi:10.15252/embr.201642738.
Vassar, R. et al.; "Function, therapeutic potential and cell biology of BACE proteases: current status and future prospects"; J Neurochem, vol. 130; 2014; pp. 4-28, doi:10.1111/jnc.12715.
Vassar, R. et al.; "The ß-Secretase Enzyme BACE in Health and Alzheimer's Disease: Regulation, Cell Biology, Function, and Therapeutic Potential"; The Journal of Neuroscience, vol. 29, Issue No. 41; 2009 pp. 12787-12794.
Veres, A. et al.; "Low Incidence of Off-Target Mutations in Individual CRISPR-Cas9 and TALEN Targeted Human Stem Cell Clones Detected by Whole-Genome Sequencing"; Cell Stem Cell, vol. 15, Issue No. 1; 2014; pp. 27-30.
Vickers, J. et al.; "A Vaccine Against Alzheimer's Disease: Developments to Date"; Drugs and Aging, vol. 19, Issue No. 7; 2002; pp. 487-494.
Wang, L. et al.; "α-Synuclein Multimers Clusters Synaptic Vesicles and Attenuate Recycling"; Current Biology: CB, vol. 24, Issue No. 19; 2014; pp. 2319-2326.
Wiley, D. et al.; "Transcytosis and brain uptake of transferrin-containing nanoparticles by tuning avidity to transferrin receptor"; PNAS, vol. 110, Issue No. 21; 2013; pp. 8662-8667.
Yang, S. et al.; "CRISPR/Cas9-mediated gene editing ameliorates neurotoxicity in mouse model of Huntington's disease"; J Clin Invest, vol. 127; 2017; pp. 2719-2724; doi:10.1172/JCI92087.
Zeitler, B. et al.; "Sustained Tau Reduction via Zinc Finger Protein Transcription Factors as a Potential Next-Generation Therapy for Alzheimer's Disease and Other Tauopathies"; available online at https://d1io3yog0oux5.cloudfront.net/sangamo/files/documents/051017.Zeitler.ZFP-TFs.tau.Final.pdf, retrieved Jun. 28, 2021; 18 pages.

* cited by examiner

FIGS. 2A-2H CONTINUED

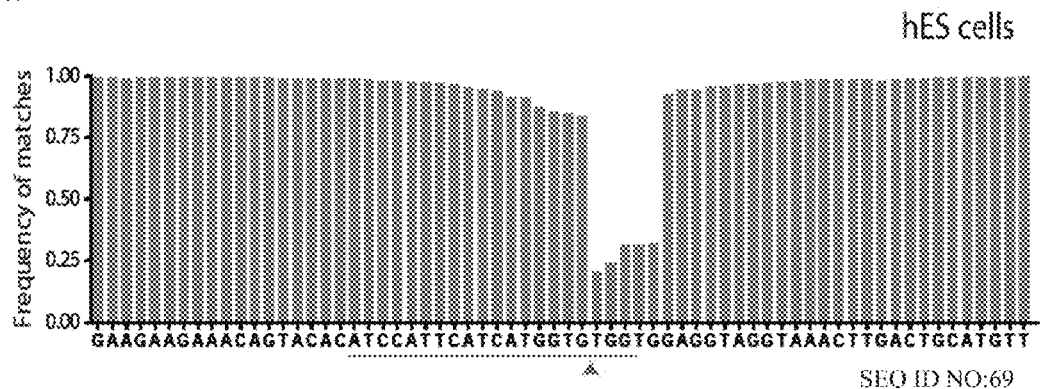

f.

g.

| | | | Freq (%) | |
|---|---|---|---|---|
| WT | AACAGTACACATCCATTCATCATGGTGTGGTGGAGGTAGGTAAAC | SEQ ID NO:70 | | |
| C1 | AACAGTACACATCCATTCATCATGGTG-----GAGGTAGGTAAAC | | 81.8 | SEQ ID NO:71 |
| C2 | AACAGTACACATCCATTCATCATGGTG--GTGGAGGTAGGTAAAC | | 0.3 | SEQ ID NO:72 |
| C3 | AACAGTACACATCCATTCATCAT----TGGTGGAGGTAGGTAAAC | | 0.2 | SEQ ID NO:73 |
| C4 | AACAGTACACATCCATTCATCATGGTG-GGTGGAGGTAGGTAAAC | | 0.2 | SEQ ID NO:74 |
| C5 | AACAGTACACATCCATTCATC------TGGTGGAGGTAGGTAAAC | | 0.2 | SEQ ID NO:75 | h.

Human APP translation (hES)

| | | Freq (%) | |
|---|---|---|---|
| WT | GGVVIATVIVITLVMLKKKQYTSIHHGVVEVDAAVTPEERHLSKMQ...(stop) | | SEQ ID NO:76 |
| C1 | GGVVIATVIVITLVMLKKKQYTSIHHG... (stop) | 81.8 | SEQ ID NO:77 |
| C2 | GGVVIATVIVITLVMLKKKQYTSIHHG... (stop) | 0.3 | SEQ ID NO:78 |
| C3 | GGVVIATVIVITLVMLKKKQYTSIHH-...60 missense aa(stop) | 0.2 | SEQ ID NO:79 |
| C4 | GGVVIATVIVITLVMLKKKQYTSIHHG...60 missense aa(stop) | 0.2 | SEQ ID NO:80 |
| C5 | GGVVIATVIVITLVMLKKKQYTSIH-LVEVDAAVTPEERHLSKMQ...(stop) | 0.2 | SEQ ID NO:81 |

659

FIGS. 3A-3G
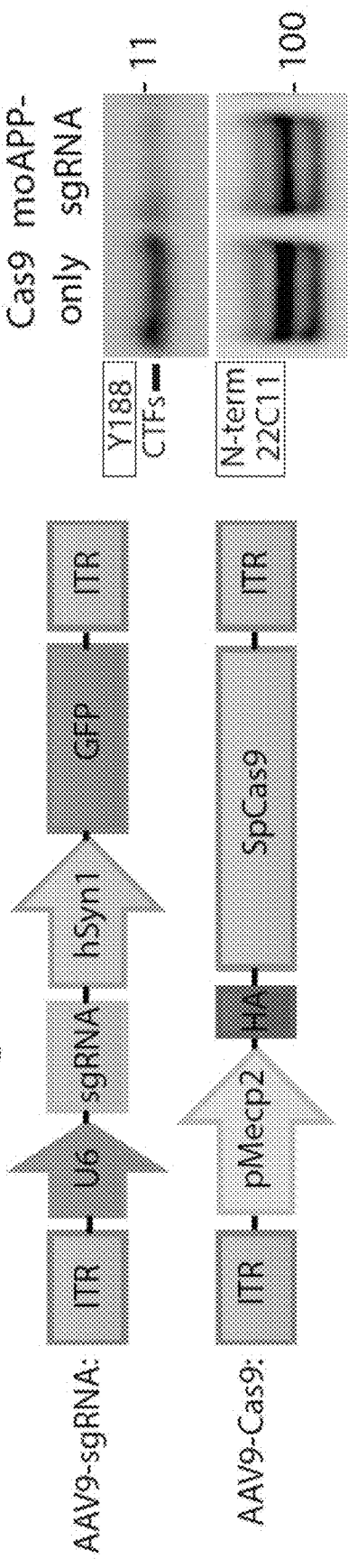
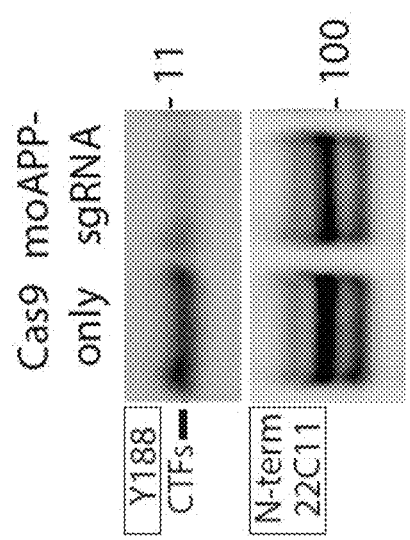
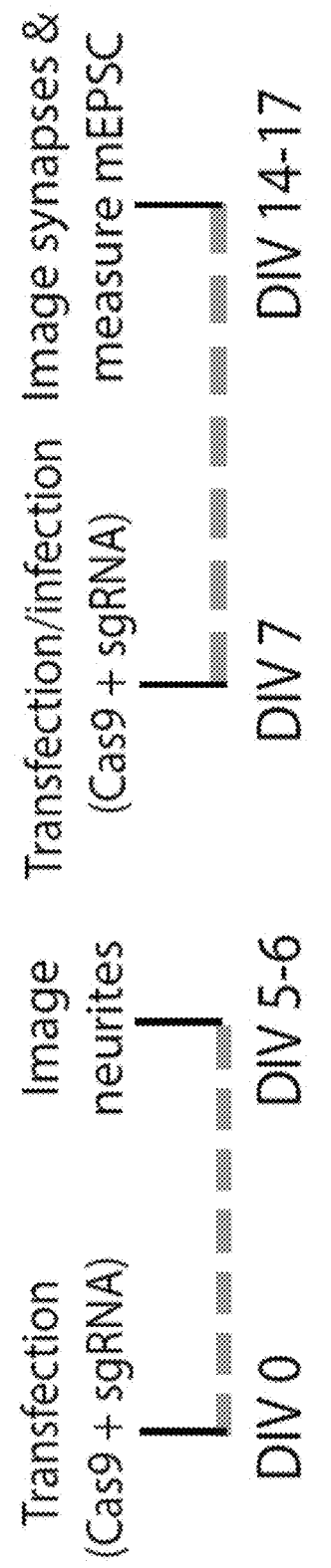

FIGS. 3A-3G CONTINUED
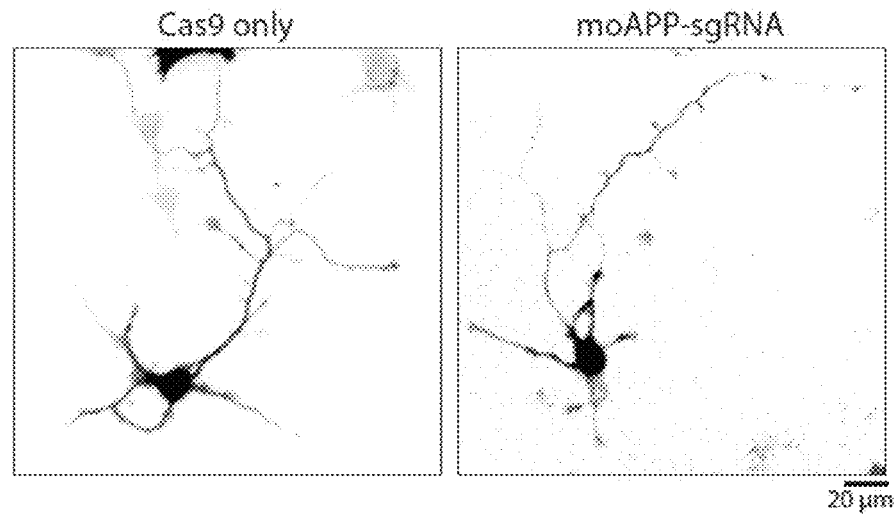
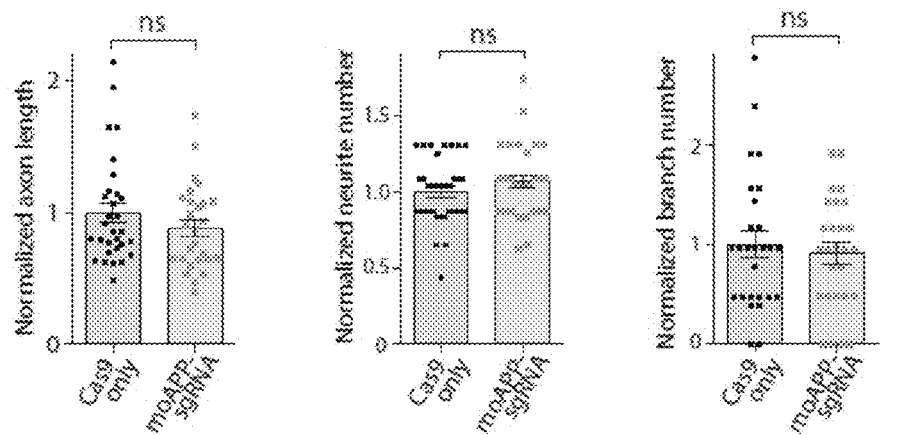
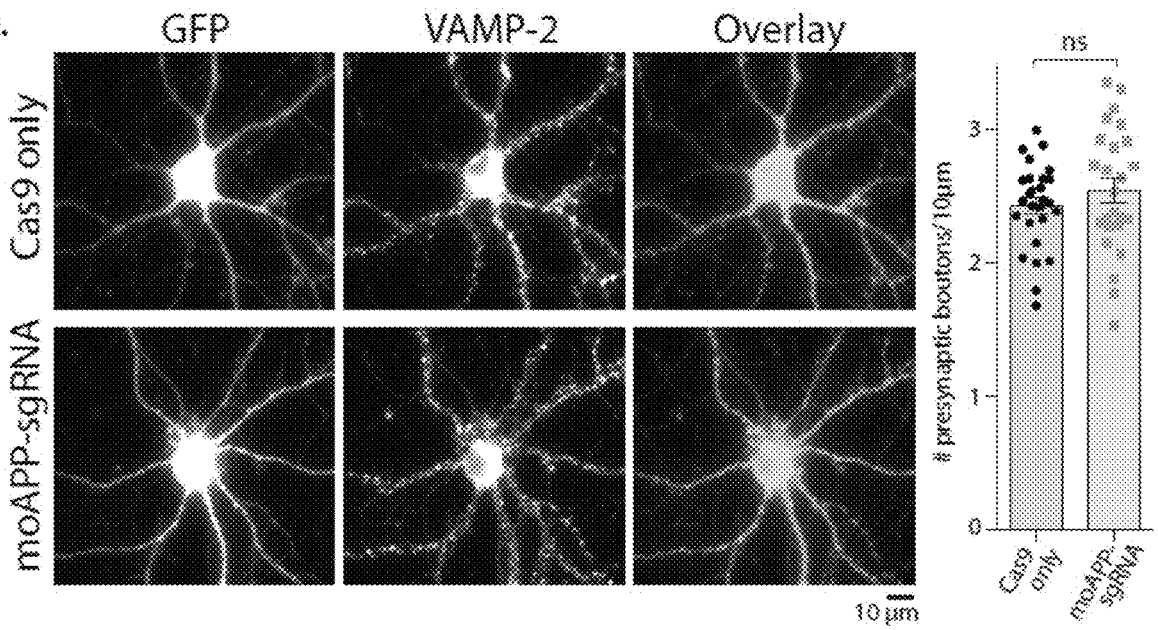

FIGS. 4A-4G
a. Hippocampal AAV9 injections (schematic)
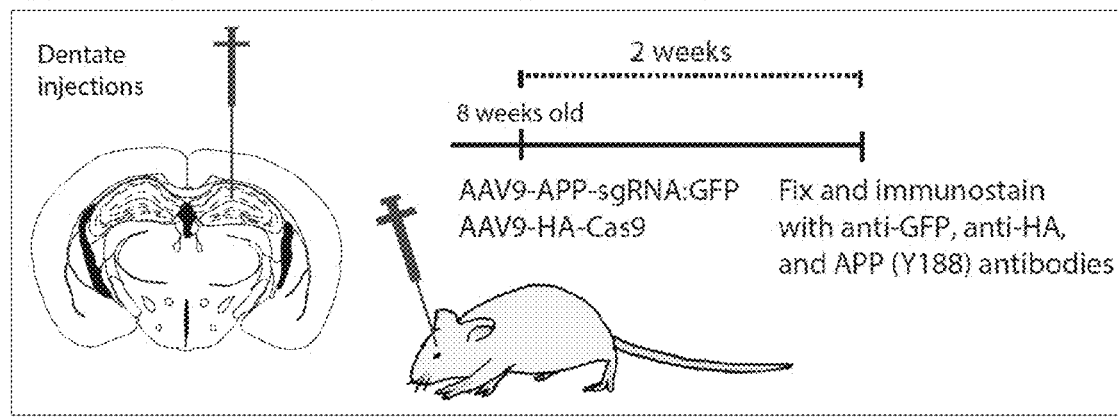
b. 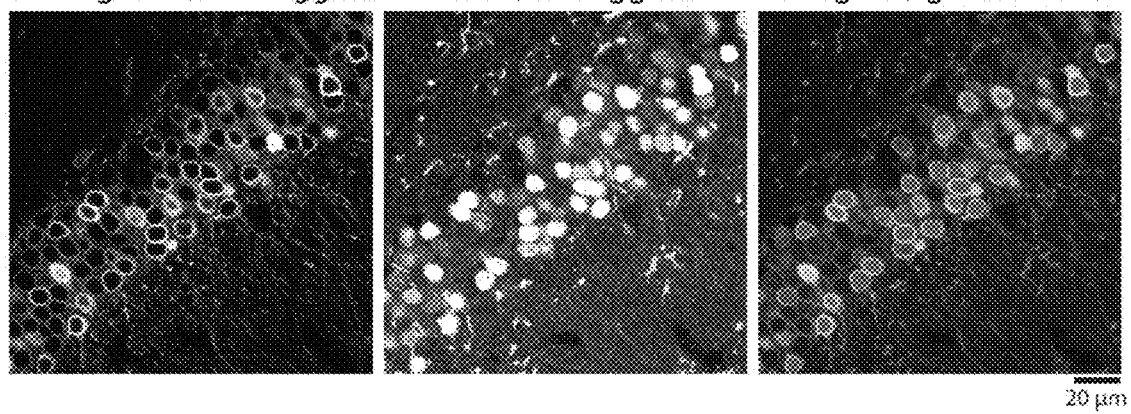

FIGS. 4A-4G CONTINUED
e. ICV AAV9 injections (schematic)
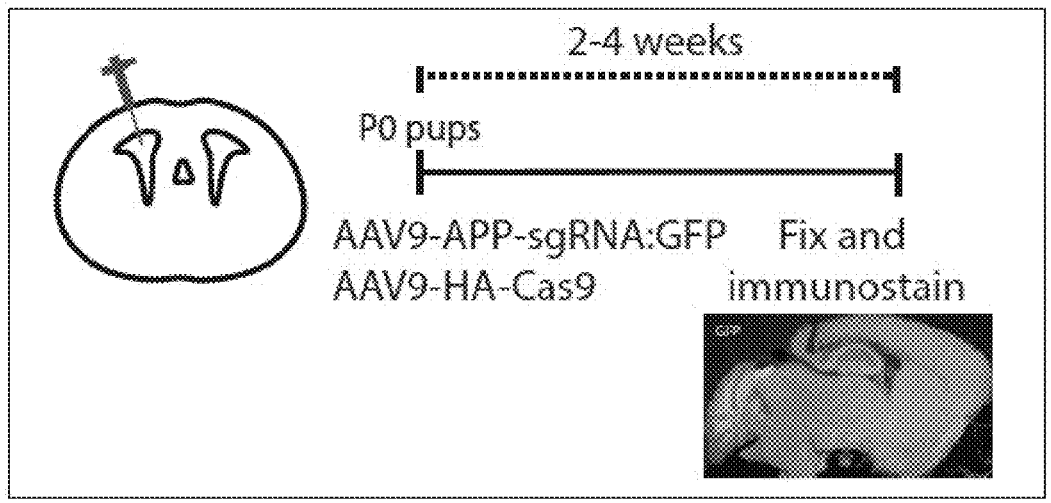
f. APP (Y188) staining
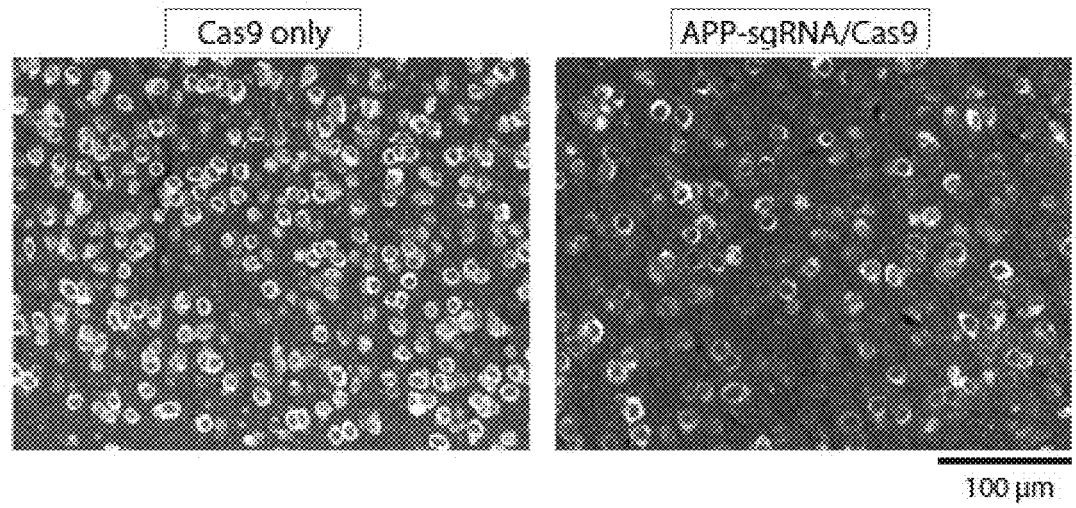
g.
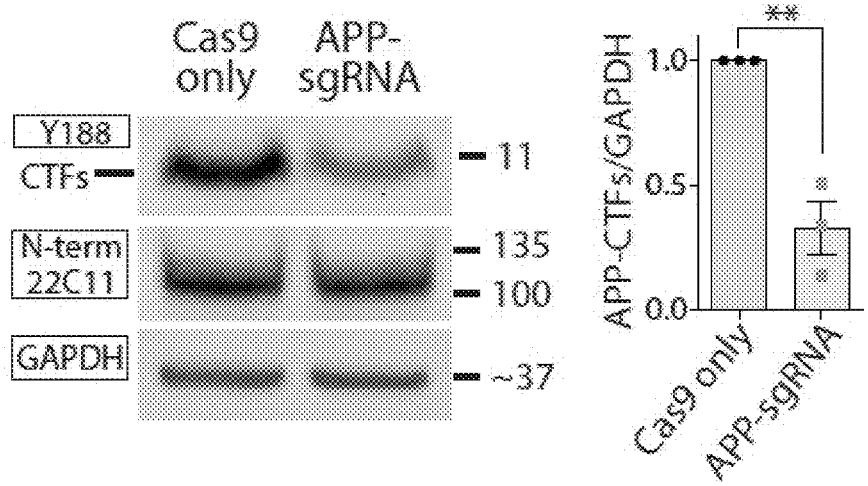

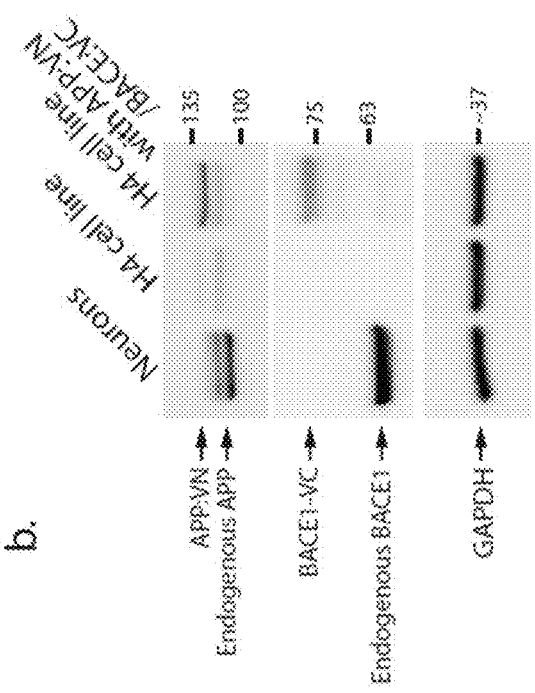
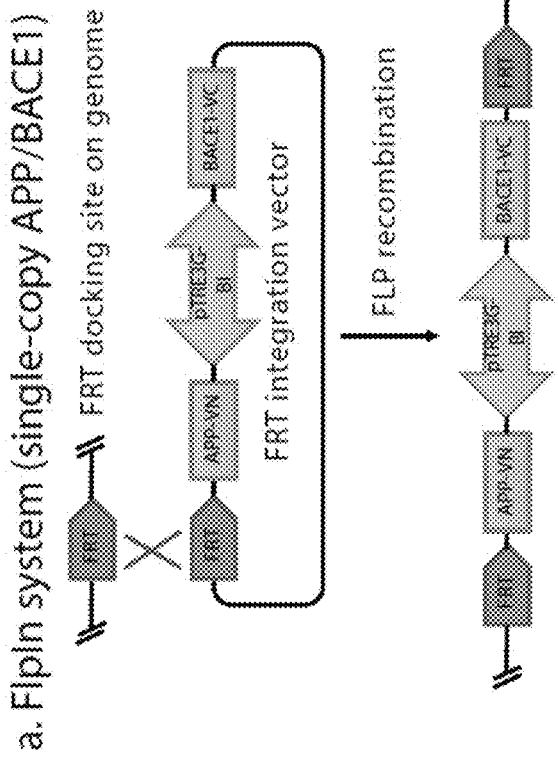
FIGS. 6A-6E

FIGS. 6A-6E CONTINUED
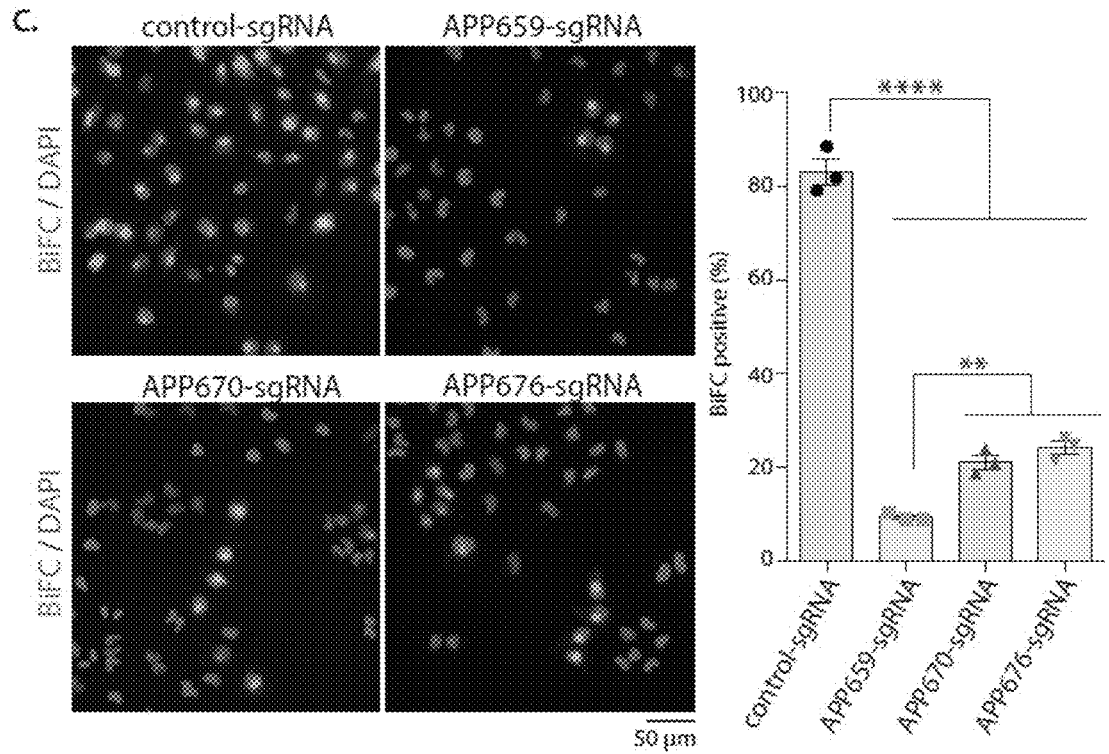
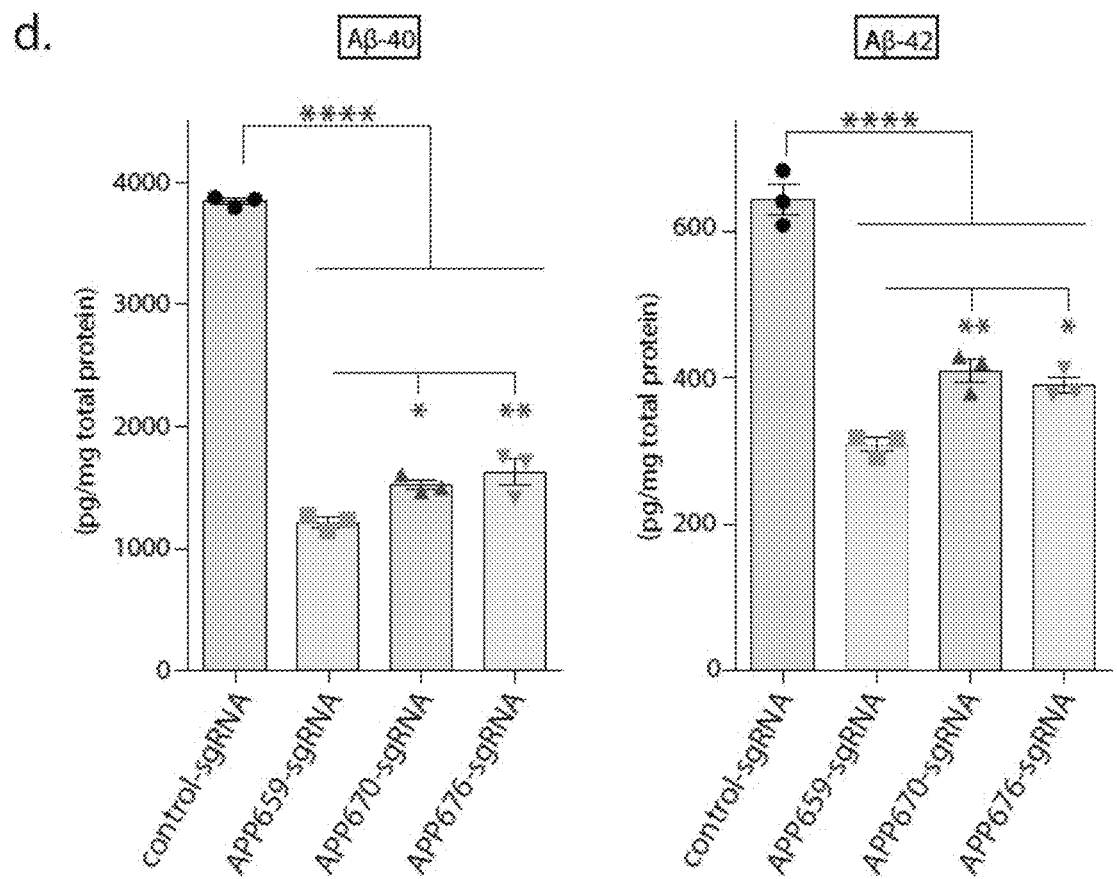

FIGS. 6A-6E CONTINUED e. Left

HEK APP659-sgRNA
Human APP genomic sequence

| | | Freq (%) | |
|---|---|---|---|
| WT | AACAGTACACATCCATTCATCATGGTGTGTGGAGGTAGGTAAAC | | SEQ ID NO:83 |
| C1 | AACAGTACACATCCATTCATCATGGTG------GAGGTAGGTAAAC | 42.9 | SEQ ID NO:84 |
| C2 | AACAGTACACATCCATTCATCATGGTG---GTGGGAGGTAGGTAAAC | 10.2 | SEQ ID NO:85 |
| C3 | AACAGTACACATCCATTCATCATGGTG-GCTGGAGGTAGGTAAAC | 3.6 | SEQ ID NO:86 |
| C4 | AACAGTACACATCCATTCATCATCAT------TGGTGGAGGTAGGTAAAC | 2.3 | SEQ ID NO:87 |
| C5 | AACAGTACACATCCATTCATCATCATG----TGGTGGAGGTAGGTAAAC | 1.9 | SEQ ID NO:88 |

HEK APP670-sgRNA
Human APP genomic sequence

| | | Freq (%) | |
|---|---|---|---|
| WT | TGCTGCATCTTGGACAGGTGGCGCTCCTCTGGGGTGACAGCGGCG | | SEQ ID NO:89 |
| C1 | TGCTGCATCTTGGACAGGTGGCGCTCCNTCTGGGGTGACAGCGGCG | 17.8 | SEQ ID NO:90 |
| C2 | TGCTGCATCTTGGACAGGTGGCGCT-----TCTGGGGTGACAGCGGCG | 12.5 | SEQ ID NO:91 |
| C3 | TGCTGCATCTTGGACAGGTGGC-------TCTGGGGTGACAGCGGCG | 8.4 | SEQ ID NO:92 |
| C4 | TGCTGCATCTTGGACAGGTGGCGC----TCTGGGGTGACAGCGGCG | 8.1 | SEQ ID NO:93 |
| C5 | TGCTGCATCTTGGACAGGTGGCGCTC-TCTGGGGTGACAGCGGCG | 5.7 | SEQ ID NO:94 |

HEK APP676-sgRNA
Human APP genomic sequence

| | | Freq (%) | |
|---|---|---|---|
| WT | TTGGATTTTCGTAGCCGTTCTGCTGCATCTTGGACAGGTGGCGCT | | SEQ ID NO:95 |
| C1 | TTGGATTTTCGTAGCCGTTCTGCTGCTGCANTCTTGGACAGGTGGCGCT | 24.1 | SEQ ID NO:96 |
| C2 | TTGGATTTTCGTAGCCGTTCT------TGGACAGGTGGCGCT | 10.2 | SEQ ID NO:97 |
| C3 | TTGGATTTTCGTAGCCGTTCTGCTGC-TCTTGGACAGGTGGCGCT | 8.8 | SEQ ID NO:98 |
| C4 | TTGGATTTTCGTAGCCGTTCTGCT----TCTTGGACAGGTGGCGCT | 8.4 | SEQ ID NO:99 |
| C5 | TTGGATTTTCGTAGCCGTTCT------TCTTGGACAGGTGGCGCT | 4.4 | SEQ ID NO:100 |

FIGS. 6A-6E CONTINUED e. CONTINUED Right
Human APP translational products

[Sequence alignment illustration showing WT and C1-C5 variants with frequencies and SEQ ID NOs 101-106, aligned at position 659]

Human APP translational products

[Sequence alignment illustration showing WT and C1-C5 variants with frequencies and SEQ ID NOs 107-112, aligned at position 670]

Human APP translational products

[Sequence alignment illustration showing WT and C1-C5 variants with frequencies and SEQ ID NOs 107, 113-117, aligned at position 676]

FIGS. 7A-7D CONTINUED

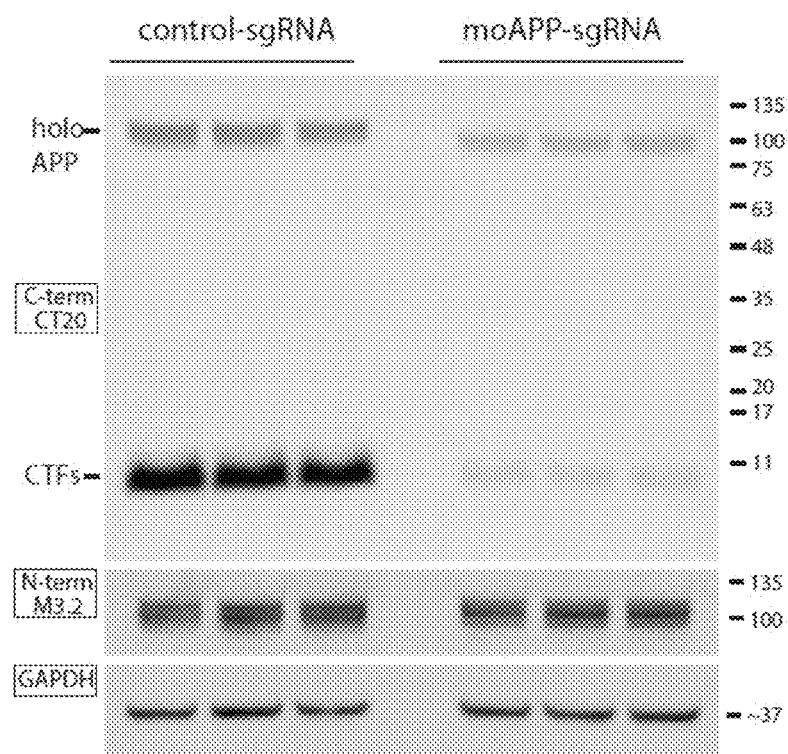

d. Mouse translational products (post-editing)

| | Mouse APP translation (neuro2a) | Freq (%) | |
|---|---|---|---|
| WT | GGVVIATVIVITLVMLKKKQYTSIHHGVVEVDAAVTPEERHLSKMQ...(stop) | | SEQ ID NO:118 |
| C1 | GGVVIATVIVITLVMLKKKQYTSIHHG-RRRRDPRGAPSLQDAAERI (stop) | 22.4 | SEQ ID NO:119 |
| C2 | GGVVIATVIVITLVMLKKKQYTSIHHG-RRRRDPRGAPSLQDAAERI (stop) | 6.8 | SEQ ID NO:119 |
| C3 | GGVVIATVIVITLVMLKKKQYTSIHHG-RRRRDPRGAPSLQDAAERI (stop) | 5.9 | SEQ ID NO:120 |
| C4 | GGVVIATVIVITLVMLKKKQYTSIHHG-RRRRDPRGAPSLQDAAERI (stop) | 3.8 | SEQ ID NO:121 |
| C5 | GGVVIATVIVITLVMLKKKQYTSIHHG-RRRRDPRGAPSLQDAAERI (stop) | 3.4 | SEQ ID NO:121 |

659

FIGS. 8A-8G
a. HEK cells
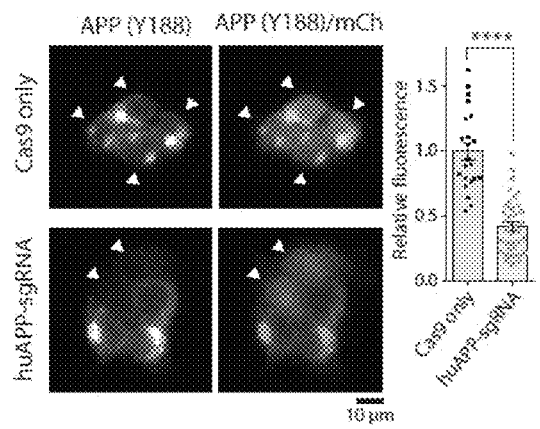
b.
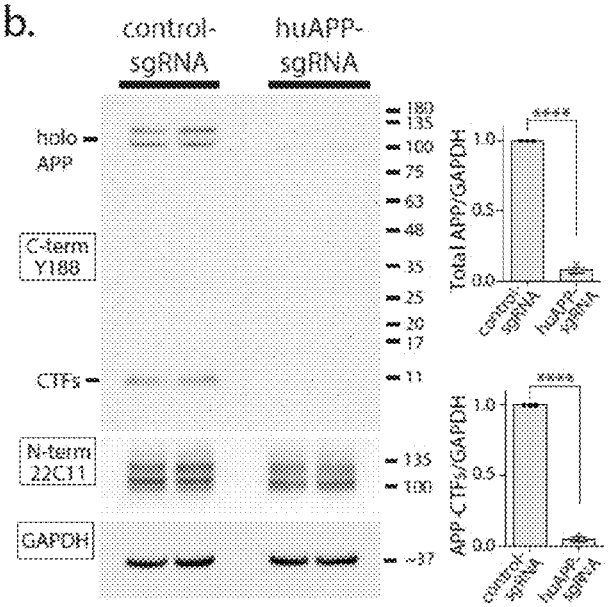
c.
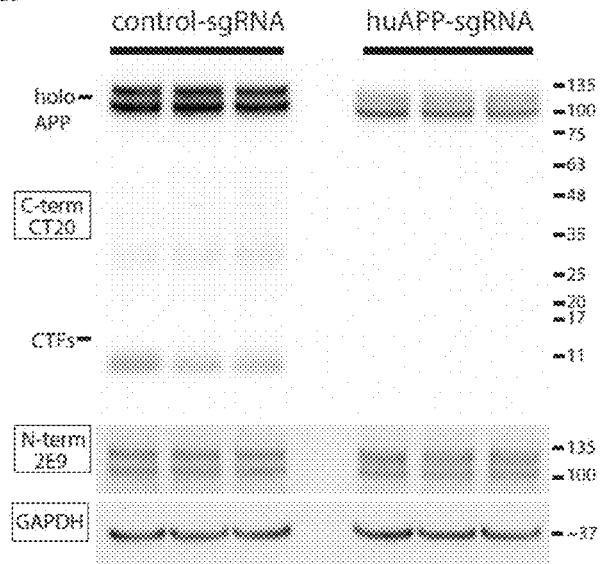

FIGS. 8A-8G CONTINUED
d. Human embryonic stem cells
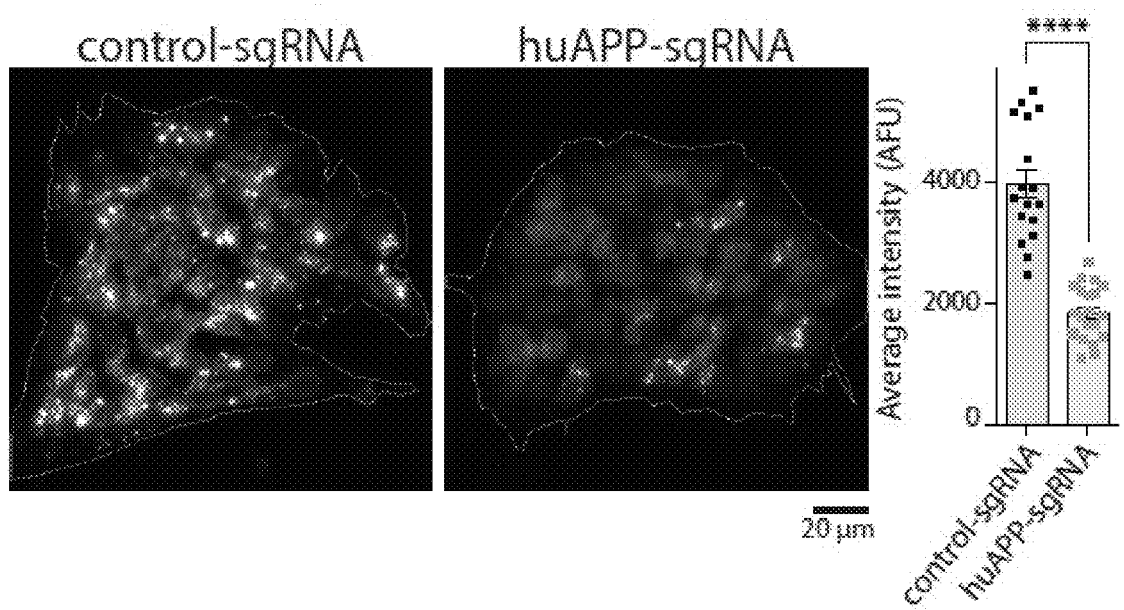
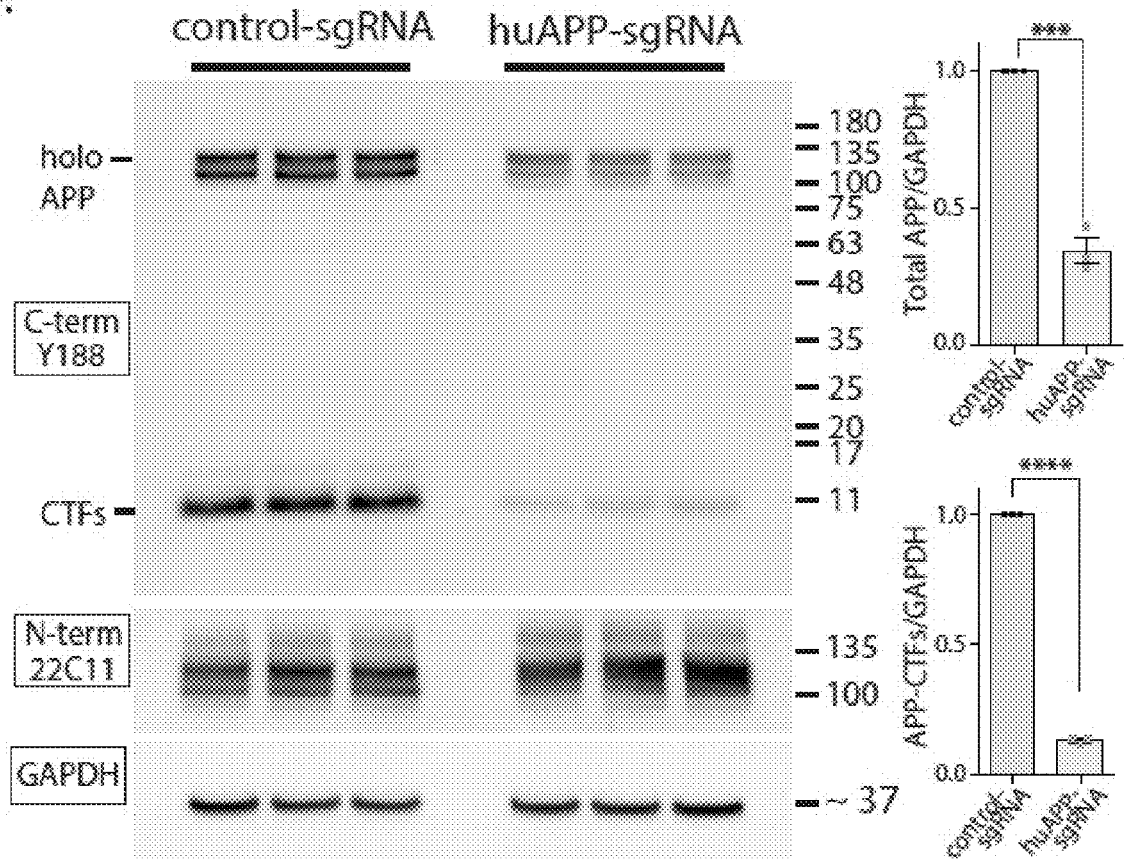

FIGS. 10A-10G a. Off-target sites

| | | Sequence | Location | Coding region | |
|---|---|---|---|---|---|
| Mouse | OT1 | GTCCATCCATCATGGCCTGG | chr18:+82500985 | No | SEQ ID NO:122 |
| | OT2 | TTCCATCCATCATGGCTTGG | chr15:+83079515 | No | SEQ ID NO:123 |
| | OT3 | GTCCCTCCATCATGGCCTGG | chr8:+54570804 | No | SEQ ID NO:124 |
| | OT4 | GGCCATCATTCATGGCGTGG | chr12:-30225859 | No | SEQ ID NO:125 |
| | OT5 | ATAAATATATCATGGCGTGG | chr2:+85075854 | No | SEQ ID NO:126 |
| Human | OT1 | CTCCCTTCATCTTGGTGTGG | chr17:+42059975 | No | SEQ ID NO:127 |
| | OT2 | ATGCAATCAGCATGGTGTGG | chr11:+45935195 | Yes, PHF21A | SEQ ID NO:128 |
| | OT3 | TTCTGTTCAGCATGGTGTGG | chr19:+13830088 | No | SEQ ID NO:129 |
| | OT4 | TTAAATTCAACATGGTGTGG | chrX:+78686020 | No | SEQ ID NO:130 |
| | OT5 | AGCCATTTATCAAGGTGTGG | chr8:+61517706 | No | SEQ ID NO:131 |

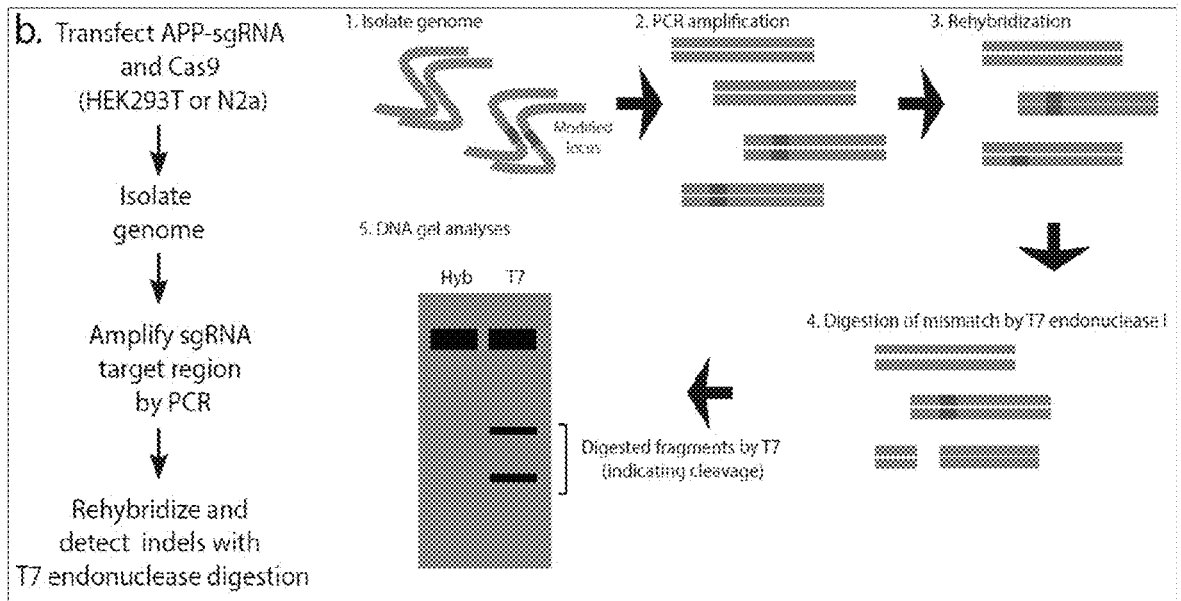

FIG. 13

>human APP (nucleotide sequence SEQ ID NO:11, amino acid sequence SEQ ID NO:12)

```
atgctgccoggtttggcactgctcctgctggccgctggacggctcggggcgctggaggta
 M  L  P  G  L  A  L  L  L  A  A  W  T  A  R  A  L  E  V
cccactgatggtaatgctggcctgctggctgaacccagatagccatgttctgtggcaga
 P  T  D  G  N  A  G  L  L  A  E  P  Q  I  A  M  F  C  G  R
ctgaacatgagcaataatgtccagaatgggaagtgggattcagatccatcagggaccaaa
 L  N  M  S  N  N  V  Q  N  G  K  W  D  S  D  P  S  G  T  K
acctgcattgatacccaggaaggcatcctgcagtattgccaagaagtctaccctgaactg
 T  C  I  D  T  K  E  G  I  L  Q  Y  C  Q  E  V  Y  P  E  L
cagatcaccaatgtggtagaagccaaccaaccagtgaccatccagaactggtgcaagcgg
 Q  I  T  N  V  V  E  A  N  Q  P  V  T  I  Q  N  W  C  K  R
ggccgcaagcagtgcaagacccatcccactttgtgattccctaccgctgcttagttggt
 G  R  K  Q  C  K  T  H  P  H  F  V  I  P  Y  R  C  L  V  G
gagtttgtaagtgatgccctctcgttcctgacaagtgcaaattcttaccaggagagg
 E  F  V  S  D  A  L  L  V  P  D  K  C  K  F  L  H  Q  E  R
atggatgttgcgaaactcatcttcactggcacaccgtcgccaaagagacatgcagtgag
 M  D  V  C  E  T  H  L  H  W  H  T  V  A  K  E  T  C  S  E
aagagtaccaacttgcatgactacggcatgttgctgccctgcggaattgacaagttccga
 K  S  T  N  L  H  D  Y  G  M  L  L  P  C  G  I  D  K  F  R
ggggtagagttttgtgtgttgcccactggctgaagaaagtgacaatgtgattctgctgat
 G  V  E  F  V  C  C  P  L  A  E  E  S  D  N  V  D  S  A  D
gcggaggaggatgactcggatgtctggtgggcggagcagacacagactatgcagatggg
 A  E  D  D  S  D  V  W  W  G  G  A  D  T  D  Y  A  D  G
agtgaagacaaagtagtagaagtagcagaggaggaagaagtggctgaggtggaagaagaa
 S  E  D  K  V  V  E  V  A  E  E  E  E  V  A  E  V  E  E  E
gaagccgatgatgacgaggacgatgaggatggtgatgaggtagaggaagaggctgaggaa
 E  A  D  D  D  E  D  D  E  D  G  D  E  V  E  E  E  A  E  E
ccctacgaagaagccacagagagaaccaccagcattgccaccaccaccaccaccacca
 P  Y  E  E  A  T  E  R  T  T  S  I  A  T  T  T  T  T  T
gagtctgtggaagaggtggttcgagttcctacaacagcagctagtacccctgatgccgtt
 E  S  V  E  E  V  V  R  V  P  T  T  A  A  S  T  P  D  A  V
gacaagtatctcgagacacctggggatgagaatgaacatgcccattttcagaaagccaaa
 D  K  Y  L  E  T  P  G  D  E  N  E  H  A  H  F  Q  K  A  K
gagaggcttgaggccaagcaccgagagaatgcccaggtcatgagaatggaagag
 E  R  L  E  A  K  H  R  E  R  M  S  Q  V  M  R  E  W  E  E
gcagaacgtcaagcaaagaacttgcctaaagctgataagaaggcagttatccagcattc
 A  E  R  Q  A  K  N  L  P  K  A  D  K  K  A  V  I  Q  H  F
caggagaaagtggaatctttggaacaggaagcagccaacgagagacagcagctggtggag
 Q  E  K  V  E  S  L  E  Q  E  A  A  N  E  R  Q  Q  L  V  E
acacatatggccagagtggaagccatgctcaatgaccgccgccgcctggccctggagaac
 T  H  M  A  R  V  E  A  M  L  N  D  R  R  R  L  A  L  E  N
tacatcaccgctctgcaggctgttcctcctcggcctcgtcacgtgttcaatatgctaaag
 Y  I  T  A  L  Q  A  V  P  P  R  P  R  H  V  F  N  M  L  K
aagtatgtccgcgcagaacagaaggacagacagcacccctaaagcatttcgagcatgtg
 K  Y  V  R  A  E  Q  K  D  R  Q  H  T  L  K  H  F  E  H  V
cgcatggtggatcccaagaaagccgctcagatccggtcccaggttatgacacacctccgt
 R  M  V  D  P  K  K  A  A  Q  I  R  S  Q  V  M  T  H  L  R
gtgatttatgagcgcatgaatcagtctctctcctgctctacaacgtgctgcagtggcc
 V  I  Y  E  R  M  N  Q  S  L  S  L  L  Y  N  V  P  A  V  A
gaggagattcaggatgaagttgatgagctggttcagaaagagcaaaactattcagatgac
 E  E  I  Q  D  E  V  D  E  L  L  Q  K  E  Q  N  Y  S  D  D
gtcttggccaacatgattagtgaaccaaggatcagttacggaaacgatgctctcatgcca
 V  L  A  N  M  I  S  E  P  R  I  S  Y  G  N  D  A  L  M  P
tctttgaccgaaacgaaaaccacgtggagctcctcccgtgaatggagagttcagcctg
```

FIG. 13 CONTINUED

```
         S  L  T  E  T  K  T  V  E  L  L  P  V  N  G  E  F  S  L
gacgatctccagccgtggcattcttttggggctgactctgtgccagccaacacagaaaac
         D  D  L  Q  P  W  H  S  F  G  A  D  S  V  P  A  N  T  E  N
gaagttgagcctgtgatgcccgccctgctgccgaccgaggactgaccactcgaccaggt
         E  V  E  P  V  D  A  R  P  A  A  D  R  G  L  T  T  R  P  G
tctgggttgacaaatatcaagacgggaggagatctctgaagtgaagatggatgcagaattc
         S  G  L  T  N  I  K  T  E  E  I  S  E  V  K  M  D  A  E  F
cgacatgactcaggatatgaagttcatcatcaaaaattggtgttctttgcagaagatgtg
         R  H  D  S  G  Y  E  V  H  H  Q  K  L  V  F  F  A  E  D  V
ggttcaaacaaagtgcaatcattggactcatggtggcggtgttgtcatagcgacagtg
         G  S  N  K  G  A  I  I  G  L  M  V  G  G  V  V  I  A  T  V
atcgtcatccttggtgatgctgaagaagaaacagtacac█████████████████████
         I  V  I  T  L  V  M  L  K  K  K  Q  Y  T  S  I  H  R  G  V
█tggaggttgacgccgctgtcacccc█████████████████████████████████
         V  E  V  D  A  A  V  T  P  E  E  R  H  L  S  K  M  Q  N
████████gaaatcca████████████████gatgcagaactag
         G  Y  E  N  P  T  Y  K  F  F  E  Q  M  Q  N  -
```

Sense:
659 gRNA
Antisense:
660 gRNA
616 gRNA
686 gRNA
670 gRNA

>mouse APP (nucleotide sequence SEQ ID NO:13, amino acid sequence SEQ ID NO:14)
```
atgctgcccagcttggcactgctcctgctggccgctggacgttcgggctctggaggta
         M  L  P  S  L  A  L  L  L  L  A  A  W  T  V  R  A  L  E  V
cccactgatggcaacgccgggctgctggcagaaccccagatcgccatgttctgtggtaaa
         P  T  D  G  N  A  G  L  L  A  E  P  Q  I  A  M  F  C  G  K
ctcaacatgcacatgaatgtgcagaatggaaagtggagtcagacccgtcaggaccaaa
         L  N  M  H  M  N  V  Q  N  G  K  W  E  S  D  P  S  G  T  K
acctgcattggcaccaaggaggggatcctgcagtactgccaagaggtctacccctgaactg
         T  C  I  G  T  K  E  G  I  L  Q  Y  C  Q  E  V  Y  P  E  L
cagatcacaaacgtggtggaagccaaccagccagtgaccatccagaactggtgcaagcgg
         Q  I  T  N  V  V  E  A  N  Q  P  V  T  I  Q  N  W  C  K  R
ggccgcaagcagtgcaagacacacacccacatcgtgattccttaccgttgcctagttggt
         G  R  K  Q  C  K  T  H  T  H  I  V  I  P  Y  R  C  L  V  G
gagtttgtgagcgacgcccttctcgtgccggacaagtgcaagttcctacaccaggagcgg
         E  F  V  S  D  A  L  L  V  P  D  K  C  K  F  L  H  Q  E  R
atggatgtttgtgagacccatcttcactggcacacggtcgccaaagagacatgcagcgag
         M  D  V  C  E  T  H  L  H  W  H  T  V  A  K  E  T  C  S  E
aagagcactaacttgcacgactatggcatgctgctgccctgcggcatcgacaagttccga
         K  S  T  N  L  H  D  Y  G  M  L  L  P  C  G  I  D  K  F  R
ggggtagagtttgtatgctgtccgttggctgaggaaagcgacagcgtggattctgcggat
         G  V  E  F  V  C  C  P  L  A  E  E  S  D  S  V  D  S  A  D
gcagaggaggatgactctgatgtctggtggggtggagcggacacagactacgctgatggc
         A  E  E  D  D  S  D  V  W  W  G  G  A  D  T  D  Y  A  D  G
ggtgaagacaaagtagtagaagtcgccgaagaggaggaagtggctgatgttgaggaagag
         G  E  D  K  V  V  E  V  A  E  E  E  E  V  A  D  V  E  E  E
gaagctgatgatgatgaggatgtggaggatggggacgagtggaggaggaggccgaggag
         E  A  D  D  D  E  D  V  E  D  G  D  E  V  E  E  E  A  E  E
```

FIG. 13 CONTINUED

```
ccctacgaagaggtcaccgagagaacaaccagcactgtcaccaccaccacaaccaccact
 P  Y  E  E  A  T  E  R  T  T  S  T  A  T  T  T  T  T  T
gagtccgtggaggaggtggtccgagttcccgatagcagccagcacccctgacgccgtc
 E  S  V  E  E  V  V  R  V  P  T  T  A  A  S  T  P  D  A  V
gacaagtacctggagacaccggggacgagaacgagcatgccattccagaaagccaaa
 D  K  Y  L  E  T  P  G  D  E  N  E  H  A  H  F  Q  K  A  K
gagaggctggaagccaagcacgagagaatgtccaggtcatgagagaatgggaagag
 E  R  L  E  A  K  S  R  E  R  M  S  Q  V  M  R  E  W  E
gcagagcgtcaagccaagaacttgcccaaagctgacaagaaggccgttatccagcatttc
 A  E  R  Q  A  K  N  L  P  K  A  D  K  K  A  V  I  Q  H  F
caggagaaagtggaatctctggaacaggaagcagccaatgagagacagcagcttgtagag
 Q  E  K  V  E  S  L  E  Q  E  A  A  N  E  R  Q  Q  L  V  E
acacacatggccagagttgaagccatgctcaatgaccgccgcgcctggccttcgagaat
 T  H  M  A  R  V  E  A  M  L  N  D  R  R  P  L  A  E  N
tacatcactgcactgcaggcggtgccccaaggcctcatcatgtgttcaacatgctgaag
 Y  I  T  A  L  Q  A  V  P  P  R  P  H  H  V  F  N  M  L  K
aagtacgtccgtgcggagcagaaagaccagacagcacaccctaaagcattttgaacatgtg
 K  Y  V  R  A  E  Q  K  D  R  Q  H  T  L  K  H  F  E  H  V
cgcatggtggaccccaagaaagctgctcagatccggtccaggttatgacacacctccgt
 R  M  V  D  P  K  K  A  A  Q  I  R  S  Q  V  M  T  R  L  R
gtgatctacgagcgcatgaaccagtctctgtccctgctctacaatgtccctgcggtggct
 V  I  Y  E  R  M  N  Q  S  L  S  L  L  Y  N  V  P  A  V  A
gaggagattcaagatgaagtcgatgagctgcttcagaaggagtagaactactccgacgat
 E  E  I  Q  D  E  V  D  E  L  L  Q  K  E  Q  N  Y  S  D  D
gtcttggccaacatgatcagtgagcccagaatcagctacggaaacgacgctctcatgcct
 V  L  A  N  M  I  S  E  P  R  I  S  Y  G  N  D  A  L  M  P
tcgctgacgaaaaccaagaccaccgtggagctccttcccgtgaatgggaattcagcctg
 S  L  T  E  K  T  T  V  E  L  L  P  V  N  G  F  S  L
gatgacctccagccgtggcaccttttggggtggactctgtgccagccaataccgaaaat
 D  D  L  Q  P  W  H  P  F  G  V  D  S  V  P  A  N  T  E  N
gaagtcgagctgttgacgcccgcccgctgctgaccgaggactgaccactgaccaggt
 E  V  E  P  V  D  A  P  P  A  A  D  R  G  L  T  T  R  P  G
tctggctgacaaacatcaagacggaagagatctggaagtgaagatggatgcagaattc
 S  G  L  T  N  I  K  T  E  E  I  S  E  V  K  M  D  A  E  F
ggacatgattcaggatttgaagtccgccatcaaaaactggtgttcttgctgaagatgtg
 G  H  D  S  G  F  E  V  R  H  Q  K  L  V  F  A  E  D  V
ggttcgaacaaaggcgccatcatcggactcatggtgggcggttgtcatagcaaccgtg
 G  S  N  K  G  A  I  I  G  L  M  V  G  G  V  V  I  A  T  V
attgtcatccctggtgatgttgaagaagaaacagtacac▓▓▓▓▓▓▓▓▓▓▓▓▓▓▓
 I  V  I  T  L  V  M  L  K  K  Q  Y  T  S  I  H  H  G  V
▓tggaggtcgacgctgcctgtaccct▓▓▓▓▓▓▓▓▓▓▓▓▓▓▓▓▓▓▓▓▓▓▓▓▓▓▓
 V  E  V  D  A  A  V  T  P  E  E  R  L  S  K  M  Q  N
▓▓▓▓▓▓▓gagaatcca▓▓▓▓▓▓▓▓▓▓▓▓▓aatgcagaactaa
 G  Y  E  N  P  T  Y  F  F  E  Q  M  Q  N  -
```

Sense:
659 gRNA
Antisense:
670 gRNA
686 gRNA
670 gRNA

FIG. 13 CONTINUED

>mouse APP

[Illegible nucleotide and amino acid sequence text]

(nucleotide sequence SEQ ID NO:13, amino acid sequence SEQ ID NO:14)

----- 653 gRNA
----- 669 gRNA
----- 670 gRNA
----- 676 gRNA
----- 686 gRNA

FIG. 13 CONTINUED

>human APP (nucleotide sequence SEQ ID NO:11, amino acid sequence SEQ ID NO:12)

------ 653 gRNA
------ 669 gRNA
—— 670 gRNA
—— 676 gRNA
------ 686 gRNA

FIG. 14

>SpCas9 (SEQ ID NO:15)
ATGGGTATCCACGGAGTCCCAGCAGCCGACAAGAAGTACAGCATCGGCCTGGACAT
CGGCACCAACTCTGTGGGCTGGGCCGTGATCACCGACGAGTACAAGGTGCCCAGCA
AGAAATTCAAGGTGCTGGGCAACACCGACCGGCACAGCATCAAGAAGAACCTGATC
GGAGCCCTGCTGTTCGACAGCGGCGAAACAGCCGAGGCCACCCGGCTGAAGAGAAC
CGCCAGAAGAAGATACACCAGACGGAAGAACCGGATCTGCTATCTGCAAGAGATCT
TCAGCAACGAGATGGCCAAGGTGGACGACAGCTTCTTCCACAGACTGGAAGAGTCC
TTCCTGGTGGAAGAGGATAAGAAGCACGAGCGGCACCCATCTTCGGCAACATCGT
GGACGAGGTGGCCTACCACGAGAAGTACCCCACCATCTACCACCTGAGAAAGAAAC
TGGTGGACAGCACCGACAAGGCCGACCTGCGGCTGATCTATCTGGCCCTGGCCCAC
ATGATCAAGTTCCGGGGCCACTTCCTGATCGAGGGCGACCTGAACCCCGACAACAG
CGACGTGGACAAGCTGTTCATCCAGCTGGTGCAGACCTACAACCAGCTGTTCGAGG
AAAACCCCATCAACGCCAGCGGCGTGGACGCCAAGGCCATCCTGTCTGCCAGACTG
AGCAAGAGCAGACGGCTGGAAAATCTGATCGCCCAGCTGCCCGGCGAGAAGAAGA
ATGGCCTGTTCGGAAACCTGATTGCCCTGAGCCTGGGCCTGACCCCAACTTCAAGA
GCAACTTCGACCTGGCCGAGGATGCCAAACTGCAGCTGAGCAAGGACACCTACGAC
GACGACCTGGACAACCTGCTGGCCCAGATCGGCGACCAGTACGCCGACCTGTTTCTG
GCCGCCAAGAACCTGTCCGACGCCATCCTGCTGAGCGACATCCTGAGAGTGAACAC
CGAGATCACCAAGGCCCCCCTGAGCGCCTCTATGATCAAGAGATACGACGAGCACC
ACCAGGACCTGACCCTGCTGAAAGCTCTCGTGCGGCAGCAGCTGCCTGAGAAGTAC
AAAGAGATTTTCTTCGACCAGAGCAAGAACGGCTACGCCGGCTACATTGACGGCGG
AGCCAGCCAGGAAGAGTTCTACAAGTTCATCAAGCCCATCCTGGAAAAGATGGACG
GCACCGAGGAACTGCTCGTGAAGCTGAACAGAGAGGACCTGCTGCGGAAGCAGCG
GACCTTCGACAACGGCAGCATCCCCCACCAGATCCACCTGGGAGAGCTGCACGCCA
TTCTGCGGCGGCAGGAAGATTTTACCCATTCCTGAAGGACAACCGGGAAAAGATC
GAGAAGATCCTGACCTTCCGCATCCCCTACTACGTGGGCCCTCTGGCCAGGGGAAAC
AGCAGATTCGCCTGGATGACCAGAAAGAGCGAGGAAACCATCACCCCCTGGAACTT
CGAGGAAGTGGTGGACAAGGGCGCTTCCGCCCAGAGCTTCATCGAGCGGATGACCA
ACTTCGATAAGAACCTGCCCAACGAGAAGGTGCTGCCCAAGCACAGCCTGCTGTAC
GAGTACTTCACCGTGTATAACGAGCTGACCAAAGTGAAATACGTGACCGAGGGAAT
GAGAAAGCCCGCCTTCCTGAGCGGCGAGCAGAAAAAGGCCATCGTGGACCTGCTGT
TCAAGACCAACCGGAAAGTGACCGTGAAGCAGCTGAAAGAGGACTACTTCAAGAAA
ATCGAGTGCTTCGACTCCGTGGAAATCTCCGGCGTGGAAGATCGGTTCAACGCCTCC
CTGGGCACATACCACGATCTGCTGAAAATTATCAAGGACAAGGACTTCCTGGACAA
TGAGGAAAACGAGGACATTCTGGAAGATATCGTGCTGACCCTGACACTGTTTGAGG
ACAGAGAGATGATCGAGGAACGGCTGAAAACCTATGCCCACCTGTTCGACGACAAA
GTGATGAAGCAGCTGAAGCGGCGGAGATACACCGGCTGGGGCAGGCTGAGCCGGA
AGCTGATCAACGGCATCCGGGACAAGCAGTCCGGCAAGACAATCCTGGATTTCCTG
AAGTCCGACGGCTTCGCCAACAGAAACTTCATGCAGCTGATCCACGACGACAGCCT

FIG. 14 CONTINUED

GACCTTTAAAGAGGACATCCAGAAAGCCCAGGTGTCCGGCCAGGGCGATAGCCTGC
ACGAGCACATTGCCAATCTGGCCGGCAGCCCCGCCATTAAGAAGGGCATCCTGCAG
ACAGTGAAGGTGGTGGACGAGCTCGTGAAAGTGATGGGCCGGCACAAGCCCGAGA
ACATCGTGATCGAAATGGCCAGAGAGAACCAGACCACCCAGAAGGGACAGAAGAA
CAGCCGCGAGAGAATGAAGCGGATCGAAGAGGGCATCAAGAGCTGGGCAGCCAG
ATCCTGAAAGAACACCCCGTGGAAAACACCCAGCTGCAGAACGAGAAGCTGTACCT
GTACTACCTGCAGAATGGGCGGGATATGTACGTGGACCAGGAACTGGACATCAACC
GGCTGTCCGACTACGATGTGGACCATATCGTGCCTCAGAGCTTTCTGAAGGACGACT
CCATCGACAACAAGGTGCTGACCAGAAGCGACAAGAACCGGGGCAAGAGCGACAA
CGTGCCCTCCGAAGAGGTCGTGAAGAAGATGAAGAACTACTGGCGGCAGCTGCTGA
ACGCCAAGCTGATTACCCAGAGAAAGTTCGACAATCTGACCAAGGCCGAGAGAGGC
GGCCTGAGCGAACTGGATAAGGCCGGCTTCATCAAGAGACAGCTGGTGGAAACCCG
GCAGATCACAAAGCACGTGGCACAGATCCTGGACTCCCGGATGAACACTAAGTACG
ACGAGAATGACAAGCTGATCCGGGAAGTGAAAGTGATCACCCTGAAGTCCAAGCTG
GTGTCCGATTTCCGGAAGGATTTCCAGTTTTACAAAGTGCGCGAGATCAACAACTAC
CACCACGCCCACGACGCCTACCTGAACGCCGTCGTGGGAACCGCCCTGATCAAAAA
GTACCCTAAGCTGGAAAGCGAGTTCGTGTACGGCGACTACAAGGTGTACGACGTGC
GGAAGATGATCGCCAAGAGCGAGCAGGAAATCGGCAAGGCTACCGCCAAGTACTTC
TTCTACAGCAACATCATGAACTTTTTCAAGACCGAGATTACCCTGGCCAACGGCGAG
ATCCGGAAGCGGCCTCTGATCGAGACAAACGGCGAAACCGGGGAGATCGTGTGGGA
TAAGGGCCGGGATTTTGCCACCGTGCGGAAAGTGCTGAGCATGCCCCAAGTGAATA
TCGTGAAAAAGACCGAGGTGCAGACAGGCGGCTTCAGCAAAGAGTCTATCCTGCCC
AAGAGGAACAGCGATAAGCTGATCGCCAGAAAGAAGGACTGGGACCCTAAGAAGT
ACGGCGGCTTCGACAGCCCCACCGTGGCCTATTCTGTGCTGGTGGTGGCCAAAGTGG
AAAAGGGCAAGTCCAAGAAACTGAAGAGTGTGAAAGAGCTGCTGGGGATCACCATC
ATGGAAAGAAGCAGCTTCGAGAAGAATCCCATCGACTTCTGGAAGCCAAGGGCTA
CAAAGAAGTGAAAAAGGACCTGATCATCAAGCTGCCTAAGTACTCCCTGTTCGAGC
TGGAAAACGGCCGGAAGAGAATGCTGGCCTCTGCCGGCGAACTGCAGAAGGGAAA
CGAACTGGCCCTGCCCTCCAAATATGTGAACTTCCTGTACCTGGCCAGCCACTATGA
GAAGCTGAAGGGCTCCCCCGAGGATAATGAGCAGAAACAGCTGTTTGTGGAACAGC
ACAAGCACTACCTGGACGAGATCATCGAGCAGATCAGCGAGTTCTCCAAGAGAGTG
ATCCTGGCCGACGCTAATCTGGACAAAGTGCTGTCCGCCTACAACAAGCACCGGGA
TAAGCCCATCAGAGAGCAGGCCGAGAATATCATCCACCTGTTTACCCTGACCAATCT
GGGAGCCCCTGCCGCCTTCAAGTACTTTGACACCACCATCGACCGGAAGAGGTACA
CCAGCACCAAAGAGGTGCTGGACGCCACCCTGATCCACCAGAGCATCACCGGCCTG
TACGAGACACGGATCGACCTGTCTCAGCTGGGAGGCGACAAAAGGCCGGCGGCCAC
GAAAAAGGCCGGCCAGGCAAAAAAGAAAAAG

FIG. 15

APP 659 gRNA Cas9 vector (SEQ ID NO:17)

CCCCACGAGGGCCTATTTCCCATGATTCCTTCATATTTGCATATACGATACAAGGCT
GTTAGAGAGATAATTGGAATTAATTTGACTGTAAACACAAGATATTAGTACAAAA
TACGTGACGTAGAAAGTAATAATTTCTTGGGTAGTTTGCAGTTTTAAAATTATGTTTT
AAAATGGACTATCATATGCTTACCGTAACTTGAAAGTATTTCGATTTCTTGGCTTTAT
ATATCTTGTGGAAAGGACGAAACACC*gatccattcatcatggtgtgg*GTTTTAGAGCTAGAAAT
AGCAAGTTAAAATAAGGCTAGTCCGTTATCAACTTGAAAAAGTGGCACCGAGTCGG
TGCTTTTTTGTTTTAGAGCTAGAAATAGCAAGTTAAAATAAGGCTAGTCCGTTTTAG
CGCGTGCGCCAATTCTGCAGACAAATGGCTCTAGAGGTACCCGTTACATAACTTACG
GTAAATGGCCCGCCTGGCTGACCGCCCAACGACCCCGCCCATTGACGTCAATAGTA
ACGCCAATAGGGACTTTCCATTGACGTCAATGGGTGGAGTATTTACGGTAAACTGCC
CACTTGGCAGTACATCAAGTGTATCATATGCCAAGTACGCCCCCTATTGACGTCAAT
GACGGTAAATGGCCCGCCTGGCATTGTGCCCAGTACATGACCTTATGGGACTTTCCT
ACTTGGCAGTACATCTACGTATTAGTCATCGCTATTACCATGGTCGAGGTGAGCCCC
ACGTTCTGCTTCACTCTCCCCATCTCCCCCCCTCCCCACCCCAATTTTGTATTTATT
TATTTTTAATTATTTTGTGCAGCGATGGGGGCGGGGGGGGGGGGGGCGCGCGC
CAGGCGGGGCGGGGCGGGGCGAGGGGCGGGGCGGGGCGAGGCGGAGAGGTGCGG
CGGCAGCCAATCAGAGCGGCGCGCTCCGAAAGTTTCCTTTTATGGCGAGGCGGCGG
CGGCGGCGGCCCTATAAAAGCGAAGCGCGCGGCGGGCGGGAGTCGCTGCGACGCT
GCCTTCGCCCCGTGCCCCGCTCCGCCGCCGCCTCGCGCCGCCCGCCCCGGCTCTGAC
TGACCGCGTTACTCCCACAGGTGAGCGGGCGGGACGGCCCTTCTCCTCCGGGCTGTA
ATTAGCTGAGCAAGAGGTAAGGGTTTAAGGGATGGTTGGTTGGTGGGGTATTAATG
TTTAATTACCTGGAGCACCTGCCTGAAATCACTTTTTTTCAGGTTGGACCGGTGCCAC
CATGGACTATAAGGACCACGACGGAGACTACAAGGATCATGATATTGATTACAAAG
ACGATGACGATAAGATGGCCCCAAAGAAGAAGCGGAAGGTCGGTATCCACGGAGTC
CCAGCAGCCGACAAGAAGTACAGCATCGGCCTGGACATCGGCACCAACTCTGTGGG
CTGGGCCGTGATCACCGACGAGTACAAGGTGCCCAGCAAGAAATTCAAGGTGCTGG
GCAACACCGACCGGCACAGCATCAAGAAGAACCTGATCGGAGCCCTGCTGTTCGAC
AGCGGCGAAACAGCCGAGGCCACCCGGCTGAAGAGAACCGCCAGAAGAAGATACA
CCAGACGGAAGAACCGGATCTGCTATCTGCAAGAGATCTTCAGCAACGAGATGGCC
AAGGTGGACGACAGCTTCTTCCACAGACTGGAAGAGTCCTTCCTGGTGGAAGAGGA
TAAGAAGCACGAGCGGCACCCCATCTTCGGCAACATCGTGGACGAGGTGGCCTACC
ACGAGAAGTACCCCACCATCTACCACCTGAGAAAGAAACTGGTGGACAGCACCGAC
AAGGCCGACCTGCGGCTGATCTATCTGGCCCTGGCCCACATGATCAAGTTCCGGGGC
CACTTCCTGATCGAGGGCGACCTGAACCCCGACAACAGCGACGTGGACAAGCTGTT
CATCCAGCTGGTGCAGACCTACAACCAGCTGTTCGAGGAAAACCCCATCAACGCCA
GCGGCGTGGACGCCAAGGCCATCCTGTCTGCCAGACTGAGCAAGAGCAGACGGCTG
GAAAATCTGATCGCCCAGCTGCCCGGCGAGAAGAAGAATGGCCTGTTCGGAAACCT

FIG. 15 CONTINUED

GATTGCCCTGAGCCTGGGCCTGACCCCCAACTTCAAGAGCAACTTCGACCTGGCCGA
GGATGCCAAACTGCAGCTGAGCAAGGACACCTACGACGACGACCTGGACAACCTGC
TGGCCCAGATCGGCGACCAGTACGCCGACCTGTTTCTGGCCGCCAAGAACCTGTCCG
ACGCCATCCTGCTGAGCGACATCCTGAGAGTGAACACCGAGATCACCAAGGCCCCC
CTGAGCGCCTCTATGATCAAGAGATACGACGAGCACCACCAGGACCTGACCCTGCT
GAAAGCTCTCGTGCGGCAGCAGCTGCCTGAGAAGTACAAAGAGATTTTCTTCGACC
AGAGCAAGAACGGCTACGCCGGCTACATTGACGGCGGAGCCAGCCAGGAAGAGTTC
TACAAGTTCATCAAGCCCATCCTGGAAAAGATGGACGGCACCGAGGAACTGCTCGT
GAAGCTGAACAGAGAGGACCTGCTGCGGAAGCAGCGGACCTTCGACAACGGCAGC
ATCCCCCACCAGATCCACCTGGGAGAGCTGCACGCCATTCTGCGGCGGCAGGAAGA
TTTTTACCCATTCCTGAAGGACAACCGGGAAAGATCGAGAAGATCCTGACCTTCCG
CATCCCCTACTACGTGGGCCCTCTGGCCAGGGGAAACAGCAGATTCGCCTGGATGA
CCAGAAAGAGCGAGGAAACCATCACCCCCTGGAACTTCGAGGAAGTGGTGGACAA
GGGCGCTTCCGCCCAGAGCTTCATCGAGCGGATGACCAACTTCGATAAGAACCTGC
CCAACGAGAAGGTGCTGCCCAAGCACAGCCTGCTGTACGAGTACTTCACCGTGTAT
AACGAGCTGACCAAAGTGAAATACGTGACCGAGGGAATGAGAAAGCCCGCCTTCCT
GAGCGGCGAGCAGAAAAAGGCCATCGTGGACCTGCTGTTCAAGACCAACCGGAAA
GTGACCGTGAAGCAGCTGAAAGAGGACTACTTCAAGAAAATCGAGTGCTTCGACTC
CGTGGAAATCTCCGGCGTGGAAGATCGGTTCAACGCCTCCCTGGGCACATACCACG
ATCTGCTGAAAATTATCAAGGACAAGGACTTCCTGGACAATGAGGAAAACGAGGAC
ATTCTGGAAGATATCGTGCTGACCCTGACACTGTTTGAGGACAGAGAGATGATCGA
GGAACGGCTGAAAACCTATGCCCACCTGTTCGACGACAAAGTGATGAAGCAGCTGA
AGCGGCGGAGATACACCGGCTGGGGCAGGCTGAGCCGGAAGCTGATCAACGGCATC
CGGGACAAGCAGTCCGGCAAGACAATCCTGGATTTCCTGAAGTCCGACGGCTTCGC
CAACAGAAACTTCATGCAGCTGATCCACGACGACAGCCTGACCTTTAAAGAGGACA
TCCAGAAAGCCCAGGTGTCCGGCCAGGGCGATAGCCTGCACGAGCACATTGCCAAT
CTGGCCGGCAGCCCCGCCATTAAGAAGGGCATCCTGCAGACAGTGAAGGTGGTGGA
CGAGCTCGTGAAAGTGATGGGCCGGCACAAGCCCGAGAACATCGTGATCGAAATGG
CCAGAGAGAACCAGACCACCCAGAAGGGACAGAAGAACAGCCGCGAGAGAATGAA
GCGGATCGAAGAGGGCATCAAAGAGCTGGGCAGCCAGATCCTGAAAGAACACCCC
GTGGAAAACACCCAGCTGCAGAACGAGAAGCTGTACCTGTACTACCTGCAGAATGG
GCGGGATATGTACGTGGACCAGGAACTGGACATCAACCGGCTGTCCGACTACGATG
TGGACCATATCGTGCCTCAGAGCTTTCTGAAGGACGACTCCATCGACAACAAGGTGC
TGACCAGAAGCGACAAGAACCGGGGCAAGAGCGACAACGTGCCTCCGAAGAGGT
CGTGAAGAAGATGAAGAACTACTGGCGGCAGCTGCTGAACGCCAAGCTGATTACCC
AGAGAAAGTTCGACAATCTGACCAAGGCCGAGAGAGGCGGCCTGAGCGAACTGGAT
AAGGCCGGCTTCATCAAGAGACAGCTGGTGGAAACCCGGCAGATCACAAAGCACGT
GGCACAGATCCTGGACTCCCGGATGAACACTAAGTACGACGAGAATGACAAGCTGA
TCCGGGAAGTGAAAGTGATCACCCTGAAGTCCAAGCTGGTGTCCGATTTCCGGAAG
GATTTCCAGTTTTACAAAGTGCGCGAGATCAACAACTACCACCACGCCCACGACGCC

FIG. 15 CONTINUED

TACCTGAACGCCGTCGTGGGAACCGCCCTGATCAAAAAGTACCCTAAGCTGGAAAG
CGAGTTCGTGTACGGCGACTACAAGGTGTACGACGTGCGGAAGATGATCGCCAAGA
GCGAGCAGGAAATCGGCAAGGCTACCGCCAAGTACTTCTTCTACAGCAACATCATG
AACTTTTTCAAGACCGAGATTACCCTGGCCAACGGCGAGATCCGGAAGCGGCCTCT
GATCGAGACAAACGGCGAAACCGGGGAGATCGTGTGGGATAAGGGCCGGGATTTTG
CCACCGTGCGGAAAGTGCTGAGCATGCCCCAAGTGAATATCGTGAAAAAGACCGAG
GTGCAGACAGGCGGCTTCAGCAAGAGTCTATCCTGCCCAAGAGGAACAGCGATAA
GCTGATCGCCAGAAAGAAGGACTGGGACCCTAAGAAGTACGGCGGCTTCGACAGCC
CCACCGTGGCCTATTCTGTGCTGGTGGTGGCCAAAGTGGAAAAGGGCAAGTCCAAG
AAACTGAAGAGTGTGAAAGAGCTGCTGGGGATCACCATCATGGAAAGAAGCAGCTT
CGAGAAGAATCCCATCGACTTTCTGGAAGCCAAGGGCTACAAAGAAGTGAAAAAGG
ACCTGATCATCAAGCTGCCTAAGTACTCCCTGTTCGAGCTGGAAAACGGCCGGAAG
AGAATGCTGGCCTCTGCCGGCGAACTGCAGAAGGGAAACGAACTGGCCCTGCCCTC
CAAATATGTGAACTTCCTGTACCTGGCCAGCCACTATGAGAAGCTGAAGGGCTCCCC
CGAGGATAATGAGCAGAAACAGCTGTTTGTGGAACAGCACAAGCACTACCTGGACG
AGATCATCGAGCAGATCAGCGAGTTCTCCAAGAGAGTGATCCTGGCCGACGCTAAT
CTGGACAAAGTGCTGTCCGCCTACAACAAGCACCGGGATAAGCCCATCAGAGAGCA
GGCCGAGAATATCATCCACCTGTTTACCCTGACCAATCTGGGAGCCCTGCCGCCTT
CAAGTACTTTGACACCACCATCGACCGGAAGAGGTACACCAGCACCAAAGAGGTGC
TGGACGCCACCCTGATCCACCAGAGCATCACCGGCCTGTACGAGACACGGATCGAC
CTGTCTCAGCTGGGAGGCGACAAAAGGCCGGCGGCCACGAAAAGGCCGGCCAGG
CAAAAAAGAAAAAGCTTGAGGGCAGAGGAAGTCTGCTAACATGCGGTGACGTGGA
GGAGAATCCCGGCCCTGCTAGCATGGTGAGCAAGGGCGAGGAGGATAACATGGCCA
TCATCAAGGAGTTCATGCGCTTCAAGGTGCACATGGAGGGCTCCGTGAACGGCCAC
GAGTTCGAGATCGAGGGCGAGGGCGAGGGCCGCCCTACGAGGGCACCCAGACCG
CCAAGCTGAAGGTGACCAAGGGTGGCCCCCTGCCCTTCGCCTGGGACATCCTGTCCC
CTCAGTTCATGTACGGCTCCAAGGCCTACGTGAAGCACCCCGCCGACATCCCCGACT
ACTTGAAGCTGTCCTTCCCCGAGGGCTTCAAGTGGGAGCGCGTGATGAACTTCGAGG
ACGGCGGCGTGGTGACCGTGACCCAGGACTCCTCCCTGCAGGACGGCGAGTTCATC
TACAAGGTGAAGCTGCGCGGCACCAACTTCCCCTCAGACGGCCCCGTAATGCAGAA
GAAAACCATGGGCTGGGAGGCCTCCTCCGAGCGGATGTACCCCGAGGACGGCGCCC
TGAAGGGCGAGATCAAGCAGAGGCTGAAGCTGAAGGACGGCGGCCACTACGACGC
TGAGGTCAAGACCACCTACAAGGCCAAGAAGCCCGTGCAGCTGCCCGGCGCCTACA
ACGTCAACATCAAGTTGGACATCACCTCCCACAACGAGGACTACACCATCGTGGAA
CAGTACGAACGCGCCGAGGGCCGCCACTCCACCGGCGGCATGGACGAGCTGTACAA
GTAAGAATTCCTAGAGCTCGCTGATCAGCCTCGACTGTGCCTTCTAGTTGCCAGCCA
TCTGTTGTTTGCCCCTCCCCGTGCCTTCCTTGACCCTGGAAGGTGCCACTCCCACTG
TCCTTTCCTAATAAAATGAGGAAATTGCATCGCATTGTCTGAGTAGGTGTCATTCTAT
TCTGGGGGGTGGGGTGGGCAGGACAGCAAGGGGGAGGATTGGGAAGAGAATAGC
AGGCATGCTGGGGAGCGGCCGCAGGAACCCCTAGTGATGGAGTTGGCCACTCCCTC

FIG. 15 CONTINUED

TCTGCGCGCTCGCTCGCTCACTGAGGCCGGGCGACCAAAGGTCGCCCGACGCCCGG
GCTTTGCCCGGGCGGCCTCAGTGAGCGAGCGAGCGCGCAGCTGCCTGCAGGGGCGC
CTGATGCGGTATTTTCTCCTTACGCATCTGTGCGGTATTTCACACCGCATACGTCAAA
GCAACCATAGTACGCGCCTGTAGCGGCGCATTAAGCGCGGCGGGTGTGGTGGTTA
CGCGCAGCGTGACCGCTACACTTGCCAGCGCCCTAGCGCCCGCTCCTTTCGCTTTCTT
CCCTTCCTTTCTCGCCACGTTCGCCGGCTTTCCCCGTCAAGCTCTAAATCGGGGGCTC
CCTTTAGGGTTCCGATTTAGTGCTTTACGGCACCTCGACCCCAAAAAACTTGATTTG
GGTGATGGTTCACGTAGTGGGCCATCGCCCTGATAGACGGTTTTCGCCCTTTGACG
TTGGAGTCCACGTTCTTTAATAGTGGACTCTTGTTCCAAACTGGAACAACACTCAAC
CCTATCTCGGGCTATTCTTTTGATTTATAAGGGATTTTGCCGATTTCGGCCTATTGGT
TAAAAAATGAGCTGATTTAACAAAAATTTAACGCGAATTTTAACAAAATATTAACGT
TTACAATTTTATGGTGCACTCTCAGTACAATCTGCTCTGATGCCGCATAGTTAAGCCA
GCCCCGACACCCGCCAACACCCGCTGACGCGCCCTGACGGGCTTGTCTGCTCCCGGC
ATCCGCTTACAGACAAGCTGTGACCGTCTCCGGGAGCTGCATGTGTCAGAGGTTTTC
ACCGTCATCACCGAAACGCGCGAGACGAAAGGGCCTCGTGATACGCCTATTTTATA
GGTTAATGTCATGATAATAATGGTTTCTTAGACGTCAGGTGGCACTTTTCGGGGAAA
TGTGCGCGGAACCCCTATTTGTTTATTTTCTAAATACATTCAAATATGTATCCGCTC
ATGAGACAATAACCCTGATAAATGCTTCAATAATATTGAAAAAGGAAGAGTATGAG
TATTCAACATTTCCGTGTCGCCCTTATTCCCTTTTTGCGGCATTTTGCCTTCCTGTTT
TTGCTCACCCAGAAACGCTGGTGAAAGTAAAAGATGCTGAAGATCAGTTGGGTGCA
CGAGTGGGTTACATCGAACTGGATCTCAACAGCGGTAAGATCCTTGAGAGTTTTCGC
CCCGAAGAACGTTTTCCAATGATGAGCACTTTAAAGTTCTGCTATGTGGCGCGGTA
TTATCCCGTATTGACGCCGGGCAAGAGCAACTCGGTCGCCGCATACACTATTCTCAG
AATGACTTGGTTGAGTACTCACCAGTCACAGAAAAGCATCTTACGGATGGCATGAC
AGTAAGAGAATTATGCAGTGCTGCCATAACCATGAGTGATAACACTGCGGCCAACT
TACTTCTGACAACGATCGGAGGACCGAAGGAGCTAACCGCTTTTTGCACAACATGG
GGGATCATGTAACTCGCCTTGATCGTTGGGAACCGGAGCTGAATGAAGCCATACCA
AACGACGAGCGTGACACCACGATGCCTGTAGCAATGGCAACAACGTTGCGCAAACT
ATTAACTGGCGAACTACTTACTCTAGCTTCCCGGCAACAATTAATAGACTGGATGGA
GGCGGATAAAGTTGCAGGACCACTTCTGCGCTCGGCCCTTCCGGCTGGCTGGTTTAT
TGCTGATAAATCTGGAGCCGGTGAGCGTGGAAGCCGCGGTATCATTGCAGCACTGG
GGCCAGATGGTAAGCCCTCCCGTATCGTAGTTATCTACACGACGGGGAGTCAGGCA
ACTATGGATGAACGAAATAGACAGATCGCTGAGATAGGTGCCTCACTGATTAAGCA
TTGGTAACTGTCAGACCAAGTTTACTCATATATACTTTAGATTGATTTAAAACTTCAT
TTTTAATTTAAAAGGATCTAGGTGAAGATCCTTTTTGATAATCTCATGACCAAAATC
CCTTAACGTGAGTTTTCGTTCCACTGAGCGTCAGACCCCGTAGAAAGATCAAAGGA
TCTTCTTGAGATCCTTTTTTTCTGCGCGTAATCTGCTGCTTGCAAACAAAAAAACCAC
CGCTACCAGCGGTGGTTTGTTTGCCGGATCAAGAGCTACCAACTCTTTTTCCGAAGG
TAACTGGCTTCAGCAGAGCGCAGATACCAAATACTGTCCTTCTAGTGTAGCCGTAGT
TAGGCCACCACTTCAAGAACTCTGTAGCACCGCCTACATACCTCGCTCTGCTAATCC

FIG. 15 CONTINUED

TGTTACCAGTGGCTGCTGCCAGTGGCGATAAGTCGTGTCTTACCGGGTTGGACTCAA
GACGATAGTTACCGGATAAGGCGCAGCGGTCGGGCTGAACGGGGGGTTCGTGCACA
CAGCCCAGCTTGGAGCGAACGACCTACACCGAACTGAGATACCTACAGCGTGAGCT
ATGAGAAAGCGCCACGCTTCCCGAAGGGAGAAAGGCGGACAGGTATCCGGTAAGC
GGCAGGGTCGGAACAGGAGAGCGCACGAGGGAGCTTCCAGGGGGAAACGCCTGGT
ATCTTTATAGTCCTGTCGGGTTTCGCCACCTCTGACTTGAGCGTCGATTTTTGTGATG
CTCGTCAGGGGGGCGGAGCCTATGGAAAAACGCCAGCAACGCGGCCTTTTTACGGT
TCCTGGCCTTTTGCTGGCCTTTTGCTCACATGT

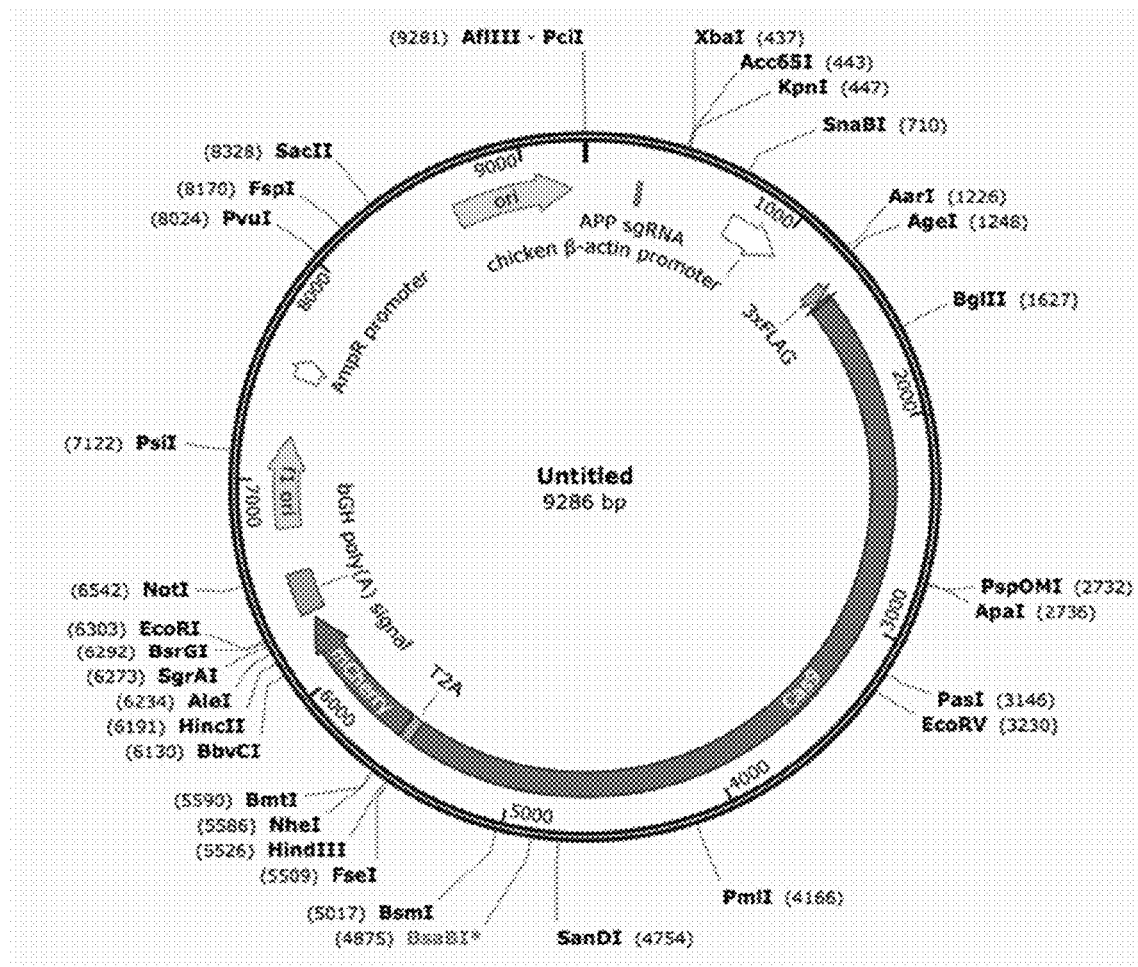

FIG. 16

PX551 Cas9 vector (SEQ ID NO:18)

cctgcaggcagctgcgcgctcgctcgctcactgaggccgcccgggcaaagcccgggcgtcgggcgacctttggtcgcccggcctcagt
gagcgagcgagcgcgcagagagggagtggccaactccatcactagggggttcctgcggcctctagaaagcttAGCTGAATGGG
GTCCGCCTCTTTTCCCTGCCTAAACAGACAGGAACTCCTGCCAATTGAGGGCGTCAC
CGCTAAGGCTCCGCCCCAGCCTGGGCTCCACAACCAATGAAGGGTAATCTCGACAA
AGAGCAAGGGGTGGGGCGCGGGCGCGCAGGTGCAGCAGCACACAGGCTGGTCGGG
AGGGCGGGGCGCGACGTCTGCCGTGCGGGGTCCCGGCATCGGTTGCGCGaccggtgcca
ccatgtacccatacgatgttccagattacgcttcgccgaagaaaaagcgcaaggtcgaagcgtccgacaagaagtacagcatcggcctgg
acatcggcaccaactctgtgggctgggccgtgatcaccgacgagtacaaggtgcccagcaagaaattcaaggtgctgggcaacaccgac
cggcacagcatcaagaagaacctgatcggagccctgctgttcgacagcggcgaaacagccgaggccaccggctgaagagaaccgcc
agaagaagatacaccagacggaagaaccggatctgctatctgcaagagatcttcagcaacgagatggccaaggtggacgacagcttcttc
cacagactggaagagtccttcctggtggaagaggataagaagcacgagcggcacccccatcttcggcaacatcgtggacgaggtggccta
ccacgagaagtaccccaccatctaccacctgagaaagaaactggtggacagcaccgacaaggccgacctgcggctgatctatctggccct
ggcccacatgatcaagttccggggccacttcctgatcgagggcgacctgaaccccgacaacagcgacgtggacaagctgttcatccagct
ggtgcagacctacaaccagctgttcgaggaaaaccccatcaacgccagcggcgtggacgccaaggccatcctgtctgccagactgagca
agagcagacggctggaaaatctgatcgcccagctgcccggcgagaagaagaatggcctgttcggcaacctgattgccctgagcctgggc
ctgacccccaacttcaagagcaacttcgacctggccgaggatgccaaactgcagctgagcaaggacacctacgacgacgacctggacaa
cctgctggcccagatcggcgaccagtacgccgacctgtttctggccgccaagaacctgtccgacgccatcctgctgagcgacatcctgag
agtgaacaccgagatcaccaaggcccccctgagcgcctctatgatcaagagatacgacgagcaccaccaggacctgaccctgctgaaag
ctctcgtgcggcagcagctgcctgagaagtacaaagagattttcttcgaccagagcaagaacggctacgccggctacattgacggcggag
ccagccaggaagagttctacaagttcatcaagcccatcctggaaaagatggacggcaccgaggaactgctcgtgaagctgaacagagag
gacctgctgcggaagcagcggaccttcgacaacggcagcatccccaccagatccacctgggagagctgcacgccattctgcggcggc
aggaagatttttacccattcctgaaggacaaccgggaaaagatcgagaagatcctgaccttccgcatcccctactacgtgggccctctggcc
aggggaaacagcagattcgcctggatgaccagaaagagcgaggaaaccatcacccctggaacttcgaggaagtggtggacaagggc
gcttccgcccagagcttcatcgagcggatgaccaacttcgataagaacctgcccaacgagaaggtgctgcccaagcacagcctgctgtac
gagtacttcaccgtgtataacgagctgaccaaagtgaaatacgtgaccgagggaatgagaaagcccgccttcctgagcggcgagcagaa
aaaggccatcgtggacctgctgttcaagaccaaccggaaagtgaccgtgaagcagctgaaagaggactacttcaagaaaatcgagtgctt
cgactccgtggaaatctccggcgtggaagatcggttcaacgcctccctgggcacataccacgatctgctgaaaattatcaaggacaaggac
ttcctggacaatgaggaaaacgaggacattctggaagatatcgtgctgaccctgacactgtttgaggacagagagatgatcgaggaacggc
tgaaaacctatgcccacctgttcgacgacaaagtgatgaagcagctgaagcggcggagatacaccggctggggcaggctgagccggaa
gctgatcaacggcatccgggacaagcagtccggcaagacaatcctggatttcctgaagtccgacggcttcgccaacagaaacttcatgca
gctgatccacgacgacagcctgaccttaaagaggacatccagaaagcccaggtgtccggccagggcgatagcctgcacgagcacattg
ccaatctggccggcagccccgccattaagaagggcatcctgcagacagtgaaggtggtggacgagctcgtgaaagtgatgggccggca
caagcccgagaacatcgtgatcgaaatggccagagagaaccagaccacccagaagggacagaagaacagccgcgagagaatgaagc
ggatcgaagagggcatcaaagagctgggcagccagatcctgaaagaacaccccgtggaaaacacccagctgcagaacgagaagctgt
acctgtactacctgcagaatgggcgggatatgtacgtggaccaggaactggacatcaaccggctgtccgactacgatgtggaccatatcgt
gcctcagagctttctgaaggacgactccatcgacaacaaggtgctgaccagaagcgacaagaaccggggcaagagcgacaacgtgccc
tccgaagaggtcgtgaagaagatgaagaactactggcggcagctgctgaacgccaagctgattacccagagaaagttcgacaatctgacc

FIG. 16 CONTINUED aaggccgagagaggcggcctgagcgaactggataaggccggcttcatcaagagacagctggtggaaacccggcagatcacaaagcac
gtggcacagatcctggactcccggatgaacactaagtacgacgagaatgacaagctgatccgggaagtgaaagtgatcaccctgaagtcc
aagctggtgtccgatttccggaaggatttccagttttacaaagtgcgcgagatcaacaactaccaccacgcccacgacgcctacctgaacgc
cgtcgtgggaaccgccctgatcaaaaagtaccctaagctggaaagcgagttcgtgtacggcgactacaaggtgtacgacgtgcggaagat
gatcgccaagagcgagcaggaaatcggcaaggctaccgccaagtacttcttctacagcaacatcatgaacttttcaagaccgagattaccc
tggccaacggcgagatccggaagcggcctctgatcgagacaaacggcgaaaccggggagatcgtgtgggataagggccgggattttgc
caccgtgcggaaagtgctgagcatgccccaagtgaatatcgtgaaaaagaccgaggtgcagacaggcggcttcagcaaagagtctatcct
gcccaagaggaacagcgataagctgatcgccagaaagaaggactgggaccctaagaagtacggcggcttcgacagccccaccgtggc
ctattctgtgctggtggtggccaaagtggaaaagggcaagtccaagaaactgaagagtgtgaaagagctgctggggatcaccatcatgga
aagaagcagcttcgagaagaatcccatcgactttctggaagccaaggggctacaaagaagtgaaaaaggacctgatcatcaagctgcctaa
gtactccctgttcgagctggaaaacggccggaagagaatgctggcctctgccggcgaactgcagaagggaaacgaactggccctgccct
ccaaatatgtgaacttcctgtacctggccagccactatgagaagctgaagggctcccccgaggataatgagcagaaacagctgtttgtgga
acagcacaagcactacctggacgagatcatcgagcagatcagcgagttctccaagagagtgatcctggccgacgctaatctggacaaagt
gctgtccgcctacaacaagcaccgggataagcccatcagagagcaggccgagaatatcatccacctgtttaccctgaccaatctgggagc
ccctgccgccttcaagtactttgacaccaccatcgaccggaagaggtacaccagcaccaaagaggtgctggacgccaccctgatccacca
gagcatcaccggcctgtacgagacacggatcgacctgtctcagctgggaggcgacagccccaagaagaagagaaaggtggaggccag
ctaagaattcAATAAAAGATCTTTATTTTCATTAGATCTGTGTGTTGGTTTTTGTGTgcggcc
gcaggaaccccctagtgatggagttggccactccctctgcgcgctcgctcgctcactgaggccgggcgaccaaaggtcgcccgacgcc
cgggctttgcccgggcggcctcagtgagcgagcgagcgcgcagctgcctgcaggggcgcctgatgcggtattttctccttacgcatctgtg
cggtatttcacaccgcatacgtcaaagcaaccatagtacgcgccctgtagcggcgcattaagcgcggcgggtgtggtggttacgcgcagc
gtgaccgctacacttgccagcgccctagcgcccgctcctttcgctttcttcccttcctttctcgccacgttcgccggctttccccgtcaagctcta
aatcgggggctcccttagggttccgatttagtgctttacggcacctcgaccccaaaaaacttgatttgggtgatggttcacgtagtgggccat
cgccctgatagacggtttttcgccctttgacgttggagtccacgttctttaatagtggactcttgttccaaactggaacaacactcaaccctatct
cgggctattcttttgatttataagggattttgccgatttcggcctattggttaaaaaatgagctgatttaacaaaaatttaacgcgaattttaacaaa
atattaacgtttacaattttatggtgcactctcagtacaatctgctctgatgccgcatagttaagccagccccgacacccgccaacacccgctg
acgcgccctgacgggcttgtctgctcccggcatccgcttacagacaagctgtgaccgtctccgggagctgcatgtgtcagaggttttcaccg
tcatcaccgaaacgcgcgagacgaaagggcctcgtgatacgcctatttttataggttaatgtcatgataataatggtttcttagacgtcaggtg
gcacttttcggggaaatgtgcgcggaaccccctatttgtttatttttctaaatacattcaaatatgtatccgctcatgagacaataaccctgataaat
gcttcaataatattgaaaaaggaagagtatgagtattcaacatttccgtgtcgcccttattcccttttttgcggcattttgccttcctgttttgctcac
ccagaaacgctggtgaaagtaaaagatgctgaagatcagttgggtgcacgagtgggttacatcgaactggatctcaacagcggtaagatcc
ttgagagttttcgccccgaagaacgttttccaatgatgagcacttttaaagttctgctatgtggcgcggtattatcccgtattgacgccgggcaa
gagcaactcggtcgccgcatacactattctcagaatgacttggttgagtactcaccagtcacagaaaagcatcttacggatggcatgacagta
agagaattatgcagtgctgccataaccatgagtgataacactgcggccaacttacttctgacaacgatcggaggaccgaaggagctaaccg
cttttttgcacaacatgggggatcatgtaactcgccttgatcgttgggaaccggagctgaatgaagccataccaaacgacgagcgtgacacc
acgatgcctgtagcaatggcaacaacgttgcgcaaactattaactggcgaactacttactctagcttcccggcaacaattaatagactggatg
gaggcggataaagttgcaggaccacttctgcgctcggcccttccggctggctggtttattgctgataaatctggagccggtgagcgtggaag
ccgcggtatcattgcagcactggggccagatggtaagccctcccgtatcgtagttatctacacgacggggagtcaggcaactatggatgaa
cgaaatagacagatcgctgagataggtgcctcactgattaagcattggtaactgtcagaccaagtttactcatatatactttagattgatttaaaa
cttcatttttaatttaaaaggatctaggtgaagatcctttttgataatctcatgaccaaaatcccttaacgtgagttttcgttccactgagcgtcaga
ccccgtagaaaagatcaaaggatcttcttgagatcctttttttctgcgcgtaatctgctgcttgcaaacaaaaaaaccaccgctaccagcggtg

FIG. 16 CONTINUED gtttgtttgccggatcaagagctaccaactcttttttccgaaggtaactggcttcagcagagcgcagataccaaatactgtccttctagtgtagcc
gtagttaggccaccacttcaagaactctgtagcaccgcctacatacctcgctctgctaatcctgttaccagtggctgctgccagtggcgataa
gtcgtgtcttaccgggttggactcaagacgatagttaccggataaggcgcagcggtcgggctgaacggggggttcgtgcacacagcccag
cttggagcgaacgacctacaccgaactgagatacctacagcgtgagctatgagaaagcgccacgcttcccgaagggagaaaggcggac
aggtatccggtaagcggcagggtcggaacaggagagcgcacgagggagcttccaggggaaacgcctggtatctttatagtcctgtcgg
gtttcgccacctctgacttgagcgtcgatttttgtgatgctcgtcaggggggcggagcctatggaaaaacgccagcaacgcggccttttacg
gttcctggccttttgctggccttttgctcacatgt

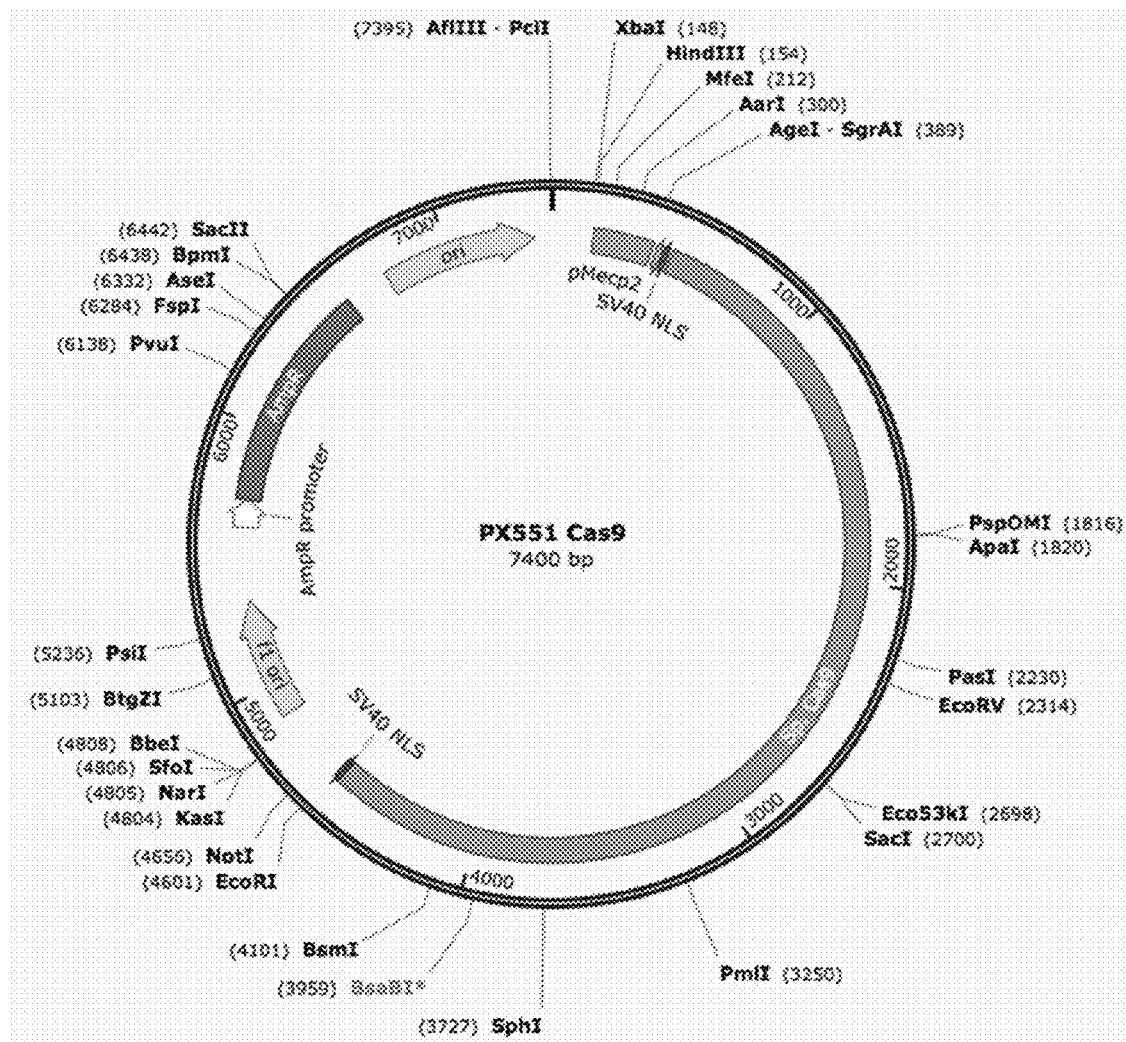

FIG. 17

PX552 APP sgRNA vector (SEQ ID NO:19)

cctgcaggcagctgcgcgctcgctcgctcactgaggccgcccgggcaaagcccgggcgtcggcgacctttggtcgcccggcctcagtgagcgagc
gagcgcgcagagagggagtggccaactccatcactagggggttcctgcggccgcacgcgtgagggcctatttcccatgattccttcatatttgcatatacg
atacaaggctgttagagagataattggaattaatttgactgtaaacacaaagatattagtacaaaatacgtgacgtagaaagtaataatttcttgggtagtttgc
agttttaaaattatgttttaaaatggactatcatatgcttaccgtaactgaaagtattcgatttcttggctttatatatcttGTGGAAAGGACGAAA
CACCATCCATCCATCATGGCGTGGGTTttagagctaGAAAtagcaagttaaaataaggctagtccgttatcaacttgaaaaag
tggcaccgagtcggtgcTTTTTTctagactgcagagggccctgcgtatgagtgcaagtgggttttaggaccaggatgaggcggggtgggggtgc
ctacctgacgaccgaccccgacccactggacaagcacccaacccccattccccaaattgcgcatccctatcagagaggggggagggggaaacaggatg
cggcgaggcgcgtgcgcactgccagcttcagcaccgcggacagtgccttcgccccgcctggcggcgcgcgccaccgccgcctcagcactgaagg
cgcgctgacgtcactcgccggtcccccgcaaactccccttcccggccaccttggtcgcgtccgcgccgccgccgggcccagccggaccgcaccacgc
gaggcgcgagataggggggcacgggcgcgaccatctgcgctgcggcgccggcgactcagcgctgcctcagtctgcggtgggcagcggaggagtc
gtgtcgtgcctgagagcgcagtcgagaaggtaccggatcctctagagtcgacgccaccatggtgagcaagggcgaggagctgttcaccggggtggtg
cccatcctggtcgagctggacggcgacgtaaacggccacaagttcagcgtgtccggcgagggcgagggcgatgccacctacggcaagctgaccctg
aagttcatctgcaccaccggcaagctgcccgtgccctggcccaccctcgtgaccaccctgacctacggcgtgcagtgcttcagccgctaccccgaccac
atgaagcagcacgacttcttcaagtccgccatgcccgaaggctacgtccaggagcgcaccatcttcttcaaggacgacggcaactacaagacccgcgc
cgaggtgaagttcgagggcgacaccctggtgaaccgcatcgagctgaagggcatcgacttcaaggaggacggcaacatcctggggcacaagctgga
gtacaactacaacagccacaacgtctatatcatggccgacaagcagaagaacggcatcaaggtgaacttcaagatccgccacaacatcgaggacggca
gcgtgcagctcgccgaccactaccagcagaacacccccatcggcgacggccccgtgctgctgcccgacaaccactacctgagcacccagtccgccct
gagcaaagaccccaacgagaagcgcgatcacatggtcctgctggagttcgtgaccgccgccgggatcactctcggcatggacgagctgtacaagtcc
ggactcagatctcgagaggaggaggaggagacagacagcaggatgcccacctcgacagccccggcagctcccagccgagacgctccttcctctca
agggtgatcagggcagcgctaccgttgcagctgcttctgctgctgctgctgctcctggcctgcctgctacctgcctctgaagatgactacagctgcaccca
ggccaacaactttgcccgatccttctaccccatgctgcggtacaccaacggggccacctcccacctaggaattcgatatcaagcttatcgataccgagcgct
gctcgagagatctacgggtggcatccctgtgacccctccccagtgcctctcctggccctggaagttgccactccagtgcccaccagccttgtcctaataaa
attaagttgcatcattttgtctgactaggtgtccttctataatatatgggggtggaggggggtggtatggagcaaggggcaagttgggaagacaacctgtag
ggcctgcggggtctattgggaaccaagctggagtgcagtggcacaatcttggctcactgcaatctccgcctcctgggttcaagcgattctcctgcctcagc
ctcccgagttgttgggattccaggcatgcatgaccaggctcagctaatttttgtttttttggtagagacggggtttcaccatattggccaggctggtctccaact
cctaatctcaggtgatctaccacctggcctcccaaattgctgggattacaggcgtgaaccactgctccttccctgtccttctgattttgtaggtaaccacg
tgcggaccgagcggccgcaggaaccccctagtgatggagttggccactccctctgcgcgctcgctcgctcactgaggccgggcgaccaaaggtcgc
ccgacgcccgggctttgcccgggcggcctcagtgagcgagcgagcgcgcagctgcctgcaggggcgcctgatgcggtattttctccttacgcatctgt
gcggtatttcacaccgcatacgtcaaagcaaccatagtacgcgccctgtagcggcgcattaagcgcggcgggtgtggtggttacgcgcagcgtgaccg
ctacacttgccagcgccctagcgcccgctcctttcgctttcttcccttcctttctcgccacgttcgccggctttccccgtcaagctctaaatcgggggctcccttt
agggttccgatttagtgctttacggcacctcgaccccaaaaaacttgatttgggtgatggttcacgtagtgggccatcgccctgatagacggttttcgccct
ttgacgttggagtccacgttctttaatagtggactcttgttccaaactggaacaacactcaaccctatctcgggctatcttttgatttataagggattttgccgat
ttcggcctattggttaaaaaatgagctgatttaacaaaaatttaacgcgaattttaacaaaatattaacgttacaattttatggtgcactctcagtacaatctgct
ctgatgccgcatagttaagccagccccgacacccgccaacacccgctgacgcgccctgacgggcttgtctgctcccggcatccgcttacagacaagct
gtgaccgtctccgggagctgcatgtgtcagaggttttcaccgtcatcaccgaaacgcgcgagacgaaagggcctcgtgatacgcctatttttataggttaat
gtcatgataataatggtttcttagacgtcaggtggcacttttcggggaaatgtgcgcggaacccctatttgtttatttttctaaatacattcaaatatgtatccgct
catgagacaataaccctgataaatgcttcaataatattgaaaaaggaagagtatgagtattcaacatttccgtgtcgcccttattcccttttttgcggcattttgc
cttcctgtttttgctcacccagaaacgctggtgaaagtaaaagatgctgaagatcagttgggtgcacgagtgggttacatcgaactggatctcaacagcggt
aagatcctgagagttttcgccccgaagaacgttttccaatgatgagcacttttaaagttctgctatgtggcgcggtattatcccgtattgacgccgggcaag
agcaactcggtcgccgcatacactattctcagaatgacttggttgagtactcaccagtcacagaaaagcatcttacggatggcatgacagtaagagaattat
gcagtgctgccataaccatgagtgataacactgcggccaacttacttctgacaacgatcggaggaccgaaggagctaaccgcttttttgcacaacatggg

FIG. 17 CONTINUED ggatcatgtaactcgccttgatcgttgggaaccggagctgaatgaagccataccaaacgacgagcgtgacaccacgatgcctgtagcaatggcaacaa
cgttgcgcaaactattaactggcgaactacttactctagcttcccggcaacaattaatagactggatggaggcggataaagttgcaggaccacttctgcgct
cggcccttccggctggctggtttattgctgataaatctggagccggtgagcgtgggtctcgcggtatcattgcagcactggggccagatggtaagccctc
ccgtatcgtagttatctacacgacggggagtcaggcaactatggatgaacgaaatagacagatcgctgagataggtgcctcactgattaagcattggtaac
tgtcagaccaagtttactcatatatactttagattgatttaaaacttcatttttaatttaaaaggatctaggtgaagatcctttttgataatctcatgaccaaaatccc
ttaacgtgagttttcgttccactgagcgtcagaccccgtagaaaagatcaaaggatcttcttgagatcctttttttctgcgcgtaatctgctgcttgcaaacaaa
aaaaccaccgctaccagcggtggtttgtttgccggatcaagagctaccaactctttttccgaaggtaactggcttcagcagagcgcagataccaaatactg
tccttctagtgtagccgtagttaggccaccacttcaagaactctgtagcaccgcctacatacctcgctctgctaatcctgttaccagtggctgctgccagtgg
cgataagtcgtgtcttaccgggttggactcaagacgatagttaccggataaggcgcagcggtcgggctgaacggggggttcgtgcacacagcccagctt
ggagcgaacgacctacaccgaactgagatacctacagcgtgagctatgagaaagcgccacgcttcccgaagggagaaaggcggacaggtatccggt
aagcggcagggtcggaacaggagagcgcacgagggagcttccaggggggaaacgcctggtatctttatagtcctgtcgggtttcgccacctctgacttga
gcgtcgatttttgtgatgctcgtcaggggggcggagcctatggaaaaacgccagcaacgcggccttttacggttcctggccttttgctggccttttgctcac
atgt

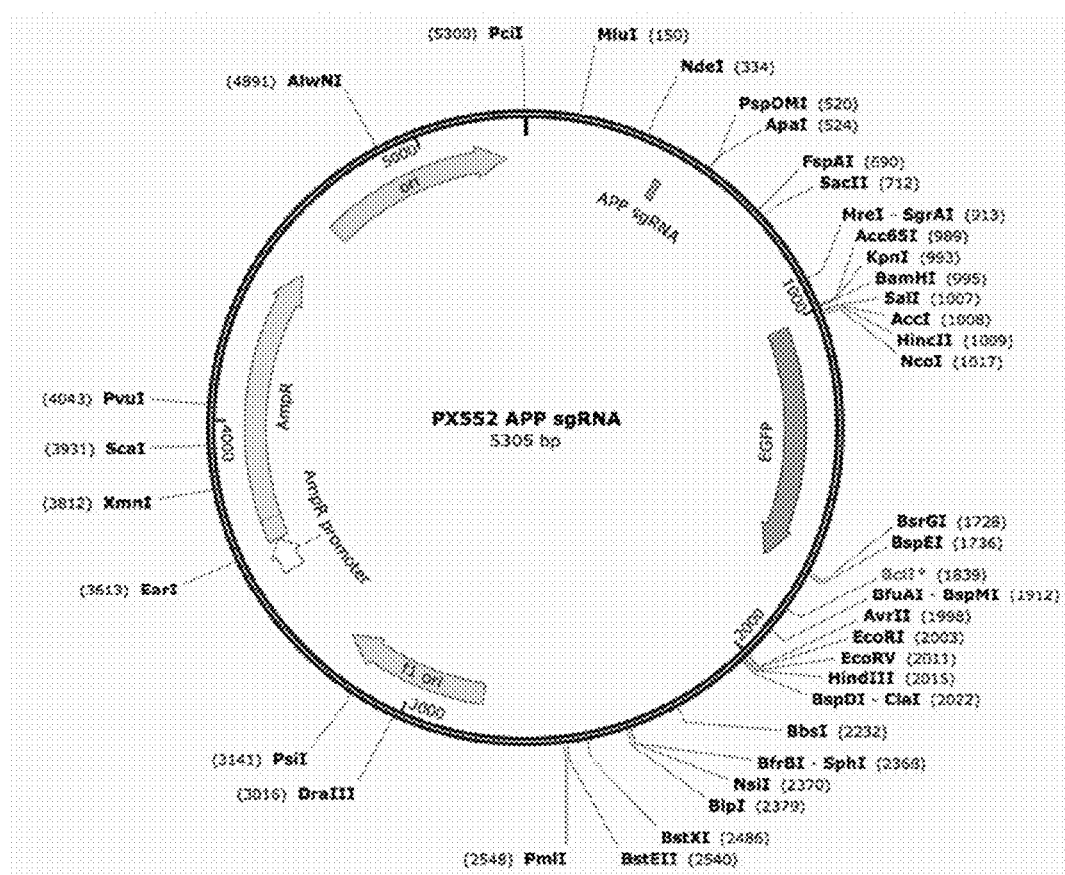

FIG. 18

LentiCRISPRv2 APP sgRNA vector (SEQ ID NO:20)

tgatgcggttttggcagtacatcaatgggcgtggatagcggtttgactcacggggatttccaagtctccacccccattgacgtcaatgggagttt
gttttggcaccaaaatcaacgggactttccaaaatgtcgtaacaactccgccccattgacgcaaatgggcggtaggcgtgtacggtgggag
gtctatataagcagcgcgttttgcctgtactgggtctctctggttagaccagatctgagcctgggagctctctggctaactagggaacccactg
cttaagcctcaataaagcttgccttgagtgcttcaagtagtgtgtgcccgtctgttgtgtgactctggtaactagagatccctcagacccttttagt
cagtgtggaaaatctctagcagtggcgcccgaacagggacttgaaagcgaaagggaaaccagaggagctctctcgacgcaggactcgg
cttgctgaagcgcgcacggcaagaggcgaggggcggcgactggtgagtacgccaaaaattttgactagcggaggctagaaggagaga
gatgggtgcgagagcgtcagtattaagcgggggagaattagatcgcgatgggaaaaaattcggttaaggccagggggaaagaaaaaata
taaattaaaacatatagtatgggcaagcagggagctagaacgattcgcagttaatcctggcctgttagaaacatcagaaggctgtagacaaa
tactgggacagctacaaccatcccttcagacaggatcagaagaacttagatcattatataatacagtagcaaccctctattgtgtgcatcaaag
gatagagataaaagacaccaaggaagctttagacaagatagaggaagagcaaaacaaaagtaagaccaccgcacagcaagcggccgct
gatcttcagacctggaggaggagatatgagggacaattggagaagtgaattatataaatataaagtagtaaaaattgaaccattaggagtag
cacccaccaaggcaaagagaagagtggtgcagagagaaaaaagagcagtgggaataggagctttgttccttgggttcttgggagcagca
ggaagcactatgggcgcagcgtcaatgacgctgacggtacaggccagacaattattgtctggtatagtgcagcagcagaacaatttgctga
gggctattgaggcgcaacagcatctgttgcaactcacagtctggggcatcaagcagctccaggcaagaatcctggctgtggaaagatacct
aaaggatcaacagctcctggggatttggggttgctctggaaaactcatttgcaccactgctgtgccttggaatgctagttggagtaataaatct
ctgaacagatttggaatcacacgacctggatggagtgggacagagaaattaacaattacacaagcttaatacactccttaattgaagaatcg
caaaaccagcaagaaaagaatgaacaagaattattggaattagataaatgggcaagtttgtggaattggtttaacataacaaattggctgtggt
atataaaattattcataatgatagtaggaggcttggtaggtttaagaatagtttttgctgtactttctatagtgaatagagttaggcagggatattca
ccattatcgtttcagacccacctcccaaccccgaggggacccgacaggcccgaaggaatagaagaagaaggtggagagagagacaga
gacagatccattcgattagtgaacggatcggcactgcgtgcgccaattctgcagacaaatggcagtattcatccacaattttaaaagaaaagg
ggggattggggggtacagtgcaggggaaagaatagtagacataatagcaacagacatacaaactaaagaattacaaaaacaaattacaaa
aattcaaaattttcgggtttattacagggacagcagagatccagtttggttaattaaggtaccgagggcctatttcccatgattccttcatatttgc
atatacgatacaaggctgttagagagataattagaattaatttgactgtaaacacaaagatattagtacaaaatacgtgacgtagaaagtaataa
tttcttgggtagtttgcagttttaaaattatgttttaaaatggactatcatatgcttaccgtaacttgaaagtatttcgatttcttggctttatatatcttG
TGGAAAGGACGAAACACCgatccattcatcatggtgtgggtttagagctaGAAAtagcaagttaaaataaggctagtc
cgttatcaacttgaaaaagtggcaccgagtcggtgcTTTTTTgaattcgctagctaggtcttgaaaggagtgggaattggctccggtgc
ccgtcagtgggcagagcgcacatcgcccacagtccccgagaagttggggggaggggtcggcaattgatccggtgcctagagaaggtgg
cgcggggtaaactgggaaagtgatgtcgtgtactggctccgcctttttcccgagggtgggggagaaccgtatataagtgcagtagtcgccg
tgaacgttctttttcgcaacgggtttgccgccagaacacaggaccggttctagagcgctgccaccATGGACAAGAAGTACA
GCATCGGCCTGGACATCGGCACCAACTCTGTGGGCTGGGCCGTGATCACCGACGAG
TACAAGGTGCCCAGCAAGAAATTCAAGGTGCTGGGCAACACCGACCGGCACAGCAT
CAAGAAGAACCTGATCGGAGCCCTGCTGTTCGACAGCGGCGAAACAGCCGAGGCCA
CCCGGCTGAAGAGAACCGCCAGAAGAAGATACACCAGACGGAAGAACCGGATCTG
CTATCTGCAAGAGATCTTCAGCAACGAGATGGCCAAGGTGGACGACAGCTTCTTCCA
CAGACTGGAAGAGTCCTTCCTGGTGGAAGAGGATAAGAAGCACGAGCGGCACCCCA
TCTTCGGCAACATCGTGGACGAGGTGGCCTACCACGAGAAGTACCCCACCATCTACC
ACCTGAGAAAGAAACTGGTGGACAGCACCGACAAGGCCGACCTGCGGCTGATCTAT

FIG. 18 CONTINUED

CTGGCCCTGGCCCACATGATCAAGTTCCGGGGCCACTTCCTGATCGAGGGCGACCTG
AACCCCGACAACAGCGACGTGGACAAGCTGTTCATCCAGCTGGTGCAGACCTACAA
CCAGCTGTTCGAGGAAAACCCCATCAACGCCAGCGGCGTGGACGCCAAGGCCATCC
TGTCTGCCAGACTGAGCAAGAGCAGACGGCTGGAAAATCTGATCGCCCAGCTGCCC
GGCGAGAAGAAGAATGGCCTGTTCGGAAACCTGATTGCCCTGAGCCTGGGCCTGAC
CCCCAACTTCAAGAGCAACTTCGACCTGGCCGAGGATGCCAAACTGCAGCTGAGCA
AGGACACCTACGACGACGACCTGGACAACCTGCTGGCCCAGATCGGCGACCAGTAC
GCCGACCTGTTTCTGGCCGCCAAGAACCTGTCCGACGCCATCCTGCTGAGCGACATC
CTGAGAGTGAACACCGAGATCACCAAGGCCCCCCTGAGCGCCTCTATGATCAAGAG
ATACGACGAGCACCACCAGGACCTGACCCTGCTGAAAGCTCTCGTGCGGCAGCAGC
TGCCTGAGAAGTACAAAGAGATTTTCTTCGACCAGAGCAAGAACGGCTACGCCGGC
TACATTGACGGCGGAGCCAGCCAGGAAGAGTTCTACAAGTTCATCAAGCCCATCCT
GGAAAAGATGGACGGCACCGAGGAACTGCTCGTGAAGCTGAACAGAGAGGACCTG
CTGCGGAAGCAGCGGACCTTCGACAACGGCAGCATCCCCCACCAGATCCACCTGGG
AGAGCTGCACGCCATTCTGCGGCGGCAGGAAGATTTTACCCATTCCTGAAGGACAA
CCGGGAAAAGATCGAGAAGATCCTGACCTTCCGCATCCCCTACTACGTGGGCCCTCT
GGCCAGGGGAAACAGCAGATTCGCCTGGATGACCAGAAAGAGCGAGGAAACCATC
ACCCCCTGGAACTTCGAGGAAGTGGTGGACAAGGGCGCTTCCGCCCAGAGCTTCAT
CGAGCGGATGACCAACTTCGATAAGAACCTGCCCAACGAGAAGGTGCTGCCCAAGC
ACAGCCTGCTGTACGAGTACTTCACCGTGTATAACGAGCTGACCAAAGTGAAATAC
GTGACCGAGGGAATGAGAAAGCCCGCCTTCCTGAGCGGCGAGCAGAAAAAGGCCA
TCGTGGACCTGCTGTTCAAGACCAACCGGAAAGTGACCGTGAAGCAGCTGAAAGAG
GACTACTTCAAGAAAATCGAGTGCTTCGACTCCGTGGAAATCTCCGGCGTGGAAGAT
CGGTTCAACGCCTCCCTGGGCACATACCACGATCTGCTGAAAATTATCAAGGACAA
GGACTTCCTGGACAATGAGGAAAACGAGGACATTCTGGAAGATATCGTGCTGACCC
TGACACTGTTTGAGGACAGAGAGATGATCGAGGAACGGCTGAAAACCTATGCCCAC
CTGTTCGACGACAAAGTGATGAAGCAGCTGAAGCGGCGGAGATACACCGGCTGGGG
CAGGCTGAGCCGGAAGCTGATCAACGGCATCCGGGACAAGCAGTCCGGCAAGACA
ATCCTGGATTTCCTGAAGTCCGACGGCTTCGCCAACAGAAACTTCATGCAGCTGATC
CACGACGACAGCCTGACCTTTAAAGAGGACATCCAGAAAGCCCAGGTGTCCGGCCA
GGGCGATAGCCTGCACGAGCACATTGCCAATCTGGCCGGCAGCCCCGCCATTAAGA
AGGGCATCCTGCAGACAGTGAAGGTGGTGGACGAGCTCGTGAAAGTGATGGGCCGG
CACAAGCCCGAGAACATCGTGATCGAAATGGCCAGAGAGAACCAGACCACCCAGA
AGGGACAGAAGAACAGCCGCGAGAGAATGAAGCGGATCGAAGAGGGCATCAAAGA
GCTGGGCAGCCAGATCCTGAAAGAACACCCCGTGGAAAACACCCAGCTGCAGAACG
AGAAGCTGTACCTGTACTACCTGCAGAATGGGCGGGATATGTACGTGGACCAGGAA
CTGGACATCAACCGGCTGTCCGACTACGATGTGGACCATATCGTGCCTCAGAGCTTT
CTGAAGGACGACTCCATCGACAACAAGGTGCTGACCAGAAGCGACAAGAACCGGG
GCAAGAGCGACAACGTGCCCTCCGAAGAGGTCGTGAAGAAGATGAAGAACTACTGG
CGGCAGCTGCTGAACGCCAAGCTGATTACCCAGAGAAAGTTCGACAATCTGACCAA

FIG. 18 CONTINUED

GGCCGAGAGAGGCGGCCTGAGCGAACTGGATAAGGCCGGCTTCATCAAGAGACAG
CTGGTGGAAACCCGGCAGATCACAAAGCACGTGGCACAGATCCTGGACTCCCGGAT
GAACACTAAGTACGACGAGAATGACAAGCTGATCCGGGAAGTGAAAGTGATCACCC
TGAAGTCCAAGCTGGTGTCCGATTTCCGGAAGGATTTCCAGTTTTACAAAGTGCGCG
AGATCAACAACTACCACCACGCCCACGACGCCTACCTGAACGCCGTCGTGGGAACC
GCCCTGATCAAAAAGTACCCTAAGCTGGAAAGCGAGTTCGTGTACGGCGACTACAA
GGTGTACGACGTGCGGAAGATGATCGCCAAGAGCGAGCAGGAAATCGGCAAGGCT
ACCGCCAAGTACTTCTTCTACAGCAACATCATGAACTTTTTCAAGACCGAGATTACC
CTGGCCAACGGCGAGATCCGGAAGCGGCCTCTGATCGAGACAAACGGCGAAACCGG
GGAGATCGTGTGGGATAAGGGCCGGGATTTTGCCACCGTGCGGAAAGTGCTGAGCA
TGCCCCAAGTGAATATCGTGAAAAAGACCGAGGTGCAGACAGGCGGCTTCAGCAAA
GAGTCTATCCTGCCCAAGAGGAACAGCGATAAGCTGATCGCCAGAAAGAAGGACTG
GGACCCTAAGAAGTACGGCGGCTTCGACAGCCCCACCGTGGCCTATTCTGTGCTGGT
GGTGGCCAAAGTGGAAAAGGGCAAGTCCAAGAAACTGAAGAGTGTGAAAGAGCTG
CTGGGGATCACCATCATGGAAAGAAGCAGCTTCGAGAAGAATCCCATCGACTTTCT
GGAAGCCAAGGGCTACAAAGAAGTGAAAAAGGACCTGATCATCAAGCTGCCTAAGT
ACTCCCTGTTCGAGCTGGAAAACGGCCGGAAGAGAATGCTGGCCTCTGCCGGCGAA
CTGCAGAAGGGAAACGAACTGGCCCTGCCCTCCAAATATGTGAACTTCCTGTACCTG
GCCAGCCACTATGAGAAGCTGAAGGGCTCCCCCGAGGATAATGAGCAGAAACAGCT
GTTTGTGGAACAGCACAAGCACTACCTGGACGAGATCATCGAGCAGATCAGCGAGT
TCTCCAAGAGAGTGATCCTGGCCGACGCTAATCTGGACAAAGTGCTGTCCGCCTACA
ACAAGCACCGGGATAAGCCCATCAGAGAGCAGGCCGAGAATATCATCCACCTGTTT
ACCCTGACCAATCTGGGAGCCCCTGCCGCCTTCAAGTACTTTGACACCACCATCGAC
CGGAAGAGGTACACCAGCACCAAGGAGGTGCTGGACGCCACCCTGATCCACCAGAG
CATCACCGGCCTGTACGAGACACGGATCGACCTGTCTCAGCTGGGAGGCGACAAGC
GACCTGCCGCCACAAAGAAGGCTGGACAGGCTAAGAAGAAGAAAGATTACAAAGA
CGATGACGATAAGGGATCCGGCGCAACAAACTTCTCTCTGCTGAAACAAGCCGGAG
ATGTCGAAGAGAATCCTGGACCGACCGAGTACAAGCCCACGGTGCGCCTCGCCACC
CGCGACGACGTCCCCAGGGCCGTACGCACCCTCGCCGCCGCGTTCGCCGACTACCCC
GCCACGCGCCACACCGTCGATCCGGACCGCCACATCGAGCGGGTCACCGAGCTGCA
AGAACTCTTCCTCACGCGCGTCGGGCTCGACATCGGCAAGGTGTGGGTCGCGGACG
ACGGCGCCGCGGTGGCGGTCTGGACCACGCCGGAGAGCGTCGAAGCGGGGCGGT
GTTCGCCGAGATCGGCCCGCGCATGGCCGAGTTGAGCGGTTCCCGGCTGGCCGCGC
AGCAACAGATGGAAGGCCTCCTGGCGCCGCACCGGCCCAAGGAGCCCGCGTGGTTC
CTGGCCACCGTCGGAGTCTCGCCCGACCACCAGGGCAAGGGTCTGGGCAGCGCCGT
CGTGCTCCCCGGAGTGGAGGCGGCCGAGCGCGCCGGGGTGCCCGCCTTCCTGGAGA
CCTCCGCGCCCCGCAACCTCCCCTTCTACGAGCGGCTCGGCTTCACCGTCACCGCCG
ACGTCGAGGTGCCCGAAGGACCGCGCACCTGGTGCATGACCCGCAAGCCCGGTGCC
TGAACGCGTTAAGTCGACAATCAACCTCTGGATTACAAAATTTGTGAAAGATTGACT
GGTATTCTTAACTATGTTGCTCCTTTTACGCTATGTGGATACGCTGCTTTAATGCCTT

FIG. 18 CONTINUED

TGTATCATGCTATTGCTTCCCGTATGGCTTTCATTTTCTCCTCCTTGTATAAATCCTGG
TTGCTGTCTCTTTATGAGGAGTTGTGGCCCGTTGTCAGGCAACGTGGCGTGGTGTGC
ACTGTGTTTGCTGACGCAACCCCACTGGTTGGGGCATTGCCACCACCTGTCAGCTC
CTTTCCGGGACTTTCGCTTTCCCCCTCCCTATTGCCACGGCGGAACTCATCGCCGCCT
GCCTTGCCCGCTGCTGGACAGGGGCTCGGCTGTTGGGCACTGACAATTCCGTGGTGT
TGTCGGGGAAATCATCGTCCTTTCCTTGGCTGCTCGCCTGTGTTGCCACCTGGATTCT
GCGCGGGACGTCCTTCTGCTACGTCCCTTCGGCCCTCAATCCAGCGGACCTTCCTTCC
CGCGGCCTGCTGCCGGCTCTGCGGCCTCTTCCGCGTCTTCGCCTTCGCCCTCAGACG
AGTCGGATCTCCCTTTGGGCCGCCTCCCCGCGTCGACTTTAAGACCAATGACTTACA
AGGCAGCTGTAGATCTTAGCCACTTTTAAAAGAAAAGGGGGGACTGGAAGGGCTA
ATTCACTCCCAACGAAGACAAGATCTGCTTTTTGCTTGTACTGGGTCTCTCTGGTTAG
ACCAGATCTGAGCCTGGGAGCTCTCTGGCTAACTAGGGAACCCACTGCTTAAGCCTC
AATAAAGCTTGCCTTGAGTGCTTCAAGTAGTGTGTGCCCGTCTGTTGTGTGACTCTG
GTAACTAGAGATCCCTCAGACCCTTTTAGTCAGTGTGGAAATCTCTAGCAGggcccgttt
aaacccgctgatcagcctcgactgtgccttctagttgccagccatctgttgtttgcccctcccccgtgccttccttgaccctggaaggtgccact
cccactgtccttttcctaataaaatgaggaaattgcatcgcattgtctgagtaggtgtcattctattctggggggtggggtggggcaggacagc
aaggggggaggattgggaagacaatagcaggcatgctggggatgcggtgggctctatggcttctgaggcggaaagaaccagctggggct
ctaggggtatccccacgcgccctgtagcggcgcattaagcgcggcgggtgtggtggttacgcgcagcgtgaccgctacacttgccagc
gccctagcgcccgctcctttcgctttcttcccttcctttctcgccacgttcgccggctttccccgtcaagctctaaatcggggggctcccttaggg
ttccgatttagtgctttacggcacctcgacccccaaaaaacttgattagggtgatggttcacgtagtgggccatcgccctgatagacggttttcg
cccttttgacgttggagtccacgttctttaatagtggactcttgttccaaactggaacaacactcaaccctatctcggtctattctttttgatttataag
ggattttgccgatttcggcctattggttaaaaaatgagctgatttaacaaaaatttaacgcgaattaattctgtggaatgtgtgtcagttagggtgt
ggaaagtccccaggctccccagcaggcagaagtatgcaaagcatgcatctcaattagtcagcaaccaggtgtggaaagtccccaggctcc
ccagcaggcagaagtatgcaaagcatgcatctcaattagtcagcaaccatagtcccgcccctaactccgcccatcccgcccctaactccgc
ccagttccgcccattctccgccccatggctgactaatttttttttatttatgcagaggccgaggccgcctctgcctctgagctattccagaagtagt
gaggaggcttttttggaggcctaggcttttgcaaaaagctcccgggagcttgtatatccatttcggatctgatcagcacgtgttgacaattaat
catcggcatagtatatcggcatagtataatacgacaaggtgaggaactaaaccatggccaagttgaccagtgccgttccggtgctcaccgc
gcgcgacgtcgccggagcggtcgagttctggaccgaccggctcgggttctcccgggacttcgtggaggacgacttcgccggtgtggtcc
gggacgacgtgaccctgttcatcagcgcggtccaggaccaggtggtgccggacaacacccctggcctgggtgtgggtgcgcggcctgga
cgagctgtacgccgagtggtcggaggtcgtgtccacgaacttccgggacgcctccgggccggccatgaccgagatcggcgagcagccg
tgggggcgggagttcgccctgcgcgacccggccggcaactgcgtgcacttcgtggccgaggagcaggactgacacgtgctacgagattt
cgattccaccgccgccttctatgaaaggttgggcttcggaatcgttttccgggacgccggctggatgatcctccagcgcggggatctcatgc
tggagttcttcgcccacccccaacttgtttattgcagcttataatggttacaaataaagcaatagcatcacaaatttcacaaataaagcatttttttca
ctgcattctagttgtggtttgtccaaactcatcaatgtatcttatcatgtctgtataccgtcgacctctagctagagcttggcgtaatcatggtcata
gctgtttcctgtgtgaaattgttatccgctcacaattccacacaacatacgagccggaagcataaagtgtaaagcctggggtgcctaatgagt
gagctaactcacattaattgcgttgcgctcactgcccgctttccagtcgggaaacctgtcgtgccagctgcattaatgaatcggccaacgcgc
ggggagaggcggtttgcgtattgggcgctcttccgcttcctcgctcactgactcgctgcgctcggtcgttcggctgcggcgagcggtatcag
ctcactcaaaggcggtaatacggttatccacagaatcaggggataacgcaggaaagaacatgtgagcaaaaggccagcaaaaggccag
gaaccgtaaaaaggccgcgttgctggcgtttttccataggctccgcccccctgacgagcatcacaaaaatcgacgctcaagtcagaggtgg
cgaaacccgacaggactataaagataccaggcgtttccccctggaagctccctcgtgcgctctcctgttccgaccctgccgcttaccggata

FIG. 18 CONTINUED cctgtccgcctttctcccttcgggaagcgtggcgctttctcatagctcacgctgtaggtatctcagttcggtgtaggtcgttcgctccaagctgg
gctgtgtgcacgaaccccccgttcagcccgaccgctgcgccttatccggtaactatcgtcttgagtccaacccggtaagacacgacttatcg
ccactggcagcagccactggtaacaggattagcagagcgaggtatgtaggcggtgctacagagttcttgaagtggtggcctaactacggct
acactagaagaacagtatttggtatctgcgctctgctgaagccagttaccttcggaaaaagagttggtagctcttgatccggcaaacaaacca
ccgctggtagcggtggttttttgtttgcaagcagcagattacgcgcagaaaaaaaggatctcaagaagatcctttgatcttttctacggggtct
gacgctcagtggaacgaaaactcacgttaagggattttggtcatgagattatcaaaaaggatcttcacctagatccttttaaattaaaaatgaag
ttttaaatcaatctaaagtatatatgagtaaacttggtctgacagttaccaatgcttaatcagtgaggcacctatctcagcgatctgtctatttcgtt
catccatagttgcctgactccccgtcgtgtagataactacgatacgggagggcttaccatctggccccagtgctgcaatgataccgcgagac
ccacgctcaccggctccagatttatcagcaataaaccagccagccggaagggccgagcgcagaagtggtcctgcaactttatccgcctcc
atccagtctattaattgttgccgggaagctagagtaagtagttcgccagttaatagtttgcgcaacgttgttgccattgctacaggcatcgtggt
gtcacgctcgtcgtttggtatggcttcattcagctccggttcccaacgatcaaggcgagttacatgatcccccatgttgtgcaaaaaagcggtt
agctccttcggtcctccgatcgttgtcagaagtaagttggccgcagtgttatcactcatggttatggcagcactgcataattctcttactgtcatg
ccatccgtaagatgcttttctgtgactggtgagtactcaaccaagtcattctgagaatagtgtatgcggcgaccgagttgctcttgcccggcgt
caatacgggataataccgcgccacatagcagaactttaaaagtgctcatcattggaaaacgttcttcggggcgaaaactctcaaggatcttac
cgctgttgagatccagttcgatgtaacccactcgtgcacccaactgatcttcagcatctttactttcaccagcgtttctgggtgagcaaaaaca
ggaaggcaaaatgccgcaaaaaagggaataagggcgacacggaaatgttgaatactcatactcttcctttttcaatattattgaagcatttatc
agggttattgtctcatgagcggatacatatttgaatgtatttagaaaaataaacaatagggggttccgcgcacatttccccgaaaagtgccacct
gacgtcgacggatcgggagatctcccgatcccctatggtgcactctcagtacaatctgctctgatgccgcatagttaagccagtatctgctcc
ctgcttgtgtgttggaggtcgctgagtagtgcgcgagcaaaatttaagctacaacaaggcaaggcttgaccgacaattgcatgaagaatctg
cttagggttaggcgttttgcgctgcttcgcgatgtacgggccagatatacgcgttgacattgattattgactagttattaatagtaatcaattacgg
ggtcattagttcatagcccatatatggagttccgcgttacataacttacggtaaatggcccgcctggctgaccgcccaacgacccccgcccat
tgacgtcaataatgacgtatgttcccatagtaacgccaatagggactttccattgacgtcaatgggtggagtatttacggtaaactgcccacttg
gcagtacatcaagtgtatcatatgccaagtacgccccctattgacgtcaatgacggtaaatggcccgcctggcattatgcccagtacatgacc
ttatgggactttcctacttggcagtacatctacgtattagtcatcgctattaccatgg

SEQUENCE LISTING

<160> NUMBER OF SEQ ID NOS: 138

<210> SEQ ID NO 1
<211> LENGTH: 20
<212> TYPE: DNA
<213> ORGANISM: Artificial Sequence
<220> FEATURE:

<223> OTHER INFORMATION: synthetic

<400> SEQUENCE: 1
atccattcat catggtgtgg                                               20

<210> SEQ ID NO 2
<211> LENGTH: 20
<212> TYPE: DNA
<213> ORGANISM: Artificial Sequence
<220> FEATURE:
<223> OTHER INFORMATION: synthetic

<400> SEQUENCE: 2
tggacaggtg gcgctcctct                                               20

<210> SEQ ID NO 3
<211> LENGTH: 20
<212> TYPE: DNA
<213> ORGANISM: Artificial Sequence
<220> FEATURE:
<223> OTHER INFORMATION: synthetic

<400> SEQUENCE: 3
ttggacaggt ggcgctcctc                                               20

<210> SEQ ID NO 4
<211> LENGTH: 20
<212> TYPE: DNA
<213> ORGANISM: Artificial Sequence
<220> FEATURE:
<223> OTHER INFORMATION: synthetic

<400> SEQUENCE: 4
gtagccgttc tgctgcatct                                               20

<210> SEQ ID NO 5
<211> LENGTH: 20
<212> TYPE: DNA
<213> ORGANISM: Artificial Sequence
<220> FEATURE:
<223> OTHER INFORMATION: synthetic

<400> SEQUENCE: 5
tgctcaaaga acttgtaggt                                               20

<210> SEQ ID NO 6
<211> LENGTH: 20
<212> TYPE: DNA
<213> ORGANISM: Artificial Sequence
<220> FEATURE:
<223> OTHER INFORMATION: synthetic

<400> SEQUENCE: 6
atccatccat catggcgtgg                                               20

<210> SEQ ID NO 7
<211> LENGTH: 20
<212> TYPE: DNA
<213> ORGANISM: Artificial Sequence
<220> FEATURE:
<223> OTHER INFORMATION: synthetic

<400> SEQUENCE: 7
tggagagatg gcgctcctct                                               20

```
<210> SEQ ID NO 8
<211> LENGTH: 20
<212> TYPE: DNA
<213> ORGANISM: Artificial Sequence
<220> FEATURE:
<223> OTHER INFORMATION: synthetic

<400> SEQUENCE: 8
ttggagagat ggcgctcctc                                                 20

<210> SEQ ID NO 9
<211> LENGTH: 20
<212> TYPE: DNA
<213> ORGANISM: Artificial Sequence
<220> FEATURE:
<223> OTHER INFORMATION: synthetic

<400> SEQUENCE: 9
atatccgttc tgctgcatct                                                 20

<210> SEQ ID NO 10
<211> LENGTH: 20
<212> TYPE: DNA
<213> ORGANISM: Artificial Sequence
<220> FEATURE:
<223> OTHER INFORMATION: synthetic

<400> SEQUENCE: 10
tgctcaaaga acttgtaagt                                                 20

<210> SEQ ID NO 11
<211> LENGTH: 2088
<212> TYPE: DNA
<213> ORGANISM: Homo sapiens

<400> SEQUENCE: 11
atgctgcccg gtttggcact gctcctgctg gccgcctgga cggctcgggc gctggaggta     60
cccactgatg gtaatgctgg cctgctggct gaaccccaga ttgccatgtt ctgtggcaga    120
ctgaacatgc acatgaatgt ccagaatggg aagtgggatt cagatccatc agggaccaaa    180
acctgcattg ataccaagga aggcatcctg cagtattgcc aagaagtcta ccctgaactg    240
cagatcacca atgtggtaga agccaaccaa ccagtgacca tccagaactg gtgcaagcgg    300
ggccgcaagc agtgcaagac ccatccccac tttgtgattc cctaccgctg cttagttggt    360
gagtttgtaa gtgatgccct tctcgttcct gacaagtgca aattcttaca ccaggagagg    420
atggatgttt gcgaaactca tcttcactgg cacaccgtcg ccaaagagac atgcagtgag    480
aagagtacca acttgcatga ctacggcatg ttgctgccct gcggaattga caagttccga    540
ggggtagagt ttgtgtgttg cccactggct gaagaaagtg acaatgtgga ttctgctgat    600
gcggaggagg atgactcgga tgtctggtgg ggcggagcag acacagacta tgcagatggg    660
agtgaagaca aagtagtaga agtagcgagg aggaagaag tggctgaggt ggaagaagaa    720
gaagccgatg atgacgagga cgatgaggat ggtgatgagg tagaggaaga ggctgaggaa    780
ccctacgaag aagccacaga gagaaccacc agcattgcca ccaccaccac caccaccaca    840
gagtctgtgg aagaggtggt tcgagttcct acaacagcag ccagtacccc tgatgccgtt    900
gacaagtatc tcgagacacc tggggatgag aatgaacatg cccatttcca gaaagccaaa    960
gagaggcttg aggccaagca ccgagagaga atgtccaggg tcatgagaga atgggaagag   1020
gcagaacgtc aagcaaagaa cttgcctaaa gctgataaga aggcagttat ccagcatttc   1080
```

-continued

```
caggagaaag tggaatcttt ggaacaggaa gcagccaacg agagacagca gctggtggag     1140
acacacatgg ccagagtgga agccatgctc aatgaccgcc gccgcctggc cctggagaac     1200
tacatcaccg ctctgcaggc tgttcctcct cggcctcgtc acgtgttcaa tatgctaaag     1260
aagtatgtcc gcgcagaaca gaaggacaga cagcacaccc taaagcattt cgagcatgtg     1320
cgcatggtgg atcccaagaa agccgctcag atccggtccc aggttatgac acacctccgt     1380
gtgatttatg agcgcatgaa tcagtctctc tccctgctct acaacgtgcc tgcagtggcc     1440
gaggagattc aggatgaagt tgatgagctg cttcagaaag agcaaaacta ttcagatgac     1500
gtcttggcca acatgattag tgaaccaagg atcagttacg aaacgatgc tctcatgcca      1560 tctttgaccg aaacgaaaac caccgtggag ctccttcccg tgaatggaga gttcagcctg     1620
gacgatctcc agccgtggca ttcttttggg gctgactctg tgccagccaa cacagaaaac     1680
gaagttgagc ctgttgatgc ccgccctgct gccgaccgag gactgaccac tcgaccaggt     1740
tctgggttga caaatatcaa gacggaggag atctctgaag tgaagatgga tgcagaattc     1800
cgacatgact caggatatga agttcatcat caaaaattgg tgttctttgc agaagatgtg     1860
ggttcaaaca aggtgcaat cattggactc atggtgggcg tgttgtcat agcgacagtg       1920 atcgtcatca ccttggtgat gctgaagaag aaacagtaca catccattca tcatggtgtg     1980
gtggaggttg acgccgctgt caccccagag gagcgccacc tgtccaagat gcagcagaac     2040
ggctacgaaa atccaaccta caagttcttt gagcagatgc agaactag                  2088
```

```
<210> SEQ ID NO 12
<211> LENGTH: 695
<212> TYPE: PRT
<213> ORGANISM: Homo sapiens

<400> SEQUENCE: 12

Met Leu Pro Gly Leu Ala Leu Leu Leu Ala Ala Trp Thr Ala Arg
1               5                   10                  15

Ala Leu Glu Val Pro Thr Asp Gly Asn Ala Gly Leu Leu Ala Glu Pro
            20                  25                  30

Gln Ile Ala Met Phe Cys Gly Arg Leu Asn Met His Met Asn Val Gln
        35                  40                  45

Asn Gly Lys Trp Asp Ser Asp Pro Ser Gly Thr Lys Thr Cys Ile Asp
    50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
        115                 120                 125

Val Pro Asp Lys Cys Lys Phe Leu His Gln Glu Arg Met Asp Val Cys
    130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190
```

```
Ser Asp Asn Val Asp Ser Ala Asp Ala Glu Glu Asp Ser Asp Val
        195                 200                 205

Trp Trp Gly Gly Ala Asp Thr Asp Tyr Ala Asp Gly Ser Glu Asp Lys
    210                 215                 220

Val Val Glu Val Ala Glu Glu Glu Val Ala Glu Val Glu Glu Glu
225                 230                 235                 240

Glu Ala Asp Asp Asp Glu Asp Asp Glu Asp Gly Asp Glu Val Glu Glu
                245                 250                 255

Glu Ala Glu Glu Pro Tyr Glu Glu Ala Thr Glu Arg Thr Thr Ser Ile
                260                 265                 270

Ala Thr Thr Thr Thr Thr Thr Glu Ser Val Glu Val Val Arg
        275                 280                 285

Val Pro Thr Thr Ala Ala Ser Thr Pro Asp Ala Val Asp Lys Tyr Leu
        290                 295                 300

Glu Thr Pro Gly Asp Glu Asn Glu His Ala His Phe Gln Lys Ala Lys
305                 310                 315                 320

Glu Arg Leu Glu Ala Lys His Arg Glu Arg Met Ser Gln Val Met Arg
                325                 330                 335

Glu Trp Glu Glu Ala Glu Arg Gln Ala Lys Asn Leu Pro Lys Ala Asp
                340                 345                 350

Lys Lys Ala Val Ile Gln His Phe Gln Glu Lys Val Glu Ser Leu Glu
        355                 360                 365

Gln Glu Ala Ala Asn Glu Arg Gln Gln Leu Val Glu Thr His Met Ala
        370                 375                 380

Arg Val Glu Ala Met Leu Asn Asp Arg Arg Arg Leu Ala Leu Glu Asn
385                 390                 395                 400

Tyr Ile Thr Ala Leu Gln Ala Val Pro Pro Arg Pro Arg His Val Phe
                405                 410                 415

Asn Met Leu Lys Lys Tyr Val Arg Ala Glu Gln Lys Asp Arg Gln His
                420                 425                 430

Thr Leu Lys His Phe Glu His Val Arg Met Val Asp Pro Lys Lys Ala
        435                 440                 445

Ala Gln Ile Arg Ser Gln Val Met Thr His Leu Arg Val Ile Tyr Glu
        450                 455                 460

Arg Met Asn Gln Ser Leu Ser Leu Leu Tyr Asn Val Pro Ala Val Ala
465                 470                 475                 480

Glu Glu Ile Gln Asp Glu Val Asp Glu Leu Leu Gln Lys Glu Gln Asn
                485                 490                 495

Tyr Ser Asp Asp Val Leu Ala Asn Met Ile Ser Glu Pro Arg Ile Ser
                500                 505                 510

Tyr Gly Asn Asp Ala Leu Met Pro Ser Leu Thr Glu Thr Lys Thr Thr
        515                 520                 525

Val Glu Leu Leu Pro Val Asn Gly Glu Phe Ser Leu Asp Asp Leu Gln
        530                 535                 540

Pro Trp His Ser Phe Gly Ala Asp Ser Val Pro Ala Asn Thr Glu Asn
545                 550                 555                 560

Glu Val Glu Pro Val Asp Ala Arg Pro Ala Ala Asp Arg Gly Leu Thr
                565                 570                 575

Thr Arg Pro Gly Ser Gly Leu Thr Asn Ile Lys Thr Glu Glu Ile Ser
                580                 585                 590

Glu Val Lys Met Asp Ala Glu Phe Arg His Asp Ser Gly Tyr Glu Val
        595                 600                 605
```

| | | | | | | | | | | | | | |
|---|---|---|---|---|---|---|---|---|---|---|---|---|---|
| His | His | Gln | Lys | Leu | Val | Phe | Phe | Ala | Glu | Asp | Val | Gly | Ser | Asn | Lys |
| 610 | | | | | 615 | | | | | 620 | | | | | |

Gly Ala Ile Ile Gly Leu Met Val Gly Gly Val Val Ile Ala Thr Val
625 630 635 640

Ile Val Ile Thr Leu Val Met Leu Lys Lys Lys Gln Tyr Thr Ser Ile
645 650 655

His His Gly Val Val Glu Val Asp Ala Ala Val Thr Pro Glu Glu Arg
660 665 670

His Leu Ser Lys Met Gln Gln Asn Gly Tyr Glu Asn Pro Thr Tyr Lys
675 680 685

Phe Phe Glu Gln Met Gln Asn
690 695

<210> SEQ ID NO 13
<211> LENGTH: 2088
<212> TYPE: DNA
<213> ORGANISM: Mus musculus

<400> SEQUENCE: 13

```
atgctgccca gcttggcact gctcctgctg gccgcctgga cggttcgggc tctggaggta      60
cccactgatg caacgccgg gctgctggca gaacccagga tcgccatgtt ctgtggtaaa      120
ctcaacatgc acatgaatgt gcagaatgga agtgggagt cagacccgtc agggaccaaa      180
acctgcattg gcaccaagga gggcatcttg cagtactgcc aagaggtcta ccctgaactg      240
cagatcacaa acgtggtgga agccaaccag ccagtgacca tccagaactg gtgcaagcgg      300
ggccgcaagc agtgcaagac acacacccac atcgtgattc cttaccgttg cctagttggt      360
gagtttgtga gcgacgccct tctcgtgccc gacaagtgca agttcctaca ccaggagcgg      420
atggatgttt gtgagaccca tcttcactgg cacaccgtcg ccaaagagac atgcagcgag      480
aagagcacta acttgcacga ctatggcatg ctgctgccct gcggcatcga caagttccga      540
ggggtagagt ttgtatgctg cccgttggcc gaggaaagcg acagcgtgga ttctgcggat      600
gcagaggagg atgactctga tgtctggtgg ggtggagcgg acacagacta cgctgatggc      660
ggtgaagaca aagtagtaga agtcgccgaa gaggaggaag tggctgatgt tgaggaagag      720
gaagctgatg atgatgagga tgtggaggat ggggacgagg tggaggagga ggccgaggag      780
ccctacgaag aggccaccga gagaacaacc agcactgcca ccaccaccac aaccaccact      840
gagtccgtgg aggaggtggt ccgagttccc acgacagcag ccagcacccc gacgccgtc      900
gacaagtacc tggagacacc cggggacgag aacgagcatg cccatttcca gaaagccaaa      960
gagaggctgg aagccaagca ccgagagaga atgtcccagg tcatgagaga atgggaagag     1020
gcagagcgtc aagccaagaa cttgcccaaa gctgacaaga aggccgttat ccagcatttc     1080
caggagaaag tggaatctct ggaacaggaa gcagccaatg agacagca gcttgtagag     1140
acacacatgg ccagagttga agccatgctc aatgaccgcc gccgcctggc cctcgagaat     1200
tacatcactg cactgcaggc ggtgcccca aggcctcatc atgtgttcaa catgctgaag     1260
aagtacgtcc gtgcggagca gaaagacaga cagcacaccc taaagcattt tgaacatgtg     1320
cgcatggtgg accccaagaa agctgctcag atccggtccc aggttatgac acacctccgt     1380
gtgatctacg agcgcatgaa ccagtctctg tccctgctct acaatgtccc tgcggtggct     1440
gaggagattc aagatgaagt cgatgagctg cttcagaagg agcagaacta ctccgacgat     1500
gtcttggcca acatgatcag tgagcccaga atcagctacg aaacgacgc tctcatgcct     1560
tcgctgacgg aaaccaagac caccgtggag ctccttcccg tgaatgggga attcagcctg     1620
```

```
gatgacctcc agccgtggca ccctttgggg gtggactctg tgccagccaa taccgaaaat    1680
gaagtcgagc ctgttgacgc ccgccccgct gctgaccgag gactgaccac tcgaccaggt    1740
tctgggctga caaacatcaa gacggaagag atctcggaag tgaagatgga tgcagaattc    1800
ggacatgatt caggatttga agtccgccat caaaaactgg tgttctttgc tgaagatgtg    1860
ggttcgaaca aaggcgccat catcggactc atggtgggcg gcgttgtcat agcaaccgtg    1920
attgtcatca ccctggtgat gttgaagaag aaacagtaca catccatcca tcatggcgtg    1980
gtggaggtcg acgccgccgt gaccccagag gagcgccatc tctccaagat gcagcagaac    2040
ggatatgaga atccaactta caagttcttt gagcaaatgc agaactaa                 2088

<210> SEQ ID NO 14
<211> LENGTH: 695
<212> TYPE: PRT
<213> ORGANISM: Mus musculus

<400> SEQUENCE: 14

Met Leu Pro Ser Leu Ala Leu Leu Leu Ala Ala Trp Thr Val Arg
1               5                   10                  15

Ala Leu Glu Val Pro Thr Asp Gly Asn Ala Gly Leu Leu Ala Glu Pro
            20                  25                  30

Gln Ile Ala Met Phe Cys Gly Lys Leu Asn Met His Met Asn Val Gln
        35                  40                  45

Asn Gly Lys Trp Glu Ser Asp Pro Ser Gly Thr Lys Thr Cys Ile Gly
    50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Thr His Ile Val
            100                 105                 110

Ile Pro Tyr Arg Cys Leu Val Gly Glu Phe Val Ser Asp Ala Leu Leu
        115                 120                 125

Val Pro Asp Lys Cys Lys Phe Leu His Gln Glu Arg Met Asp Val Cys
    130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190

Ser Asp Ser Val Asp Ser Ala Asp Ala Glu Glu Asp Asp Ser Asp Val
        195                 200                 205

Trp Trp Gly Gly Ala Asp Thr Asp Tyr Ala Asp Gly Gly Glu Asp Lys
    210                 215                 220

Val Val Glu Val Ala Glu Glu Glu Val Ala Asp Val Glu Glu Glu
225                 230                 235                 240

Glu Ala Asp Asp Asp Glu Asp Val Glu Asp Gly Asp Glu Val Glu Glu
                245                 250                 255

Glu Ala Glu Glu Pro Tyr Glu Glu Ala Thr Glu Arg Thr Thr Ser Thr
            260                 265                 270

Ala Thr Thr Thr Thr Thr Thr Glu Ser Val Glu Glu Val Val Arg
        275                 280                 285
```

```
Val Pro Thr Thr Ala Ala Ser Thr Pro Asp Ala Val Asp Lys Tyr Leu
    290                 295                 300
Glu Thr Pro Gly Asp Glu Asn Glu His Ala His Phe Gln Lys Ala Lys
305                 310                 315                 320
Glu Arg Leu Glu Ala Lys His Arg Glu Arg Met Ser Gln Val Met Arg
                325                 330                 335
Glu Trp Glu Glu Ala Glu Arg Gln Ala Lys Asn Leu Pro Lys Ala Asp
            340                 345                 350
Lys Lys Ala Val Ile Gln His Phe Gln Glu Lys Val Glu Ser Leu Glu
        355                 360                 365
Gln Glu Ala Ala Asn Glu Arg Gln Gln Leu Val Glu Thr His Met Ala
    370                 375                 380
Arg Val Glu Ala Met Leu Asn Asp Arg Arg Arg Leu Ala Leu Glu Asn
385                 390                 395                 400
Tyr Ile Thr Ala Leu Gln Ala Val Pro Pro Arg Pro His His Val Phe
                405                 410                 415
Asn Met Leu Lys Lys Tyr Val Arg Ala Glu Gln Lys Asp Arg Gln His
            420                 425                 430
Thr Leu Lys His Phe Glu His Val Arg Met Val Asp Pro Lys Lys Ala
        435                 440                 445
Ala Gln Ile Arg Ser Gln Val Met Thr His Leu Arg Val Ile Tyr Glu
    450                 455                 460
Arg Met Asn Gln Ser Leu Ser Leu Leu Tyr Asn Val Pro Ala Val Ala
465                 470                 475                 480
Glu Glu Ile Gln Asp Glu Val Asp Glu Leu Leu Gln Lys Glu Gln Asn
                485                 490                 495
Tyr Ser Asp Asp Val Leu Ala Asn Met Ile Ser Glu Pro Arg Ile Ser
            500                 505                 510
Tyr Gly Asn Asp Ala Leu Met Pro Ser Leu Thr Glu Thr Lys Thr Thr
        515                 520                 525
Val Glu Leu Leu Pro Val Asn Gly Glu Phe Ser Leu Asp Asp Leu Gln
    530                 535                 540
Pro Trp His Pro Phe Gly Val Asp Ser Val Pro Ala Asn Thr Glu Asn
545                 550                 555                 560
Glu Val Glu Pro Val Asp Ala Arg Pro Ala Ala Asp Arg Gly Leu Thr
                565                 570                 575
Thr Arg Pro Gly Ser Gly Leu Thr Asn Ile Lys Thr Glu Glu Ile Ser
            580                 585                 590
Glu Val Lys Met Asp Ala Glu Phe Gly His Asp Ser Gly Phe Glu Val
        595                 600                 605
Arg His Gln Lys Leu Val Phe Phe Ala Glu Asp Val Gly Ser Asn Lys
    610                 615                 620
Gly Ala Ile Ile Gly Leu Met Val Gly Gly Val Val Ile Ala Thr Val
625                 630                 635                 640
Ile Val Ile Thr Leu Val Met Leu Lys Lys Lys Gln Tyr Thr Ser Ile
                645                 650                 655
His His Gly Val Val Glu Val Asp Ala Ala Val Thr Pro Glu Glu Arg
            660                 665                 670
His Leu Ser Lys Met Gln Gln Asn Gly Tyr Glu Asn Pro Thr Tyr Lys
        675                 680                 685
Phe Phe Glu Gln Met Gln Asn
    690                 695
```

<210> SEQ ID NO 15
<211> LENGTH: 4176
<212> TYPE: DNA
<213> ORGANISM: Streptococcus pyogenes M1

<400> SEQUENCE: 15

| | | | | | |
|---|---|---|---|---|---|
| atgggtatcc | acggagtccc | agcagccgac | aagaagtaca | gcatcggcct | ggacatcggc | 60 |
| accaactctg | tgggctgggc | cgtgatcacc | gacgagtaca | aggtgcccag | caagaaattc | 120 |
| aaggtgctgg | gcaacaccga | ccggcacagc | atcaagaaga | acctgatcgg | agccctgctg | 180 |
| ttcgacagcg | gcgaaacagc | cgaggccacc | cggctgaaga | gaaccgccag | aagaagatac | 240 |
| accagacgga | agaaccggat | ctgctatctg | caagagatct | tcagcaacga | gatggccaag | 300 |
| gtggacgaca | gcttcttcca | cagactggaa | gagtccttcc | tggtggaaga | ggataagaag | 360 |
| cacgagcggc | accccatctt | cggcaacatc | gtggacgagg | tggcctacca | cgagaagtac | 420 |
| cccaccatct | accacctgag | aaagaaactg | gtggacagca | ccgacaaggc | cgacctgcgg | 480 |
| ctgatctatc | tggccctggc | ccacatgatc | aagttccggg | gccacttcct | gatcgagggc | 540 |
| gacctgaacc | ccgacaacag | cgacgtggac | aagctgttca | tccagctggt | gcagacctac | 600 |
| aaccagctgt | tcgaggaaaa | ccccatcaac | gccagcggcg | tggacgccaa | ggccatcctg | 660 |
| tctgccagac | tgagcaagag | cagacggctg | gaaaatctga | tcgcccagct | gcccggcgag | 720 |
| aagaagaatg | gcctgttcgg | aaacctgatt | gccctgagcc | tgggcctgac | ccccaacttc | 780 |
| aagagcaact | tcgacctggc | cgaggatgcc | aaactgcagc | tgagcaagga | cacctacgac | 840 |
| gacgacctgg | acaacctgct | ggcccagatc | ggcgaccagt | acgccgacct | gtttctggcc | 900 |
| gccaagaacc | tgtccgacgc | catcctgctg | agcgacatcc | tgagagtgaa | caccgagatc | 960 |
| accaaggccc | ccctgagcgc | ctctatgatc | aagagatacg | acgagcacca | ccaggacctg | 1020 |
| accctgctga | aagctctcgt | gcggcagcag | ctgcctgaga | agtacaaaga | gattttcttc | 1080 |
| gaccagagca | agaacggcta | cgccggctac | attgacggcg | gagccagcca | ggaagagttc | 1140 |
| tacaagttca | tcaagcccat | cctggaaaag | atggacggca | ccgaggaact | gctcgtgaag | 1200 |
| ctgaacagag | aggacctgct | gcggaagcag | cggaccttcg | acaacggcag | catccccac | 1260 |
| cagatccacc | tgggagagct | gcacgccatt | ctgcggcggc | aggaagattt | ttacccattc | 1320 |
| ctgaaggaca | accgggaaaa | gatcgagaag | atcctgacct | tccgcatccc | ctactacgtg | 1380 |
| ggccctctgg | ccaggggaaa | cagcagattc | gcctggatga | ccagaaagag | cgaggaaacc | 1440 |
| atcacccct | ggaacttcga | ggaagtggtg | acaagggcg | cttccgccca | gagcttcatc | 1500 |
| gagcggatga | ccaacttcga | taagaacctg | cccaacgaga | ggtgctgcc | caagcacagc | 1560 |
| ctgctgtacg | agtacttcac | cgtgtataac | gagctgacca | agtgaaata | cgtgaccgag | 1620 |
| ggaatgagaa | agcccgcctt | cctgagcggc | gagcagaaaa | aggccatcgt | ggacctgctg | 1680 |
| ttcaagacca | accggaaagt | gaccgtgaag | cagctgaaag | aggactactt | caagaaaatc | 1740 |
| gagtgcttcg | actccgtgga | aatctccggc | gtggaagatc | ggttcaacgc | ctccctgggc | 1800 |
| acataccacg | atctgctgaa | aattatcaag | gacaaggact | tcctggacaa | tgaggaaaac | 1860 |
| gaggacattc | tggaagatat | cgtgctgacc | ctgacactgt | ttgaggacag | agagatgatc | 1920 |
| gaggaacggc | tgaaaaccta | tgcccacctg | ttcgacgaca | aagtgatgaa | gcagctgaag | 1980 |
| cggcggagat | acaccggctg | gggcaggctg | agccggaagc | tgatcaacgg | catccgggac | 2040 |
| aagcagtccg | gcaagacaat | cctggatttc | ctgaagtccg | acggcttcgc | caacagaaac | 2100 |
| ttcatgcagc | tgatccacga | cgacagcctg | accttaaag | aggacatcca | gaaagcccag | 2160 |

```
gtgtccggcc agggcgatag cctgcacgag cacattgcca atctggccgg cagccccgcc    2220
attaagaagg gcatcctgca gacagtgaag gtggtggacg agctcgtgaa agtgatgggc    2280
cggcacaagc ccgagaacat cgtgatcgaa atggccagag agaaccagac cacccagaag    2340
ggacagaaga acagccgcga gagaatgaag cggatcgaag agggcatcaa agagctgggc    2400
agccagatcc tgaaagaaca ccccgtggaa acacccagc tgcagaacga gaagctgtac    2460
ctgtactacc tgcagaatgg gcgggatatg tacgtggacc aggaactgga catcaaccgg    2520
ctgtccgact acgatgtgga ccatatcgtg cctcagagct ttctgaagga cgactccatc    2580
gacaacaagg tgctgaccag aagcgacaag aaccggggca gagcgacaa cgtgccctcc    2640 gaagaggtcg tgaagaagat gaagaactac tggcggcagc tgctgaacgc caagctgatt    2700
acccagagaa agttcgacaa tctgaccaag gccgagagag cggcctgag cgaactggat    2760 aaggccggct tcatcaagag acagctggtg gaaacccggc agatcacaaa gcacgtggca    2820
cagatcctgg actcccggat gaacactaag tacgacgaga atgacaagct gatccgggaa    2880
gtgaaagtga tcaccctgaa gtccaagctg gtgtccgatt tccggaagga tttccagttt    2940
tacaaagtgc gcgagatcaa caactaccac cacgcccacg acgcctacct gaacgccgtc    3000
gtgggaaccg ccctgatcaa aaagtaccct aagctggaaa gcgagttcgt gtacggcgac    3060
tacaaggtgt acgacgtgcg gaagatgatc gccaagagcg agcaggaaat cggcaaggct    3120
accgccaagt acttcttcta cagcaacatc atgaactttt tcaagaccga gattaccctg    3180
gccaacggcg agatccggaa gcggcctctg atcgagacaa acggcgaaac cggggagatc    3240
gtgtgggata agggccggga ttttgccacc gtgcggaaag tgctgagcat gccccaagtg    3300
aatatcgtga aaagaccga ggtgcagaca ggcggcttca gcaaagagtc tatcctgccc    3360
aagaggaaca gcgataagct gatcgccaga aagaaggact gggaccctaa gaagtacggc    3420
ggcttcgaca gcccccaccgt ggcctattct gtgctggtgg tggccaaagt ggaaaagggc    3480
aagtccaaga aactgaagag tgtgaaagag ctgctgggga tcaccatcat ggaaagaagc    3540
agcttcgaga agaatcccat cgactttctg gaagccaagg gctacaaaga agtgaaaaag    3600
gacctgatca tcaagctgcc taagtactcc ctgttcgagc tggaaaacgg ccggaagaga    3660
atgctggcct ctgccggcga actgcagaag ggaaacgaac tggccctgcc ctccaaatat    3720
gtgaacttcc tgtacctggc cagccactat gagaagctga agggctcccc cgaggataat    3780
gagcagaaac agctgtttgt ggaacagcac aagcactacc tggacgagat catcgagcag    3840
atcagcgagt tctccaagag agtgatcctg gccgacgcta atctggacaa agtgctgtcc    3900
gcctacaaca gcaccgggga taagcccatc agagagcagg ccgagaatat catccacctg    3960
tttaccctga ccaatctggg agcccctgcc gccttcaagt actttgacac caccatcgac    4020
cggaagaggt acaccagcac caaagaggtg ctggacgcca ccctgatcca ccagagcatc    4080
accggcctgt acgagacacg gatcgacctg tctcagctgg aggcgacaa aaggccggcg    4140 gccacgaaaa aggccggcca ggcaaaaaag aaaaag    4176
```

<210> SEQ ID NO 16
<211> LENGTH: 80
<212> TYPE: DNA
<213> ORGANISM: Artificial Sequence
<220> FEATURE:
<223> OTHER INFORMATION: synthetic

```
<400> SEQUENCE: 16
gttttagagc tagaaatagc aagttaaaat aaggctagtc cgttatcaac ttgaaaaagt    60
ggcaccgagt cggtgctttt                                                80

<210> SEQ ID NO 17
<211> LENGTH: 9286
<212> TYPE: DNA
<213> ORGANISM: Artificial Sequence
<220> FEATURE:
<223> OTHER INFORMATION: synthetic

<400> SEQUENCE: 17
ccccacgagg gcctatttcc catgattcct tcatatttgc atatacgata caaggctgtt    60
agagagataa ttggaattaa tttgactgta aacacaaaga tattagtaca aaatacgtga   120
cgtagaaagt aataatttct tgggtagttt gcagttttaa aattatgttt taaaatggac   180
tatcatatgc ttaccgtaac ttgaaagtat ttcgatttct tggctttata tatcttgtgg   240
aaaggacgaa acaccgatcc attcatcatg gtgtgggttt tagagctaga aatagcaagt   300
taaaataagg ctagtccgtt atcaacttga aaaagtggca ccgagtcggt gcttttttgt   360
tttagagcta gaaatagcaa gttaaaataa ggctagtccg ttttagcgc gtgcgccaat    420 tctgcagaca aatggctcta gaggtacccg ttacataact tacggtaaat ggcccgcctg   480
gctgaccgcc caacgacccc cgcccattga cgtcaatagt aacgccaata gggactttcc   540
attgacgtca atgggtggag tatttacggt aaactgccca cttggcagta catcaagtgt   600
atcatatgcc aagtacgccc cctattgacg tcaatgacgg taaatggccc gcctggcatt   660
gtgcccagta catgacctta tgggactttc ctacttggca gtacatctac gtattagtca   720
tcgctattac catggtcgag gtgagcccca cgttctgctt cactctcccc atctcccccc   780
cctccccacc cccaattttg tatttattta tttttttaatt attttgtgca gcgatggggg   840
cggggggggg ggggggcgc gcgccaggcg gggcggggcg gggcgagggg cggggcgggg   900
cgaggcggag aggtgcggcg gcagccaatc agagcggcgc gctccgaaag tttccttttta   960 tggcgaggcg gcggcggcgg cggccctata aaaagcgaag cgcgcggcgg gcgggagtcg  1020
ctgcgacgct gccttcgccc cgtgccccgc tccgccgccg cctcgcgccg cccgccccgg  1080
ctctgactga ccgcgttact cccacaggtg agcgggcggg acggcccttc tcctccgggc  1140
tgtaattagc tgagcaagag gtaagggttt aagggatggt tggttggtgg ggtattaatg  1200
tttaattacc tggagcacct gcctgaaatc acttttttc aggttggacc ggtgccacca   1260
tggactataa ggaccacgac ggagactaca aggatcatga tattgattac aaagacgatg  1320
acgataagat ggcccaaag aagaagcgga aggtcggtat ccacggagtc ccagcagccg  1380
acaagaagta cagcatcggc ctggacatcg gcaccaactc tgtgggctgg gccgtgatca  1440
ccgacgagta caaggtgccc agcaagaaat tcaaggtgct gggcaacacc gaccggcaca  1500
gcatcaagaa gaacctgatc ggagccctgc tgttcgacag cggcgaaaca gccgaggcca  1560
cccggctgaa gagaaccgcc agaagaagat acaccagacg gaagaaccgg atctgctatc  1620
tgcaagagat cttcagcaac gagatggcca aggtggacga cagcttcttc cacagactgg  1680
aagagtcctt cctggtggaa gaggataaga gcacgagcg gcaccccatc ttcggcaaca  1740
tcgtggacga ggtggcctac cacgagaagt accccaccat ctaccacctg agaaagaaac  1800
tggtggacag caccgacaag gccgacctgc ggctgatcta tctggccctg gcccacatga  1860
```

```
tcaagttccg gggccacttc ctgatcgagg gcgacctgaa ccccgacaac agcgacgtgg    1920
acaagctgtt catccagctg gtgcagacct acaaccagct gttcgaggaa aaccccatca    1980
acgccagcgg cgtggacgcc aaggccatcc tgtctgccag actgagcaag agcagacggc    2040
tggaaaatct gatcgcccag ctgccggcg agaagaagaa tggcctgttc ggaaacctga    2100
ttgccctgag cctgggcctg accccaact tcaagagcaa cttcgacctg ccgaggatg    2160 ccaaactgca gctgagcaag gacacctacg acgacgacct ggacaacctg ctggcccaga    2220
tcggcgacca gtacgccgac ctgtttctgg ccgccaagaa cctgtccgac gccatcctgc    2280
tgagcgacat cctgagagtg aacaccgaga tcaccaaggc ccccctgagc gcctctatga    2340
tcaagagata cgacgagcac caccaggacc tgaccctgct gaaagctctc gtgcggcagc    2400
agctgcctga agtacaaa gagattttct cgaccagag caagaacggc tacgccggct    2460
acattgacgg cggagccagc caggaagagt tctacaagtt catcaagccc atcctggaaa    2520
agatggacgg caccgaggaa ctgctcgtga agctgaacag agaggacctg ctgcggaagc    2580 agcggaccctt cgacaacggc agcatccccc accagatcca cctgggagag ctgcacgcca    2640
ttctgcggcg gcaggaagat ttttaccccat tcctgaagga caaccgggaa agatcgaga    2700 agatcctgac cttccgcatc ccctactacg tgggccctct ggccagggga acagcagat    2760 tcgcctggat gaccagaaag agcgaggaaa ccatcaccc ctggaacttc gaggaagtgg    2820
tggacaaggg cgcttccgcc cagagcttca tcgagcggat gaccaacttc gataagaacc    2880
tgcccaacga aaggtgctg cccaagcaca gcctgctgta cgagtacttc accgtgtata    2940
acgagctgac caaagtgaaa tacgtgaccg agggaatgag aaagccccgcc ttcctgagcg    3000 gcgagcagaa aaaggccatc gtggacctgc tgttcaagac caaccggaaa gtgaccgtga    3060
agcagctgaa agaggactac ttcaagaaaa tcgagtgctt cgactccgtg aaatctccg    3120 gcgtggaaga tcggttcaac gcctccctgg gcacatacca cgatctgctg aaaattatca    3180
aggacaagga cttcctggac aatgaggaaa acgaggacat tctggaagat atcgtgctga    3240
ccctgacact gtttgaggac agagagatga tcgaggaacg gctgaaaacc tatgcccacc    3300
tgttcgacga caaagtgatg aagcagctga agcggcggag atacaccggc tggggcaggc    3360
tgagccggaa gctgatcaac ggcatccggg acaagcagtc cggcaagaca atcctggatt    3420
tcctgaagtc cgacggcttc gccaacagaa acttcatgca gctgatccac gacgacagcc    3480
tgacctttaa agaggacatc cagaaagccc aggtgtccgg ccaggcgat agcctgcacg    3540 agcacattgc caatctggcc ggcagccccg ccattaagaa gggcatcctg cagacagtga    3600
aggtggtgga cgagctcgtg aaagtgatgg gccggcacaa gcccgagaac atcgtgatcg    3660
aaatggccag agagaaccag accacccaga gggacagaa aacagccgc gagagaatga    3720 agcggatcga agagggcatc aaagagctgg gcagccagat cctgaaagaa caccccgtgg    3780
aaaacaccca gctgcagaac gagaagctgt acctgtacta cctgcagaat gggcgggata    3840
tgtacgtgga ccaggaactg gacatcaacc ggctgtccga ctacgatgtg gaccatatcg    3900
tgcctcagag ctttctgaag gacgactcca tcgacaacaa ggtgctgacc agaagcgaca    3960
agaaccgggg caagagcgac aacgtgccct ccgaagaggt cgtgaagaag atgaagaact    4020
actggcggca gctgctgaac gccaagctga ttacccagag aaagttcgac aatctgacca    4080
aggccgagag aggcggcctg agcgaactgg ataaggccgg cttcatcaag agacagctgg    4140
tggaaacccg gcagatcaca aagcacgtgg cacagatcct ggactccgg atgaacacta    4200 agtacgacga gaatgacaag ctgatccgg aagtgaaagt gatcacctg aagtccaagc    4260
```

```
tggtgtccga tttccggaag gatttccagt tttacaaagt gcgcgagatc aacaactacc   4320
accacgccca cgacgcctac ctgaacgccg tcgtgggaac cgccctgatc aaaaagtacc   4380
ctaagctgga aagcgagttc gtgtacggcg actacaaggt gtacgacgtg cggaagatga   4440
tcgccaagag cgagcaggaa atcggcaagg ctaccgccaa gtacttcttc tacagcaaca   4500
tcatgaactt tttcaagacc gagattaccc tggccaacgg cgagatccgg aagcggcctc   4560
tgatcgagac aaacggcgaa accggggaga tcgtgtggga taagggccgg gattttgcca   4620
ccgtgcggaa agtgctgagc atgccccaag tgaatatcgt gaaaaagacc gaggtgcaga   4680
caggcggctt cagcaaagag tctatcctgc caagaggaa cagcgataag ctgatcgcca   4740
gaaagaagga ctgggaccct aagaagtacg gcggcttcga cagccccacc gtggcctatt   4800
ctgtgctggt ggtggccaaa gtggaaaagg gcaagtccaa gaaactgaag agtgtgaaag   4860
agctgctggg gatcaccatc atggaaagaa gcagcttcga gaagaatccc atcgactttc   4920
tggaagccaa gggctacaaa gaagtgaaaa aggacctgat catcaagctg cctaagtact   4980
ccctgttcga gctggaaaac ggccggaaga gaatgctggc ctctgccggc gaactgcaga   5040
agggaaacga actggcccctg ccctccaaat atgtgaactt cctgtacctg gccagccact   5100
atgagaagct gaagggctcc cccgaggata tgagcagaa acagctgttt gtggaacagc   5160
acaagcacta cctggacgag atcatcgagc agatcagcga gttctccaag agagtgatcc   5220
tggccgacgc taatctggac aaagtgctgt ccgcctacaa caagcaccgg gataagccca   5280
tcagagagca ggccgagaat atcatccacc tgtttaccct gaccaatctg ggagcccctg   5340
ccgccttcaa gtactttgac accaccatcg accggaagag gtacaccagc accaaagagg   5400
tgctggacgc caccctgatc caccagagca tcaccggcct gtacgagaca cggatcgacc   5460
tgtctcagct gggggagcgac aaaaggccgg cggccacgaa aaaggccggc caggcaaaaa   5520
agaaaaagct gagggcaga ggaagtctgc taacatgcgg tgacgtggag gagaatcccg   5580
gccctgctag catggtgagc aagggcgagg aggataacat ggccatcatc aaggagttca   5640
tgcgcttcaa ggtgcacatg gagggctccg tgaacggcca cgagttcgag atcgagggcg   5700
agggcgaggg ccgcccctac gagggcaccc agaccgccaa gctgaaggtg accaagggtg   5760
gccccctgcc cttcgcctgg gacatcctgt cccctcagtt catgtacggc tccaaggcct   5820
acgtgaagca ccccgccgac atccccgact acttgaagct gtccttcccc gagggcttca   5880
agtgggagcg cgtgatgaac ttcgaggacg gcggcgtggt gaccgtgacc caggactcct   5940
ccctgcagga cggcgagttc atctacaagg tgaagctgcg cggcaccaac ttcccctcag   6000
acggccccgt aatgcagaag aaaaccatgg gctgggaggc ctcctccgag cggatgtacc   6060
ccgaggacgg cgccctgaag ggcgagatca gcagaggct gaagctgaag gacggcggcc   6120
actacgacgc tgaggtcaag accacctaca aggccaagaa gcccgtgcag ctgcccggcg   6180
cctacaacgt caacatcaag ttggacatca cctcccacaa cgaggactac accatcgtgg   6240
aacagtacga acgcgccgag ggccgccact ccaccggcgg catggacgag ctgtacaagt   6300
aagaattcct agagctcgct gatcagcctc gactgtgcct tctagttgcc agccatctgt   6360
tgtttgcccc tccccgtgc cttccttgac cctggaaggt gccactccca ctgtcctttc   6420
ctaataaaat gaggaaattg catcgcattg tctgagtagg tgtcattcta ttctgggggg   6480
tggggtgggg caggacagca agggggagga ttgggaagag aatagcaggc atgctggga   6540 gcggccgcag gaacccctag tgatggagtt ggccactccc tctctgcgcg ctcgctcgct   6600
```

```
cactgaggcc gggcgaccaa aggtcgcccg acgcccgggc tttgcccggg cggcctcagt      6660
gagcgagcga gcgcgcagct gcctgcaggg gcgcctgatg cggtattttc tccttacgca      6720
tctgtgcggt atttcacacc gcatacgtca aagcaaccat agtacgcgcc ctgtagcggc      6780
gcattaagcg cggcggtgt ggtggttacg cgcagcgtga ccgctacact tgccagcgcc       6840
ctagcgcccg ctcctttcgc tttcttccct tcctttctcg ccacgttcgc cggctttccc      6900
cgtcaagctc taaatcgggg ctccctttta gggttccgat ttagtgcttt acggcacctc      6960
gaccccaaaa aacttgattt gggtgatggt tcacgtagtg ggccatcgcc ctgatagacg      7020 gttttcgcc ctttgacgtt ggagtccacg ttctttaata gtggactctt gttccaaact       7080
ggaacaacac tcaaccctat ctcgggctat tcttttgatt tataagggat tttgccgatt      7140
tcggcctatt ggttaaaaaa tgagctgatt taacaaaaat ttaacgcgaa ttttaacaaa      7200
atattaacgt ttacaatttt atggtgcact ctcagtacaa tctgctctga tgccgcatag      7260
ttaagccagc cccgacaccc gccaacaccc gctgacgcgc cctgacgggc ttgtctgctc      7320
ccggcatccg cttacagaca agctgtgacc gtctccggga gctgcatgtg tcagaggttt      7380
tcaccgtcat caccgaaacg cgcgagacga agggcctcg tgatacgcct attttttatag      7440 gttaatgtca tgataataat ggtttcttag acgtcaggtg gcacttttcg gggaaatgtg      7500
cgcggaaccc ctatttgttt attttttctaa atacattcaa atatgtatcc gctcatgaga      7560
caataaccct gataaatgct tcaataatat tgaaaaagga agagtatgag tattcaacat      7620
ttccgtgtcg cccttattcc cttttttgcg gcattttgcc ttcctgtttt tgctcaccca      7680
gaaacgctgg tgaaagtaaa agatgctgaa gatcagttgg gtgcacgagt gggttacatc      7740
gaactggatc tcaacagcgg taagatcctt gagagttttc gccccgaaga acgttttcca      7800
atgatgagca cttttaaagt tctgctatgt ggcgcggtat tatcccgtat tgacgccggg      7860
caagagcaac tcggtcgccg catacactat tctcagaatg acttggttga gtactcacca      7920
gtcacagaaa agcatcttac ggatggcatg acagtaagag aattatgcag tgctgccata      7980
accatgagtg ataacactgc ggccaactta cttctgacaa cgatcggagg accgaaggag      8040
ctaaccgctt ttttgcacaa catgggggat catgtaactc gccttgatcg ttgggaaccg      8100
gagctgaatg aagccatacc aaacgacgag cgtgacacca cgatgcctgt agcaatggca      8160
acaacgttgc gcaaactatt aactggcgaa ctacttactc tagcttcccg gcaacaatta      8220
atagactgga tggaggcgga taaagttgca ggaccacttc tgcgctcggc ccttccggct      8280
ggctggttta ttgctgataa atctggagcc ggtgagcgtg aagccgcgg tatcattgca       8340 gcactggggc cagatggtaa gccctcccgt atcgtagtta tctacacgac ggggagtcag      8400
gcaactatgg atgaacgaaa tagacagatc gctgagatag gtgcctcact gattaagcat      8460
tggtaactgt cagaccaagt ttactcatat atactttaga ttgatttaaa acttcatttt      8520
taatttaaaa ggatctaggt gaagatcctt tttgataatc tcatgaccaa aatcccttaa      8580
cgtgagtttt cgttccactg agcgtcagac cccgtagaaa agatcaaagg atcttcttga      8640 gatcctttt tctgcgcgt aatctgctgc ttgcaaacaa aaaaaccacc gctaccagcg       8700
gtggtttgtt tgccggatca agagctacca actctttttc cgaaggtaac tggcttcagc      8760
agagcgcaga taccaaatac tgtccttcta gtgtagccgt agttaggcca ccacttcaag      8820
aactctgtag caccgcctac atacctcgct ctgctaatcc tgttaccagt ggctgctgcc      8880
agtggcgata agtcgtgtct taccgggttg gactcaagac gatagttacc ggataaggcg      8940
cagcggtcgg gctgaacggg gggttcgtgc acacagccca gcttggagcg aacgacctac      9000
```

| | |
|---|---|
| accgaactga gatacctaca gcgtgagcta tgagaaagcg ccacgcttcc cgaagggaga | 9060 |
| aaggcggaca ggtatccggt aagcggcagg gtcggaacag gagagcgcac gagggagctt | 9120 |
| ccagggggaa acgcctggta tctttatagt cctgtcgggt ttcgccacct ctgacttgag | 9180 |
| cgtcgatttt tgtgatgctc gtcagggggg cggagcctat ggaaaaacgc cagcaacgcg | 9240 |
| gccttttttac ggttcctggc cttttgctgg ccttttgctc acatgt | 9286 |

<210> SEQ ID NO 18
<211> LENGTH: 7400
<212> TYPE: DNA
<213> ORGANISM: Artificial Sequence
<220> FEATURE:
<223> OTHER INFORMATION: synthetic

<400> SEQUENCE: 18

| | |
|---|---|
| cctgcaggca gctgcgcgct cgctcgctca ctgaggccgc ccgggcaaag cccgggcgtc | 60 |
| gggcgacctt tggtcgcccg gcctcagtga gcgagcgagc gcgcagagag ggagtggcca | 120 |
| actccatcac tagggggttcc tgcggcctct agaaagctta gctgaatggg gtccgcctct | 180 |
| tttccctgcc taaacagaca ggaactcctg ccaattgagg gcgtcaccgc taaggctccg | 240 |
| ccccagcctg gctccacaa ccaatgaagg gtaatctcga caaagagcaa ggggtggggc | 300 |
| gcgggcgcgc aggtgcagca gcacacaggc tggtcgggag ggcggggcgc gacgtctgcc | 360 |
| gtgcggggtc ccggcatcgg ttgcgcgcac cggtgccacc atgtacccat acgatgttcc | 420 |
| agattacgct tcgccgaaga aaaagcgcaa ggtcgaagcg tccgacaaga agtacagcat | 480 |
| cggcctggac atcggcacca actctgtggg ctgggccgtg atcaccgacg agtacaaggt | 540 |
| gcccagcaag aaattcaagg tgctgggcaa caccgaccgg cacagcatca agaagaacct | 600 |
| gatcggagcc ctgctgttcg acagcggcga acagccgag gccacccggc tgaagagaac | 660 |
| cgccagaaga agatacacca gacgaagaa ccggatctgc tatctgcaag agatcttcag | 720 |
| caacgagatg gccaaggtgg acgacagctt cttccacaga ctggaagagt ccttcctggt | 780 |
| ggaagaggat aagaagcacg agcggcaccc catcttcggc aacatcgtgg acgaggtggc | 840 |
| ctaccacgag aagtacccca ccatctacca cctgagaaaa aaactggtgg acagcaccga | 900 |
| caaggccgac ctgcggctga tctatctggc cctggcccac atgatcaagt tccggggcca | 960 |
| cttcctgatc gagggcgacc tgaaccccga caacagcgac gtggacaagc tgttcatcca | 1020 |
| gctggtgcag acctacaacc agctgttcga ggaaaacccc atcaacgcca gcggcgtgga | 1080 |
| cgccaaggcc atcctgtctg ccagactgag caagagcaga cggctggaaa tctgatcgc | 1140 |
| ccagctgccc ggcgagaaga gaatggcct gttcggcaac ctgattgccc tgagcctggg | 1200 |
| cctgaccccc aacttcaaga gcaacttcga cctggccgag gatgccaaac tgcagctgag | 1260 |
| caaggacacc tacgacgacg acctggacaa cctgctggcc cagatcggcg accagtacgc | 1320 |
| cgacctgttt ctggccgcca gaacctgtc cgacgccatc ctgctgagcg acatcctgag | 1380 |
| agtgaacacc gagatcacca aggccccct gagcgcctct atgatcaaga gatacgacga | 1440 |
| gcaccaccag gacctgaccc tgctgaaagc tctcgtgcgg cagcagctgc ctgagaagta | 1500 |
| caaagagatt ttcttcgacc agagcaagaa cggctacgcc ggctacattg acggcggagc | 1560 |
| cagccaggaa gagttctaca gttcatcaa gcccatcctg gaaaagatgg acggcaccga | 1620 |
| ggaactgctc gtgaagctga acagagagga cctgctgcgg aagcagcgga ccttcgacaa | 1680 |
| cggcagcatc ccccaccaga tccacctggg agagctgcac gccattctgc ggcggcagga | 1740 |

```
agatttttac ccattcctga aggacaaccg ggaaaagatc gagaagatcc tgaccttccg   1800
catcccctac tacgtgggcc ctctggccag gggaaacagc agattcgcct ggatgaccag   1860
aaagagcgag gaaaccatca cccccCtggaa cttcgaggaa gtggtggaca agggcgcttc   1920
cgcccagagc ttcatcgagc ggatgaccaa cttcgataag aacctgccca acgagaaggt   1980
gctgcccaag cacagcctgc tgtacgagta cttcaccgtg tataacgagc tgaccaaagt   2040
gaaatacgtg accgagggaa tgagaaagcc cgccttcctg agcggcgagc agaaaaaggc   2100
catcgtggac ctgctgttca agaccaaccg gaaagtgacc gtgaagcagc tgaaagagga   2160
ctacttcaag aaaatcgagt gcttcgactc cgtggaaatc tccggcgtgg aagatcggtt   2220
caacgcctcc ctgggcacat accacgatct gctgaaaatt atcaaggaca aggacttcct   2280
ggacaatgag gaaaacgagg acattctgga agatatcgtg ctgaccctga cactgtttga   2340
ggacagagag atgatcgagg aacggctgaa aacctatgcc cacctgttcg acgacaaagt   2400
gatgaagcag ctgaagcggc ggagatacac cggctggggc aggctgagcc ggaagctgat   2460
caacggcatc cgggacaagc agtccggcaa gacaatcctg gatttcctga agtccgacgg   2520
cttcgccaac agaaacttca tgcagctgat ccacgacgac agcctgacct ttaaagagga   2580
catccagaaa gcccaggtgt ccggccaggg cgatagcctg cacgagcaca ttgccaatct   2640
ggccggcagc cccgccatta gaagggcat cctgcagaca gtgaaggtgg tggacgagct   2700
cgtgaaagtg atgggccggc acaagcccga gaacatcgtg atcgaaatgg ccagagagaa   2760
ccagaccacc cagaagggac agaagaacag ccgcgagaga atgaagcgga tcgaagaggg   2820
catcaaagag ctgggcagcc agatcctgaa agaacacccc gtggaaaaca cccagctgca   2880
gaacgagaag ctgtacctgt actacctgca gaatgggcgg gatatgtacg tggaccagga   2940
actggacatc aaccggctgt ccgactacga tgtggaccat atcgtgcctc agagctttct   3000
gaaggacgac tccatcgaca caaggtgct gaccagaagc gacaagaacc ggggcaagag   3060
cgacaacgtg ccctccgaag aggtcgtgaa gaagatgaag aactactggc ggcagctgct   3120
gaacgccaag ctgattaccc agagaaagtt cgacaatctg accaaggccg agagaggcgg   3180
cctgagcgaa ctggataagg ccggcttcat caagagacag ctggtggaaa cccggcagat   3240
cacaaagcac gtggcacaga tcctggactc ccggatgaac actaagtacg acgagaatga   3300
caagctgatc cgggaagtga aagtgatcac cctgaagtcc aagctggtgt ccgatttccg   3360
gaaggatttc cagtttttaca aagtgcgcga gatcaacaac taccaccacg cccacgacgc   3420
ctacctgaac gccgtcgtgg gaaccgcccct gatcaaaaag taccctaagc tggaaagcga   3480
gttcgtgtac ggcgactaca aggtgtacga cgtgcggaag atgatcgcca agagcgagca   3540
ggaaatcggc aaggctaccg ccaagtactt cttctacagc aacatcatga actttttcaa   3600
gaccgagatt accctggcca acggcgagat ccggaagcgg cctctgatcg agacaaacgg   3660
cgaaaccggg gagatcgtgt gggataaggg ccgggatttt gccaccgtgc ggaaagtgct   3720
gagcatgccc caagtgaata tcgtgaaaaa gaccgaggtg cagacaggcg gcttcagcaa   3780
agagtctatc ctgcccaaga ggaacagcga taagctgatc gccagaaaga aggactggga   3840
ccctaagaag tacggcggct cgacagccc caccgtggcc tattctgtgc tggtggtggc   3900
caaagtggaa aagggcaagt ccaagaaact gaagagtgtg aaagagctgc tggggatcac   3960
catcatggaa agaagcagct tcgagaagaa tcccatcgac tttctggaag ccaagggcta   4020
caaagaagtg aaaaaggacc tgatcatcaa gctgcctaag tactccctgt tcgagctgga   4080
aaacggccgg aagagaatgc tggcctctgc cggcgaactg cagaagggaa acgaactggc   4140
```

```
cctgccctcc aaatatgtga acttcctgta cctggccagc cactatgaga agctgaaggg    4200
ctcccccgag gataatgagc agaaacagct gtttgtggaa cagcacaagc actacctgga    4260
cgagatcatc gagcagatca gcgagttctc caagagagtg atcctggccg acgctaatct    4320
ggacaaagtg ctgtccgcct acaacaagca ccgggataag cccatcagag agcaggccga    4380
gaatatcatc cacctgttta ccctgaccaa tctgggagcc cctgccgcct tcaagtactt    4440
tgacaccacc atcgaccgga gaggtacac cagcaccaaa gaggtgctgg acgccaccct    4500
gatccaccag agcatcaccg gcctgtacga gacacggatc gacctgtctc agctgggagg    4560 cgacagccc aagaagaaga gaaaggtgga ggccagctaa gaattcaata aaagatcttt    4620
attttcatta gatctgtgtg ttggttttt gtgtgcggcc gcaggaaccc ctagtgatgg    4680
agttggccac tccctctctg cgcgctcgct cgctcactga ggccgggcga ccaaaggtcg    4740
cccgacgccc gggctttgcc cgggcggcct cagtgagcga gcgagcgcgc agctgcctgc    4800
aggggcgcct gatgcggtat tttctcctta cgcatctgtg cggtatttca caccgcatac    4860
gtcaaagcaa ccatagtacg cgccctgtag cggcgcatta agcgcggcgg gtgtggtggt    4920
tacgcgcagc gtgaccgcta cacttgccag cgccctagcg cccgctcctt tcgctttctt    4980
cccttccttt ctcgccacgt tcgccggctt tccccgtcaa gctctaaatc ggggctccc    5040 tttagggttc cgatttagtg ctttacggca cctcgacccc aaaaaacttg atttgggtga    5100
tggttcacgt agtgggccat cgccctgata gacggttttt cgccctttga cgttggagtc    5160
cacgttcttt aatagtggac tcttgttcca aactggaaca acactcaacc ctatctcggg    5220 ctattcttt gatttataag ggattttgcc gatttcggcc tattggttaa aaaatgagct    5280
gatttaacaa aaatttaacg cgaattttaa caaaatatta acgtttacaa ttttatggtg    5340
cactctcagt acaatctgct ctgatgccgc atagttaagc cagccccgac acccgccaac    5400
acccgctgac gcgccctgac gggcttgtct gctcccggca tccgcttaca gacaagctgt    5460
gaccgtctcc gggagctgca tgtgtcagag gttttcaccg tcatcaccga aacgcgcgag    5520
acgaaagggc ctcgtgatac gcctattttt ataggttaat gtcatgataa taatggtttc    5580
ttagacgtca ggtggcactt ttcggggaaa tgtgcgcgga acccctattt gtttatttt    5640 ctaaatacat tcaaatatgt atccgctcat gagacaataa ccctgataaa tgcttcaata    5700
atattgaaaa aggaagagta tgagtattca acatttccgt gtcgccctta ttcccttttt    5760
tgcggcattt tgccttcctg ttttttgctca cccagaaacg ctggtgaaag taaaagatgc    5820
tgaagatcag ttgggtgcac gagtgggtta catcgaactg gatctcaaca gcggtaagat    5880
ccttgagagt tttcgccccg aagaacgttt tccaatgatg agcactttta aagttctgct    5940
atgtggcgcg gtattatccc gtattgacgc cgggcaagag caactcggtc gccgcataca    6000
ctattctcag aatgacttgg ttgagtactc accagtcaca gaaaagcatc ttacggatgg    6060
catgacagta agagaattat gcagtgctgc cataaccatg agtgataaca ctgcggccaa    6120
cttacttctg acaacgatcg gaggaccgaa ggagctaacc gcttttttgc acaacatggg    6180
ggatcatgta actcgcctgg atcgttggga accggagctg aatgaagcca taccaaacga    6240
cgagcgtgac accacgatgc ctgtagcaat ggcaacaacg ttgcgcaaac tattaactgg    6300
cgaactactt actctagctt cccggcaaca attaatagac tggatggagg cggataaagt    6360
tgcaggacca cttctgcgct cggccctcc ggctggctgg tttattgctg ataaatctgg    6420
agccggtgag cgtggaagcc gcggtatcat tgcagcactg gggccagatg gtaagccctc    6480
```

```
ccgtatcgta gttatctaca cgacggggag tcaggcaact atggatgaac gaaatagaca    6540
gatcgctgag ataggtgcct cactgattaa gcattggtaa ctgtcagacc aagtttactc    6600
atatatactt tagattgatt taaaacttca tttttaattt aaaaggatct aggtgaagat    6660 ccttttttgat aatctcatga ccaaaatccc ttaacgtgag ttttcgttcc actgagcgtc    6720 agacccgta gaaaagatca aaggatcttc ttgagatcct ttttttctgc gcgtaatctg    6780
ctgcttgcaa acaaaaaaac caccgctacc agcggtggtt tgtttgccgg atcaagagct    6840
accaactctt tttccgaagg taactggctt cagcagagcg cagataccaa atactgtcct    6900
tctagtgtag ccgtagttag gccaccactt caagaactct gtagcaccgc ctacatacct    6960
cgctctgcta atcctgttac cagtggctgc tgccagtggc gataagtcgt gtcttaccgg    7020
gttggactca agacgatagt taccggataa ggcgcagcgg tcgggctgaa cggggggttc    7080
gtgcacacag cccagcttgg agcgaacgac ctacaccgaa ctgagatacc tacagcgtga    7140
gctatgagaa agcgccacgc ttcccgaagg gagaaaggcg gacaggtatc cggtaagcgg    7200
cagggtcgga acaggagagc gcacgaggga gcttccaggg ggaaacgcct ggtatcttta    7260
tagtcctgtc gggtttcgcc acctctgact tgagcgtcga ttttgtgat gctcgtcagg    7320 ggggcggagc ctatgaaaaa cgccagcaa cgcggccttt ttacggttcc tggccttttg    7380
ctggcctttt gctcacatgt                                                 7400
```

<210> SEQ ID NO 19
<211> LENGTH: 5305
<212> TYPE: DNA
<213> ORGANISM: Artificial Sequence
<220> FEATURE:
<223> OTHER INFORMATION: synthetic

<400> SEQUENCE: 19

```
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac tagggggttcc tgcggccgca cgcgtgaggg cctatttccc atgattcctt     180
catatttgca tatacgatac aaggctgtta gagagatat tggaattaat ttgactgtaa     240
acacaaagat attagtacaa aatacgtgac gtagaaagta ataatttctt gggtagtttg     300
cagttttaaa attatgtttt aaaatggact atcatatgct taccgtaact tgaaagtatt     360
tcgatttctt ggctttatat atcttgtgga aaggacgaaa caccatccat ccatcatggc     420 gtgggttta gagctagaaa tagcaagtta aaataaggct agtccgttat caacttgaaa     480
aagtggcacc gagtcggtgc tttttttcta gactgcagag ggccctgcgt atgagtgcaa     540
gtgggtttta ggaccaggat gaggcggggt ggggtgcct acctgacgac cgaccccgac     600
ccactggaca agcacccaac ccccattccc caaattgcgc atcccctatc agagaggggg     660
aggggaaaca ggatgcggcg aggcgcgtgc gcactgccag cttcagcacc gcggacagtg     720
ccttcgcccc cgcctggcgg cgcgcgccac cgccgcctca gcactgaagg cgcgctgacg     780
tcactcgccg gtccccccgca aactcccctt cccggccacc ttggtcgcgt ccgcgccgcc     840
gccgccccag ccggaccgca ccacgcgagg cgcgagatag gggggcacgg gcgcgaccat     900
ctgcgctgcg gcgccggcga ctcagcgctg cctcagtctg cggtgggcag cggaggagtc     960
gtgtcgtgcc tgagagcgca gtcgagaagg taccggatcc tctagagtcg acgccaccat    1020
ggtgagcaag ggcgaggagc tgttcaccgg ggtggtgccc atcctggtcg agctggacgg    1080
cgacgtaaac ggccacaagt tcagcgtgtc cggcgagggc gagggcgatg ccacctacgg    1140
```

```
caagctgacc ctgaagttca tctgcaccac cggcaagctg cccgtgccct ggcccaccct   1200
cgtgaccacc ctgacctacg gcgtgcagtg cttcagccgc tacccgacc acatgaagca    1260 gcacgacttc ttcaagtccg ccatgcccga aggctacgtc caggagcgca ccatcttctt   1320
caaggacgac ggcaactaca agacccgcgc cgaggtgaag ttcgagggcg acaccctggt   1380
gaaccgcatc gagctgaagg gcatcgactt caaggaggac ggcaacatcc tggggcacaa   1440
gctggagtac aactacaaca gccacaacgt ctatatcatg gccgacaagc agaagaacgg   1500
catcaaggtg aacttcaaga tccgccacaa catcgaggac ggcagcgtgc agctcgccga   1560
ccactaccag cagaacaccc ccatcggcga cggccccgtg ctgctgcccg acaaccacta   1620
cctgagcacc cagtccgccc tgagcaaaga ccccaacgag aagcgcgatc acatggtcct   1680
gctggagttc gtgaccgccg ccgggatcac tctcggcatg gacgagctgt acaagtccgg   1740
actcagatct cgagaggagg aggaggagac agacagcagg atgccccacc tcgacagccc   1800
cggcagctcc cagccgagac gctccttcct ctcaagggtg atcagggcag cgctaccgtt   1860
gcagctgctt ctgctgctgc tgctgctcct ggcctgcctg ctacctgcct ctgaagatga   1920
ctacagctgc acccaggcca caactttgc ccgatccttc tacccatgc tgcggtacac    1980 caacgggcca cctcccacct aggaattcga tatcaagctt atcgataccg agcgctgctc   2040
gagagatcta cgggtggcat ccctgtgacc cctccccagt gcctctcctg gccctggaag   2100
ttgccactcc agtgcccacc agccttgtcc taataaaatt aagttgcatc attttgtctg   2160
actaggtgtc cttctataat attatggggt ggaggggggt ggtatggagc aaggggcaag   2220
ttgggaagac aacctgtagg gcctgcgggg tctattggga accaagctgg agtgcagtgg   2280
cacaatcttg gctcactgca atctccgcct cctgggttca agcgattctc ctgcctcagc   2340
ctcccgagtt gttgggattc caggcatgca tgaccaggct cagctaattt tgttttttt    2400 ggtagagacg gggtttcacc atattggcca ggctggtctc caactcctaa tctcaggtga   2460
tctacccacc ttggcctccc aaattgctgg gattacaggc gtgaaccact gctcccttcc   2520
ctgtccttct gattttgtag gtaaccacgt gcggaccgag cggccgcagg aaccctagt    2580 gatggagttg gccactccct ctctgcgcgc tcgctcgctc actgaggccg ggcgaccaaa   2640
ggtcgcccga cgcccgggct ttgcccgggc ggcctcagtg agcgagcgag cgcgcagctg   2700
cctgcagggg cgcctgatgc ggtattttct ccttacgcat ctgtgcggta tttcacaccg   2760
catacgtcaa agcaaccata gtacgcgccc tgtagcggcg cattaagcgc ggcgggtgtg   2820
gtggttacgc gcagcgtgac cgctacactt gccagcgccc tagcgcccgc tcctttcgct   2880
ttcttccctt cctttctcgc cacgttcgcc ggctttcccc gtcaagctct aaatcggggg   2940
ctccctttag ggttccgatt tagtgcttta cggcacctcg accccaaaaa acttgatttg   3000
ggtgatggtt cacgtagtgg gccatcgccc tgatagacgg ttttcgccc tttgacgttg    3060 gagtccacgt tctttaatag tggactcttg ttccaaactg gaacaacact caaccctatc   3120
tcgggctatt cttttgattt ataagggatt ttgccgattt cggcctattg gttaaaaaat   3180
gagctgattt aacaaaaatt taacgcgaat tttaacaaaa tattaacgtt tacaatttta   3240
tggtgcactc tcagtacaat ctgctctgat gccgcatagt taagccagcc ccgacacccg   3300
ccaacacccg ctgacgcgcc ctgacgggct tgtctgctcc cggcatccgc ttacagacaa   3360
gctgtgaccg tctccgggag ctgcatgtgt cagaggtttt caccgtcatc accgaaacgc   3420
gcgagacgaa agggcctcgt gatacgccta tttttatagg ttaatgtcat gataataatg   3480
```

| | |
|---|---|
| gtttcttaga cgtcaggtgg cacttttcgg ggaaatgtgc gcggaacccc tatttgttta | 3540 |
| tttttctaaa tacattcaaa tatgtatccg ctcatgagac aataaccctg ataaatgctt | 3600 |
| caataatatt gaaaaaggaa gagtatgagt attcaacatt tccgtgtcgc ccttattccc | 3660 |
| ttttttgcgg cattttgcct tcctgttttt gctcacccag aaacgctggt gaaagtaaaa | 3720 |
| gatgctgaag atcagttggg tgcacgagtg ggttacatcg aactggatct caacagcggt | 3780 |
| aagatccttg agagttttcg ccccgaagaa cgttttccaa tgatgagcac ttttaaagtt | 3840 |
| ctgctatgtg gcgcggtatt atcccgtatt gacgccgggc aagagcaact cggtcgccgc | 3900 |
| atacactatt ctcagaatga cttggttgag tactcaccag tcacagaaaa gcatcttacg | 3960 |
| gatggcatga cagtaagaga attatgcagt gctgccataa ccatgagtga taacactgcg | 4020 |
| gccaacttac ttctgacaac gatcggagga ccgaaggagc taaccgcttt tttgcacaac | 4080 |
| atgggggatc atgtaactcg ccttgatcgt tgggaaccgg agctgaatga agccatacca | 4140 |
| aacgacgagc gtgacaccac gatgcctgta gcaatggcaa caacgttgcg caaactatta | 4200 |
| actggcgaac tacttactct agcttcccgg caacaattaa tagactggat ggaggcggat | 4260 |
| aaagttgcag gaccacttct gcgctcggcc cttccggctg gctggtttat tgctgataaa | 4320 |
| tctggagccg gtgagcgtgg gtctcgcggt atcattgcag cactggggcc agatggtaag | 4380 |
| ccctcccgta tcgtagttat ctacacgacg gggagtcagg caactatgga tgaacgaaat | 4440 |
| agacagatcg ctgagatagg tgcctcactg attaagcatt ggtaactgtc agaccaagtt | 4500 |
| tactcatata tactttagat tgatttaaaa cttcattttt aatttaaaag gatctaggtg | 4560 |
| aagatccttt ttgataatct catgaccaaa atcccttaac gtgagttttc gttccactga | 4620 |
| gcgtcagacc ccgtagaaaa gatcaaagga tcttcttgag atcctttttt tctgcgcgta | 4680 |
| atctgctgct tgcaaacaaa aaaaccaccg ctaccagcgg tggtttgttt gccggatcaa | 4740 |
| gagctaccaa ctctttttcc gaaggtaact ggcttcagca gagcgcagat accaaatact | 4800 |
| gtccttctag tgtagccgta gttaggccac cacttcaaga actctgtagc accgcctaca | 4860 |
| tacctcgctc tgctaatcct gttaccagtg gctgctgcca gtggcgataa gtcgtgtctt | 4920 |
| accgggttgg actcaagacg atagttaccg gataaggcgc agcggtcggg ctgaacgggg | 4980 |
| ggttcgtgca cacagcccag cttggagcga acgacctaca ccgaactgag atacctacag | 5040 |
| cgtgagctat gagaaagcgc cacgcttccc gaagggagaa aggcggacag gtatccggta | 5100 |
| agcggcaggg tcggaacagg agagcgcacg agggagcttc caggggggaaa cgcctggtat | 5160 |
| ctttatagtc ctgtcgggtt tcgccacctc tgacttgagc gtcgattttt gtgatgctcg | 5220 |
| tcaggggggc ggagcctatg gaaaaacgcc agcaacgcgg cctttttacg gttcctggcc | 5280 |
| ttttgctggc cttttgctca catgt | 5305 |

<210> SEQ ID NO 20
<211> LENGTH: 13013
<212> TYPE: DNA
<213> ORGANISM: Artificial Sequence
<220> FEATURE:
<223> OTHER INFORMATION: synthetic

<400> SEQUENCE: 20

| | |
|---|---|
| tgatgcggtt ttggcagtac atcaatgggc gtggatagcg gtttgactca cggggatttc | 60 |
| caagtctcca ccccattgac gtcaatggga gtttgttttg gcaccaaaat caacgggact | 120 |
| ttccaaaatg tcgtaacaac tccgccccat tgacgcaaat gggcggtagg cgtgtacggt | 180 |
| gggaggtcta tataagcagc gcgttttgcc tgtactgggt ctctctggtt agaccagatc | 240 |

```
tgagcctggg agctctctgg ctaactaggg aacccactgc ttaagcctca ataaagcttg    300
ccttgagtgc ttcaagtagt gtgtgcccgt ctgttgtgtg actctggtaa ctagagatcc    360
ctcagaccct tttagtcagt gtggaaaatc tctagcagtg gcgcccgaac agggacttga    420
aagcgaaagg gaaaccagag gagctctctc gacgcaggac tcggcttgct gaagcgcgca    480
cggcaagagg cgaggggcgg cgactggtga gtacgccaaa aattttgact agcggaggct    540
agaaggagag agatgggtgc gagagcgtca gtattaagcg gggagaatt agatcgcgat    600 gggaaaaaat tcggttaagg ccaggggggaa agaaaaaata taaattaaaa catatagtat    660
gggcaagcag ggagctagaa cgattcgcag ttaatcctgg cctgttagaa acatcagaag    720
gctgtagaca atactggga cagctacaac catcccttca gacaggatca gaagaactta    780
gatcattata taatacagta gcaaccctct attgtgtgca tcaaaggata gagataaaag    840
acaccaagga agctttagac aagatagagg aagagcaaaa caaaagtaag accaccgcac    900
agcaagcggc cgctgatctt cagacctgga ggaggagata tgaggacaa ttggagaagt    960 gaattatata aatataaagt agtaaaaatt gaaccattag gagtagcacc caccaaggca    1020
aagagaagag tggtgcagag agaaaaaaga gcagtgggaa taggagcttt gttccttggg    1080
ttcttgggag cagcaggaag cactatgggc gcagcgtcaa tgacgctgac ggtacaggcc    1140
agacaattat tgtctggtat agtgcagcag cagaacaatt tgctgagggc tattgaggcg    1200
caacagcatc tgttgcaact cacagtctgg ggcatcaagc agctccaggc aagaatcctg    1260
gctgtggaaa gatacctaaa ggatcaacag ctcctgggga tttggggttg ctctggaaaa    1320
ctcatttgca ccactgctgt gccttggaat gctagttgga gtaataaatc tctggaacag    1380
atttggaatc acacgacctg gatggagtgg gacagagaaa ttaacaatta cacaagctta    1440
atacactcct taattgaaga atcgcaaaac cagcaagaaa agaatgaaca agaattattg    1500
gaattagata aatgggcaag tttgtggaat tggtttaaca taacaaattg gctgtggtat    1560
ataaaattat tcataatgat agtaggaggc ttggtaggtt taagaatagt ttttgctgta    1620
ctttctatag tgaatagagt taggcaggga tattcaccat tatcgtttca gacccacctc    1680
ccaaccccga ggggacccga caggcccgaa ggaatagaag aagaaggtgg agagagagac    1740
agagacagat ccattcgatt agtgaacgga tcggcactgc gtgcgccaat tctgcagaca    1800
aatggcagta ttcatccaca ttttaaaag aaaggggggg attgggggggt acagtgcagg    1860 ggaaagaata gtagacataa tagcaacaga catacaaact aaagaattac aaaaacaaat    1920
tacaaaaatt caaaattttc gggtttatta cagggacagc agagatccag tttggttaat    1980
taaggtaccg agggcctatt tcccatgatt ccttcatatt tgcatatacg atacaaggct    2040
gttagagaga taattagaat taatttgact gtaaacacaa agatattgt acaaaatacg    2100 tgacgtagaa agtaataatt tcttgggtag tttgcagttt taaaattatg ttttaaaatg    2160
gactatcata tgcttaccgt aacttgaaag tatttcgatt tcttggcttt atatatcttg    2220
tggaaaggac gaaacaccga tccattcatc atggtgtggg tttagagct agaaatagca    2280 agttaaaata aggctagtcc gttatcaact tgaaaaagtg gcaccgagtc ggtgcttttt    2340
tgaattcgct agctaggtct tgaaaggagt gggaattggc tccggtgccc gtcagtgggc    2400
agagcgcaca tcgcccacag tccccgagaa gttgggggga gggtcggca attgatccgg    2460 tgcctagaga aggtggcgcg gggtaaactg ggaaagtgat gtcgtgtact ggctccgcct    2520
ttttcccgag ggtgggggag aaccgtatat aagtgcagta gtcgccgtga acgttctttt    2580
```

-continued

```
tcgcaacggg tttgccgcca gaacacagga ccggttctag agcgctgcca ccatggacaa    2640
gaagtacagc atcggcctgg acatcggcac caactctgtg gctgggccg tgatcaccga     2700 cgagtacaag gtgcccagca agaaattcaa ggtgctgggc aacaccgacc ggcacagcat    2760
caagaagaac ctgatcggag ccctgctgtt cgacagcggc gaaacagccg aggccacccg    2820
gctgaagaga accgccagaa agagatacac cagacggaag aaccggatct gctatctgca    2880
agagatcttc agcaacgaga tggccaaggt ggacgacagc ttcttccaca gactggaaga    2940
gtccttcctg gtggaagagg ataagaagca cgagcggcac cccatcttcg gcaacatcgt    3000
ggacgaggtg gcctaccacg agaagtaccc caccatctac cacctgagaa agaaactggt    3060
ggacagcacc gacaaggccg acctgcggct gatctatctg gccctggccc acatgatcaa    3120
gttccggggc cacttcctga tcgagggcga cctgaacccc gacaacagcg acgtggacaa    3180
gctgttcatc cagctggtgc agacctacaa ccagctgttc gaggaaaacc ccatcaacgc    3240
cagcggcgtg gacgccaagg ccatcctgtc tgccagactg agcaagagca gacggctgga    3300
aaatctgatc gcccagctgc ccggcgagaa gaagaatggc ctgttcggaa acctgattgc    3360
cctgagcctg ggcctgaccc ccaacttcaa gagcaacttc gacctggccg aggatgccaa    3420
actgcagctg agcaaggaca cctacgacga cgacctggac aacctgctgg cccagatcgg    3480
cgaccagtac gccgacctgt ttctggccgc caagaacctg tccgacgcca tcctgctgag    3540
cgacatcctg agagtgaaca ccgagatcac caaggccccc ctgagcgcct ctatgatcaa    3600
gagatacgac gagcaccacc aggacctgac cctgctgaaa gctctcgtgc ggcagcagct    3660
gcctgagaag tacaaagaga ttttcttcga ccagagcaag aacggctacg ccggctacat    3720
tgacggcgga gccagccagg aagagttcta caagttcatc aagcccatcc tggaaaagat    3780
ggacggcacc gaggaactgc tcgtgaagct gaacagagag gacctgctgc ggaagcagcg    3840
gaccttcgac aacggcagca tcccccacca gatccacctg ggagagctgc acgccattct    3900
gcggcggcag gaagattttt acccattcct gaaggacaac cgggaaaaga tcgagaagat    3960
cctgaccttc cgcatcccct actacgtggg ccctctggcc aggggaaaca gcagattcgc    4020
ctggatgacc agaaagagcg aggaaaccat caccccctgg aacttcgagg aagtggtgga    4080
caagggcgct tccgcccaga gcttcatcga gcggatgacc aacttcgata agaacctgcc    4140
caacgagaag gtgctgccca agcacagcct gctgtacgag tacttcaccg tgtataacga    4200
gctgaccaaa gtgaaatacg tgaccgaggg aatgagaaag cccgccttcc tgagcggcga    4260
gcagaaaaag gccatcgtgg acctgctgtt caagaccaac cggaaagtga ccgtgaagca    4320
gctgaaagag gactacttca gaaaaatcga gtgcttcgac tccgtggaaa tctccggcgt    4380
ggaagatcgg ttcaacgcct ccctgggcac ataccacgat ctgctgaaaa ttatcaagga    4440
caaggacttc ctggacaatg aggaaaacga ggacattctg gaagatatcg tgctgaccct    4500
gacactgttt gaggacagag agatgatcga ggaacggctg aaaacctatg cccacctgtt    4560
cgacgacaaa gtgatgaagc agctgaagcg gcggagatac accggctggg gcaggctgag    4620
ccggaagctg atcaacggca tccgggacaa gcagtccggc aagacaatcc tggatttcct    4680
gaagtccgac ggcttcgcca acagaaactt catgcagctg atccacgacg acagcctgac    4740
ctttaaagag gacatccaga aagcccaggt gtccggccag ggcgatagcc tgcacgagca    4800
cattgccaat ctggccggca gccccgccat taagaagggc atcctgcaga cagtgaaggt    4860
ggtggacgag ctcgtgaaag tgatgggccg gcacaagccc gagaacatcg tgatcgaaat    4920
ggccagagag aaccagacca cccagaaggg acagaagaac agccgcgaga atgaagcg     4980
```

```
gatcgaagag ggcatcaaag agctgggcag ccagatcctg aaagaacacc ccgtggaaaa    5040
cacccagctg cagaacgaga agctgtacct gtactacctg cagaatgggc gggatatgta    5100
cgtggaccag gaactggaca tcaaccggct gtccgactac gatgtggacc atatcgtgcc    5160
tcagagcttt ctgaaggacg actccatcga caacaaggtg ctgaccagaa gcgacaagaa    5220
ccggggcaag agcgacaacg tgccctccga gaggtcgtg aagaagatga agaactactg     5280
gcggcagctg ctgaacgcca agctgattac ccagagaaag ttcgacaatc tgaccaaggc    5340
cgagagaggc ggcctgagcg aactggataa ggccggcttc atcaagagac agctggtgga    5400
aacccggcag atcacaaagc acgtggcaca gatcctggac tcccggatga cactaagta    5460
cgacgagaat gacaagctga tccgggaagt gaaagtgatc accctgaagt ccaagctggt    5520
gtccgatttc cggaaggatt tccagtttta caaagtgcgc gagatcaaca actaccacca    5580
cgcccacgac gcctacctga cgccgtcgt gggaaccgcc ctgatcaaaa agtaccctaa     5640
gctggaaagc gagttcgtgt acggcgacta caaggtgtac gacgtgcgga agatgatcgc    5700
caagagcgag caggaaatcg gcaaggctac cgccaagtac ttcttctaca gcaacatcat    5760
gaacttttc aagaccgaga ttaccctggc caacggcgag atccggaagc ggcctctgat     5820
cgagacaaac ggcgaaaccg gggagatcgt gtgggataag gcgggat ttgccaccgt       5880
gcggaaagtg ctgagcatgc cccaagtgaa tatcgtgaaa aagaccgagg tgcagacagg    5940
cggcttcagc aaagagtcta tcctgcccaa gaggaacagc gataagctga tcgccagaaa    6000
gaaggactgg gaccctaaga gtacggcgcg cttcgacagc cccaccgtgg cctattctgt    6060
gctggtggtg gccaaagtgg aaaagggcaa gtccaagaaa ctgaagagtg tgaaagagct    6120
gctgggatc accatcatgg aaaagaagcag cttcgagaag aatcccatcg actttctgga   6180
agccaagggc tacaaagaag tgaaaaagga cctgatcatc aagctgccta agtactccct    6240
gttcgagctg gaaaacggcc ggaagagaat gctggcctct gccggcgaac tgcagaaggg    6300
aaacgaactg gccctgcct caaatatgt gaacttcctg tacctggcca gccactatga     6360
gaagctgaag ggctcccccg aggataatga gcagaaacag ctgtttgtgg aacagcacaa    6420
gcactacctg gacgagatca tcgagcagat cagcgagttc tccaagagag tgatcctggc    6480
cgacgctaat ctggacaaag tgctgtccgc ctacaacaag caccggata agcccatcag     6540
agagcaggcc gagaatatca tccacctgtt taccctgacc aatctgggag cccctgccgc    6600
cttcaagtac tttgacacca ccatcgaccg gaagaggtac accagcacca agaggtgct     6660
ggacgccacc ctgatccacc agagcatcac cggcctgtac gagacacgga tcgacctgtc    6720
tcagctggga ggcgacaagc gacctgccgc cacaaagaag gctggacagg ctaagaagaa    6780
gaaagattac aaagacgatg acgataaggg atccggcgca acaaacttct ctctgctgaa    6840
acaagccgga gatgtcgaag agaatcctgg accgaccgag tacaagccca cggtgcgcct    6900
cgccacccgc gacgacgtcc ccagggccgt acgcaccctc gccgccgcgt tcgccgacta    6960
ccccgccacg cgccacaccg tcgatccgga ccgccacatc gagcgggtca ccgagctgca    7020
agaactcttc ctcacgcgcg tcgggctcga catcggcaag gtgtgggtcg cggacgacgg    7080
cgccgcggtg gcggtctgga ccacgccgga gagcgtcgaa gcggggcgg tgttcgccga    7140
gatcggcccg cgcatggccg agttgagcgg ttcccggctg ccgcgcagc aacagatgga    7200
aggcctcctg gcgccgcacc ggcccaagga gcccgcgtgg ttcctggcca ccgtcggagt    7260
ctcgcccgac caccagggca aggtctgg cagcgccgtc gtgctccccg gagtggaggc    7320
```

```
ggccgagcgc gccggggtgc ccgccttcct ggagacctcc gcgccccgca acctccccctt    7380 ctacgagcgg ctcggcttca ccgtcaccgc cgacgtcgag gtgcccgaag gaccgcgcac     7440
ctggtgcatg acccgcaagc ccggtgcctg aacgcgttaa gtcgacaatc aacctctgga     7500
ttacaaaatt tgtgaaagat tgactggtat tcttaactat gttgctcctt ttacgctatg     7560
tggatacgct gctttaatgc cttttgtatca tgctattgct tcccgtatgg ctttcatttt    7620
ctcctccttg tataaatcct ggttgctgtc tctttatgag gagttgtggc ccgttgtcag     7680
gcaacgtggc gtggtgtgca ctgtgtttgc tgacgcaacc cccactggtt ggggcattgc     7740
caccacctgt cagctccttt ccgggacttt cgctttcccc ctccctattg ccacggcgga     7800
actcatcgcc gcctgccttg cccgctgctg acagggget cggctgttgg gcactgacaa      7860
ttccgtggtg ttgtcgggga aatcatcgtc ctttccttgg ctgctcgcct gtgttgccac     7920
ctggattctg cgcgggacgt ccttctgcta cgtcccttcg gccctcaatc cagcggacct     7980
tccttcccgc ggcctgctgc cggctctgcg gcctcttccg cgtcttcgcc ttcgccctca     8040
gacgagtcgg atctcccttt gggccgcctc cccgcgtcga ctttaagacc aatgacttac     8100
aaggcagctg tagatcttag ccacttttta aagaaaagg ggggactgga agggctaatt      8160
cactcccaac gaagacaaga tctgcttttt gcttgtactg ggtctctctg gttagaccag     8220
atctgagcct gggagctctc tggctaacta gggaacccac tgcttaagcc tcaataaagc     8280
ttgccttgag tgcttcaagt agtgtgtgcc cgtctgttgt gtgactctgg taactagaga     8340
tccctcagac ccttttagtc agtgtggaaa atctctagca gggcccgttt aaacccgctg     8400
atcagcctcg actgtgcctt ctagttgcca gccatctgtt gtttgcccct cccccgtgcc     8460
ttccttgacc ctggaaggtg ccactcccac tgtcctttcc taataaaatg aggaaattgc     8520
atcgcattgt ctgagtaggt gtcattctat tctgggggt ggggtggggc aggacagcaa      8580
gggggaggat tgggaagaca atagcaggca tgctggggat gcggtgggct ctatggcttc     8640
tgaggcggaa agaaccagct ggggctctag ggggtatccc cacgcgccct gtagcggcgc     8700
attaagcgcg gcgggtgtgg tggttacgcg cagcgtgacc gctacacttg ccagcgccct     8760
agcgcccgct cctttcgctt tcttcccttc ctttctcgcc acgttcgccg gctttccccg     8820
tcaagctcta aatcgggggc tccctttagg gttccgattt agtgctttac ggcacctcga     8880
ccccaaaaaa cttgattagg gtgatggttc acgtagtggg ccatcgccct gatagacggt     8940
ttttcgccct ttgacgttgg agtccacgtt ctttaatagt ggactcttgt tccaaactgg     9000
aacaacactc aaccctatct cggtctattc ttttgattta agggattt tgccgatttc       9060 ggcctattgg ttaaaaaatg agctgattta acaaaaattt aacgcgaatt aattctgtgg     9120
aatgtgtgtc agttagggtg tggaaagtcc ccaggctccc cagcaggcag aagtatgcaa     9180
agcatgcatc tcaattagtc agcaaccagg tgtggaaagt ccccaggctc cccagcaggc     9240
agaagtatgc aaagcatgca tctcaattag tcagcaacca tagtcccgcc cctaactccg     9300
cccatcccgc ccctaactcc gcccagttcc gcccattctc cgccccatgg ctgactaatt     9360
ttttttattt atgcagaggc cgaggccgcc tctgcctctg agctattcca gaagtagtga     9420
ggaggctttt ttggaggcct aggcttttgc aaaaagctcc cggagccttg tatatccatt     9480
ttcggatctg atcagcacgt gttgacaatt aatcatcggc atagtatatc ggcatagtat     9540
aatacgacaa ggtgaggaac taaaccatgg ccaagttgac cagtgccgtt ccggtgctca     9600
ccgcgcgcga cgtcgccgga gcggtcgagt tctggaccga ccggctcggg ttctcccggg     9660
acttcgtgga ggacgacttc gccggtgtgg tccgggacga cgtgaccctg ttcatcagcg     9720
```

```
cggtccagga ccaggtggtg ccggacaaca ccctggcctg ggtgtgggtg cgcggcctgg    9780
acgagctgta cgccgagtgg tcggaggtcg tgtccacgaa cttccgggac gcctccgggc    9840
cggccatgac cgagatcggc gagcagccgt ggggcggga gttcgccctg cgcgacccgg     9900
ccggcaactg cgtgcacttc gtggccgagg agcaggactg acacgtgcta cgagatttcg    9960
attccaccgc cgccttctat gaaaggttgg gcttcggaat cgttttccgg gacgccggct    10020
ggatgatcct ccagcgcggg gatctcatgc tggagttctt cgcccacccc aacttgttta    10080
ttgcagctta taatggttac aaataaagca atagcatcac aaatttcaca aataaagcat    10140
ttttttcact gcattctagt tgtggtttgt ccaaactcat caatgtatct tatcatgtct    10200
gtataccgtc gacctctagc tagagcttgg cgtaatcatg gtcatagctg tttcctgtgt    10260
gaaattgtta tccgctcaca attccacaca acatacgagc cggaagcata agtgtaaag     10320 cctggggtgc ctaatgagtg agctaactca cattaattgc gttgcgctca ctgcccgctt    10380
tccagtcggg aaacctgtcg tgccagctgc attaatgaat cggccaacgc gcggggagag    10440
gcggtttgcg tattgggcgc tcttccgctt cctcgctcac tgactcgctg cgctcggtcg    10500
ttcggctgcg gcgagcggta tcagctcact caaaggcggt aatacggtta tccacagaat    10560
caggggataa cgcaggaaag aacatgtgag caaaaggcca gcaaaaggcc aggaaccgta    10620
aaaaggccgc gttgctggcg ttttttccata ggctccgccc ccctgacgag catcacaaaa    10680
atcgacgctc aagtcagagg tggcgaaacc cgacaggact ataaagatac caggcgtttc    10740 ccctggaag ctccctcgtg cgctctcctg ttccgaccct gccgcttacc ggatacctgt     10800
ccgcctttct cccttcggga agcgtggcgc tttctcatag ctcacgctgt aggtatctca    10860
gttcggtgta ggtcgttcgc tccaagctgg gctgtgtgca cgaaccccc gttcagcccg     10920 accgctgcgc cttatccggt aactatcgtc ttgagtccaa cccggtaaga cacgacttat    10980
cgccactggc agcagccact ggtaacagga ttagcagagc gaggtatgta ggcggtgcta    11040
cagagttctt gaagtggtgg cctaactacg gctacactag aagaacagta tttggtatct    11100
gcgctctgct gaagccagtt accttcggaa aaagagttgg tagctcttga tccggcaaac    11160
aaaccaccgc tggtagcggt ggtttttttg tttgcaagca gcagattacg cgcagaaaaa    11220
aaggatctca agaagatcct ttgatctttt ctacggggtc tgacgctcag tggaacgaaa    11280
actcacgtta agggattttg gtcatgagat tatcaaaaag gatcttcacc tagatccttt    11340
taaattaaaa atgaagtttt aaatcaatct aaagtatata tgagtaaact tggtctgaca    11400
gttaccaatg cttaatcagt gaggcaccta tctcagcgat ctgtctattt cgttcatcca    11460
tagttgcctg actccccgtc gtgtagataa ctacgatacg ggagggctta ccatctggcc    11520
ccagtgctgc aatgataccg cgagacccac gctcaccggc tccagattta tcagcaataa    11580
accagccagc cggaagggcc gagcgcagaa gtggtcctgc aactttatcc gcctccatcc    11640
agtctattaa ttgttgccgg gaagctagag taagtagttc gccagttaat agtttgcgca    11700
acgttgttgc cattgctaca ggcatcgtgg tgtcacgctc gtcgtttggt atggcttcat    11760
tcagctccgg ttcccaacga tcaaggcgag ttacatgatc ccccatgttg tgcaaaaaag    11820
cggttagctc cttcggtcct ccgatcgttg tcagaagtaa gttggccgca gtgttatcac    11880
tcatggttat ggcagcactg cataattctc ttactgtcat gccatccgta agatgctttt    11940
ctgtgactgg tgagtactca accaagtcat tctgagaata gtgtatgcgg cgaccgagtt    12000
gctcttgccc ggcgtcaata cgggataata ccgcgccaca tagcagaact ttaaaagtgc    12060
```

-continued

```
tcatcattgg aaaacgttct tcggggcgaa aactctcaag gatcttaccg ctgttgagat    12120
ccagttcgat gtaacccact cgtgcaccca actgatcttc agcatctttt actttcacca    12180
gcgtttctgg gtgagcaaaa acaggaaggc aaaatgccgc aaaaaaggga ataagggcga    12240
cacggaaatg ttgaatactc atactcttcc tttttcaata ttattgaagc atttatcagg    12300
gttattgtct catgagcgga tacatatttg aatgtattta gaaaaataaa caaataggggg   12360 ttccgcgcac atttccccga aaagtgccac ctgacgtcga cggatcggga gatctcccga    12420 tccccctatgg tgcactctca gtacaatctg ctctgatgcc gcatagttaa gccagtatct   12480
gctccctgct tgtgtgttgg aggtcgctga gtagtgcgcg agcaaaattt aagctacaac    12540
aaggcaaggc ttgaccgaca attgcatgaa gaatctgctt agggttaggc gttttgcgct    12600
gcttcgcgat gtacgggcca gatatacgcg ttgacattga ttattgacta gttattaata    12660
gtaatcaatt acggggtcat tagttcatag cccatatatg gagttccgcg ttacataact    12720
tacggtaaat ggcccgcctg gctgaccgcc caacgacccc cgcccattga cgtcaataat    12780
gacgtatgtt cccatagtaa cgccaatagg gactttccat tgacgtcaat gggtggagta    12840
tttacggtaa actgcccact tggcagtaca tcaagtgtat catatgccaa gtacgccccc    12900
tattgacgtc aatgacggta aatggcccgc ctggcattat gcccagtaca tgaccttatg    12960
ggactttcct acttggcagt acatctacgt attagtcatc gctattacca tgg           13013
```

```
<210> SEQ ID NO 21
<211> LENGTH: 22
<212> TYPE: DNA
<213> ORGANISM: Artificial Sequence
<220> FEATURE:
<223> OTHER INFORMATION: synthetic

<400> SEQUENCE: 21
aggaacggag tgacctgttt cc                                              22

<210> SEQ ID NO 22
<211> LENGTH: 22
<212> TYPE: DNA
<213> ORGANISM: Artificial Sequence
<220> FEATURE:
<223> OTHER INFORMATION: synthetic

<400> SEQUENCE: 22
ttcctccatg gtaaccacgc at                                              22

<210> SEQ ID NO 23
<211> LENGTH: 22
<212> TYPE: DNA
<213> ORGANISM: Artificial Sequence
<220> FEATURE:
<223> OTHER INFORMATION: synthetic

<400> SEQUENCE: 23
tggggaagcc acatgttgta ca                                              22

<210> SEQ ID NO 24
<211> LENGTH: 22
<212> TYPE: DNA
<213> ORGANISM: Artificial Sequence
<220> FEATURE:
<223> OTHER INFORMATION: synthetic

<400> SEQUENCE: 24
atgttttggt gggccatttg gt                                              22
```

<210> SEQ ID NO 25
<211> LENGTH: 26
<212> TYPE: DNA
<213> ORGANISM: Artificial Sequence
<220> FEATURE:
<223> OTHER INFORMATION: synthetic

<400> SEQUENCE: 25
aaattatggg tgttctgcaa tcttgg                                    26

<210> SEQ ID NO 26
<211> LENGTH: 23
<212> TYPE: DNA
<213> ORGANISM: Artificial Sequence
<220> FEATURE:
<223> OTHER INFORMATION: synthetic

<400> SEQUENCE: 26
acttgtgtta cagcacagct gtc                                       23

<210> SEQ ID NO 27
<211> LENGTH: 21
<212> TYPE: DNA
<213> ORGANISM: Artificial Sequence
<220> FEATURE:
<223> OTHER INFORMATION: synthetic

<400> SEQUENCE: 27
gccctccaga agtattggct t                                         21

<210> SEQ ID NO 28
<211> LENGTH: 21
<212> TYPE: DNA
<213> ORGANISM: Artificial Sequence
<220> FEATURE:
<223> OTHER INFORMATION: synthetic

<400> SEQUENCE: 28
gtcagggcct tgctctacaa a                                         21

<210> SEQ ID NO 29
<211> LENGTH: 20
<212> TYPE: DNA
<213> ORGANISM: Artificial Sequence
<220> FEATURE:
<223> OTHER INFORMATION: synthetic

<400> SEQUENCE: 29
cgcaaaaact ggctgcgtat                                           20

<210> SEQ ID NO 30
<211> LENGTH: 20
<212> TYPE: DNA
<213> ORGANISM: Artificial Sequence
<220> FEATURE:
<223> OTHER INFORMATION: synthetic

<400> SEQUENCE: 30
tgtaggcgca catgcagaag                                           20

<210> SEQ ID NO 31
<211> LENGTH: 21
<212> TYPE: DNA
<213> ORGANISM: Artificial Sequence
<220> FEATURE:

<223> OTHER INFORMATION: synthetic

<400> SEQUENCE: 31
caggtagagc gtggaaactc a                                              21

<210> SEQ ID NO 32
<211> LENGTH: 20
<212> TYPE: DNA
<213> ORGANISM: Artificial Sequence
<220> FEATURE:
<223> OTHER INFORMATION: synthetic

<400> SEQUENCE: 32
tgtgcgcatt aggaccagat                                                20

<210> SEQ ID NO 33
<211> LENGTH: 20
<212> TYPE: DNA
<213> ORGANISM: Artificial Sequence
<220> FEATURE:
<223> OTHER INFORMATION: synthetic

<400> SEQUENCE: 33
cacctgacaa tgctgtccca                                                20

<210> SEQ ID NO 34
<211> LENGTH: 21
<212> TYPE: DNA
<213> ORGANISM: Artificial Sequence
<220> FEATURE:
<223> OTHER INFORMATION: synthetic

<400> SEQUENCE: 34
agacaaggtc tgtctccttg c                                              21

<210> SEQ ID NO 35
<211> LENGTH: 20
<212> TYPE: DNA
<213> ORGANISM: Artificial Sequence
<220> FEATURE:
<223> OTHER INFORMATION: synthetic

<400> SEQUENCE: 35
ccaactcttt gcttaggggc                                                20

<210> SEQ ID NO 36
<211> LENGTH: 20
<212> TYPE: DNA
<213> ORGANISM: Artificial Sequence
<220> FEATURE:
<223> OTHER INFORMATION: synthetic

<400> SEQUENCE: 36
atcgtccctg gtgcattctc                                                20

<210> SEQ ID NO 37
<211> LENGTH: 20
<212> TYPE: DNA
<213> ORGANISM: Artificial Sequence
<220> FEATURE:
<223> OTHER INFORMATION: synthetic

<400> SEQUENCE: 37
ggaaaaccag gtagaggggg                                                20

<210> SEQ ID NO 38
<211> LENGTH: 20
<212> TYPE: DNA
<213> ORGANISM: Artificial Sequence
<220> FEATURE:
<223> OTHER INFORMATION: synthetic

<400> SEQUENCE: 38
tctctggctc gagggtacat          20

<210> SEQ ID NO 39
<211> LENGTH: 20
<212> TYPE: DNA
<213> ORGANISM: Artificial Sequence
<220> FEATURE:
<223> OTHER INFORMATION: synthetic

<400> SEQUENCE: 39
ctgcatgcca tgggtaggta          20

<210> SEQ ID NO 40
<211> LENGTH: 19
<212> TYPE: DNA
<213> ORGANISM: Artificial Sequence
<220> FEATURE:
<223> OTHER INFORMATION: synthetic

<400> SEQUENCE: 40
caggctgttt cgggtcctt          19

<210> SEQ ID NO 41
<211> LENGTH: 21
<212> TYPE: DNA
<213> ORGANISM: Artificial Sequence
<220> FEATURE:
<223> OTHER INFORMATION: synthetic

<400> SEQUENCE: 41
agactcttct ccgattccag c          21

<210> SEQ ID NO 42
<211> LENGTH: 20
<212> TYPE: DNA
<213> ORGANISM: Artificial Sequence
<220> FEATURE:
<223> OTHER INFORMATION: synthetic

<400> SEQUENCE: 42
tccagcacga tctggtaggc          20

<210> SEQ ID NO 43
<211> LENGTH: 22
<212> TYPE: DNA
<213> ORGANISM: Artificial Sequence
<220> FEATURE:
<223> OTHER INFORMATION: synthetic

<400> SEQUENCE: 43
agtgcttttc tttgcctttg ct          22

<210> SEQ ID NO 44
<211> LENGTH: 20
<212> TYPE: DNA
<213> ORGANISM: Artificial Sequence
<220> FEATURE:
<223> OTHER INFORMATION: synthetic

<400> SEQUENCE: 44
tgctcgggag gtgtttctac                                                    20

<210> SEQ ID NO 45
<211> LENGTH: 20
<212> TYPE: DNA
<213> ORGANISM: Artificial Sequence
<220> FEATURE:
<223> OTHER INFORMATION: synthetic

<400> SEQUENCE: 45
aacaaggcag ctcctcaact                                                    20

<210> SEQ ID NO 46
<211> LENGTH: 21
<212> TYPE: DNA
<213> ORGANISM: Artificial Sequence
<220> FEATURE:
<223> OTHER INFORMATION: synthetic

<400> SEQUENCE: 46
gacgtcagaa ttgagggtgg a                                                  21

<210> SEQ ID NO 47
<211> LENGTH: 22
<212> TYPE: DNA
<213> ORGANISM: Artificial Sequence
<220> FEATURE:
<223> OTHER INFORMATION: synthetic

<400> SEQUENCE: 47
ccagcgggat gaactggtaa ga                                                 22

<210> SEQ ID NO 48
<211> LENGTH: 22
<212> TYPE: DNA
<213> ORGANISM: Artificial Sequence
<220> FEATURE:
<223> OTHER INFORMATION: synthetic

<400> SEQUENCE: 48
cccaggtcac cttaaggagc aa                                                 22

<210> SEQ ID NO 49
<211> LENGTH: 22
<212> TYPE: DNA
<213> ORGANISM: Artificial Sequence
<220> FEATURE:
<223> OTHER INFORMATION: synthetic

<400> SEQUENCE: 49
gagagagttg gaggccttga gg                                                 22

<210> SEQ ID NO 50
<211> LENGTH: 22
<212> TYPE: DNA
<213> ORGANISM: Artificial Sequence
<220> FEATURE:
<223> OTHER INFORMATION: synthetic

<400> SEQUENCE: 50
aaccacagtg acaagtggct ct                                                 22

<210> SEQ ID NO 51
<211> LENGTH: 22

<212> TYPE: DNA
<213> ORGANISM: Artificial Sequence
<220> FEATURE:
<223> OTHER INFORMATION: synthetic

<400> SEQUENCE: 51
gtgaatgcgt ctgttccaag gg         22

<210> SEQ ID NO 52
<211> LENGTH: 22
<212> TYPE: DNA
<213> ORGANISM: Artificial Sequence
<220> FEATURE:
<223> OTHER INFORMATION: synthetic

<400> SEQUENCE: 52
gctgctggga ctatctggga at         22

<210> SEQ ID NO 53
<211> LENGTH: 22
<212> TYPE: DNA
<213> ORGANISM: Artificial Sequence
<220> FEATURE:
<223> OTHER INFORMATION: synthetic

<400> SEQUENCE: 53
ttttaggggc tcgaccttcc ag         22

<210> SEQ ID NO 54
<211> LENGTH: 22
<212> TYPE: DNA
<213> ORGANISM: Artificial Sequence
<220> FEATURE:
<223> OTHER INFORMATION: synthetic

<400> SEQUENCE: 54
tgcactaatt tcccagggct ca         22

<210> SEQ ID NO 55
<211> LENGTH: 30
<212> TYPE: DNA
<213> ORGANISM: Artificial Sequence
<220> FEATURE:
<223> OTHER INFORMATION: synthetic

<400> SEQUENCE: 55
cacatccatc catcatggcg tggtggaggt         30

<210> SEQ ID NO 56
<211> LENGTH: 30
<212> TYPE: DNA
<213> ORGANISM: Artificial Sequence
<220> FEATURE:
<223> OTHER INFORMATION: synthetic

<400> SEQUENCE: 56
tcttggagag atggcgctcc tctgggtca         30

<210> SEQ ID NO 57
<211> LENGTH: 30
<212> TYPE: DNA
<213> ORGANISM: Artificial Sequence
<220> FEATURE:
<223> OTHER INFORMATION: synthetic

<400> SEQUENCE: 57
ctcatatccg ttctgctgca tcttggagag                                          30

<210> SEQ ID NO 58
<211> LENGTH: 303
<212> TYPE: DNA
<213> ORGANISM: Mus musculus

<400> SEQUENCE: 58
atggatgcag aattcggaca tgattcagga tttgaagtcc gccatcaaaa actggtgttc         60
tttgctgaag atgtgggttc gaacaaaggc gccatcatcg gactcatggt gggcggcgtt        120
gtcatagcaa ccgtgattgt catcaccctg gtgatgttga agaagaaaca gtacacatcc        180
atccatcatg gcgtggtgga ggtcgacgcc gccgtgaccc cagaggagcg ccatctctcc        240
aagatgcagc agaacggata tgagaatcca acttacaagt tctttgagca aatgcagaac        300
taa                                                                      303

<210> SEQ ID NO 59
<211> LENGTH: 100
<212> TYPE: PRT
<213> ORGANISM: Mus musculus

<400> SEQUENCE: 59

Met Asp Ala Glu Phe Gly His Asp Ser Gly Phe Glu Val Arg His Gln
1               5                   10                  15

Lys Leu Val Phe Phe Ala Glu Asp Val Gly Ser Asn Lys Gly Ala Ile
            20                  25                  30

Ile Gly Leu Met Val Gly Gly Val Val Ile Ala Thr Val Ile Val Ile
        35                  40                  45

Thr Leu Val Met Leu Lys Lys Lys Gln Tyr Thr Ser Ile His His Gly
    50                  55                  60

Val Val Glu Val Asp Ala Ala Val Thr Pro Glu Glu Arg His Leu Ser
65                  70                  75                  80

Lys Met Gln Gln Asn Gly Tyr Glu Asn Pro Thr Tyr Lys Phe Phe Glu
                85                  90                  95

Gln Met Gln Asn
            100

<210> SEQ ID NO 60
<211> LENGTH: 66
<212> TYPE: DNA
<213> ORGANISM: Artificial Sequence
<220> FEATURE:
<223> OTHER INFORMATION: synthetic

<400> SEQUENCE: 60
gaagaagaaa cagtacacat ccatccatca tggcgtggtg gaggtaggta aacctggagg         60
cttgtc                                                                   66

<210> SEQ ID NO 61
<211> LENGTH: 46
<212> TYPE: DNA
<213> ORGANISM: Artificial Sequence
<220> FEATURE:
<223> OTHER INFORMATION: synthetic

<400> SEQUENCE: 61
aacagtacac atccatccat catggcgtgg tggaggtagg taaacc                        46

-continued

<210> SEQ ID NO 62
<211> LENGTH: 41
<212> TYPE: DNA
<213> ORGANISM: Artificial Sequence
<220> FEATURE:
<223> OTHER INFORMATION: synthetic

<400> SEQUENCE: 62
aacagtacac atccatccat catggtggag gtaggtaaac c       41

<210> SEQ ID NO 63
<211> LENGTH: 41
<212> TYPE: DNA
<213> ORGANISM: Artificial Sequence
<220> FEATURE:
<223> OTHER INFORMATION: synthetic

<400> SEQUENCE: 63
aacagtacac atccatccat catggcggag gtaggtaaac c       41

<210> SEQ ID NO 64
<211> LENGTH: 38
<212> TYPE: DNA
<213> ORGANISM: Artificial Sequence
<220> FEATURE:
<223> OTHER INFORMATION: synthetic

<400> SEQUENCE: 64
aacagtacac atccatccat catggaggta ggtaaacc          38

<210> SEQ ID NO 65
<211> LENGTH: 44
<212> TYPE: DNA
<213> ORGANISM: Artificial Sequence
<220> FEATURE:
<223> OTHER INFORMATION: synthetic

<400> SEQUENCE: 65
aacagtacac atccatccat catggcggtg gaggtaggta aacc    44

<210> SEQ ID NO 66
<211> LENGTH: 44
<212> TYPE: DNA
<213> ORGANISM: Artificial Sequence
<220> FEATURE:
<223> OTHER INFORMATION: synthetic

<400> SEQUENCE: 66
aacagtacac atccatccat catggtggtg gaggtaggta aacc    44

<210> SEQ ID NO 67
<211> LENGTH: 23
<212> TYPE: DNA
<213> ORGANISM: Mus musculus

<400> SEQUENCE: 67
atccatccat catggcgtgg tgg                          23

<210> SEQ ID NO 68
<211> LENGTH: 23
<212> TYPE: DNA
<213> ORGANISM: Homo sapiens

<400> SEQUENCE: 68
atccattcat catggtgtgg tgg                                          23

<210> SEQ ID NO 69
<211> LENGTH: 66
<212> TYPE: DNA
<213> ORGANISM: Artificial Sequence
<220> FEATURE:
<223> OTHER INFORMATION: synthetic

<400> SEQUENCE: 69
gaagaagaaa cagtacacat ccattcatca tggtgtggtg gaggtaggta aacttgactg    60
catgtt                                                             66

<210> SEQ ID NO 70
<211> LENGTH: 45
<212> TYPE: DNA
<213> ORGANISM: Artificial Sequence
<220> FEATURE:
<223> OTHER INFORMATION: synthetic

<400> SEQUENCE: 70
aacagtacac atccattcat catggtgtgg tggaggtagg taaac                  45

<210> SEQ ID NO 71
<211> LENGTH: 40
<212> TYPE: DNA
<213> ORGANISM: Artificial Sequence
<220> FEATURE:
<223> OTHER INFORMATION: synthetic

<400> SEQUENCE: 71
aacagtacac atccattcat catggtggag gtaggtaaac                        40

<210> SEQ ID NO 72
<211> LENGTH: 43
<212> TYPE: DNA
<213> ORGANISM: Artificial Sequence
<220> FEATURE:
<223> OTHER INFORMATION: synthetic

<400> SEQUENCE: 72
aacagtacac atccattcat catggtggtg gaggtaggta aac                    43

<210> SEQ ID NO 73
<211> LENGTH: 41
<212> TYPE: DNA
<213> ORGANISM: Artificial Sequence
<220> FEATURE:
<223> OTHER INFORMATION: synthetic

<400> SEQUENCE: 73
aacagtacac atccattcat cattggtgga ggtaggtaaa c                      41

<210> SEQ ID NO 74
<211> LENGTH: 44
<212> TYPE: DNA
<213> ORGANISM: Artificial Sequence
<220> FEATURE:
<223> OTHER INFORMATION: synthetic

<400> SEQUENCE: 74
aacagtacac atccattcat catggtgggt ggaggtaggt aaac                   44

<210> SEQ ID NO 75
<211> LENGTH: 39
<212> TYPE: DNA
<213> ORGANISM: Artificial Sequence
<220> FEATURE:
<223> OTHER INFORMATION: synthetic

<400> SEQUENCE: 75
aacagtacac atccattcat ctggtggagg taggtaaac                              39

<210> SEQ ID NO 76
<211> LENGTH: 46
<212> TYPE: PRT
<213> ORGANISM: Artificial Sequence
<220> FEATURE:
<223> OTHER INFORMATION: synthetic

<400> SEQUENCE: 76

Gly Gly Val Val Ile Ala Thr Val Ile Val Ile Thr Leu Val Met Leu
1               5                   10                  15

Lys Lys Lys Gln Tyr Thr Ser Ile His His Gly Val Val Glu Val Asp
            20                  25                  30

Ala Ala Val Thr Pro Glu Glu Arg His Leu Ser Lys Met Gln
        35                  40                  45

<210> SEQ ID NO 77
<211> LENGTH: 29
<212> TYPE: PRT
<213> ORGANISM: Artificial Sequence
<220> FEATURE:
<223> OTHER INFORMATION: synthetic

<400> SEQUENCE: 77

Gly Gly Val Val Ile Ala Thr Val Ile Val Ile Thr Leu Val Met Leu
1               5                   10                  15

Lys Lys Lys Gln Tyr Thr Ser Ile His His Gly Gly Gly
            20                  25

<210> SEQ ID NO 78
<211> LENGTH: 30
<212> TYPE: PRT
<213> ORGANISM: Artificial Sequence
<220> FEATURE:
<223> OTHER INFORMATION: synthetic

<400> SEQUENCE: 78

Gly Gly Val Val Ile Ala Thr Val Ile Val Ile Thr Leu Val Met Leu
1               5                   10                  15

Lys Lys Lys Gln Tyr Thr Ser Ile His His Gly Gly Gly Gly
            20                  25                  30

<210> SEQ ID NO 79
<211> LENGTH: 26
<212> TYPE: PRT
<213> ORGANISM: Artificial Sequence
<220> FEATURE:
<223> OTHER INFORMATION: synthetic

<400> SEQUENCE: 79

Gly Gly Val Val Ile Ala Thr Val Ile Val Ile Thr Leu Val Met Leu
1               5                   10                  15

Lys Lys Lys Gln Tyr Thr Ser Ile His His
            20                  25

```
<210> SEQ ID NO 80
<211> LENGTH: 27
<212> TYPE: PRT
<213> ORGANISM: Artificial Sequence
<220> FEATURE:
<223> OTHER INFORMATION: synthetic

<400> SEQUENCE: 80

Gly Gly Val Val Ile Ala Thr Val Ile Val Ile Thr Leu Val Met Leu
1               5                   10                  15

Lys Lys Lys Gln Tyr Thr Ser Ile His His Gly
            20                  25

<210> SEQ ID NO 81
<211> LENGTH: 44
<212> TYPE: PRT
<213> ORGANISM: Artificial Sequence
<220> FEATURE:
<223> OTHER INFORMATION: synthetic

<400> SEQUENCE: 81

Gly Gly Val Val Ile Ala Thr Val Ile Val Ile Thr Leu Val Met Leu
1               5                   10                  15

Lys Lys Lys Gln Tyr Thr Ser Ile His Leu Val Glu Val Asp Ala Ala
            20                  25                  30

Val Thr Pro Glu Glu Arg His Leu Ser Lys Met Gln
        35                  40

<210> SEQ ID NO 82
<211> LENGTH: 37
<212> TYPE: PRT
<213> ORGANISM: Artificial Sequence
<220> FEATURE:
<223> OTHER INFORMATION: synthetic

<400> SEQUENCE: 82

Gly Val Val Glu Val Asp Ala Ala Val Thr Pro Glu Glu Arg His Leu
1               5                   10                  15

Ser Lys Met Gln Gln Asn Gly Tyr Glu Asn Pro Thr Tyr Lys Phe Phe
            20                  25                  30

Glu Gln Met Gln Asn
        35

<210> SEQ ID NO 83
<211> LENGTH: 45
<212> TYPE: DNA
<213> ORGANISM: Artificial Sequence
<220> FEATURE:
<223> OTHER INFORMATION: synthetic

<400> SEQUENCE: 83
aacagtacac atccattcat catggtgtgg tggaggtagg taaac            45

<210> SEQ ID NO 84
<211> LENGTH: 40
<212> TYPE: DNA
<213> ORGANISM: Artificial Sequence
<220> FEATURE:
<223> OTHER INFORMATION: synthetic

<400> SEQUENCE: 84
aacagtacac atccattcat catggtggag gtaggtaaac                   40
```

```
<210> SEQ ID NO 85
<211> LENGTH: 43
<212> TYPE: DNA
<213> ORGANISM: Artificial Sequence
<220> FEATURE:
<223> OTHER INFORMATION: synthetic

<400> SEQUENCE: 85
aacagtacac atccattcat catggtggtg gaggtaggta aac                    43

<210> SEQ ID NO 86
<211> LENGTH: 44
<212> TYPE: DNA
<213> ORGANISM: Artificial Sequence
<220> FEATURE:
<223> OTHER INFORMATION: synthetic

<400> SEQUENCE: 86
aacagtacac atccattcat catggtgggt ggaggtaggt aaac                   44

<210> SEQ ID NO 87
<211> LENGTH: 41
<212> TYPE: DNA
<213> ORGANISM: Artificial Sequence
<220> FEATURE:
<223> OTHER INFORMATION: synthetic

<400> SEQUENCE: 87
aacagtacac atccattcat cattggtgga ggtaggtaaa c                      41

<210> SEQ ID NO 88
<211> LENGTH: 42
<212> TYPE: DNA
<213> ORGANISM: Artificial Sequence
<220> FEATURE:
<223> OTHER INFORMATION: synthetic

<400> SEQUENCE: 88
aacagtacac atccattcat catgtggtgg aggtaggtaa ac                     42

<210> SEQ ID NO 89
<211> LENGTH: 45
<212> TYPE: DNA
<213> ORGANISM: Artificial Sequence
<220> FEATURE:
<223> OTHER INFORMATION: synthetic

<400> SEQUENCE: 89
tgctgcatct tggacaggtg gcgctcctct ggggtgacag cggcg                  45

<210> SEQ ID NO 90
<211> LENGTH: 46
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (28)..(28)
<223> OTHER INFORMATION: n is a, c, g, or t

<400> SEQUENCE: 90
tgctgcatct tggacaggtg gcgctccntc tggggtgaca gcggcg                 46

<210> SEQ ID NO 91
<211> LENGTH: 43
<212> TYPE: DNA
```

```
<213> ORGANISM: Artificial Sequence
<220> FEATURE:
<223> OTHER INFORMATION: synthetic

<400> SEQUENCE: 91
tgctgcatct tggacaggtg gcgcttctgg ggtgacagcg gcg                    43

<210> SEQ ID NO 92
<211> LENGTH: 40
<212> TYPE: DNA
<213> ORGANISM: Artificial Sequence
<220> FEATURE:
<223> OTHER INFORMATION: synthetic

<400> SEQUENCE: 92
tgctgcatct tggacaggtg gctctggggt gacagcggcg                       40

<210> SEQ ID NO 93
<211> LENGTH: 42
<212> TYPE: DNA
<213> ORGANISM: Artificial Sequence
<220> FEATURE:
<223> OTHER INFORMATION: synthetic

<400> SEQUENCE: 93
tgctgcatct tggacaggtg gcgctctggg gtgacagcgg cg                    42

<210> SEQ ID NO 94
<211> LENGTH: 44
<212> TYPE: DNA
<213> ORGANISM: Artificial Sequence
<220> FEATURE:
<223> OTHER INFORMATION: synthetic

<400> SEQUENCE: 94
tgctgcatct tggacaggtg gcgctctctg gggtgacagc ggcg                  44

<210> SEQ ID NO 95
<211> LENGTH: 45
<212> TYPE: DNA
<213> ORGANISM: Artificial Sequence
<220> FEATURE:
<223> OTHER INFORMATION: synthetic

<400> SEQUENCE: 95
ttggattttc gtagccgttc tgctgcatct tggacaggtg gcgct                 45

<210> SEQ ID NO 96
<211> LENGTH: 46
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (28)..(28)
<223> OTHER INFORMATION: n is a, c, g, or t

<400> SEQUENCE: 96
ttggattttc gtagccgttc tgctgcantc ttggacaggt ggcgct                46

<210> SEQ ID NO 97
<211> LENGTH: 36
<212> TYPE: DNA
<213> ORGANISM: Artificial Sequence
<220> FEATURE:
<223> OTHER INFORMATION: synthetic
```

-continued

<400> SEQUENCE: 97
ttggattttc gtagccgttc ttggacaggt ggcgct                                36

<210> SEQ ID NO 98
<211> LENGTH: 44
<212> TYPE: DNA
<213> ORGANISM: Artificial Sequence
<220> FEATURE:
<223> OTHER INFORMATION: synthetic

<400> SEQUENCE: 98
ttggattttc gtagccgttc tgctgctctt ggacaggtgg cgct                       44

<210> SEQ ID NO 99
<211> LENGTH: 42
<212> TYPE: DNA
<213> ORGANISM: Artificial Sequence
<220> FEATURE:
<223> OTHER INFORMATION: synthetic

<400> SEQUENCE: 99
ttggattttc gtagccgttc tgcttcttgg acaggtggcg ct                         42

<210> SEQ ID NO 100
<211> LENGTH: 39
<212> TYPE: DNA
<213> ORGANISM: Artificial Sequence
<220> FEATURE:
<223> OTHER INFORMATION: synthetic

<400> SEQUENCE: 100
ttggattttc gtagccgttc ttcttggaca ggtggcgct                             39

<210> SEQ ID NO 101
<211> LENGTH: 46
<212> TYPE: PRT
<213> ORGANISM: Artificial Sequence
<220> FEATURE:
<223> OTHER INFORMATION: synthetic

<400> SEQUENCE: 101

Gly Gly Val Val Ile Ala Thr Val Ile Val Ile Thr Leu Val Met Leu
1               5                   10                  15

Lys Lys Lys Gln Tyr Thr Ser Ile His His Gly Val Val Glu Val Asp
            20                  25                  30

Ala Ala Val Thr Pro Glu Glu Arg His Leu Ser Lys Met Gln
        35                  40                  45

<210> SEQ ID NO 102
<211> LENGTH: 29
<212> TYPE: PRT
<213> ORGANISM: Artificial Sequence
<220> FEATURE:
<223> OTHER INFORMATION: synthetic

<400> SEQUENCE: 102

Gly Gly Val Val Ile Ala Thr Val Ile Val Ile Thr Leu Val Met Leu
1               5                   10                  15

Lys Lys Lys Gln Tyr Thr Ser Ile His His Gly Gly Gly
            20                  25

<210> SEQ ID NO 103
<211> LENGTH: 30

```
<212> TYPE: PRT
<213> ORGANISM: Artificial Sequence
<220> FEATURE:
<223> OTHER INFORMATION: synthetic

<400> SEQUENCE: 103

Gly Gly Val Val Ile Ala Thr Val Ile Val Thr Leu Val Met Leu
1               5                   10                  15

Lys Lys Lys Gln Tyr Thr Ser Ile His His Gly Gly Gly
            20                  25                  30

<210> SEQ ID NO 104
<211> LENGTH: 27
<212> TYPE: PRT
<213> ORGANISM: Artificial Sequence
<220> FEATURE:
<223> OTHER INFORMATION: synthetic

<400> SEQUENCE: 104

Gly Gly Val Val Ile Ala Thr Val Ile Val Thr Leu Val Met Leu
1               5                   10                  15

Lys Lys Lys Gln Tyr Thr Ser Ile His His Gly
            20                  25

<210> SEQ ID NO 105
<211> LENGTH: 26
<212> TYPE: PRT
<213> ORGANISM: Artificial Sequence
<220> FEATURE:
<223> OTHER INFORMATION: synthetic

<400> SEQUENCE: 105

Gly Gly Val Val Ile Ala Thr Val Ile Val Thr Leu Val Met Leu
1               5                   10                  15

Lys Lys Lys Gln Tyr Thr Ser Ile His His
            20                  25

<210> SEQ ID NO 106
<211> LENGTH: 45
<212> TYPE: PRT
<213> ORGANISM: Artificial Sequence
<220> FEATURE:
<223> OTHER INFORMATION: synthetic

<400> SEQUENCE: 106

Gly Gly Val Val Ile Ala Thr Val Ile Val Thr Leu Val Met Leu
1               5                   10                  15

Lys Lys Lys Gln Tyr Thr Ser Ile His His Val Val Ala Val Asp Ala
            20                  25                  30

Ala Val Thr Pro Glu Glu Arg His Leu Ser Lys Met Gln
        35                  40                  45

<210> SEQ ID NO 107
<211> LENGTH: 46
<212> TYPE: PRT
<213> ORGANISM: Artificial Sequence
<220> FEATURE:
<223> OTHER INFORMATION: synthetic

<400> SEQUENCE: 107

Lys Lys Gln Tyr Thr Ser Ile His His Gly Val Val Glu Val Asp Ala
1               5                   10                  15

Ala Val Thr Pro Glu Glu Arg His Leu Ser Lys Met Gln Gln Asn Gly
            20                  25                  30
```

Tyr Glu Asn Pro Thr Tyr Lys Phe Phe Glu Gln Met Gln Asn
            35                  40                  45

<210> SEQ ID NO 108
<211> LENGTH: 41
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (21)..(21)
<223> OTHER INFORMATION: X is D or E

<400> SEQUENCE: 108

Lys Lys Gln Tyr Thr Ser Ile His His Gly Val Val Glu Val Asp Ala
1               5                   10                  15

Ala Val Thr Pro Xaa Gly Ala Pro Pro Val Gln Asp Ala Ala Glu Arg
            20                  25                  30

Leu Arg Lys Ser Asn Leu Gln Val Leu
            35                  40

<210> SEQ ID NO 109
<211> LENGTH: 41
<212> TYPE: PRT
<213> ORGANISM: Artificial Sequence
<220> FEATURE:
<223> OTHER INFORMATION: synthetic

<400> SEQUENCE: 109

Lys Lys Gln Tyr Thr Ser Ile His His Gly Val Val Glu Val Asp Ala
1               5                   10                  15

Ala Val Thr Pro Glu Ala Arg Pro Pro Val Gln Asp Ala Ala Glu Arg
            20                  25                  30

Leu Arg Lys Ser Asn Leu Gln Val Leu
            35                  40

<210> SEQ ID NO 110
<211> LENGTH: 39
<212> TYPE: PRT
<213> ORGANISM: Artificial Sequence
<220> FEATURE:
<223> OTHER INFORMATION: synthetic

<400> SEQUENCE: 110

Lys Lys Gln Tyr Thr Ser Ile His His Gly Val Val Glu Val Asp Ala
1               5                   10                  15

Ala Val Thr Pro Glu Pro Pro Val Gln Asp Ala Ala Glu Arg Leu Arg
            20                  25                  30

Lys Ser Asn Leu Gln Val Leu
            35

<210> SEQ ID NO 111
<211> LENGTH: 45
<212> TYPE: PRT
<213> ORGANISM: Artificial Sequence
<220> FEATURE:
<223> OTHER INFORMATION: synthetic

<400> SEQUENCE: 111

Lys Lys Gln Tyr Thr Ser Ile His His Gly Val Val Glu Val Asp Ala
1               5                   10                  15

```
Ala Val Thr Pro Glu Arg His Leu Ser Lys Met Gln Gln Asn Ser Tyr
            20                  25                  30

Glu Asn Pro Thr Tyr Lys Phe Phe Glu Gln Met Gln Asn
        35                  40                  45
```

<210> SEQ ID NO 112
<211> LENGTH: 20
<212> TYPE: PRT
<213> ORGANISM: Artificial Sequence
<220> FEATURE:
<223> OTHER INFORMATION: synthetic

<400> SEQUENCE: 112

```
Lys Lys Gln Tyr Thr Ser Ile His His Gly Val Val Glu Val Asp Ala
1               5                   10                  15

Ala Val Thr Pro
            20
```

<210> SEQ ID NO 113
<211> LENGTH: 27
<212> TYPE: PRT
<213> ORGANISM: Artificial Sequence
<220> FEATURE:
<223> OTHER INFORMATION: synthetic

<400> SEQUENCE: 113

```
Lys Lys Gln Tyr Thr Ser Ile His His Gly Val Val Glu Val Asp Ala
1               5                   10                  15

Ala Val Thr Pro Glu Glu Arg His Leu Ser Lys
            20                  25
```

<210> SEQ ID NO 114
<211> LENGTH: 43
<212> TYPE: PRT
<213> ORGANISM: Artificial Sequence
<220> FEATURE:
<223> OTHER INFORMATION: synthetic

<400> SEQUENCE: 114

```
Lys Lys Gln Tyr Thr Ser Ile His His Gly Val Val Glu Val Asp Ala
1               5                   10                  15

Ala Val Thr Pro Glu Glu Arg His Leu Ser Lys Asn Gly Tyr Glu Asn
            20                  25                  30

Pro Thr Tyr Lys Phe Phe Glu Gln Met Gln Asn
        35                  40
```

<210> SEQ ID NO 115
<211> LENGTH: 27
<212> TYPE: PRT
<213> ORGANISM: Artificial Sequence
<220> FEATURE:
<223> OTHER INFORMATION: synthetic

<400> SEQUENCE: 115

```
Lys Lys Gln Tyr Thr Ser Ile His His Gly Val Val Glu Val Asp Ala
1               5                   10                  15

Ala Val Thr Pro Glu Glu Arg His Leu Ser Lys
            20                  25
```

<210> SEQ ID NO 116
<211> LENGTH: 45
<212> TYPE: PRT
<213> ORGANISM: Artificial Sequence
<220> FEATURE:
<223> OTHER INFORMATION: synthetic

<400> SEQUENCE: 116

Lys Lys Gln Tyr Thr Ser Ile His His Gly Val Val Glu Val Asp Ala
1               5                   10                  15

Ala Val Thr Pro Glu Glu Arg His Leu Ser Lys Lys Gln Asn Gly Tyr
            20                  25                  30

Glu Asn Pro Thr Tyr Lys Phe Phe Glu Gln Met Gln Asn
        35                  40                  45

<210> SEQ ID NO 117
<211> LENGTH: 44
<212> TYPE: PRT
<213> ORGANISM: Artificial Sequence
<220> FEATURE:
<223> OTHER INFORMATION: synthetic

<400> SEQUENCE: 117

Lys Lys Gln Tyr Thr Ser Ile His His Gly Val Val Glu Val Asp Ala
1               5                   10                  15

Ala Val Thr Pro Glu Glu Arg His Leu Ser Lys Lys Asn Gly Tyr Glu
            20                  25                  30

Asn Pro Thr Tyr Lys Phe Phe Glu Gln Met Gln Asn
        35                  40

<210> SEQ ID NO 118
<211> LENGTH: 46
<212> TYPE: PRT
<213> ORGANISM: Artificial Sequence
<220> FEATURE:
<223> OTHER INFORMATION: synthetic

<400> SEQUENCE: 118

Gly Gly Val Val Ile Ala Thr Val Ile Val Ile Thr Leu Val Met Leu
1               5                   10                  15

Lys Lys Lys Gln Tyr Thr Ser Ile His His Gly Val Val Glu Val Asp
            20                  25                  30

Ala Ala Val Thr Pro Glu Glu Arg His Leu Ser Lys Met Gln
        35                  40                  45

<210> SEQ ID NO 119
<211> LENGTH: 48
<212> TYPE: PRT
<213> ORGANISM: Artificial Sequence
<220> FEATURE:
<223> OTHER INFORMATION: synthetic

<400> SEQUENCE: 119

Gly Gly Val Val Ile Ala Thr Val Ile Val Ile Thr Leu Val Met Leu
1               5                   10                  15

Lys Lys Lys Gln Tyr Thr Ser Ile His His Gly Gly Gly Arg Arg Arg
            20                  25                  30

Arg Asp Pro Arg Gly Ala Pro Ser Leu Gln Asp Ala Ala Glu Arg Ile
        35                  40                  45

<210> SEQ ID NO 120
<211> LENGTH: 47
<212> TYPE: PRT
<213> ORGANISM: Artificial Sequence
<220> FEATURE:
<223> OTHER INFORMATION: synthetic

```
<400> SEQUENCE: 120

Gly Gly Val Val Ile Ala Thr Val Ile Val Ile Thr Leu Val Met Leu
1               5                   10                  15

Lys Lys Lys Gln Tyr Thr Ser Ile His His Gly Gly Arg Arg Arg Arg
            20                  25                  30

Asp Pro Arg Gly Ala Pro Ser Leu Gln Asp Ala Ala Glu Arg Ile
        35                  40                  45

<210> SEQ ID NO 121
<211> LENGTH: 49
<212> TYPE: PRT
<213> ORGANISM: Artificial Sequence
<220> FEATURE:
<223> OTHER INFORMATION: synthetic

<400> SEQUENCE: 121

Gly Gly Val Val Ile Ala Thr Val Ile Val Ile Thr Leu Val Met Leu
1               5                   10                  15

Lys Lys Lys Gln Tyr Thr Ser Ile His His Gly Gly Gly Gly Arg Arg
            20                  25                  30

Arg Arg Asp Pro Arg Gly Ala Pro Ser Leu Gln Asp Ala Ala Glu Arg
        35                  40                  45

Ile

<210> SEQ ID NO 122
<211> LENGTH: 20
<212> TYPE: DNA
<213> ORGANISM: Artificial Sequence
<220> FEATURE:
<223> OTHER INFORMATION: synthetic

<400> SEQUENCE: 122
gtccatccat catggcctgg                                              20

<210> SEQ ID NO 123
<211> LENGTH: 20
<212> TYPE: DNA
<213> ORGANISM: Artificial Sequence
<220> FEATURE:
<223> OTHER INFORMATION: synthetic

<400> SEQUENCE: 123
ttccatccat catggcttgg                                              20

<210> SEQ ID NO 124
<211> LENGTH: 20
<212> TYPE: DNA
<213> ORGANISM: Artificial Sequence
<220> FEATURE:
<223> OTHER INFORMATION: synthetic

<400> SEQUENCE: 124
gtccctccat catggcctgg                                              20

<210> SEQ ID NO 125
<211> LENGTH: 20
<212> TYPE: DNA
<213> ORGANISM: Artificial Sequence
<220> FEATURE:
<223> OTHER INFORMATION: synthetic

<400> SEQUENCE: 125
ggccatcatt catggcgtgg                                              20
```

<210> SEQ ID NO 126
<211> LENGTH: 20
<212> TYPE: DNA
<213> ORGANISM: Artificial Sequence
<220> FEATURE:
<223> OTHER INFORMATION: synthetic

<400> SEQUENCE: 126
ataaatatat catggcgtgg                                          20

<210> SEQ ID NO 127
<211> LENGTH: 20
<212> TYPE: DNA
<213> ORGANISM: Artificial Sequence
<220> FEATURE:
<223> OTHER INFORMATION: synthetic

<400> SEQUENCE: 127
ctcccttcat cttggtgtgg                                          20

<210> SEQ ID NO 128
<211> LENGTH: 20
<212> TYPE: DNA
<213> ORGANISM: Artificial Sequence
<220> FEATURE:
<223> OTHER INFORMATION: synthetic

<400> SEQUENCE: 128
atgcaatcag catggtgtgg                                          20

<210> SEQ ID NO 129
<211> LENGTH: 20
<212> TYPE: DNA
<213> ORGANISM: Artificial Sequence
<220> FEATURE:
<223> OTHER INFORMATION: synthetic

<400> SEQUENCE: 129
ttctgttcag catggtgtgg                                          20

<210> SEQ ID NO 130
<211> LENGTH: 20
<212> TYPE: DNA
<213> ORGANISM: Artificial Sequence
<220> FEATURE:
<223> OTHER INFORMATION: synthetic

<400> SEQUENCE: 130
ttaaattcaa catggtgtgg                                          20

<210> SEQ ID NO 131
<211> LENGTH: 20
<212> TYPE: DNA
<213> ORGANISM: Artificial Sequence
<220> FEATURE:
<223> OTHER INFORMATION: synthetic

<400> SEQUENCE: 131
agccatttat caaggtgtgg                                          20

<210> SEQ ID NO 132
<211> LENGTH: 23
<212> TYPE: DNA
<213> ORGANISM: Artificial Sequence
<220> FEATURE:

<223> OTHER INFORMATION: synthetic

<400> SEQUENCE: 132
atccatccat catggcgtgg tgg                                    23

<210> SEQ ID NO 133
<211> LENGTH: 23
<212> TYPE: DNA
<213> ORGANISM: Artificial Sequence
<220> FEATURE:
<223> OTHER INFORMATION: synthetic

<400> SEQUENCE: 133
gactatcagc catggagtgg tgg                                    23

<210> SEQ ID NO 134
<211> LENGTH: 23
<212> TYPE: DNA
<213> ORGANISM: Artificial Sequence
<220> FEATURE:
<223> OTHER INFORMATION: synthetic

<400> SEQUENCE: 134
atccatccat catggcgtgg tgg                                    23

<210> SEQ ID NO 135
<211> LENGTH: 23
<212> TYPE: DNA
<213> ORGANISM: Artificial Sequence
<220> FEATURE:
<223> OTHER INFORMATION: synthetic

<400> SEQUENCE: 135
caccatcagc cacgggattg tgg                                    23

<210> SEQ ID NO 136
<211> LENGTH: 23
<212> TYPE: DNA
<213> ORGANISM: Artificial Sequence
<220> FEATURE:
<223> OTHER INFORMATION: synthetic

<400> SEQUENCE: 136
atccattcat catggtgtgg tgg                                    23

<210> SEQ ID NO 137
<211> LENGTH: 23
<212> TYPE: DNA
<213> ORGANISM: Artificial Sequence
<220> FEATURE:
<223> OTHER INFORMATION: synthetic

<400> SEQUENCE: 137
ggctatcagc catggcgtgg tgg                                    23

<210> SEQ ID NO 138
<211> LENGTH: 23
<212> TYPE: DNA
<213> ORGANISM: Artificial Sequence
<220> FEATURE:
<223> OTHER INFORMATION: synthetic

<400> SEQUENCE: 138
atccattcat catggtgtgg tgg                                    23

GENE EDITING-BASED METHOD OF ATTENUATING THE BETA-AMYLOID PATHWAY

CROSS-REFERENCE TO RELATED APPLICATIONS

This application is a divisional of U.S. application Ser. No. 16/251,970, filed on Jan. 18, 2019, which claims priority to U.S. Provisional Patent Application No. 62/618,694, filed Jan. 18, 2018, which are incorporated herein by reference in their entirety.

STATEMENT REGARDING FEDERALLY SPONSORED RESEARCH

This invention was made with government support under AG048218 awarded by the National Institutes of Health. The government has certain rights in the invention.

SEQUENCE LISTING

The Instant Application contains a Sequence Listing which has been submitted electronically in ASCII format and is hereby incorporated by reference in its entirety. Said ASCII copy, created on Oct. 5, 2021, is named "WIS0059USD" and is 101,3756 bytes in size.

BACKGROUND

The gradual accumulation of Aβ in brains is a neuropathologic hallmark of Alzheimer's disease (AD). Aβ is generated by the sequential cleavage of the amyloid precursor protein (APP) by β- and γ-secretases (β-secretase aka BACE-1, and γ-secretase), with BACE-1-cleavage as the rate-limiting step. Substantial evidence indicates that accrual of APP-cleavage products plays a key role in AD, making the "amyloidogenic pathway" an important therapeutic target (1-3).

CRISPR/Cas9 gene editing is emerging as a promising tool to disrupt the expression of disease-causing genes or edit pathogenic mutations (4). Originally discovered in bacteria as part of a natural self-defense mechanism, the Cas9 nuclease—guided by a short guide RNA (sgRNA)—generates double-stranded breaks (DSB) at targeted genomic loci (5).

However, to date, the application of gene editing to neurologic diseases has been limited (6). For instance, CRISPR/Cas9 has been used in cell-based models to edit triplet-repeat expansions of Huntington's and Fragile X syndrome (7, 8). Besides significant technical caveats such as low editing efficiency and limited in vivo validation (6), such canonical approaches would only be applicable to the small fraction of cases that are inherited (i.e. <10% of AD, Parkinson's, ALS); with a different approach required for each gene. Moreover, the feasibility of CRISPR/Cas9 as a therapeutic possibility in AD has not been reported.

Needed in the art of Alzheimer's disease treatment is an improved method of using gene editing methods to treat or prevent the disease.

SUMMARY OF THE INVENTION

In a first aspect, provided herein is a method of treating or preventing Alzheimer's disease (AD) caused by formation of amyloid plaques composed of amyloid beta (Aβ) peptides, wherein the method comprises the steps of (a) obtaining a gene-editing construct specific for the amyloid precursor protein (APP), wherein the construct facilitates truncation of the APP C-terminus when combined with a Cas9 nuclease, and (b) delivering the construct and a construct encoding the Cas9 nuclease to a patient in need of AD therapy, wherein the APP molecule is truncated and production of Aβ peptides is decreased in the patient's brain. In some embodiments, the truncation of the APP C-terminus occurs at an APP residue selected from the group consisting of 659, 670, 676, and 686. In some embodiments, the gene-editing construct comprises a gRNA sequence selected from the group consisting of SEQ ID NOs: 1-10. In some embodiments, the construct and the nuclease are delivered in a composition comprising an adeno-associated viral vector and a nanocarrier delivery vehicle. In some embodiments, the composition is delivered intravenously or intrathecally.

In a second aspect, provided herein is a method of reducing the formation of amyloid plaques in a patient's brain, wherein the plaques comprise amyloid beta (Aβ) peptides, the method comprises the steps of (a) obtaining a gene-editing construct specific for the amyloid precursor protein (APP), wherein the construct facilitates truncation of the APP C-terminus when combined with a Cas9 nuclease, and (b) delivering the construct and nuclease to a patient in need of AD therapy, wherein the APP molecule is truncated and production of Aβ peptides is decreased in the patient's brain. In some embodiments, the truncation of the APP C-terminus occurs at an APP residue selected from the group consisting of 659, 670, 676, and 686. In some embodiments, the gene-editing construct comprises a gRNA sequence selected from the group consisting of SEQ ID NOs:1-10. In some embodiments, the construct and the nuclease are delivered in a composition comprising an adeno-associated viral vector and a nanocarrier delivery vehicle. In some embodiments, the composition is delivered intravenously or intrathecally.

In a third aspect, provided herein is a genetic construct comprising, a sequence encoding for a Cas9 nuclease and a sequence encoding a gRNA specific to amyloid precursor protein (APP). In some embodiments, the construct is packaged in a viral vector selected from the group consisting of a lentiviral vector and an adeno-associated viral (AAV) vector. In some embodiments, the construct further comprises at least one neuron specific promoter. In some embodiments, the neuron specific promoter is selected from the group consisting of human synapsin 1 (hSyn1) promoter, and mouse Mecp2 promoter (pMecp2). In some embodiments, the construct further comprises an RNA Pol III promoter. In some embodiments, the RNA Pol III promoter is a U6 promoter. In some embodiments, the sequence of the gRNA is selected from the group consisting of SEQ ID NOs: 1-10. In some embodiments, the sequence of the Cas9 nuclease consists of SEQ ID NO: 15. In some embodiments, the construct comprises the sequence of SEQ ID NO: 17, SEQ ID NO: 18, SEQ ID NO: 19, or SEQ ID NO: 20. In some embodiments, the sequence encoding for a Cas9 nuclease in packaged on a first AAV vector and the sequence encoding a gRNA specific to amyloid precursor protein (APP) is packaged on a second AAV vector.

In a fourth aspect, provided herein is a kit for reducing the formation of amyloid plaques in a patient's brain, the kit comprising a first viral vector encoding a gRNA selected from the group consisting of SEQ ID NOs: 1-10 and a second viral vector encoding a Cas9 nuclease. In some embodiments, the viral vector is selected from the group consisting of a lentiviral vector and an adeno-associated viral (AAV) vector. In some embodiments, the first or second viral vector further comprises at least one neuron specific promoter. In some embodiments, the neuron specific promoter is selected from the group consisting of human synapsin 1 (hSyn1) promoter, and mouse Mecp2 promoter (pMecp2). In some embodiments, the first or second viral vector further comprises an RNA Pol III promoter. In some embodiments, the RNA Pol III promoter is a U6 promoter. In some embodiments, the kit comprises a viral vector encoding both a gRNA selected from the group consisting of SEQ ID NOs: 1-10 and a Cas9 nuclease.

BRIEF DESCRIPTION OF THE DRAWINGS

The patent or application file contains at least one drawing executed in color. Copies of this patent or patent application publication with color drawings will be provided by the Office upon request and payment of the necessary fee.

(FIG. 1A) Schematic and C-terminal sequence of mouse APP showing PAM sites (yellow) and genomic targets for the three APP-sgRNAs (APP-659 sgRNA used henceforth and referred to as 'APP-sgRNA'—see text). Note that the C-terminal antibody Y188 recognizes the last 20 amino acids of APP. (FIG. 1B) Neuro2A cells were transfected with APP-sgRNA and Cas9 (or Cas9 only), and immunostained with the Y188 antibody (after 5 days; mCherry labels transfected cells). Note decreased APP (Y188) fluorescence, indicating APP editing (quantified on right, mean±SEM of 39 cells from two independent experiments per condition, p<0.0001). (FIGS. 1C-1D) Neuro2A cells were transduced by lentiviral vectors carrying APP-sgRNA and Cas9 (or non-targeting control-sgRNA/Cas9 as control) and immunoblotted with Y188 and 22C11 antibodies (latter recognizes APP N-terminus). A gamma secretase inhibitor (GSI) was added to allow detection of accumulated APP CTF's (see methods, GAPDH used as loading controls). Note attenuated signal with the Y188 antibody in APP-sgRNA treated samples, but no change in 22C11 signal. Blots quantified in (d), mean±SEM of six independent experiments, p<0.0001. (FIG. 1E) Time course of APP-editing in neuro2a cells. Cells were transfected with a vector carrying APP-sgRNA and Cas9, and APP-CTFs were analyzed by Western blotting (in the presence of GSI). (FIG. 1F) Deep sequencing of APP C-terminus in neuro2A cells. Top: Frequency of base-pair matches between gRNA-edited and WT mouse sequence. Red underline marks the sgRNA target sequence and arrowhead denotes predicted cut-site. Note extensive mismatch around predicted cut-site, indicating robust editing. Bottom: Major mutated APP loci resulting from sgRNA-editing, and their frequencies.

(FIG. 2A) Comparison of mouse and human APP-sgRNA targeting sequences (red arrowheads indicate differences; yellow bar denotes the PAM site). (FIG. 2B) Human iPSC-derived NPCs were transduced by lentiviral vectors carrying APP-sgRNA and Cas9 (or non-targeting control-sgRNA/Cas9 as control) and differentiated into neurons. After 3 weeks of differentiation, cells were immunostained with the Y188 and Tuj1 (tubulin) antibodies. Note decreased APP (Y188) fluorescence, indicating APP editing. (FIG. 2C) The iPSC-derived neurons above (or isogenic APPV717I London-mutant knock-in iPSC-neurons) were transduced and differentiated as above and immunoblotted with C- and N-terminus antibodies (GSI was added to allow detection of accumulated APP CTFs). Note attenuation of APP signal with Y188 after APP-sgRNA treatment in both wild type and isogenic APP London iPSCs (quantified on right, mean±SEM of three independent experiments,  p<0.01, *p<0.001, **p<0.0001). (FIG. 2D) Media from the iPSC-derived neurons above was immunoblotted for secreted sAPPα (6E10 antibody). Note increased sAPPα in sgRNA-treated samples, indicating upregulation of the non-amyloidogenic pathway. (FIG. 2E) ELISA of media from iPSC derived neurons. Note decreased Aβ in the sgRNA-treated samples (mean±SEM of three independent experiments,  p<0.01, *p<0.001, **p<0.0001). (FIG. 2F) Deep sequencing of APP C-terminus in human ESCs. Red underline marks the sgRNA target sequence and arrowhead denotes predicted cut-site. Note extensive mismatch around predicted cut-site, indicating robust editing. (FIG. 2G) Major mutated APP-loci resulting from CRISPR editing, and their frequencies. (FIG. 2H) Predicted APP translational products (post-editing) for the major mutant alleles observed in deep sequencing. Note that after editing, APP is translated up-to amino acid 659 (red arrowheads; similar results were seen in HEK cells, see FIG. 6E).

(FIG. 3A) AAV9-sgRNA and AAV9-Cas9 expression vectors. Note that the sgRNA vector co-expresses GFP and the Cas9 is tagged to HA, for identification of transduced neurons. (FIG. 3B) Cultured hippocampal neurons were transduced with AAV9s carrying APP-sgRNA/Cas9 (or Cas9 only) and immunoblotted with the Y188 and 22C11 antibodies (in the presence of GSI). Note attenuation of CTFs by the APP-sgRNA. (FIG. 3C) Neurons were transfected (at the time of plating) with a vector expressing APP-sgRNA and Cas9. Neuritic/axon outgrowth was analyzed after 5-6 days. Neurons were transfected or infected at DIV7 with APP CRISPR, and synapse structure/function was analyzed after 14-17 days. (FIG. 3D) Top: Representative images of neurons transfected with the APP-sgRNA/Cas9 (or Cas9 alone). Bottom: Axon length and number of neurites/branches in the APP-sgRNA/Cas9 (or Cas9 alone) groups; note that there was no significant difference (mean±SEM; axon length: 30 cells for Cas9 only and 27 cells for moAPP-sgRNA from two independent experiments, p=0.2462; neurite number: 35 cells for Cas9 only and 31 cells for moAPP-sgRNA from two independent experiments, p=0.2289; branch number: 27 cells for both conditions from two independent experiments, p=0.6008). (FIG. 3E) Neurons were infected with AAV9 viruses carrying APP-sgRNA/Cas9 (or Cas9 only as controls), and fixed/stained with the presynaptic marker VAMP2. Note that the presynaptic density (VAMP2 puncta) was similar in both groups (quantified on right, mean±SEM of VAMP2 staining along 27 dendrites for Cas9 only and 25 dendrites for moAPP-sgRNA from two independent experiments, p=0.3132). (FIG. 3F) Neurons were transfected with APP-sgRNA/Cas9 (or Cas9 only as controls). Spine density in the APP-sgRNA/Cas9 (or Cas9 only) groups was also similar, quantified on right (mean±SEM of 18 dendrites for Cas9 only and 16 dendrites for moAPP-sgRNA from two independent experiments, p=0.7456). (FIG. 3G) Miniature excitatory postsynaptic currents (mEPSC) were recorded from neurons infected with AAV9-APP-sgRNA/Cas9 or AAV9-Cas9 alone. Top: Representative mEPSC traces in control and APP-sgRNA transduced neurons. Corresponding alignments of mEPSCs with average (white traces) are shown on right. Bottom: Cumulative histograms of mEPSC amplitude, 20-80% rise-time and inter-event interval in APP-sgRNA/Cas9 and the Cas9-only infected neurons (note no significant differences).

(FIG. 4A) AAV9-sgRNA and AAV9-Cas9 were stereotactically co-injected into dentate gyrus of 8-week old mouse brains (bottom). Two weeks after viral delivery, brains were perfused, fixed, and immunostained with anti-GFP, anti-HA and anti-APP(Y188) antibodies. (FIG. 4B) Co-expression of AAV9-sgRNA-GFP and AAV9-HA-Cas9 in the dentate gyrus. Note that majority of neurons are positive for both GFP and HA (~87% of the cells were positive for both; sampling from 3 brains). (FIGS. 4C-4D) Coronal section of a mouse hippocampi injected on one side (marked by arrow) with the AAV viruses as described above. Note attenuated Y188 staining of neurons on the injected side, indicating APP-editing. The image of mouse hippocampus injected with Cas9 only is not shown. Fluorescence quantified in (d), mean±SEM, data from three brains. One-way ANOVA: $p<0.0001$. Tukey's multiple comparisons: $p=0.4525$ (Un-injected vs Cas9 only); $p<0.0001$ (Un-injected vs APP-sgRNA); $p<0.0001$ (Cas9 only vs APP-sgRNA). (FIG. 4E) Intracerebroventrical injection of the AAV9 viruses into P0 pups. Note widespread delivery of gRNA into brain, as evident by GFP fluorescence. (FIG. 4F) Brain sections from above were immunostained with the Y188 antibody. Note attenuated Y188 staining in the APP-sgRNA/Cas9 transduced sample, suggesting APP-editing. (FIG. 4G) Western blots of the brains from (e). Note decreased expression of CTFs in the APP-sgRNA/Cas9 transduced brains; blots quantified on right (mean±SEM of three independent experiments, **$p<0.01$).

(FIG. 5A) APP/BACE-1 interaction—as evaluated by fluorescence complementation in cultured hippocampal neurons—was attenuated in neurons transfected with an APP C-terminus truncation mimicking the post-edited translational product (APP659:VN; quantified below, mean±SEM of 12 cells for APP(WT) and 13 cells for APP(659) from two independent experiments, $p<0.0001$). (FIG. 5B) APP β-cleavage is also attenuated in cells transfected with APP659. HEK cells were co-transfected with APPWT (or APP659) tagged to VN, and BACE-1:VC; and immunoblotted with the 6E10 antibody. Note decreased β-CTFs in cells carrying the truncated APP plasmid. (FIG. 5C) Schematic showing the CRISPR-edited C-terminus portion of APP. Note that the threonine at the 668 position, and the endocytic YENPTY motif (dashed boxes) are thought to play roles in Aβ production (see text). (FIG. 5D) APP/BACE-1 interaction—as evaluated by fluorescence complementation in cultured hippocampal neurons—was most markedly attenuated in neurons transfected with mutant YENPTY (mean±SEM of 32 cells for APP(WT), 37 cells for APP(T668A), 45 cells for APP(YENPTY) and 49 cells for APP(T668A+YENPTY) from two independent experiments). One-way ANOVA: $p<0.0001$. Tukey's multiple comparisons: $p=0.0022$ (APP vs APP$^{T668A}$); $p<0.0001$ (APP vs APP$^{YENPTY}$); $p<0.0001$ (APP vs APP$^{T668A+YENPTY}$); $p<0.0001$ (APP$^{T668A}$ vs APP$^{YENPTY}$); $p<0.0001$ (APP$^{T668A}$ vs APP$^{T668A+YENPTY}$); $p=0.7568$ (APP$^{YENPTY}$ vs APP$^{T668A+YENPTY}$). (FIG. 5E) Strategy of APP internalization assay. Neuro 2a cells are transfected with APP:GFP or APP659:GFP. After incubation with anti N-terminal APP antibody (22C11) for 10 min, the cells were fixed and stained with secondary antibody to visualize the cell surface and internalized APP. Note the cell surface accumulation and decreased internalization of APP659 (mean±SEM of 21 cells from two independent experiments, $p<0.0001$).

FIGS. 6A-6E show the choice of CRISPR editing site at APP C-terminus. (FIG. 6A) Strategy to integrate APP:VN and BACE-1:VC into the H4 genome and generation of a stable cell line expressing single copies of the two proteins (see results and methods for details). (FIG. 6B) APP and BACE-1 expression in the H4$^{single\ copy}$ cell line. Note negligible expression of endogenous proteins in native H4 cells. (FIG. 6C) The H4$^{single\ copy}$ cell line was transduced with lentiviral vectors carrying non-targeting control-sgRNA/Cas9 or various human APP C-terminus targeting sgRNAs/Cas9 (see Table 5 for targeting sequences). The APP/BACE-1 Venus complementation was visualized by fluorescence microscopy. Note attenuation of complementation, indicating editing by the APP-sgRNAs (quantified on right, mean±SEM of three independent experiments). One-way ANOVA: $p<0.0001$. Tukey's multiple comparisons: $p<0.0001$ (control-sgRNA vs APP659-sgRNA); $p<0.0001$ (control-sgRNA vs APP670-sgRNA); $p<0.0001$ (control-sgRNA vs APP676-sgRNA); $p=0.0064$ (APP659-sgRNA vs APP670-sgRNA); $p=0.0015$ (APP659-sgRNA vs APP676-sgRNA); $p=0.6207$ (APP670-sgRNA vs APP676-sgRNA). (FIG. 6D) ELISA of media from the H4$^{single\ copy}$ cell line (treated as above). Note decreased Aβ in the APP-sgRNAs treated samples (mean±SEM of three independent experiments). One-way ANOVA for Aβ 40 and 42: $p<0.0001$. Tukey's multiple comparisons for Aβ 40: $p<0.0001$ (control-sgRNA vs APP659-sgRNA; control-sgRNA vs APP670-sgRNA; control-sgRNA vs APP676-sgRNA; $p=0.0331$ (APP659-sgRNA vs APP670-sgRNA); $p=0.0071$ (APP659-sgRNA vs APP676-sgRNA); $p=0.6673$ (APP670-sgRNA vs APP676-sgRNA). Tukey's multiple comparisons for Aβ 42: $p<0.0001$ (control-sgRNA vs APP659-sgRNA; control-sgRNA vs APP670-sgRNA; control-sgRNA vs APP676-sgRNA); $p=0.0068$ (APP659-sgRNA vs APP670-sgRNA); $p=0.0221$ (APP659-sgRNA vs APP676-sgRNA); $p=0.8079$ (APP670-sgRNA vs APP676-sgRNA). (FIG. 6E) HEK cells were transduced by lentiviral vectors carrying APP-sgRNAs and Cas9 (or non-targeting control-sgRNA/Cas9 as control), and APP C-terminus was sequenced. Left: Deep sequencing of APP659-sgRNA treated cells, and Sanger sequencing followed by ICE analyses for APP670-sgRNA and APP676-sgRNA treated cells. Red underlines mark the sgRNA-targeting sequences and arrowheads denote predicted cut-sites. Right: Predicted APP translational products after CRISPR/Cas9 editing in human HEK cells for the major mutant alleles observed in sequencing analyses. Red arrowheads indicate the amino acids where APP genes were translated up to after editing.

(FIG. 7A) Neuro2a cells were co-transfected with a sgRNA that knocked out the entire APP gene and Cas9 (see Table 5 for APP targeting sequence), and immunostained with APP N-terminal and C-terminal antibodies (after 5 days in culture). Note attenuation of staining for both Y188 and 22C11. (FIG. 7B) Neuro2a cells were transfected with various APP C-terminus targeting sgRNAs (or non-targeting control-sgRNA), and immunostained with APP N-terminal and C-terminal antibodies (after 5 days in culture in the presence of GSI). Note attenuation of staining by Y188 but not 22C11, indicating selective editing of the APP C-terminus. (FIG. 7C) Neuro2A cells were transduced by lentiviral vectors carrying APP-sgRNA and Cas9 (or non-targeting control-sgRNA/Cas9 as control) and immunoblotted with the APP antibodies CT20 and M3.2 (CT20 recognizes last 20 aa; M3.2 recognizes an extracellular domain located upstream of the CRISPR/Cas9 targeting site). A GSI was added to allow detection of accumulated APP CTF's. Note attenuated signal with CT20- but not M3.2-antibody, indicating selective editing of the APP C-terminus. (FIG. 7D) Post-editing translational products in mouse (neuro 2a) cells. Note effective truncation of APP at aa 659.

(FIG. 8A) HEK cells were transfected with human-specific APP-sgRNA and Cas9 (or Cas9 only), and immunostained with the Y188 antibody (after 5 days in culture). Note attenuation of staining, quantified on right (mean±SEM of 25 cells for Cas9 only and 43 cells for huAPP-sgRNA from two independent experiments, p<0.0001). (FIG. 8B) HEK cells were transduced by lentiviral vectors carrying APP-sgRNA and Cas9 (or non-targeting control-sgRNA/Cas9 as control) and immunoblotted with the Y188 and 22C11 antibodies (in the presence of GSI). Note attenuation of APP-CTFs in APP-sgRNA treated cells, indicating CRISPR-editing (mean±SEM of three independent experiments, p<0.0001). (FIG. 8C) HEK cells above were immunoblotted with CT20 and 2E9 antibodies (CT20 recognizes last 20 aa; 2E9 recognizes APP extracellular domain upstream of the CRISPR/Cas9 targeting site). Note attenuated signal with CT20—but not 2E9—antibody, indicating selective editing of the APP C-terminus. (FIGS. 8D-8E) Human ESCs were transduced by lentiviral vectors carrying human APP-sgRNA/Cas9 (or non-targeting sgRNA/Cas9). Samples were immunostained with the Y188 antibody (d) or immunoblotted with the Y188 and 22C11 antibodies (e). Note attenuation of APP-CTFs in sgRNA-transduced group (for immunostaining, mean±SEM of 17 colonies for control-sgRNA and 20 colonies for huAPP-sgRNA from two independent experiments, p<0.0001; for western blotting, mean±SEM of three independent experiments, p=0.001 for total APP and p<0.0001 for CTFs). (FIG. 8F) Media from iPSC derived neurons were immunoblotted for extracellular sAPPβ (in the absence of GSI). Note decrease in APP β-cleavage in the APP-sgRNA treated samples. (FIG. 8G) Media from H4$^{single-copy}$ cells were immunoblotted for extracellular sAPPα with 6E10 antibody and sAPPβ (in the absence of GSI). Note enhanced APP α-cleavage and attenuated APP β-cleavage in the APP-sgRNA treated samples.

(FIG. 9A) Strategy to evaluate γ-cleavage of post-edited APP. Neuro2a cells were transfected with either full length (FL) C99, or C99 truncated at aa 659 (to mimic the post-editing translational product; all constructs were GFP-tagged to confirm expression). γ-cleavage of the FL and 659 C99 was evaluated by western blotting (note that neuro2a cells have all components of the γ-secretase complex). (FIG. 9B) Schematic showing expected C99-cleavage patterns. Note that upon γ-cleavage, both C99-fragments will be further truncated. However, if the 'CRISPR-mimic' (659) fragment did not undergo γ-cleavage, this truncation would not occur. (FIG. 9C) Western blotting of the cells from (a) indicates that both C99 fragments (FL and 659) undergo γ-cleavage—as indicated by the shift upon inhibiting γ-cleavage by GSI. These data suggest that gene editing by the APP-gRNA likely does not affect APP γ-cleavage, and that the effects seen on the amyloid pathway are likely due to modulation of APP-β-cleavage.

(FIG. 10A) Computationally predicted top five off-target (OT) sites in the genome, that can be potentially targeted by the mouse and human APP-sgRNAs (mismatched nucleotides in the targeting sequence are marked in red). Genomic locations corresponding to the sequences is shown on the right column (note most are in non-coding regions). (FIG. 10B) Strategy of T7 endonuclease digestion assay to detect genome-editing events. Genomic DNA was PCR amplified with primers bracketing the modified locus. PCR products were then rehybridized, yielding three possible structures. Duplexes containing a mismatch were digested by T7 endonuclease I. DNA gel analysis was used to calculate targeting efficiency. Note digested fragments in the gel indicates cleavage. (FIG. 10C) Gene edits at the APP locus by the APP-sgRNA, as seen by T7 endonuclease digestion. Note two digested fragments were recognized after T7 endonuclease digestion. (FIGS. 10D-10E) T7 endonuclease assays of potential off-target sites (mouse and human). No digested fragments are seen, indicating that the sgRNAs do not generate detectable gene edits at these sites. (FIG. 10F) Comparison of APLP1 and 2 sequences with APP at the sgRNA targeting site. Asterisks mark conserved nucleotide sequences, and the PAM sites are underlined. Nucleotide mis-matches are highlighted in yellow. Note extensive mismatch of the mouse and human sequences at the sgRNA targeting site. (FIG. 10G) Left: Off-target TIDE analysis of APP family members APLP1 and 2 in mouse (neuro 2a) and human (HEK) cell lines following lentiviral integration of Cas9 using TIDE. No modifications were detected below the TIDE limit of detection (dotted line) in either of the populations, indicating that the APP-gRNA was unable to edit APLP 1/2. Right: TIDE analysis of APLP1 and 2 loci in mouse and human cell lines. Neither of the populations had significant editing at either of the two loci, and all sequences had a near perfect correlation to the model.

(FIG. 11A) Cultured hippocampal neurons were transfected with APP(WT):GFP or APP(659):GFP, and kinetics of APP particles were imaged live in axons and dendrites. (FIG. 11B) Representative kymographs and quantification of APP kinetics in axons. Note that there was no change in frequency of transport, and only a modest reduction in run-length and velocity. Error bars, mean±SEM of 325 APP(WT):GFP and 310 APP(659):GFP vesicles in 10-12 neurons from two independent experiments. Frequency: p=0.4635 (APP_antero vs APP659_antero); p=0.6650 (APP_retro vs APP659_retro); p=0.7420 (APP_stat vs APP659 stat). Velocity: P<0.0001 (APP_antero vs APP659_antero); p=0.9419 (APP_retro vs APP659_retro). Run length: p<0.0001 (APP_antero vs APP659_antero); p=0.2433 (APP_retro vs APP659_retro). (FIG. 11C) Representative kymographs and quantification of APP kinetics in dendrites. Error bars, mean±SEM of 130 APP(WT):GFP and 115 APP(659):GFP particles in 10-12 neurons from two independent experiments. Frequency: p=0.3245 (APP_antero vs APP659_antero); p=0.5438 (APP_retro vs APP659_retro); p=0.2394 (APP_stat vs APP659_stat). Velocity: p=0.0120 (APP_antero vs APP659_antero); p=0.6248 (APP_retro vs APP659_retro). Run length: p=0.1352 (APP_antero vs APP659_antero); p=0.4284 (APP_retro vs APP659_retro).

(FIGS. 12A-12B) Neuro2a cells were co-transfected with untagged APP-659-GG and mCherry (or untagged WT APP and mCherry as control). After incubation with anti N-terminal APP antibody (22C11) for 10 min, the cells were fixed and stained with secondary antibody to visualize surface and internalized APP (mCherry labels transfected cells). Note accumulation of APP-659-GG on the cell surface, along with decreased internalization; quantified in FIG. 12B. Mean±SEM of 25 cells for APP(WT) and 26 cells for APP-659-GG from two independent experiments, p<0.0001.

(FIG. 12C) Expression levels of exogenous APP constructs. Note that WT and APP-659-GG were expressed at similar levels in the Neuro2a cells above.

FIG. 13 shows the sequence of human APP (nucleotide sequence SEQ ID NO: 11, amino acid sequence SEQ ID NO: 12) and mouse APP (nucleotide sequence SEQ ID NO: 13, amino acid sequence SEQ ID NO: 14) along with the corresponding sequences of the gRNA used in select gene editing embodiments described herein.

FIG. 14 shows the sequence of the Cas9 nuclease gene sequence.

FIG. 15 shows the sequence and vector map of an exemplary vector (SEQ ID NO: 17) for APP truncation at amino acid 659. The vector includes the gRNA sequence (lowercase italics) and the Cas9 nuclease sequence.

FIG. 16 shows the sequence and vector map of an exemplary Cas9 vector (SEQ ID NO: 18).

FIG. 17 shows the sequence and vector map of an exemplary APP sgRNA vector (SEQ ID NO: 19).

INCORPORATION BY REFERENCE

Figures 1A, 1B, 1C, 1D, 1E, 1F:
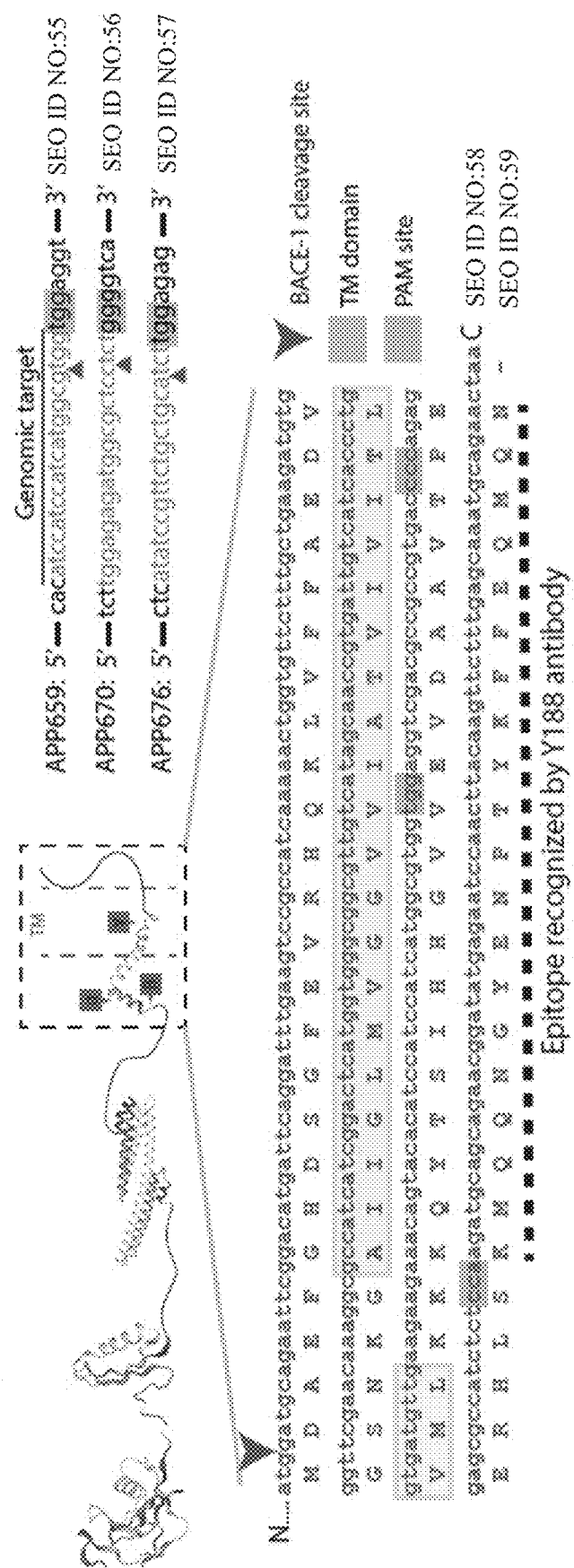
FIGS. 1A-1F show manipulation of the amyloid pathway by CRISPR/Cas9 editing.
Figures 1A, 1B, 1C, 1D, 1E, 1F:
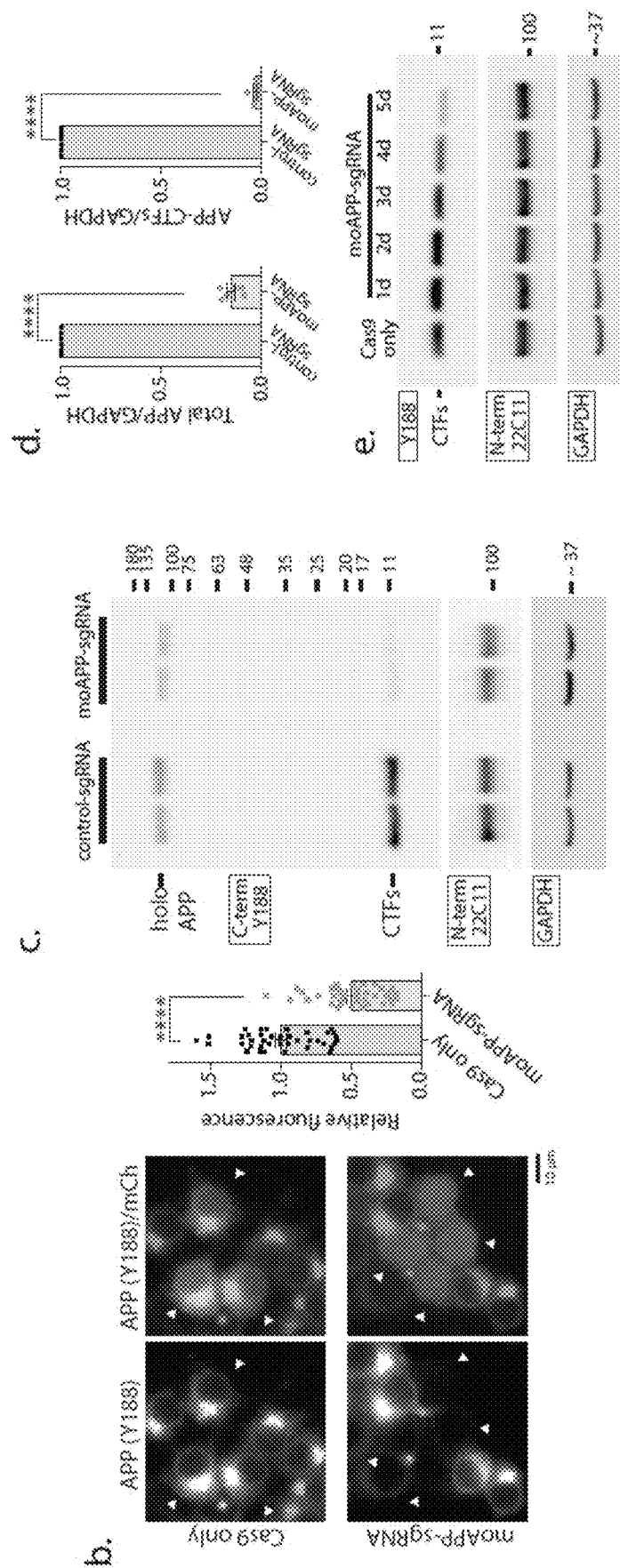
Figures 1A, 1B, 1C, 1D, 1E, 1F:
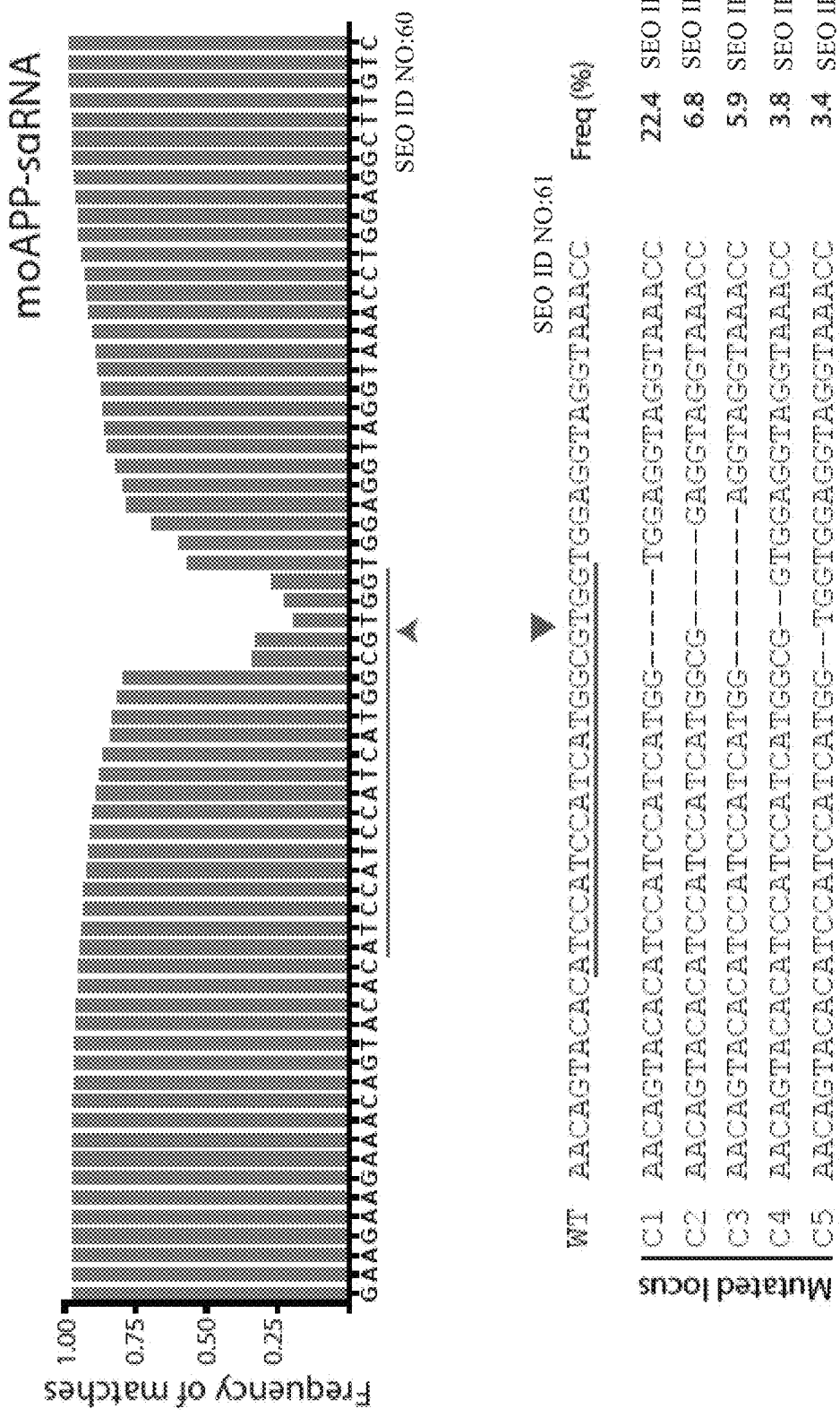

All publications, including but not limited to patents and patent applications, cited in this specification are herein incorporated by reference as though set forth in their entirety in the present application.

DETAILED DESCRIPTION OF THE INVENTION

In General

Gene-editing methods, such as CRISPR/Cas9 guided gene-editing, hold promise as a therapeutic tool. However, few studies have applied the technology to neurodegenerative diseases. Moreover, the conventional approach of mutation-correction is limited in scope to inherited diseases which are a small fraction of neurodegenerative disease cases. The present invention introduces a strategy to edit endogenous amyloid precursor protein (APP) at the extreme C-terminus and selectively attenuate the amyloidogenic pathway—a key pathologic cascade in Alzheimer's disease (AD). In the method of the present invention, the APP N-terminus remains intact and protective α-cleavage is up-regulated.

The Examples below demonstrate that robust APP-editing is demonstrated in cell lines, human stem cells, cultured neurons, and in mouse brains. Physiologic parameters remain unaffected. Without being bound by any particular theory, the present invention works by restricting the physical interaction of APP and BACE-1, said interaction being the rate-limiting step in amyloid-β (Aβ) production. The Examples below delineate underlying mechanisms that abrogate APP/BACE-1 interaction in this setting. The invention offers an innovative 'cut and silence' gene-editing strategy that could be a new therapeutic paradigm for AD.

CRISPR/Cas9 works by inducing sequence-specific double-stranded breaks (DSBs) in DNA. After such breaks, the cell undergoes an error-prone repair process called non-homologous end joining, leading to a disruption in the translational reading frame, often resulting in frameshift mutations and premature stop codons. For the system to work, at least two components must be introduced in cells: a Cas9 nuclease and a guide RNA. Described herein are CRISPR/Cas9 constructs suitable for truncation of the APP protein and disruption of amyloid-β production.

Constructs of the Present Invention

In a first aspect, the present invention provides a construct for CRISPR mediated cleavage of the APP gene. The constructs of the present invention include a nucleotide sequence encoding a Cas9 nuclease and a guide RNA (gRNA). In some embodiments the sequence encoding the Cas9 nuclease and the gRNA are included on a single vector construct. In some embodiments the sequence encoding the Cas9 nuclease is included in a vector construct separate from a vector construct encoding for the gRNA. Additionally, the construct may include a promoter, a poly(A) tail, an optional reporter element, and an optional selection marker such as an ampicillin selection marker.

As used herein "Cas9 nuclease" refers to the RNA-guided DNA endonuclease enzyme associated with the CRISPR adaptive immunity system in *Streptococcus pyogenes* and other bacteria. The Cas9 nuclease includes two nuclease domains, a RuvC-like nuclease domain located at the amino terminus, and a HNH-like nuclease domain. In some embodiments, the sequence of the Cas9 nuclease is the sequence included in FIG. 14 (SEQ ID NO: 15).

In some embodiments, the Cas nuclease is expressed under the control of a neuron specific promoter or ubiquitous promoter. The neuron specific promoter may be any neuron specific promoter known in the art (see for example, Swiech L et al., In vivo interrogation of gene function in the mammalian brain using CRISPR-Cas9. Nature Biotechnology 2015 January; 33(1): 102-6). In some embodiments the neuron specific promoter is the human synapsin 1 (hSyn1) promoter. In some embodiments the neuron specific promoter is the mouse Mecp2 promoter (pMecp2). In some embodiments the ubiquitous promoter is the chicken β-actin promoter. In some embodiments, the ubiquitous promoter is an EFS promoter.

In one embodiment of the present invention, the construct is specific for the extreme C-terminus of the APP gene. By "APP gene" or "amyloid precursor protein", we mean to include the human APP gene as disclosed in Hendricks et al (Hendriks L et al. Presenile dementia and cerebral haemorrhage linked to a mutation at codon 692 of the beta-amyloid precursor protein gene. Nature Genetics 1992 June; 1(3): 218-21) and recited herein as SEQ ID NO: 11. The amino acid sequence of the APP gene is recited as SEQ ID NO: 12.

As used herein "extreme C-terminus," refers of a portion of the C-terminus of the APP protein which, when absent, is sufficient to disrupt the interaction between APP and BACE. The truncated APP lacking the extreme C-terminus will still include its native N-terminus, the transmembrane domain and the residual C-terminal region. Typically, the extreme C-terminus of the APP protein will mean 8 or more amino acids at the C-terminus of the APP protein. This may be accomplished by CRISPR/Cas9 mediated cleavage of the APP gene such that the expressed APP protein is truncated to a length selected from the group consisting of 659, 670, 676, or 686, relative to SEQ ID NO: 12 (human) or SEQ ID NO: 14 (mouse). In some embodiments, the APP gene is cleaved following a nucleotide selected from the group consisting of 1978, 2009, 2010, 2029, and 2058 relative to SEQ ID NO: 11 (human) or SEQ ID NO: 14 (mouse). A list of these cleavage sites is included in the table below.

As used herein "guide RNA (gRNA)" refers to the 20 nucleotide target sequence which directs Cas9 mediated cleavage within the APP gene. The gRNA will be encoded on a synthetic RNA construct which additionally includes the tracrRNA sequence. While the gRNA sequence is variable and will be specific for the cleavage site of interest, the tracrRNA is the same for all gRNA sequences used. The tracrRNA sequence is SEQ ID NO: 16 The gRNA described herein are specific for the truncation of the C-terminal segment of APP. Suitable target sequences within the APP gene for design of gRNA sequences are recited below, which includes the sequence of the gRNA.

```
tracrRNA (SEQ ID NO: 16):
5'-GTTTTAGAGCTAGAAATAGCAAGTTAAAATAAGGCTAGTCCGTTAT
CAACTTGAAAAAGTGGCACCGAGTCGGTGCTTTT-3
```

TABLE 1

HUMAN APP (FULL LENGTH 695 AA)

| sgRNA name | sgRNA sequence (5'-3') | SEQ ID NO: | Position relative to APP | Cas9 cleavage between nucleotides | Length of truncated protein |
|---|---|---|---|---|---|
| sgRNA 1 | atccattcatcatggtgtgg | 1 | 1962-1981 | 1978/1979 | 659 aa |
| sgRNA 2 | tggacaggtggcgctcctct | 2 | 2007-2026 | 2009/2010 | 670 aa |
| sgRNA 3 | ttggacaggtggcgctcctc | 3 | 2008-2027 | 2010/2011 | 670 aa |
| sgRNA 4 | gtagccgttctgctgcatct | 4 | 2027-2046 | 2029/2030 | 676 aa |
| sgRNA 5 | tgctcaaagaacttgtaggt | 5 | 2056-2075 | 2058/2059 | 686 aa |

TABLE 2

MOUSE APP (FULL LENGTH 695 AA)

| sgRNA name | sgRNA sequence (5'-3') | SEQ ID NO: | Position relative to APP | Cas9 cleavage between nucleotides | Length of truncated protein |
|---|---|---|---|---|---|
| sgRNA 1 | atccatccatcatggcgtgg | 6 | 1962-1981 | 1978/1979 | 659 aa |
| sgRNA 2 | tggagagatggcgctcctct | 7 | 2007-2026 | 2009/2010 | 670 aa |
| sgRNA 3 | ttggagagatggcgctcctc | 8 | 2008-2027 | 2010/2011 | 670 aa |
| sgRNA 4 | atatccgttctgctgcatct | 9 | 2027-2046 | 2029/2030 | 676 aa |
| sgRNA 5 | tgctcaaagaacttgtaagt | 10 | 2056-2075 | 2058/2059 | 686 aa |

Cleavage of the APP gene will occur between the 3rd and 4th nucleotides from the PAM site associated with the target sequence in the APP gene. For the sgRNA 1, the PAM site is on the sense strand of the APP gene, the sgRNA of SEQ ID NOs: 1 and 6 are complementary to the antisense strand of the APP gene, and the cleavage will occur between nucleotides 1978 and 1979 relative to SEQ ID NO: 11 (human) or SEQ ID NO: 14 (mouse). For sgRNA 2, 3, 4 and 5, the PAM site is on the antisense strand of the APP gene, the sgRNA of SEQ ID NOs: 2-5 and 7-10 are complementary to the sense strand of the APP gene, and the cleavage site is between nucleotides 2009 and 2010 for sgRNA 2, between nucleotides 2010 and 2011 for sgRNA 3, between nucleotides 2029 and 2030 for sgRNA 4 and between nucleotides 2058 and 2059 for sgRNA 5, relative to SEQ ID NO: 11 (human) or SEQ ID NO: 14 (mouse).

In some embodiments, the gRNA or tracrRNA is modified by any means known in the art. Common methods for gRNA or tracrRNA modification include chemical modifications or modifications to axillary sequences appended to the RNA to increase efficiency known in the art.

In some embodiments, the gRNA is expressed under the control of an RNA Pol III promoter. Examples of RNA Pol III promoters include, but are not limited to, U6 and H1 promoters. A promoter, generally, is a region of nucleic acid that initiates transcription of a nucleic acid encoding a product. A promoter may be located upstream (e.g., 0 bp to −100 bp, −30 bp, −75 bp, or −90 bp) from the transcriptional start site of a nucleic acid encoding a product, or a transcription start site may be located within a promoter. A promoter may have a length of 100-1000 nucleotide base pairs, or 50-2000 nucleotide base pairs. In some embodiments, promoters have a length of at least 2 kilobases (e.g., 2-5 kb, 2-4 kb, or 2-3 kb).

In some embodiments, the construct comprises an optional reporter element. The reporter element may be any reporter known in the art including, but not limited to, mCherry, green fluorescent protein, and human influenza hemagglutinin (HA).

In some embodiments, the constructs are packaged in a vector suitable for delivery into a mammalian cell, including but not limited to, an adeno-associated viral (AAV) vector, a lentiviral vector, or a vector suitable for transient transfection. Suitable vector backbones are known and commercially available in the art. For example, see Deverman et al. (Cre-dependent selection yields AAV variants for widespread gene transfer to the adult brain, Nature Biotechnology, 34(2):204-209, 2016) and Chan et al. (Engineered AAVs for efficient noninvasive gene delivery to the central and peripheral nervous system, Nature Neuroscience, 20(8): 1172-1179, 2017) which are incorporated herein by reference in their entirety. In some embodiments, the vector is an AAV vector and the gRNA and Cas9 constructs are encoded on separate vectors. In some embodiments, the vector is a lentiviral vector and the gRNA and Cas9 constructs are encoded on a single vector. In some embodiments, the vector is a vector suitable for transient transfection and the gRNA and Cas9 constructs are encoded on a single vector. In one embodiment the vector includes the sequence of SEQ ID NO: 17. In some embodiment, the gRNA and Cas9 constructs are encoded on separate AAV vectors wherein the gRNA is encoded on a vector comprising SEQ ID NO: 19 and the Cas9 construct is encoded on a vector comprising SEQ ID NO: 18. In some embodiments, the vector is a lentiviral vector and comprises the sequence of SEQ ID NO: 20. The vectors of SEQ ID NOs: 17-20 are included in FIGS. 15-18.

In some embodiments, the vectors encoding the constructs described herein may optionally include a monoclonal antibody tag (e.g., FLAG), one or more origins of replication (e.g., fl ori), one or more terminator sequences (e.g. bGH), one or more polyadenylation tags (bGH poly (A)), and one or more inverted terminal repeats (ITR). The vector may also include one or more selectable markers, such as an antibacterial resistance marker such as an ampicillin selectable marker. A skilled artisan will be familiar with the elements and configurations necessary for vector construction to encode the constructs described herein.

METHODS OF THE PRESENT INVENTION

The constructs described herein may be formulated with a pharmaceutically acceptable carrier for administration to a patient in need thereof. A pharmaceutically acceptable carrier may be, but is not limited to, a nanoparticle cage including the one or more vectors of the present invention.

To function as therapeutic agents, the constructs described herein are delivered into neurons in the patient's brain, crossing the blood brain barrier (BBB). In one embodiment, one would attach or associate the CRISPR components with a delivery system, such as a nanoparticle delivery system. In some embodiments, the constructs are formulated using an AAV vector and are delivered intravenously. In some embodiments, the constructs are delivered intrathecally into the spinal fluid of the patient. In some embodiments, the constructs are delivered directly into the brain of the patient.

As used herein, the terms "treat" and "treating" refer to therapeutic measures, wherein the object is to slow down or alleviate (lessen) an undesired physiological change or pathological disorder resulting from Alzheimer's disease. For purposes of this invention, treating the disease, condition, or injury includes, without limitation, alleviating one or more clinical indications, reducing the severity of one or more clinical indications of Alzheimer's disease, diminishing the extent of the condition, stabilizing the subject's Alzheimer's disease (i.e., not worsening), delay or slowing, halting, or reversing Alzheimer's disease and bringing about partial or complete remission Alzheimer's disease. Treating Alzheimer's disease also includes prolonging survival by days, weeks, months, or years as compared to prognosis if treated according to standard medical practice not incorporating treatment with the constructs described herein.

Subjects in need of treatment can include those already having or diagnosed with Alzheimer's disease as well as those prone to, likely to develop, or suspected of having Alzheimer's disease, such as a subject with a genetic predisposition to or family history of Alzheimer's disease. Subjects in need to treatment may be those with a familial AD mutation or wild-type patients without a mutation. In some embodiments, a subject in need of treatment may be a subject who had been diagnosed by a positron emission tomography (PET) scan, a blood test or other means known in the art to have AD or to be predisposed to AD. Pre-treating or preventing Alzheimer's disease according to a method of the present invention includes initiating the administration of a therapeutic (e.g., the APP gRNA and Cas9 constructs described herein) at a time prior to the appearance or existence of the disease or injury, or prior to the exposure of a subject to factors known to induce Alzheimer's disease. Pre-treating the disorder is particularly applicable to subjects at risk of having or acquiring the disease injury.

As used herein, the terms "prevent" and "preventing" refer to prophylactic or preventive measures intended to inhibit undesirable physiological changes or the development of Alzheimer's disease. In exemplary embodiments, preventing Alzheimer's disease comprises initiating the administration of a therapeutic (e.g., the APP gRNA and Cas9 constructs described herein) at a time prior to the appearance or existence of Alzheimer's disease such that the disease, or its symptoms, pathological features, consequences, or adverse effects do not occur. In such cases, a method of the invention for preventing Alzheimer's disease comprises administering the APP gRNA and Cas9 constructs described herein to a subject in need thereof prior to the onset or development of Alzheimer's disease in a patient at risk for Alzheimer's disease such as a patient with a genetic risk factor or a patient with a family history of Alzheimer's disease.

As used herein, the terms "subject" or "patient" are used interchangeably and can encompass a human or mouse. As used herein, the phrase "in need thereof" indicates the state of the subject, wherein therapeutic or preventative measures are desirable. Such a state can include, but is not limited to, subjects having Alzheimer's disease or a pathological symptom or feature associated with Alzheimer's disease.

EXAMPLES

The embodiment described in this example demonstrates truncation of the C-terminus of the APP protein, attenuation of APP-β-cleavage and Aβ production, and manipulation of the amyloid pathway using CRISPR/Cas9 gene editing.

A common theme in neurodegenerative diseases is that proteins normally present in the brain (APP, tau, α-synuclein, TDP-43, etc.) acquire toxic properties—or trigger pathologic cascades—that ultimately lead to synaptic loss and neurodegeneration. Our broad idea is to rationally edit small segments of endogenous proteins known to play key roles in the progression of disease, with the ultimate goal of attenuating their pathologic activity. As endogenous proteins expectedly play physiologic roles, it is also important to conserve their normal function, as far as possible. Here we show conceptual proof of this 'selective silencing' approach for APP. APP is a single-pass transmembrane protein, cleaved by the enzymes β- and γ-secretases to ultimately generate Aβ—a neuropathologic hallmark of AD. APP cleavage by the β-secretase BACE-1 is the rate limiting step in this 'amyloidogenic' pathway. Alternatively, APP is cleaved by α-secretases—the 'non-amyloidogenic' pathway—that is thought to be neuroprotective because it precludes β-cleavage of APP (6,7); and studies have highlighted neuroprotective effects of APP-α-cleavage products in vivo (8,9).

We recently developed a Bi-molecular fluorescence complementation (BifC) assay to visualize the physical approximation of APP and BACE-1 in neurons (10). As a control for validation, we found that a C-terminal deletion also abrogated APP/BACE-1 complementation (10); in line with previous studies showing that deletions/mutations of the APP C-terminus can attenuate Aβ production (11-13). Collectively, these observations originally gave us the idea of using CRISPR/Cas9-mediated truncation of native APP to attenuate APP-β-cleavage and Aβ production in AD. Using CRISPR-tools, cell/molecular biology, live imaging, deep sequencing, electrophysiology and in vivo animal studies, here we highlight a strategy to favorably manipulate the amyloid pathway by gene editing.

RESULTS AND DISCUSSION

CRISPR/Cas9 editing of APP C-terminus—The CRISPR/Cas9 system consists of a Cas9 nuclease enzyme that generates double-stranded breaks in DNA, and a custom-designed single guide-RNA (sgRNA) that targets the Cas9 to specific sites in the host genomic DNA. Typically, the synthetic sgRNAs are complementary to stretches of genomic DNA containing 3-nt PAM (protospacer adjacent motif) and flanking 20-nt sequences. Since subsequent repair after DNA-breaks is naturally error-prone, insertions and deletions (indels) are generated at the cut-sites, leading to disruption of the translational reading frame and effectively truncated proteins (reviewed in 14). We identified three PAM sites at the APP C-terminus that are conserved in both human and mouse, and synthesized sgRNAs targeting these regions (FIG. 1A). To compare the editing efficiency of these sgRNAs, we engineered a stable H4 neuroglioma cell line expressing single copies of APP:VN and BACE-1:VC (APP/BACE$^{single\_copy}$), where editing efficiency of a given sgRNA could be determined as a simple fluorescence on/off readout and the effect of APP truncation could be assessed by evaluating secreted Aβ (for details, see FIGS. 6A and 6B and methods). The APP-sgRNA predicted to cut human APP at the 659 aa. (amino acid) position was the most efficient—both in editing APP as well as in attenuating Aβ—and also led to minimal indels (FIGS. 6C-6E). Accordingly, we used the APP659-sgRNA for further characterization (henceforth called 'mo-APP-sgRNA' or 'hu-APP-sgRNA' representing mouse and human specific sequences).

Figures 7A, 7B, 7C, 7D:
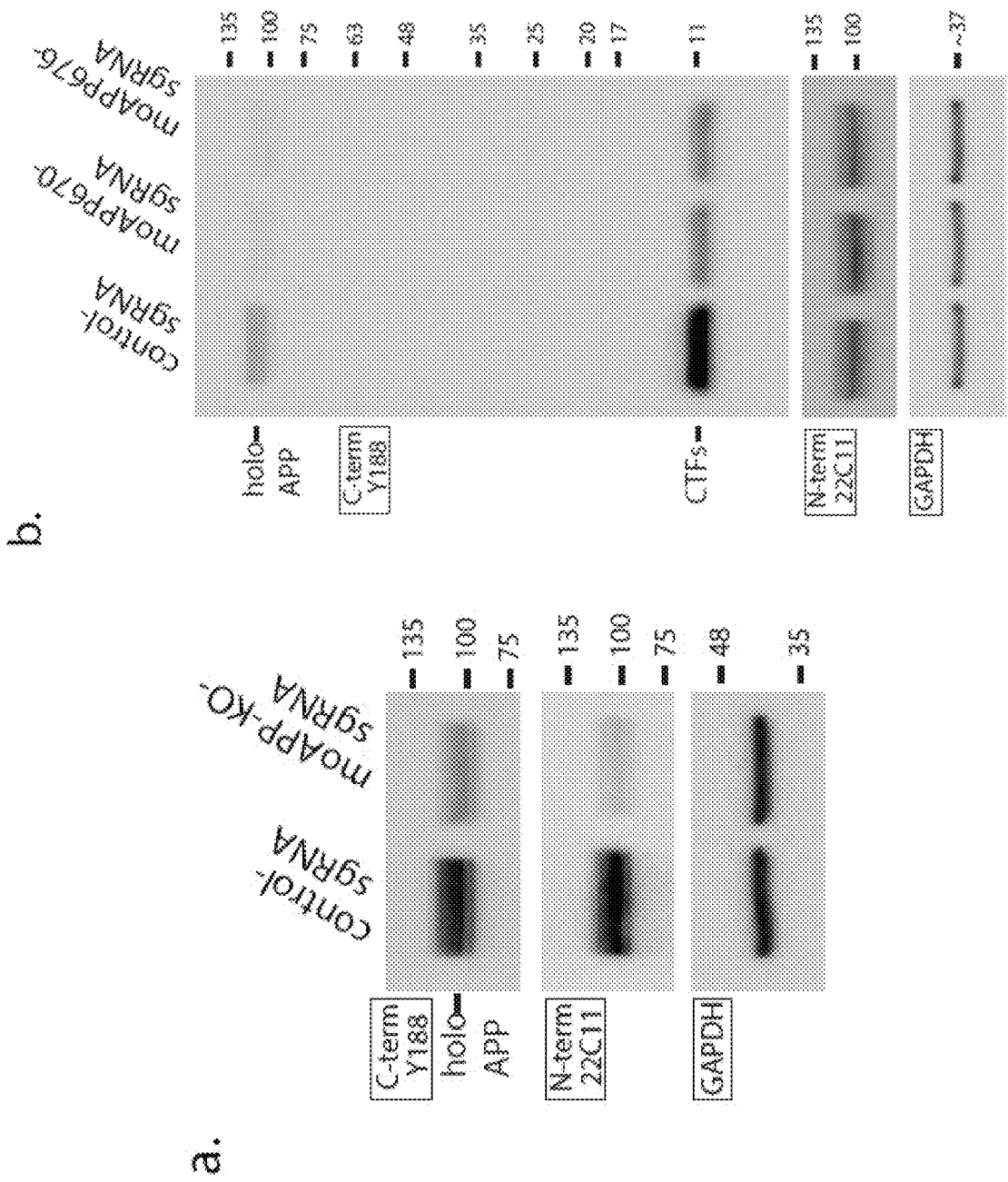
FIGS. 7A-7D show evaluation of CRISPR editing by immunoblotting in mouse Neuro2a cells.
Figures 8A, 8B, 8C, 8D, 8E, 8F, 8G:
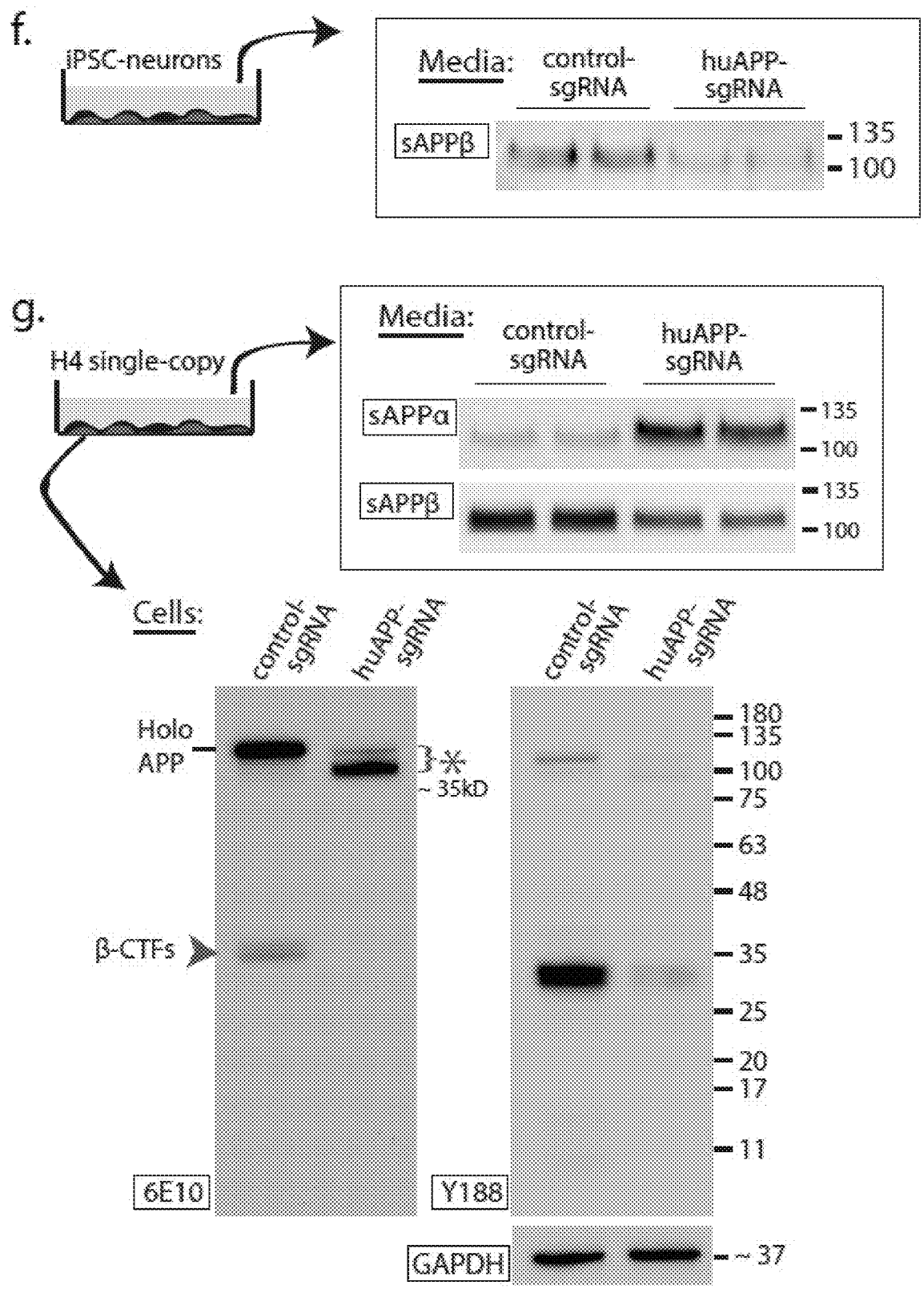
FIGS. 8A-8G show APP C-terminus editing by CRISPR/Cas9.

The TGG PAM and preceding 20-nt genomic target sequence recognized by the mo-APP-sgRNA is shown in FIG. 1A (top right); and FIGS. 1B-1F shows gene editing by this sgRNA in mouse cells. Note that upon editing, the Y188 antibody—recognizing the last 20 amino acids. of APP—would not be able to identify the resultant translational product. Robust editing of endogenous APP was seen in mouse neuroblastoma cells, as determined by attenuation of immunofluorescence with the Y188 antibody (FIG. 1B), and decreased Y188-signal in western blots (FIGS. 1C-1D; FIG. 1E shows time-course of editing). Note that the edited APP is recognized by antibodies to the N-terminus, indicating selective editing of the C-terminus by the APP-sgRNA (FIGS. 1C and 1E). However, the N-terminus antibody was unable to detect APP when the entire gene was deleted (FIG. 7A). Similar results were obtained with other sgRNAs targeting APP C-terminus and other C- and N-terminus APP antibodies (FIGS. 7B and 7C). Genomic deep-sequencing confirmed efficient editing of mouse APP at the expected loci, APP-659 (FIG. 1F). Post-editing translational products show that the last 36 amino acids. are effectively truncated by APP-sgRNA (FIG. 7D). Though the TGG PAM at this site is conserved in both mouse and human APP, and the upstream sgRNA-targeting sequences only differ by two nucleotides (FIG. 2A, arrowheads); the mouse APP-sgRNA was unable to edit human APP (not shown). However, a sgRNA specific to the human APP targeting sequence robustly edited APP in HEK293 (FIGS. 8A-8C), as well as in human embryonic stem cells (FIGS. 8D-8E). CRISPR editing of APP did not alter the steady-state levels of holo-APP (note data throughout with multiple N-terminus antibodies in various cell lines).

Figures 2A, 2B, 2C, 2D, 2E, 2F, 2G, 2H:
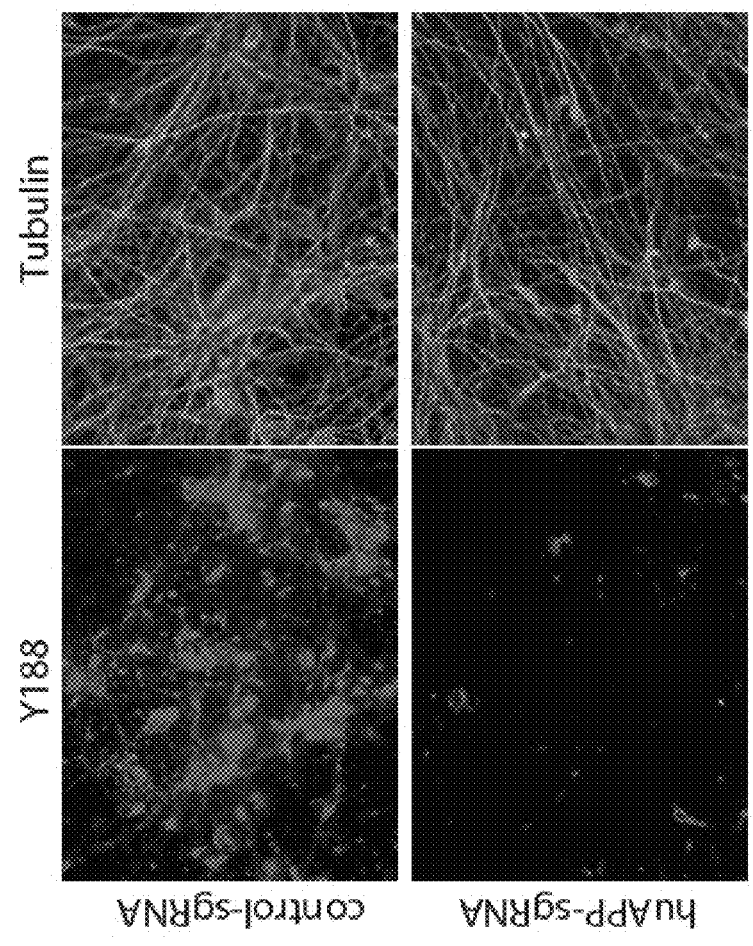
FIGS. 2A-2H show gene editing of APP C-terminus and effects on APP processing in human cells.
Figures 2A, 2B, 2C, 2D, 2E, 2F, 2G, 2H:
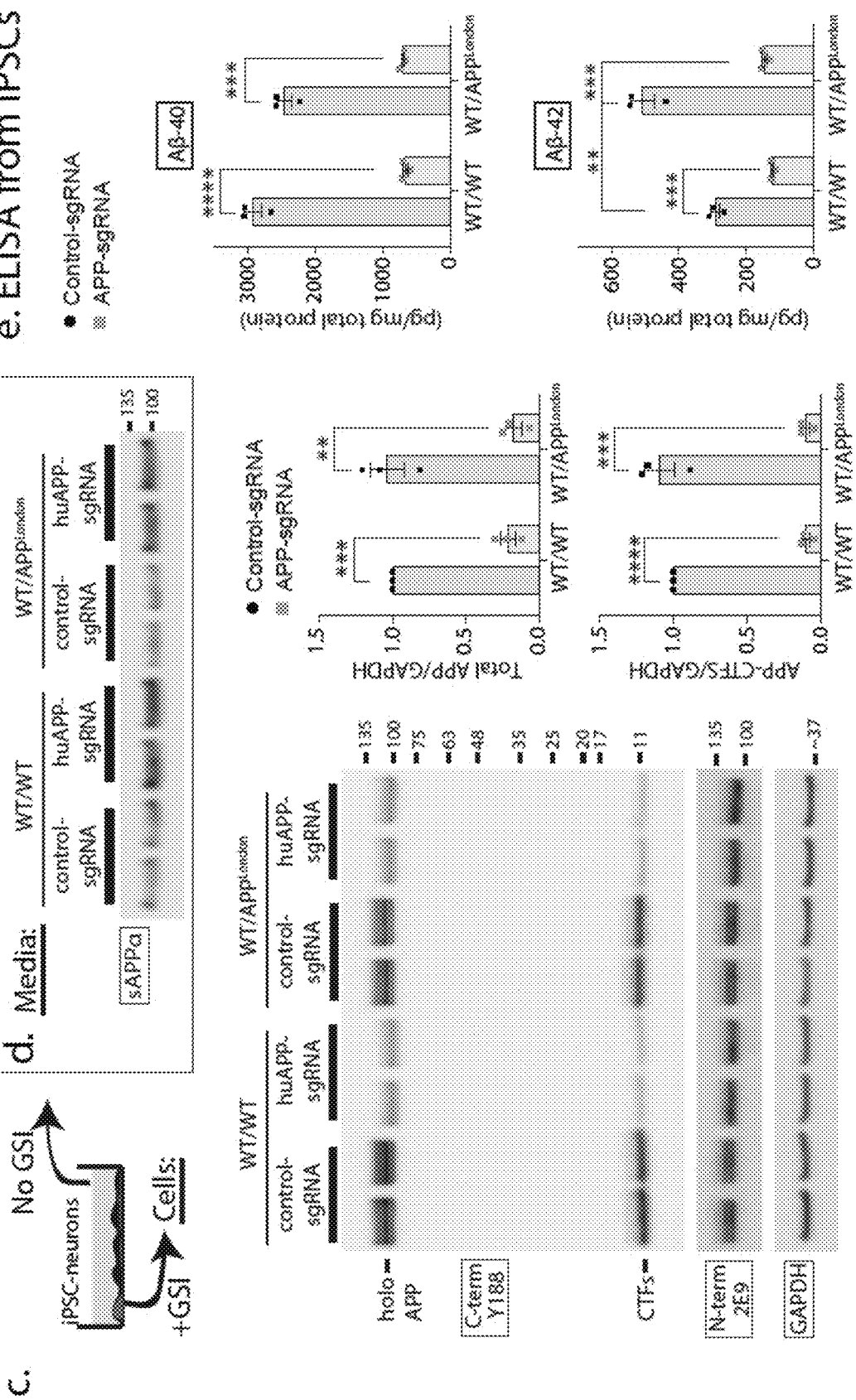

Reciprocal manipulation of the APP β/α pathway by CRISPR/Cas9 editing—Next, we examined APP editing in human iPSC-derived neurons. As shown in FIG. 2B, immunostaining with the Y188 antibody was attenuated in iPSC-neurons transduced by the hu-APP-sgRNA. To examine effects of APP editing in an "AD-like setting", we also tested the hu-APP-sgRNA in a heterozygous knock-in iPSC line carrying the most common familial AD mutation (APPV717I, also called the 'London mutation'; see methods for details of iPSC line). Both cell-lysates and supernatants were examined, to look for cellular and secreted APP products (see schematic in FIG. 2C). Immunoblotting with the Y188 antibody confirmed robust—and C-terminus selective—APP editing in both WT and APP-London iPSC lines (FIG. 2C). Examination of supernatants revealed that interestingly, APP-editing also led to increased sAPPα in both WT and London lines (FIG. 2D); suggesting upregulation of the neuroprotective α-cleavage pathway. ELISAs and western blot showed attenuated secretion of Aβ40/42 (FIG. 2E) and sAPPβ (FIG. 8F), confirming inhibition of the amyloidogenic pathway in these neurons. Genomic deep sequencing showed efficient editing of human APP by the sgRNA, with truncation of the last 36 amino acids. in human embryonic stem cells (FIGS. 2F-2H).

Figure 9A:
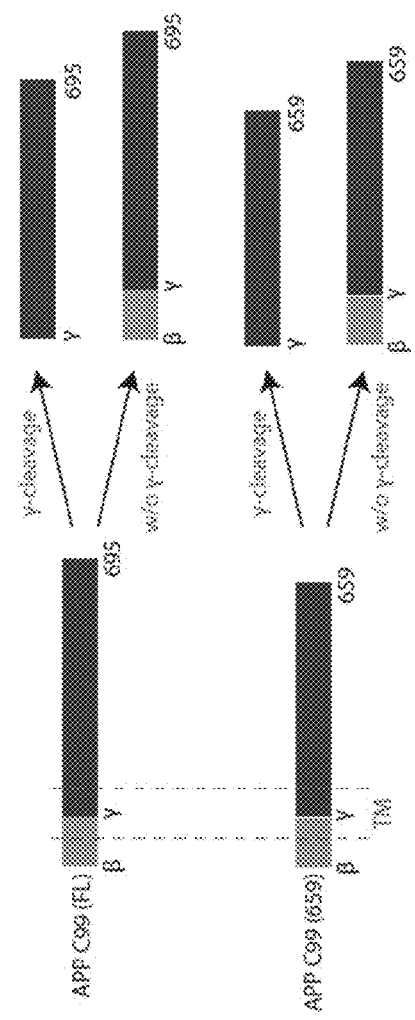
FIGS. 9A-9C show gene editing by APP-sgRNA likely does not influence APP γ-cleavage.
Figure 9B:
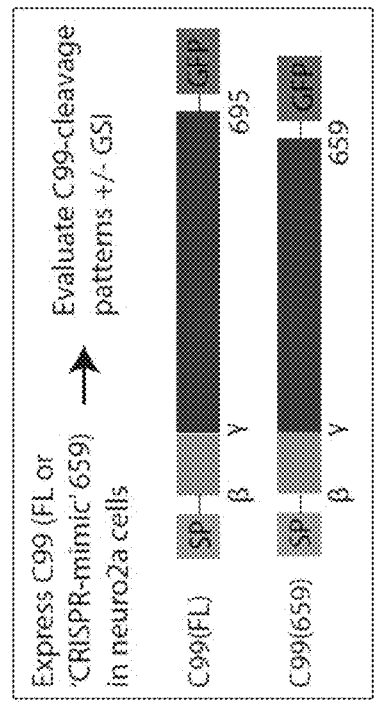
Figure 9C:
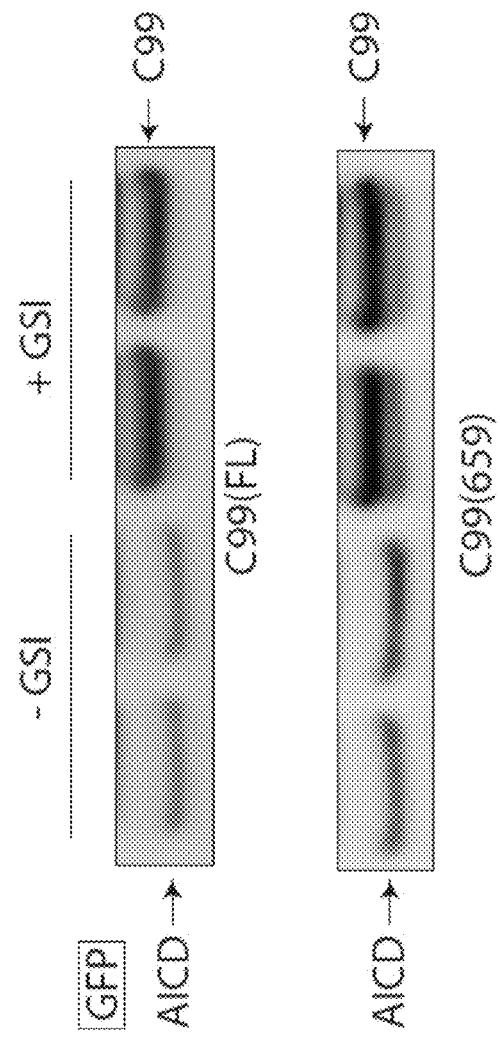

The data from iPSC-neurons suggest that the APP-sgRNA has reciprocal effects on APP β- and α-cleavage. To validate this in a more controlled setting, we tested the effects of APP editing in the H4 APP/BACE$^{single\_copy}$ cell line, where APP-cleavage is tightly regulated. In line with the data from iPSC-neurons, the hu-APP-sgRNA had reciprocal effects on APP β- and α-cleavage in APP/BACE$^{single\_copy}$ cells as well, confirming that our editing strategy has reciprocal effects on β/α cleavage (FIG. 8G). Further experiments using an APP-C99 construct (wild-type and truncated construct mimicking the CRISPR-product, APP-659) precludes an effect of the sgRNA on APP-γ-cleavage (FIGS. 9A-9C), indicating that our editing strategy is selectively affecting APP β-cleavage. Collectively, the available data strongly suggest that our gene editing strategy targeting the APP C-terminus is favorably manipulating the amyloid pathway by attenuating APP β-cleavage, while reciprocally up-regulating protective α-cleavage.

Figures 10A, 10B, 10C, 10D, 10E, 10F, 10G:
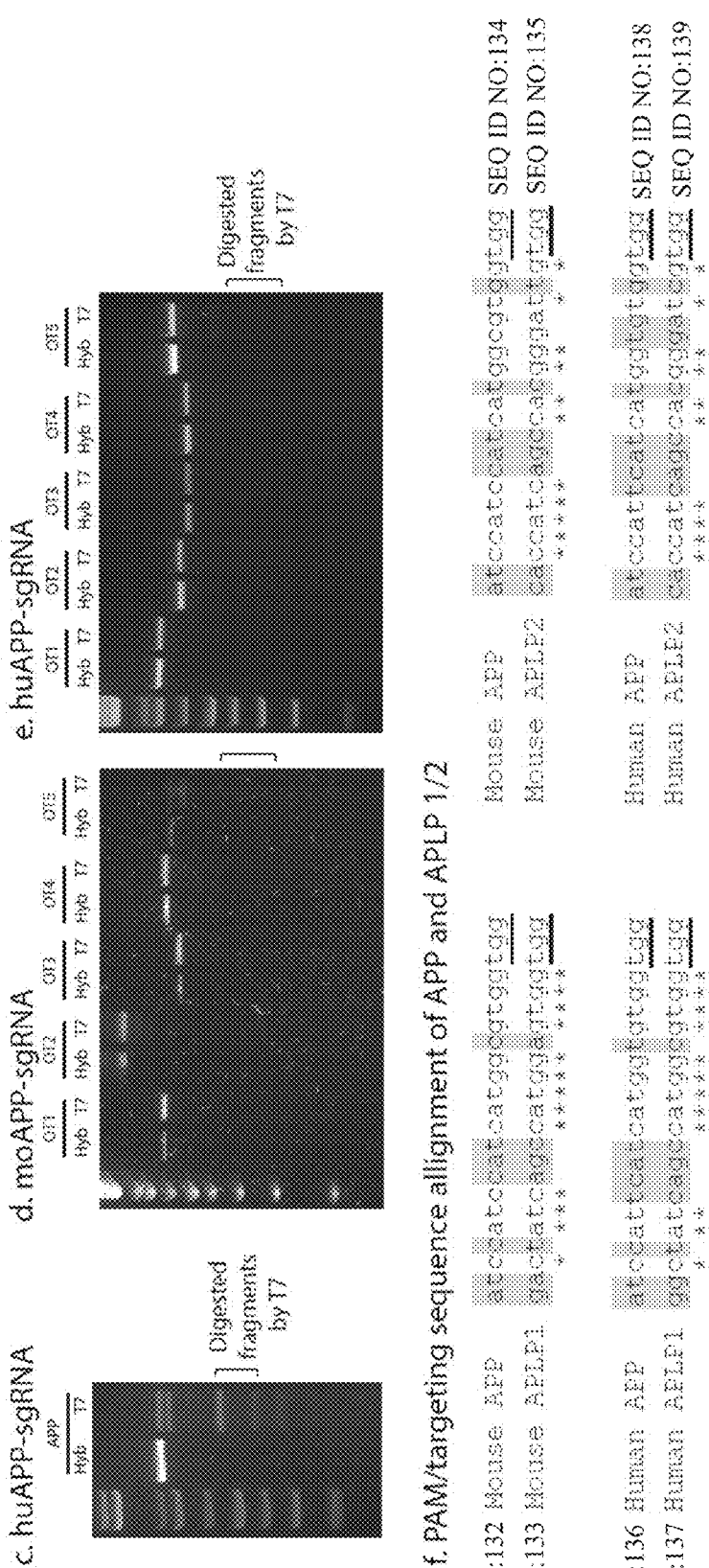
FIGS. 10A-10G show off target analyses of APP-sgRNA.
Figures 10A, 10B, 10C, 10D, 10E, 10F, 10G:
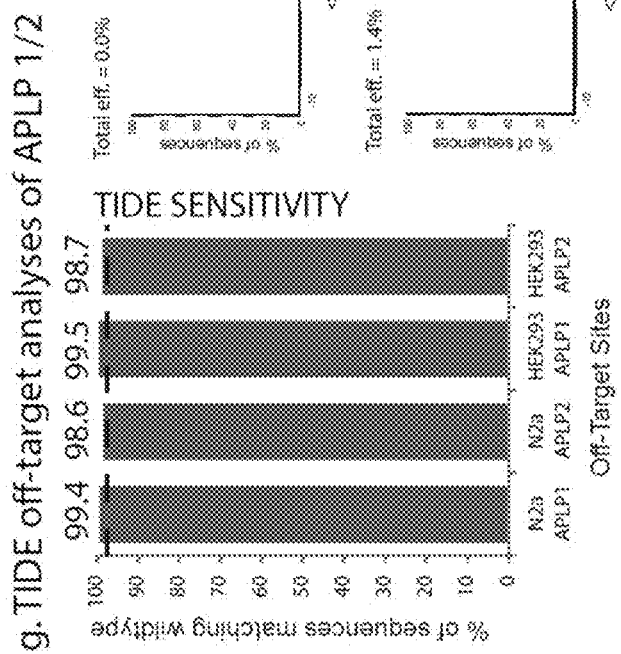

Off-target analysis and effect of APP C-terminus editing on neuronal physiology—Off-target effects of CRISPR/Cas9, due to unwanted editing of DNA-stretches resembling the targeted region, are a concern. Towards this, we asked if our mouse and human APP-sgRNA were able to edit the top five computationally predicted off-target sites (FIG. 10A; also see Table 3). No editing was seen using T7 endonuclease assays (FIGS. 10B-10E). Though APP null mice are viable, there is compensation by the two APP homologues APLP1 and 2 that undergo similar processing as APP (15,16). APLP1 and 2 were not amongst the top 50 predicted off-target sites, as their corresponding sgRNA-target sites were substantially different from APP (see sequences in FIG. 10F). For further assurance that our sgRNA was not editing the APP homologues, we performed specific off-target TIDE (Tracking of Indels by DEcomposition) analyses (17) on cells carrying the sgRNA. As shown in FIG. 10G, TIDE analyses showed no editing of APLP 1/2 by the sgRNA.

Figures 3A, 3B, 3C, 3D, 3E, 3F, 3G:
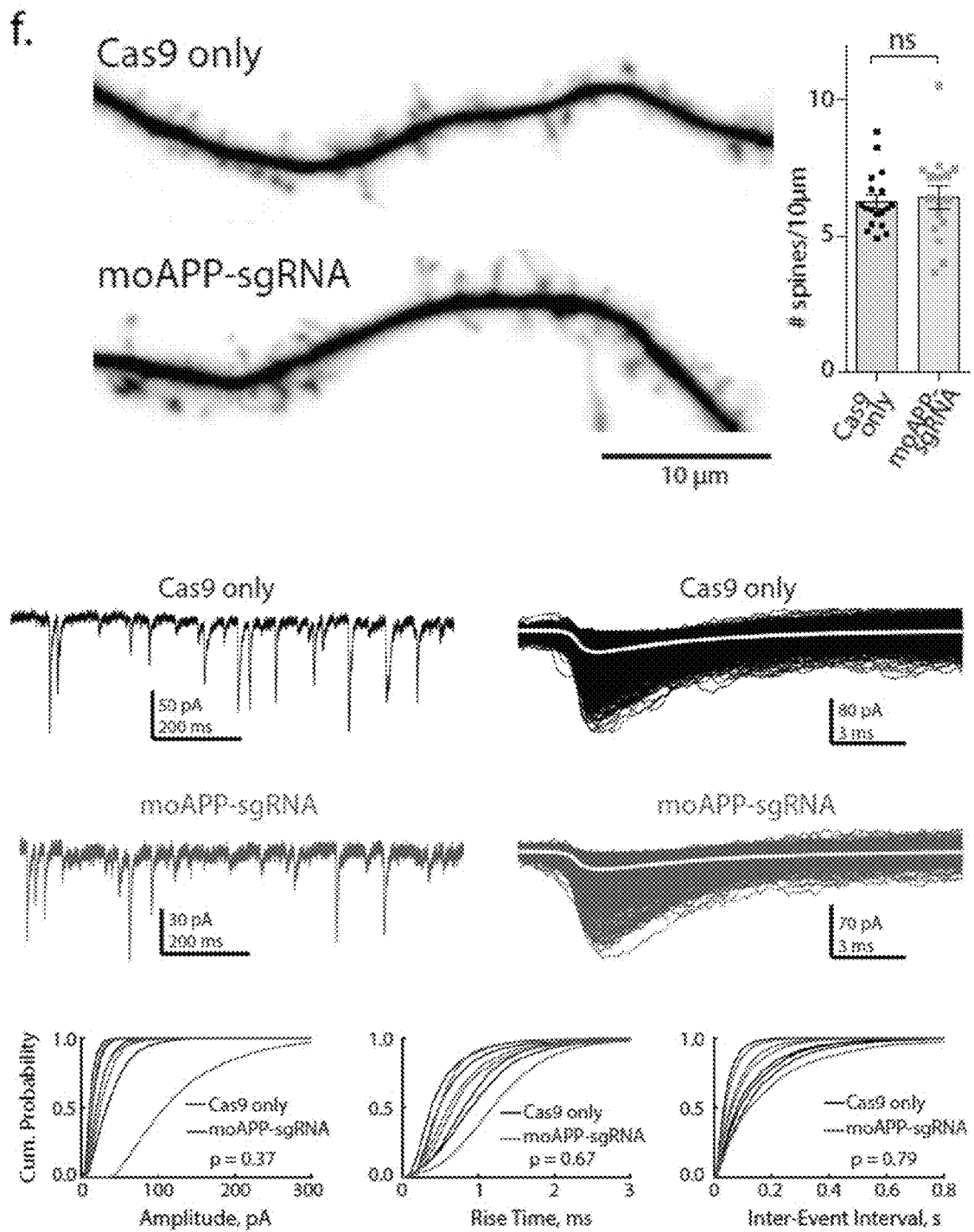
FIGS. 3A-3G show the effect of APP C-terminus editing on neuronal physiology.

APP has known physiologic roles in axon growth and signaling (18). As noted above, the N-terminus of APP— thought to play roles in axon growth and differentiation—is entirely preserved in our setting. The C-terminal APP intracellular domain (AICD) has been implicated in gene transcription, though the effect appears to be both physiologic and pathologic (19,20.) To examine potential deleterious effects of editing the extreme C-terminus of APP, we turned to cultured hippocampal neurons where various parameters like neurite outgrowth and synaptic structure/function can be confidently evaluated. To study pre-synapse structure and neuronal activity, we generated AAV9 viruses carrying the mo-APP-sgRNA and Cas9, tagged with GFP and HA respectively (see vector design in FIG. 3A) that transduced almost all cultured neurons (FIG. 3B and data not shown). In blinded analyses, we found no significant effect of the mo-APP-sgRNA on neurite outgrowth, axon-length, synaptic organization, or neuronal activity (FIGS. 3C-3G). We reason that the lack of deleterious effects upon editing is likely because: 1) most of the APP molecule remains intact after editing; 2) the APP homologues APLP1/2—that undergo similar processing as APP, generate CTFs, and are known to compensate for APP function—remain unedited; and 3) APP-cleavage is not entirely blocked by our approach.

Figures 4A, 4B, 4C, 4D, 4E, 4F, 4G:
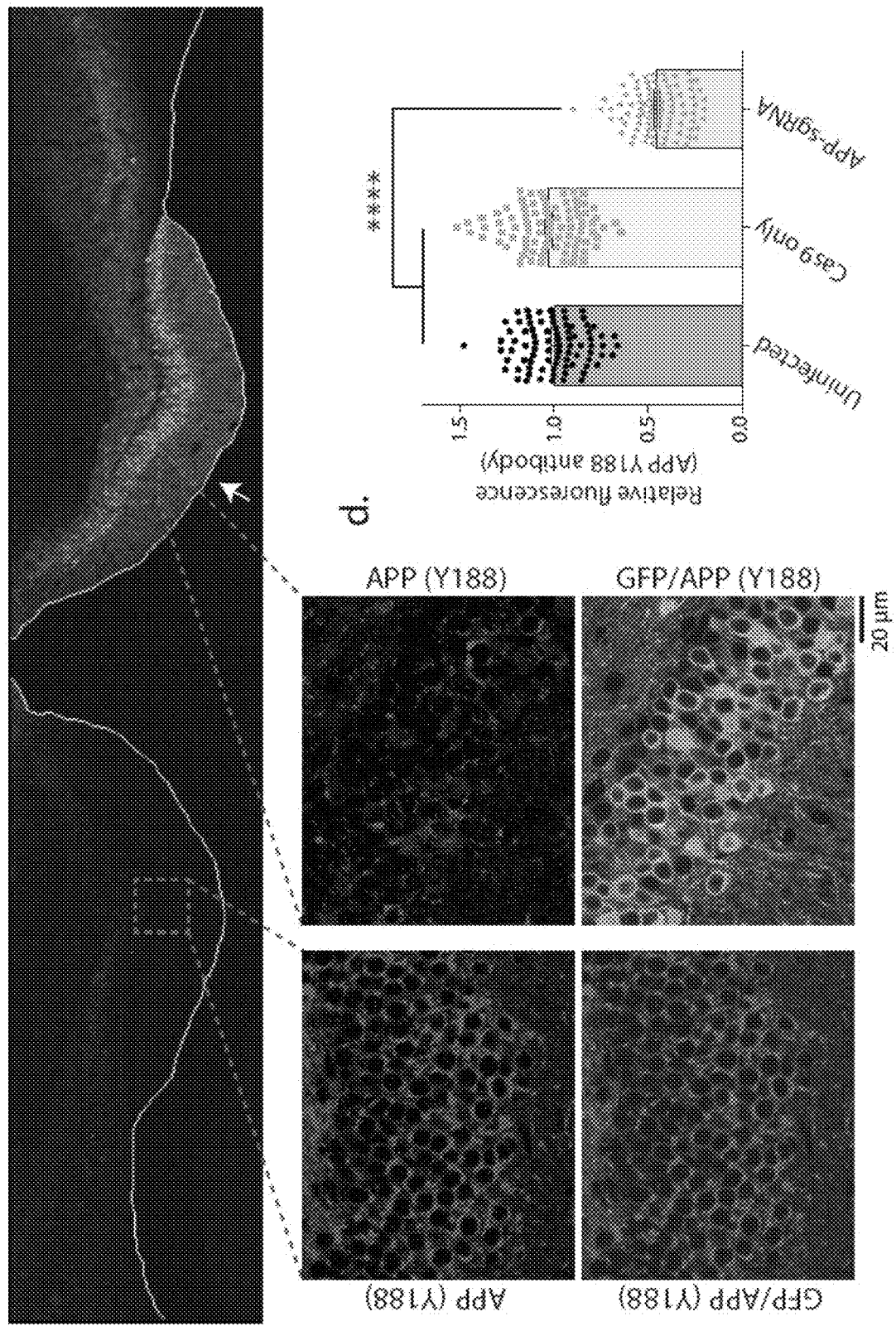
FIGS. 4A-4G show gene editing of APP C-terminus in vivo.

Editing of APP C-terminus in vivo and mechanistic details of APP β/α manipulation—Next we asked if the APP-sgRNA could edit endogenous APP in mouse brains. Injection of the AAV9s into mouse hippocampi (FIG. 4A) led to efficient transduction of both sgRNA and Cas9 in dentate neurons (86.87±2.83% neurons carrying the sgRNA also had Cas9; see representative images in FIG. 4B). Immunostaining of transduced neurons with the APP Y188 antibody showed attenuated staining, suggesting editing of endogenous APP in vivo (FIGS. 4C and 4D). To achieve a more widespread expression of the sgRNA and Cas9 in mouse brains—and also evaluate editing by biochemistry—we injected the viruses into the ventricles of neonatal (P0) mice and examined the brain after 2-4 weeks (FIG. 4E). Previous studies have shown that when AAVs are injected into the ventricles of neonatal mice, there is widespread delivery of transgenes into the brain—also called somatic transgenesis (21,22). Indeed, APP Y188 immunostaining was attenuated in cortical regions (FIG. 4F) and immunoblotting with the Y188 antibody also showed a decreased signal (FIG. 4G); indicating that the APP-sgRNA can edit APP in vivo.

Figures 5A, 5B, 5C, 5D, 5E:
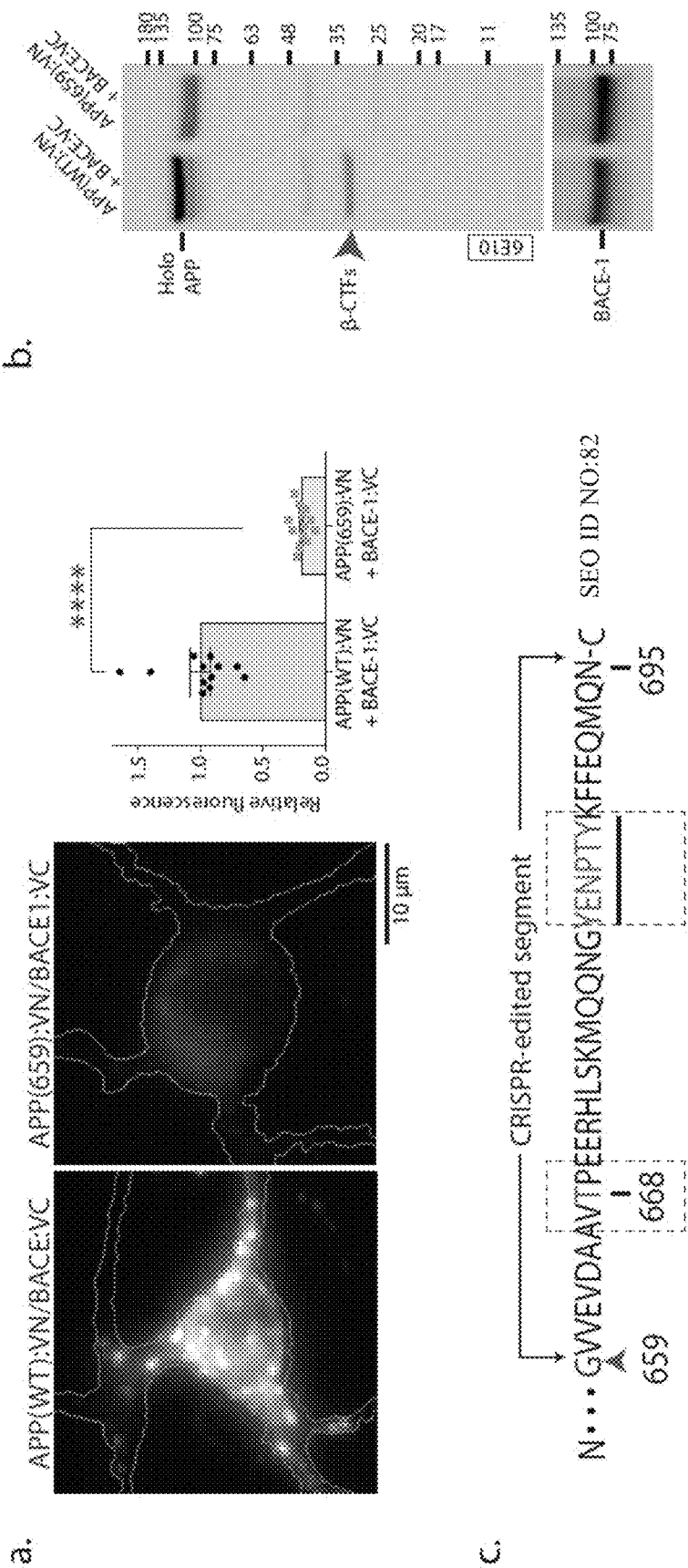
FIGS. 5A-5E show mechanistic details of CRISPR-guided APP editing.
Figures 5A, 5B, 5C, 5D, 5E:
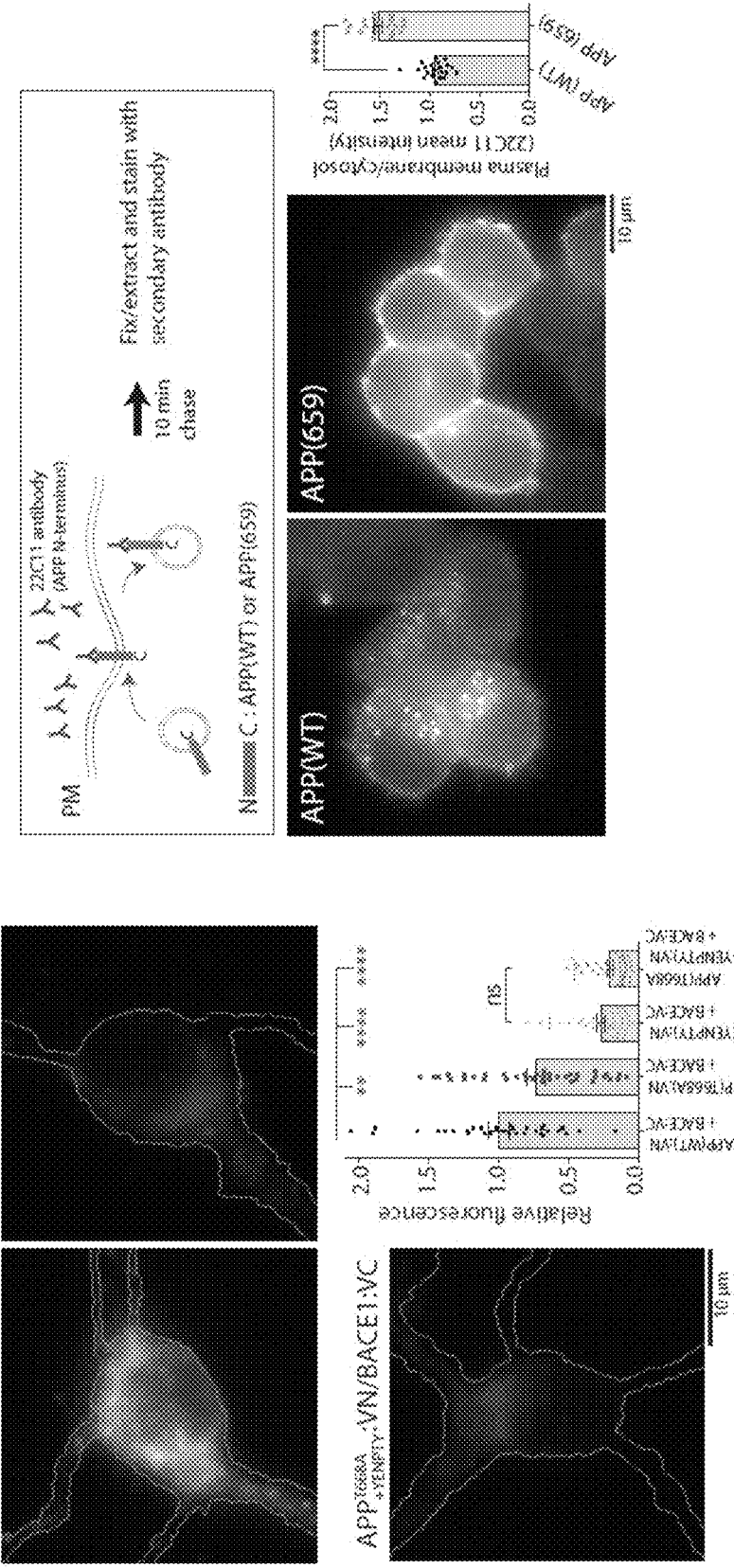
Figures 11A, 11B, 11C:
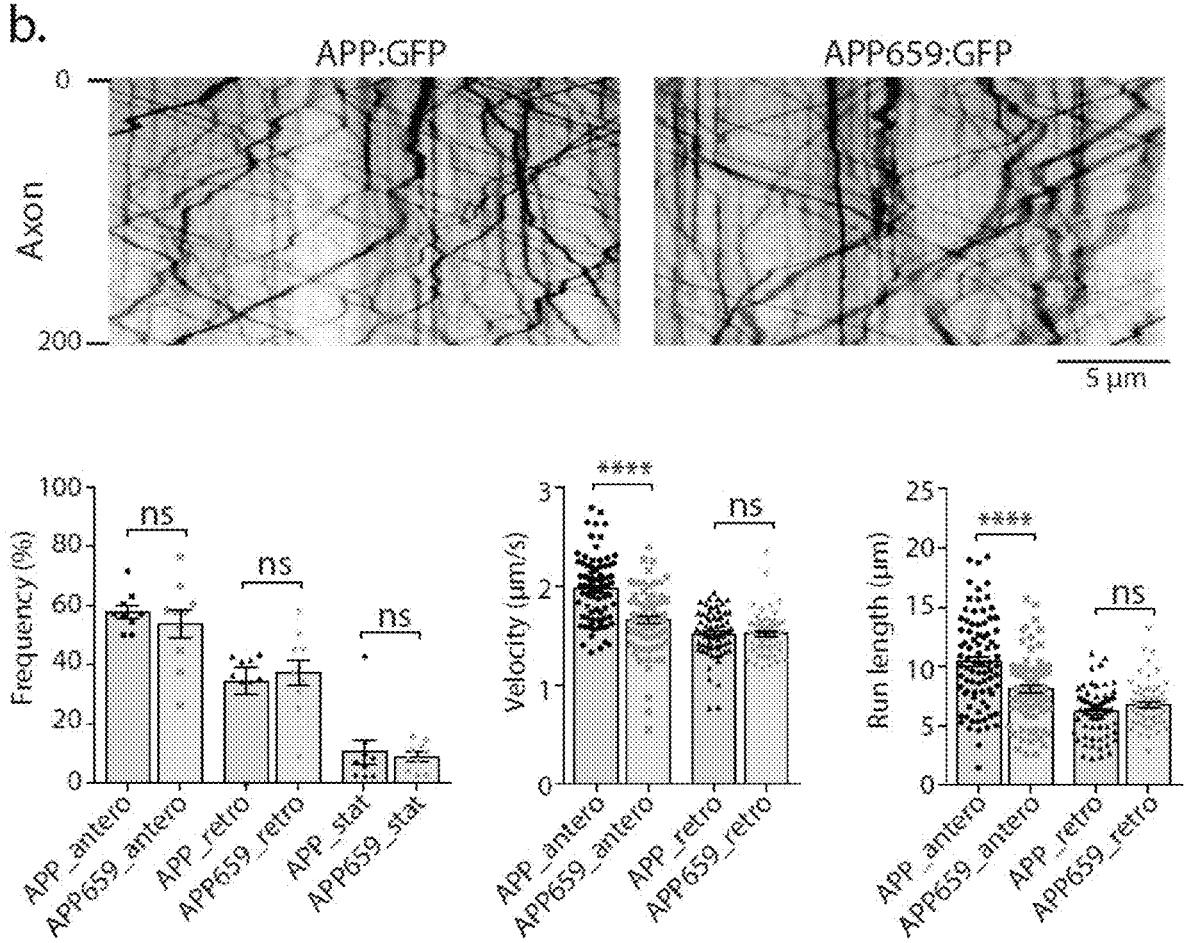
FIGS. 11A-11C show trafficking of vesicles carrying APP(WT) or APP(659).
Figures 11A, 11B, 11C:
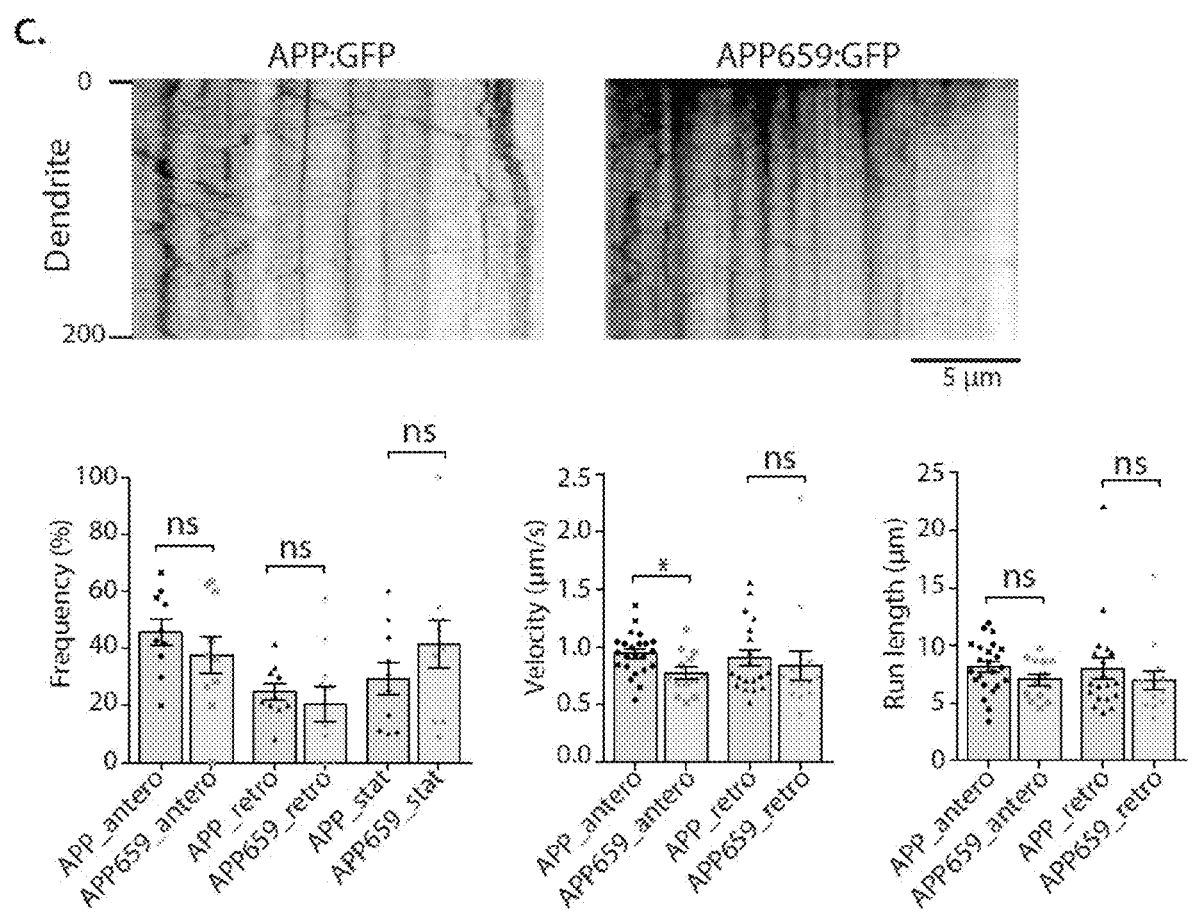

To determine the mechanism by which the APP-sgRNA manipulates the amyloid pathway, we used a "CRISPR-mimic" truncated APP construct (APP-659) that is the major post-editing translational product in both mouse and human cells (see FIG. 2H, FIG. 6E, and FIG. 7D). Using our BifC assay (10), we first asked if the CRISPR-mimic APP-659 interacted with BACE-1. APP-659/BACE-1 approximation was greatly attenuated in cultured neurons (FIG. 5A), along with a decrease in β-CTF generation (FIG. 5B). Next we visualized axonal and dendritic transport of APP-WT and APP-659. Although there were minor changes (FIGS. 11A-11C and Table 4), it seems unlikely that such small transport perturbations would lead to the dramatic attenuation of β-cleavage and Aβ-production seen in our experiments.

Figures 12A, 12B, 12C:
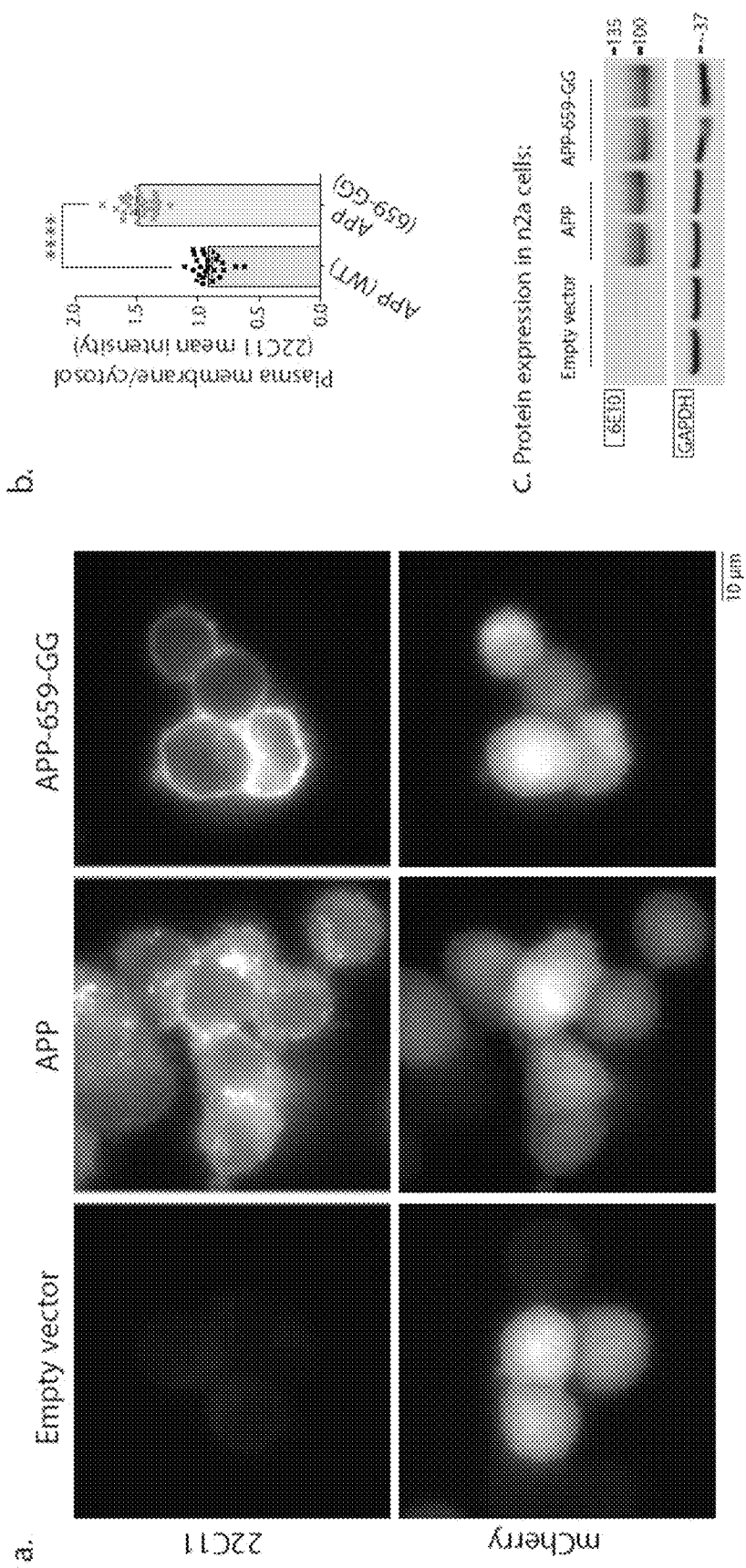
FIGS. 12A-12C show internalization of APP-659-GG (most common post-editing translational product).
Figure 18:
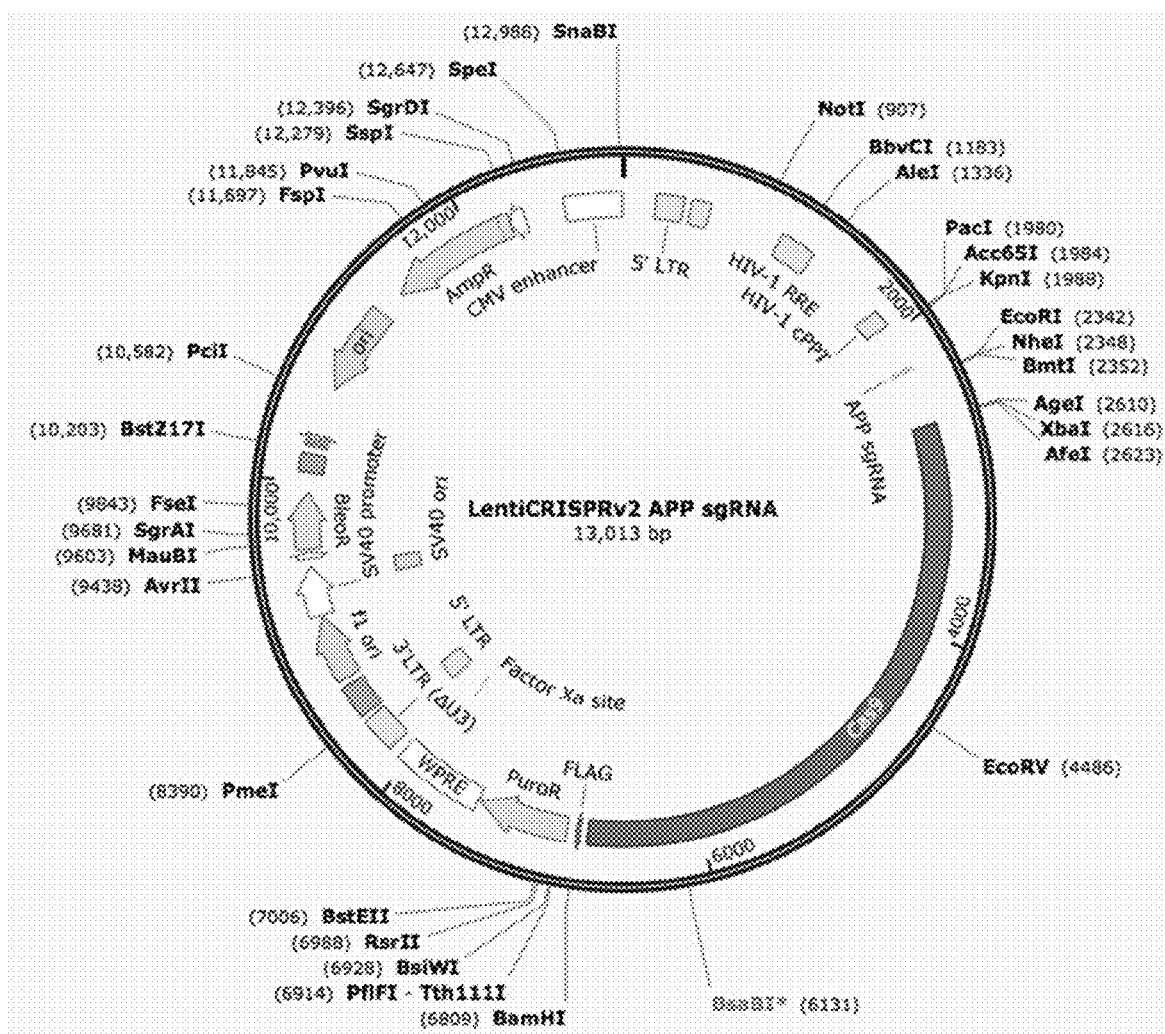
FIG. 18 shows the sequence and vector map of an exemplary lentiviral APP sgRNA vector (SEQ ID NO: 20).

The CRISPR-edited segment of APP contains the residues T668 and Y682-Y687 (YENPTY motif, see FIG. 5C; also present in APLP1/2), that have been reported to play a role in Aβ production (12,23,24). Specifically, APP phosphorylated at T668 has been reported to colocalize with BACE-1 in endosomes (23), and the YENPTY motif is known to mediate APP internalization from the plasma membrane (25). Examining the effects of these residues in APP/BACE-1 BifC assays, we saw that the extent of APP/BACE-1 attenuation by the YENPTY mutation strongly resembled the decrease in fluorescence complementation by the APP-659 construct (FIG. 5D). A prediction from these experiments is that endocytosis of the CRISPR-mimic APP from the cell surface should be attenuated; and indeed, this was the case in internalization assays (FIG. 5E). Similar results were seen with an "APP-659-GG" construct that more closely resembles the most common post-editing translational product of our sgRNA (FIGS. 12A-12C; also see post-editing products from human cells in FIG. 2H and FIG. 6E).

Collectively, the data suggest that our gene-editing approach does not have a major effect on post-Golgi trafficking of APP, but attenuates its endocytosis from cell surface, and consequently, its interaction with BACE-1 in endosomes—though we cannot exclude a direct effect of editing on APP/BACE-1 interaction. This is also consistent with previous studies showing that surface APP is internalized into endosomes, where it is cleaved by BACE-1 (26-29). Since most of the APP α-cleavage is thought to occur at the cell surface (30), this may also explain why the non-amyloidogenic pathway is enhanced by our approach.

Using CRISPR/Cas9 technology, herein we provide conceptual proof for a strategy that selectively edits the C-terminus of APP and alters the balance of APP-cleavage—attenuating β-cleavage and Aβ, while upregulating neuroprotective α-cleavage. The N-terminus of APP—known to play physiologic roles—is unaffected, along with the compensatory APP homologues APLP1/2. No deleterious effects were seen in neurophysiologic parameters. Without wishing to be bound by any particular theory, our strategy likely works by editing the terminal YENPTY motif in APP that is responsible for its internalization, subsequent APP/BACE-1 association, and initiation of the amyloidogenic pathway; while retention of APP at the plasma membrane may facilitate the upregulation of APP α-cleavage.

APP processing is regulated by α-, β-, and γ-secretases; and the various cleavage products may play physiological functions that are not fully understood (31,32). Previous studies suggest that in vivo deletion of the APP C-terminus blocks APP β-cleavage without obvious effects on neuroanatomy, behavior and neuronal activity in adult mice (13). Notably, the APP homologues APLP 1/2 also have YENPTY motifs (15,16)—that can presumably undergo endocytosis and protein-protein interactions—and are expected to compensate for the loss of the C-terminus. The precise reasoning behind enhanced α-cleavage is unclear. We propose that retention of APP at the plasma membrane might be responsible, but we cannot rule out other causes, including off-target effects, and further detailed studies may provide clarity.

Methods

Constructs, antibodies and reagents—For transient co-expression of CRISPR/Cas9 components, APP sgRNA nucleotides were synthesized and cloned into pU6-(Bbs1)_CBh-Cas9-T2A-mCherry vector at Bbs1 site. For viral transduction, a dual vector system was used to deliver CRISPR/Cas9 components using AAV9 (33). For making the AAV9 vectors, the APP sgRNA was cloned into pAAV9-U6sgRNA(SapI)_hSyn-GFP-KASH-bGH vector at Sap1 site. The CRISPR/Cas9 stable cell lines were generated by lentivirus infection as follows. The APP sgRNA was cloned into lentiCRISPR v2 vector at Bbs1 site to produce lentivirus (34). For making APP deletions and relevant constructs, the human APP659 truncation was PCR amplified and cloned at Hind3 and Sac2 sites of pVN to generate pAPP659:VN. The BBS-APP659 was PCR amplified and cloned into pBBS-APP:GFP at Hind3 and Sac2, replacing BBS-APP, to generate pBBS-APP659:GFP. The pBBS-APP$^{YENPTY}$:GFP was generated by site directed mutagenesis from pBBS-APP:GFP. The pAPP$^{T668A}$:VN and pAPP$^{T668A+YENPTY}$:VN were generated by site directed mutagenesis from pAPP:VN and pAPP$^{YENPTY}$:VN. Antibodies used were as follows: APP Y188 (ab32136; Abcam), APP 22C11 (MAB348; Millipore), APP 6E10 (803001; BioLegend), APP M3.2 (805701; BioLegend), APP 2E9 (MABN2295; Millipore), APP CT20 (171610; Millipore), sAPPβ (18957; IBL) BACE-1 (MAB931; R&D), GAPDH (MA5-15738, ThermoFisher), GFP (ab290, Abcam), GFP (A10262, Invitrogen), HA (901513, BioLegend), VAMP2 (104211, Synaptic Systems). Reagents were as follows: γ-secretase inhibitor BMS-299897 (Sigma), and Rho Kinase (ROCK)-inhibitor H-1152P (Calbiochem).

Cell cultures, transfections, viral production/infections, and biochemistry—HEK293 and neuro2a cells (ATCC) were maintained in DMEM with 10% FBS. Cells were transfected with Lipofectamine™ 2000 and collected 5 days after transfection for biochemical and immunostaining analysis. All the studies involving primary neuron culture were performed in accordance with University of Wisconsin guidelines. Primary hippocampal neurons were obtained from postnatal (P0-P1) CD1 mice (either sex), and transiently transfected using Lipofectamine™ 2000 or Amaxa™ 4 D system (Lonza). Dissociated neurons were plated at a density of 30,000 cells/cm$^2$ on poly-D-lysine-coated glass-bottom culture dishes (Mattek) and maintained in Neurobasal™/B27 medium with 5% CO$_2$. For APP/BACE-1 interaction and APP transport studies, DIV 7 neurons were cultured for ~18-20 h after transfection. For spine density analysis, DIV7 neurons were transfected with Cas9, sgRNA and soluble marker, and cultured for 7 d before imaging. For testing the effect of CRISPR/Cas9 on neuronal development, neurons were electroporated with the respective constructs before plating using an Amaxa™ 4 D-Nucleofector™ system with the P3 Primary Cell 4D-Nucleofector™ X kit S and program CL-133.

For western blotting, pre-synapse analyses and electrophysiology, DIV7 cultured neurons were infected with either AAV9-APP sgRNA-GFP (2.24×10$^{13}$ Vg/ml) and AAV9-Cas9 (2.4×10$^{14}$ Vg/ml), or AAV9-GFP (2.58×10$^{13}$ Vg/ml) and AAV9-Cas9 at a multiplicity of infection (MOI) of 1.5×10$^5$. Neurons were analyzed 7 days post-infection. Lentivirus was produced from HEK293FT cells as described (35). Briefly, HEK293FT cells (Life Technologies) were maintained in DMEM with 10% FBS, 0.1 mM NEAA, 1 mM sodium pyruvate and 2 mM Glutamine. Cells were transfected with lentiviral-target and helper plasmids at 80-90% confluency. 2 days after transfection, the supernatant was collected and filtered with 0.45 µm filter. For experiments with hESCs, cells were cultured on a Matrigel® substrate (BD Biosciences) and fed daily with TeSR-E8 culture media (StemCell Technologies). When the cells were around 60-70% confluent, they were infected with a 50/50 mixture of TeSR-E8 (with 1.0 µM H-1152P) and lentivirus supernatant. After 24 h, the virus was removed, and the cells were fed for 2 days (to recover). After 3 days, cells were treated with 0.33 µg/mL of puromycin for 72 h to select for virally-integrated hESCs. For HEK and neuro2a cell lines, cells were infected with the lentivirus carrying APP-sgRNA and Cas9 for 24 h. And then cells were fed for 1 day to recover. After 2 days, cells were treated with 1 µg/mL of puromycin for 72 h to select for virally-integrated cells.

Human NPCs were generated as has been described previously (36), using manual rosette selection and Matrigel® (Corning) to maintain them. Concentrated lentiviruses express control-sgRNA or APP-sgRNA were made as described previously (37), using Lenti-X™ concentrator (Clontech). The NPCs were transduced with either control-sgRNA or APP-sgRNA after Accutase® splitting and were submitted to puromycin selection the subsequent day. Polyclonal lines were expanded and treated with puromycin for 5 more days before banking. Neuronal differentiations were carried out by plating 165,000 cells/12 well-well in N2/B27 media (DMEM/F12 base) supplemented with BDNF (20 ng/mL; R&D) and laminin (1 ug/mL; Trevigen).

For biochemistry, cell lysates were prepared in PBS+ 0.15% Triton™ X-100 or RIPA supplemented with protease inhibitor cocktail, pH 7.4. After centrifuging at 12,000 g for 15 min at 4° C., supernatants were quantified and resolved by SDS-PAGE for western blot analysis. For sAPPα and sAPPβ detection, cell culture medium was collected and centrifuged at 2,000 g for 15 min at RT. The supernatants were resolved by SDS-PAGE for western blot analysis; band intensities were measured by ImageJ. Human Aβ40 and Aβ42 were detected using kits, according to the manufacturer's instructions (Thermo KHB3481 and KHB3544). Briefly, supernatants from H4$^{single\ copy}$ cells or human iPSC derived neurons were collected and diluted (×5 for H4 and ×2 for iPSC-neuron). The diluted supernatants and the human Aβ40/42 detection antibodies were then added into well and incubated for 3 h at RT with shaking. After washing (×4), the anti-Rabbit IgG HRP solution was added and incubated for 30 min at RT. The stabilized Chromogen was added after washing (×4) and incubated for another 30 min at RT in the dark. After addition of stop solution, absorbance at 450 nm was read using a luminescence microplate reader.

Developing a single-copy, stable APP/BACE-1 cell line— H4 tetOff FlpIn empty clone was maintained in OptiMEM® with 10% FBS, 200 µg/mL G418 and 300 µg/mL Zeocin. To generate an APP:VN/BACE-1:VC stable cell line carrying single copies of APP and BACE-1, the expressing plasmid and pOG44 plasmids were transfected with Lipofectamine™ 2000. 2 days after transfection, cells were selected with 200 µg/mL hygromycin B and 200 µg/mL G418 for 1 week. A monoclonal cell line with stable expression was selected. H4 stable cell lines were then infected with the lentivirus carrying APP-sgRNA and Cas9, as described above. After 24 h, the virus was removed, and cells were fed for 1 day to recover. After 2 days, cells were treated with 0.7 µg/mL of puromycin for 72 h to select for virally-integrated cells.

Generation of the APPLondon (V717I) knockin iPSC line—CRIPSR/Cas9 was used to knock in the APP V717I mutation (APPLon) into a commercially available control human iPSC line IMR90 (clone 4, WiCell). sgRNAs targeting Exon17 of APP were designed using the CRISPR design tool created by Feng Zhang's lab and subcloned into the MLM3636 vector (AddGene). Efficacy of multiple sgRNAs was first assessed in HEK293 cells (Geneart™ Genomic Cleavage Detection Kit, Life Technologies). The ssDNA HDR template was designed to include a silent CRISPR blocking mutation at the PAM site of most efficacious sgRNA in addition to the APPLon mutation. sgRNA, Cas9-2A-mCherry (generously provided by Hynek Wicterle), and ssDNA HDR template were electroporated (Lonza Nucleofector™) into feeder-free IMR90 iPSCs, followed by cell sorting on mCherry signal and plating at low density on MEFs (MTI-GlobalStem). Individual clones were manually picked into a 96 well format, subsequently split into duplicate plates, one of which were used to generate gDNA as had been done previously[38]. For each clone, exon 17 of APP was amplified and initially screened by restriction digest for the presence of a de novo Bcl1 site introduce by the APPLon mutation. Sanger sequencing was used to confirm the mutation, and successful knockin clones were expanded and banked. Potential off-target effects of CRISPR/Cas9 cleavage were analyzed by Sanger sequencing of the top 5 predicted off-target genomic locations, which demonstrated a lack of indels for multiple clones. Clone 88 was picked for future studies.

Immunofluorescence, microscopy/image analysis, APP trafficking and endocytosis assays—For immunostaining of endogenous APP or VAMP2, cells were fixed in 4% PFA/sucrose solution in PBS for 10 min at room temperature (RT), extracted in PBS containing 0.2% Triton™ X-100 for 10 min at RT, blocked for 2 h at RT in 1% bovine serum albumin and 5% FBS, and then incubated with rabbit anti-APP (1:200) or mouse anti-VAMP2 (1:1000) diluted in blocking buffer for 2 h at RT. After removal of primary antibody, cells were blocked for 30 min at RT, incubated with goat anti-rabbit (Alexa Fluor 488) or goat anti-mouse (Alexa Fluor® 594) secondary antibody at 1:1000 dilution for 1 h at RT and then mounted for imaging. z-stack images (0.339 μm z-step) were acquired using an inverted epifluorescence microscope (Eclipse Ti-E) equipped with CFI S Fluor VC 40× NA 1.30 (Nikon). An electron-multiplying charge-coupled device camera (QuantEM: 512SC; Photometrics) and LED illuminator (SPECTRA X; Lumencor) were used for all image acquisition. The system was controlled by Elements software (NIS Elements Advanced Research). z-stacks were subjected to a maximum intensity projection. For APP Y188 staining, the average intensity of single cell body (neuro2A, HEK293 and neurons) or the whole colony (hESCs) was quantified. All the images were analyzed in Metamorph® and ImageJ.

Spine density experiments were done as described previously (39). Briefly, DIV 7 neurons were transfected with desired constructs for 7 days, and secondary dendrites were selected for imaging. z-stack images were captured using a 100× objective (0.2 μm z-step) and subjected to a maximum intensity projection for analysis. For the APP/BACE-1 complementation assay, DIV 7 neurons were transfected with desired constructs for ~15-18 h and fixed. z-stack images were captured using a 40× objective (0.339 μm z-step) and subjected to a maximum intensity projection. The average intensity within cell bodies was quantified.

For trafficking studies in axons and dendrites, imaging parameters were set at 1 frame/s and total 200 frames. Kymographs were generated in MetaMorph®, and segmental tracks were traced on the kymographs using a line tool. The resultant velocity (distance/time) and run length data were obtained for each track, frequencies of particle movements were calculated by dividing the number of individual particles moving in a given direction by the total number of analyzed particles in the kymograph, and numbers of particles per minute were calculated by dividing the number of particles moving in a given direction by the total imaging time.

APP endocytosis assay was done as described previously (40). Cells expressing APP-GFP, APP659-GFP, untagged APP or untagged APP-659-GG were starved with serum-free medium for 30 min and incubated with anti-APP (22C11) in complete medium with 10 mM HEPES for 10 min. And then, cells were fixed, permeabilized and immunostained for 22C11. The mean intensity of 22C11 along plasma membrane was calculated by dividing the total intensity along plasma membrane (=intensity of whole cell–intensity of cytoplasm) with area of plasma membrane (=area of whole cell–area of cytoplasm). The ratio of mean intensities between plasma membrane and cytoplasm was quantified.

Stereotactic injection of AAV9s into the mouse brain and histology—All the animal procedures were performed in accordance with University of Wisconsin guidelines. In vivo injection and immunofluorescence staining was done as described previously (41). Briefly, 1.5 μl of 1:2 AAV9 mixture of AAV9-APP sgRNA-GFP (or AAV9-GFP) and AAV9-Cas9 was injected into the dentate gyrus (−2.0, ±1.6, −1.9) of 8-week old male C57BL/6 mice (either sex). 2-weeks after surgery, the mice were sacrificed by transcardiac perfusion of saline, followed by 4% PFA. The brains were dissected, post-fixed with 4% PFA overnight, immersed in 30% sucrose until saturation, and sectioned at 40 μm. Sections were immunostained with the following antibodies: mouse anti-HA (1:1000, BioLegend, clone 16B12), chicken anti-GFP (1:1000, Invitrogen, polyclonal) and rabbit anti-APP (1:200, Abcam, clone Y188). Images were acquired using Zeiss LSM800 confocal microscope. Average intensities of APP staining in cell bodies was quantified using Metamorph®.

Intracerebroventricular injections and histology—All animal procedures were approved by the Mayo Institutional Animal Care and Use Committee and are in accordance with the NIH Guide for Care and Use of Laboratory animals. Free hand bilateral intracerebroventricular (ICV) injections were performed as previously described (42) in C57BL/6 mouse pups. On post-natal day 0, newborn pups were briefly cryoanesthetized on ice until no movement was observed. A 30-gauge needle attached to a 10 μl syringe (Hamilton) was used to pierce the skull of the pups just posterior to bregma and 2 mm lateral to the midline. The needle was held at a depth of approximately 2 millimeters, and 2 μl of a mixture of AAV9 viruses (ratio 1:2 of AAV9-APP sgRNA-GFP or AAV9-GFP+AAV9-Cas9) were injected into each cerebral ventricle. After 5 minutes of recovery on a heat pad, the pups were returned into their home cages. Mice were sacrificed 15 days after viral injection. Animals were deeply anesthetized with sodium pentobarbital prior to transcardial perfusion with phosphate buffered saline (PBS), and the brain was removed and bisected along the midline. The left hemisphere was drop-fixed in 10% neutral buffered formalin (Fisher Scientific, Waltham, Mass.) overnight at 4° C. for histology, whereas the right hemisphere of each brain was snap-frozen and homogenized for biochemical analysis. Formalin fixed brains were embedded in paraffin wax, sectioned in a sagittal plane at 5-micron thickness, and mounted on glass slides. Tissue sections were then deparaffinized in xylene and rehydrated. Antigen retrieval was performed by steaming in distilled water for 30 min, followed by permeabilization with 0.5% Triton™-X, and blocking with 5% goat serum for 1 hour. Sagittal sections were then incubated with primary anti-GFP antibody (1:250, Ayes, chicken polyclonal) and anti-APP antibody (1:200, Abcam, clone Y188) overnight at 4° C. Sections were incubated with the secondary antibodies Alexa Fluor®-488-goat anti-chicken and Alexa Fluro®—568-goat anti rabbit (1:500, Invitrogen) for 2h at room temperature. Sections were washed and briefly dipped into 0.3% Sudan Black in 70% ethanol prior to mounting.

Electrophysiology—A coverslip with cultured cells at a density of 60,000 cells/cm$^2$ was placed in a continuously perfused bath, viewed under IR-DIC optics and whole-cell voltage clamp recordings were performed (−70 mV, room temp.). The extracellular solution consisted of (in mM): 145 NaCl, 2.5 KCl, 1 MgCl2, 2 CaCl2, 10 HEPES and 10 dextrose, adjusted to 7.3 pH with NaOH and 320 mOsm with sucrose. Whole-cell recordings were made with pipette solutions consisting of (in mM) 140 KCl, 10 EGTA, 10 HEPES, 2 Mg2ATP and 20 phosphocreatine, adjusted to pH 7.3 with KOH and 315 mOsm with sucrose. Excitatory synaptic events were isolated by adding 10 μM bicuculline to block GABA (subscript A) receptors. Miniature synaptic events were isolated by adding 100 nM tetrodotoxin to prevent action potentials. mEPSCs were detected using the template-matching algorithm in Axograph X, with a template that had 0.5 ms rise time and 5 ms decay. Statistics were computed using the Statistics Toolbox of Matlab.

T7 Endonuclease 1 Assay, Off-target, and ICE analyses— Genomic PCR was performed around each sgRNA target, and related off-target sites, following the manufacturer's instruction (using AccuPrime™ HiFi Taq using 500 ng of genomic DNA). Products were then purified using Wizard® SV Gel and PCR Clear-Up System (Promega) and quantified using a Qubit® 2.0 (Thermo Fischer). T7E1 assay was performed according to manufacturer's instructions (New England Biolabs). Briefly, 200 ng of genomic PCR was combined with 2 μL of NEBuffer™ 2 (New England Biolabs) and diluted to 19 μL. Products were then hybridized by denaturing at 95° C. for 5 minutes then ramped down to 85° C. at −2° C./second. This was followed by a second decrease to 25° C. at −0.1° C./second. To hybridized product, 1 μL T7E1 (M0302, New England Biolabs) was added and mixed well followed by incubation at 37° C. for 15 minutes. Reaction was stopped by adding 1.5 μL of 0.25M EDTA. Products were analyzed on a 3% agarose gel and quantified using a Gel Doc XR system (BioRad). Off-target sites were identified and scored using Benchling. The top 5 off-target sites—chosen on the basis of raw score and irrespective of being in a coding region—were identified and analyzed using T7E1 assay as previously described. For TIDE (43), PCR was performed on genomic DNA using Accuprime™ Taq HiFi (Thermo Fischer) according to manufacture specifications. Briefly, reactions were cycled at 2 min at 94° C. followed by 35 cycles of 98° C. for 30 seconds, 58° C. for 30 seconds, and 68° C. for 2 minutes 30 seconds and a final extension phase of 68° C. for 10 minutes. Products were then subjected to Sanger Sequencing and analyzed using the TIDE platform. The primers used for TIDE analyses are listed in Table 3. For analyses of indel after CRISPR editing with APP670-sgRNA and APP676-sgRNA, the edited regions of genomic DNA were PCR amplified and subjected to Sanger Sequencing. The results were analyzed using the ICE platform.

Deep Sequencing Sample Preparation and data analysis— Genomic PCR was performed using AccuPrime™ HiFi Taq (Life Technologies) following manufacturer's instructions. About 200-500 ng of genomic DNA was used for each PCR reaction. Products were then purified using AMPure® XP magnetic bead purification kit (Beckman Coulter) and quantified using a Nanodrop2000. Individual samples were pooled and run on an Illumina® HiSeq2500 High Throughput at a run length of 2×125 bp. A custom python script was developed to perform sequence analysis. For each sample, sequences with frequency of less than 100 reads were filtered from the data. Sequences in which the reads matched with primer and reverse complement subsequences classified as target sequences. These sequences were then aligned with corresponding wildtype sequence using global pairwise sequence alignment. Sequences that were misaligned through gaps or insertions around the expected cut site were classified as NHEJ events. The frequency, length, and position of matches, insertions, deletions, and mismatches were all tracked in the resulting aligned sequences.

Statistical analysis—Statistical analysis was performed and plotted using Prism software. Student's t-test (unpaired, two-tailed) was used to compare two groups. One-way ANOVA test was used to compare multiple groups, following with Tukey multiple comparison test of every pair. A P-value <0.05 was considered significant.

TABLE 3

PCR PRIMERS USED FOR ON- AND OFF- TARGET GENOMIC LOCI AMPLIFICATION

| | Forward primer sequence (5'-3') | SEQ ID NO: | Reverse primer sequence (5'-3') | SEQ ID NO: |
|---|---|---|---|---|
| Mouse APP (659) | AGGAACGGAGTGACCTGTTTCC | 21 | TTCCTCCATGGTAACCACGCAT | 22 |
| Human APP (659) | TGGGGAAGCCACATGTTGTACA | 23 | ATGTTTTGGTGGGCCATTTGGT | 24 |
| Human APP (670; 676) | AAATTATGGGTGTTCTGCAATCTTGG | 25 | ACTTGTGTTACAGCACAGCTGTC | 26 |
| Mouse OT1 | GCCCTCCAGAAGTATTGGCTT | 27 | GTCAGGGCCTTGCTCTACAAA | 28 |
| Mouse OT2 | CGCAAAAACTGGCTGCGTAT | 29 | TGTAGGCGCACATGCAGAAG | 30 |
| Mouse OT3 | CAGGTAGAGCGTGGAAACTCA | 31 | TGTGCGCATTAGGACCAGAT | 32 |
| Mouse OT4 | CACCTGACAATGCTGTCCCA | 33 | AGACAAGGTCTGTCTCCTTGC | 34 |
| Mouse OT5 | CCAACTCTTTGCTTAGGGGC | 35 | ATCGTCCCTGGTGCATTCTC | 36 |
| Human OT1 | GGAAAACCAGGTAGAGGGGG | 37 | TCTCTGGCTCGAGGGTACAT | 38 |
| Human OT2 | CTGCATGCCATGGGTAGGTA | 39 | CAGGCTGTTTCGGGTCCTT | 40 |
| Human OT3 | AGACTCTTCTCCGATTCCAGC | 41 | TCCAGCACGATCTGGTAGGC | 42 |
| Human OT4 | AGTGCTTTTCTTTGCCTTTGCT | 43 | TGCTCGGGAGGTGTTTCTAC | 44 |
| Human OT5 | AACAAGGCAGCTCCTCAACT | 45 | GACGTCAGAATTGAGGGTGGA | 46 |
| Mouse APLP1 | CCAGCGGGATGAACTGGTAAGA | 47 | CCCAGGTCACCTTAAGGAGCAA | 48 |

TABLE 3-continued

PCR PRIMERS USED FOR ON- AND OFF- TARGET GENOMIC LOCI AMPLIFICATION

|  | Forward primer sequence (5'-3') | SEQ ID NO: | Reverse primer sequence (5'-3') | SEQ ID NO: |
| --- | --- | --- | --- | --- |
| Mouse APLP2 | GAGAGAGTTGGAGGCCTTGAGG | 49 | AACCACAGTGACAAGTGGCTCT | 50 |
| Human APLP1 | GTGAATGCGTCTGTTCCAAGGG | 51 | GCTGCTGGGACTATCTGGGAAT | 52 |
| Human APLP2 | TTTTAGGGGCTCGACCTTCCAG | 53 | TGCACTAATTTCCCAGGGCTCA | 54 |

TABLE 4

TRANSPORT PARAMETERS OF WT AND APP659

|  | % Anterograde | % Retrograde | % Stationary | Anterograde Run-length (μm) | Retrograde Run-length (μm) | Anterograde velocity (μm/sec), mean ± SEM | Retrograde velocity (μm/sec), mean ± SEM |
| --- | --- | --- | --- | --- | --- | --- | --- |
| Kinetics in axons | | | | | | | |
| APP659 | 53.88 ± 4.57 | 37.13 ± 4.36 | 8.97 ± 1.51 | 8.08 ± 0.31 | 6.8 ± 0.26 | 1.66 ± 0.03 | 1.52 ± 0.03 |
| APPWT | 57.84 ± 2.22 | 34.37 ± 4.46 | 10.42 ± 4.24 | 10.44 ± 0.42 | 6.35 ± 0.26 | 1.97 ± 0.03 | 1.52 ± 0.03 |
| Kinetics in dendrites | | | | | | | |
| APP659 | 37.81 ± 6.45 | 20.55 ± 6.21 | 41.64 ± 8.37 | 7.0 ± 0.48 | 6.94 ± 0.81 | 0.76 ± 0.05 | 0.83 ± 0.12 |
| APPWT | 45.83 ± 4.58 | 24.81 ± 2.97 | 29.35 ± 5.63 | 8.12 ± 0.46 | 7.98 ± 0.94 | 0.94 ± 0.03 | 0.9 ± 0.07 |

~115 APP659:GFP and ~130 APP:GFP vesicles analyzed in dendrites; ~310 APP659:GFP and ~325 APP:GFP vesicles in axons (from 10-12 neurons from 2 separate cultures.)

TABLE 5

APP SGRNAS TARGETING SEQUENCES

|  | sgRNA targeting sequence | SEQ ID NO: |
| --- | --- | --- |
| Human APP 659 | ATCCATTCATCATGGTGTGG | 1 |
| Human APP 670 | TGGACAGGTGGCGCTCCTCT | 2 |
| Human APP 676 | GTAGCCGTTCTGCTGCATCT | 4 |
| Mouse APP 659 | ATCCATCCATCATGGCGTGG | 6 |
| Mouse APP 670 | TGGGAGAGATGGCGCTCCTCT | 7 |
| Mouse APP 676 | ATATCCGTTCTGCTGCATCT | 9 |

REFERENCES

1) Fellmann, C., Gowen, B. G., Lin, P. C., Doudna, J. A. & Corn, J. E. Cornerstones of CRISPR-Cas in drug discovery and therapy. Nat Rev Drug Discov 16, 89-100, doi: 10.1038/nrd.2016.238 (2017).
2) Yang, S. et al. CRISPR/Cas9-mediated gene editing ameliorates neurotoxicity in mouse model of Huntington's disease. J Clin Invest 127, 2719-2724, doi:10.1172/JCI92087 (2017).
3) Park, C. Y. et al. Reversion of FMR1 Methylation and Silencing by Editing the Triplet Repeats in Fragile X iPSC-Derived Neurons. Cell Rep 13, 234-241, doi: 10.1016/j.celrep.2015.08.084 (2015).
4) Gyorgy, B. et al. CRISPR/Cas9 Mediated Disruption of the Swedish APP Allele as a Therapeutic Approach for Early-Onset Alzheimer's Disease. Mol Ther Nucleic Acids 11, 429-440, doi:10.1016/j.omtn.2018.03.007 (2018).
5) McMahon, M. A. & Cleveland, D. W. Gene therapy: Gene-editing therapy for neurological disease. Nat Rev Neurol 13, 7-9, doi:10.1038/nrneurol.2016.190 (2017).
6) Mockett, B. G., Richter, M., Abraham, W. C. & Muller, U. C. Therapeutic Potential of Secreted Amyloid Precursor Protein APPsalpha. Front Mol Neurosci 10, 30, doi: 10.3389/fnmol.2017.00030 (2017).
7) O'Brien, R. J. & Wong, P. C. Amyloid precursor protein processing and Alzheimer's disease. Annu Rev Neurosci 34, 185-204, doi:10.1146/annurev-neuro-061010-113613 (2011).
8) Fol, R. et al. Viral gene transfer of APPsalpha rescues synaptic failure in an Alzheimer's disease mouse model. Acta Neuropathol 131, 247-266, doi:10.1007/s00401-015-1498-9 (2016).
9) Richter, M. C. et al. Distinct in vivo roles of secreted APP ectodomain variants APPsalpha and APPsbeta in regulation of spine density, synaptic plasticity, and cognition. EMBO J 37, doi:10.15252/embj.201798335 (2018).
10) Das, U. et al. Visualizing APP and BACE-1 approximation in neurons yields insight into the amyloidogenic pathway. Nat Neurosci 19, 55-64, doi:10.1038/nn.4188 (2016).
11) Citron, M., Teplow, D. B. & Selkoe, D. J. Generation of amyloid beta protein from its precursor is sequence specific. Neuron 14, 661-670, doi:0896-6273(95)90323-2 [pii] (1995).
12) Koo, E. H. & Squazzo, S. L. Evidence that production and release of amyloid beta-protein involves the endocytic pathway. J Biol Chem 269, 17386-17389 (1994).
13) Ring, S. et al. The secreted beta-amyloid precursor protein ectodomain APPs alpha is sufficient to rescue the anatomical, behavioral, and electrophysiological abnormalities of APP-deficient mice. J Neurosci 27, 7817-7826, doi:10.1523/JNEUROSCI.1026-07.2007 (2007).

14) Sander, J. D. & Joung, J. K. CRISPR-Cas systems for editing, regulating and targeting genomes. *Nat Biotechnol* 32, 347-355, doi:10.1038/nbt.2842 (2014).

15) Muller, U. C. & Zheng, H. Physiological functions of APP family proteins. *Cold Spring Harb Perspect Med* 2, a006288, doi:10.1101/cshperspect.a006288 (2012).

16) Muller, U. C., Deller, T. & Korte, M. Not just amyloid: physiological functions of the amyloid precursor protein family. *Nat Rev Neurosci* 18, 281-298, doi:10.1038/nrn.2017.29 (2017).

17) Carlson-Stevermer, J. et al. Assembly of CRISPR ribonucleoproteins with biotinylated oligonucleotides via an RNA aptamer for precise gene editing. *Nat Commun* 8, 1711, doi:10.1038/s41467-017-01875-9 (2017).

18) Deyts, C., Thinakaran, G. & Parent, A. T. APP Receptor? To Be or Not To Be. *Trends Pharmacol Sci* 37, 390-411, doi:10.1016/j.tips.2016.01.005 (2016).

19) Beckett, C., Nalivaeva, N. N., Belyaev, N. D. & Turner, A. J. Nuclear signalling by membrane protein intracellular domains: the AICD enigma. *Cell Signal* 24, 402-409, doi:10.1016/j.cellsig.2011.10.007 (2012).

20) Pardossi-Piquard, R. & Checler, F. The physiology of the beta-amyloid precursor protein intracellular domain AICD. *J Neurochem* 120 Suppl 1, 109-124, doi:10.1111/j.1471-4159.2011.07475.x (2012).

21) Passini, M. A. & Wolfe, J. H. Widespread gene delivery and structure-specific patterns of expression in the brain after intraventricular injections of neonatal mice with an adeno-associated virus vector. *J Virol* 75, 12382-12392, doi:10.1128/JVI.75.24.12382-12392.2001 (2001).

22) Kim, J. Y., Grunke, S. D. & Jankowsky, J. L. Widespread Neuronal Transduction of the Rodent CNS via Neonatal Viral Injection. *Methods Mol Biol* 1382, 239-250, doi:10.1007/978-1-4939-3271-9_17 (2016).

23) Lee, M. S. et al. APP processing is regulated by cytoplasmic phosphorylation. *J Cell Biol* 163, 83-95, doi:10.1083/jcb.200301115 (2003).

24) Perez, R. G. et al. Mutagenesis identifies new signals for beta-amyloid precursor protein endocytosis, turnover, and the generation of secreted fragments, including Abeta42. *J Biol Chem* 274, 18851-18856 (1999).

25) Lai, A., Sisodia, S. S. & Trowbridge, I. S. Characterization of sorting signals in the beta-amyloid precursor protein cytoplasmic domain. *J Biol Chem* 270, 3565-3573 (1995).

26) Thinakaran, G. & Koo, E. H. Amyloid precursor protein trafficking, processing, and function. *J Biol Chem* 283, 29615-29619, doi:10.1074/jbc.R800019200 (2008).

27) Vassar, R. et al. Function, therapeutic potential and cell biology of BACE proteases: current status and future prospects. *J Neurochem* 130, 4-28, doi:10.1111/jnc.12715 (2014).

28) Morel, E. et al. Phosphatidylinositol-3-phosphate regulates sorting and processing of amyloid precursor protein through the endosomal system. *Nat Commun* 4, 2250, doi:10.1038/ncomms3250 (2013).

29) Das, U. et al. Activity-induced convergence of APP and BACE-1 in acidic microdomains via an endocytosis-dependent pathway. *Neuron* 79, 447-460, doi:10.1016/j.neuron.2013.05.035 (2013).

30) Sisodia, S. S. Beta-amyloid precursor protein cleavage by a membrane-bound protease. *Proc Natl Acad Sci USA* 89, 6075-6079 (1992).

31) Chow, V. W., Mattson, M. P., Wong, P. C. & Gleichmann, M. An overview of APP processing enzymes and products. *Neuromolecular Med* 12, 1-12, doi:10.1007/s12017-009-8104-z (2010).

32) Sun, J. & Roy, S. The physical approximation of APP and BACE-1: A key event in alzheimer's disease pathogenesis. *Dev Neurobiol* 78, 340-347, doi:10.1002/dneu.22556 (2018).

33) Swiech, L. et al. In vivo interrogation of gene function in the mammalian brain using CRISPR-Cas9. *Nat Biotechnol* 33, 102-106, doi:10.1038/nbt.3055 (2015).

34) Sanjana, N. E., Shalem, 0. & Zhang, F. Improved vectors and genome-wide libraries for CRISPR screening. *Nat Methods* 11, 783-784, doi:10.1038/nmeth. 3047 (2014).

35) Joung, J. et al. Genome-scale CRISPR-Cas9 knockout and transcriptional activation screening. *Nat Protoc* 12, 828-863, doi:10.1038/nprot.2017.016 (2017).

36) Topol, A., Tran, N. N. & Brennand, K. J. A guide to generating and using hiPSC derived NPCs for the study of neurological diseases. *J Vis Exp*, e52495, doi:10.3791/52495 (2015).

37) Aime, P. et al. Trib3 Is Elevated in Parkinson's Disease and Mediates Death in Parkinson's Disease Models. *J Neurosci* 35, 10731-10749, doi:10.1523/JNEUROSCI.0614-15.2015 (2015).

38) Paquet, D. et al. Efficient introduction of specific homozygous and heterozygous mutations using CRISPR/Cas9. *Nature* 533, 125-+, doi:10.1038/nature17664 (2016).

39) Tang, Y. et al. Early and selective impairments in axonal transport kinetics of synaptic cargoes induced by soluble amyloid beta-protein oligomers. *Traffic* 13, 681-693, doi:10.1111/j.1600-0854.2012.01340.x (2012).

40) Ubelmann, F. et al. Bin1 and CD2Aβ polarise the endocytic generation of beta-amyloid. *EMBO Rep* 18, 102-122, doi:10.15252/embr.201642738 (2017).

41) Guo, W. et al. Fragile X Proteins FMRP and FXR2P Control Synaptic GluA1 Expression and Neuronal Maturation via Distinct Mechanisms. *Cell Rep* 11, 1651-1666, doi:10.1016/j.celrep.2015.05.013 (2015).

42) Chakrabarty, P. et al. Capsid serotype and timing of injection determines AAV transduction in the neonatal mice brain. *PLoS One* 8, e67680, doi:10.1371/journal.pone.0067680 (2013).

43) Brinkman, E. K., Chen, T., Amendola, M. & van Steensel, B. Easy quantitative assessment of genome editing by sequence trace decomposition. *Nucleic Acids Res* 42, e168, doi:10.1093/nar/gku936 (2014).

The invention claimed is:

1. A genetic construct encoding a Cas9 nuclease/gRNA ribonucleoprotein comprising, i. a sequence encoding for a Cas9 nuclease; and ii. a sequence encoding a gRNA specific to amyloid precursor protein (APP), wherein the encoded Cas9 nuclease/gRNA ribonucleoprotein directs cleavage of an APP gene to provide a C-terminal truncated APP having a length of 659, 670, 676, or 686 amino acids relative to a human APP amino acid sequence identified in SEQ ID NO: 12 or a mouse amino acid sequence identified in SEQ ID NO: 14.

2. The genetic construct of claim 1, wherein the genetic construct is packaged in a viral vector selected from the group consisting of a lentiviral vector and an adeno-associated viral (AAV) vector.

3. The genetic construct of claim 1, wherein the genetic construct further comprises at least one neuron specific promoter.

4. The genetic construct of claim 3, wherein the neuron specific promoter is selected from the group consisting of human synapsin 1 (hSyn1) promoter and mouse Mecp2 promoter (pMecp2).

5. The genetic construct of claim 1, wherein the genetic construct further comprises an RNA Pol III promoter.

6. The genetic construct of claim 5, wherein the RNA Pol III promoter is a U6 promoter.

7. The genetic construct of claim 1, wherein the sequence of the gRNA is selected from the group consisting of SEQ ID NOs:1-10.

8. The genetic construct of claim 1, wherein the sequence of the Cas9 nuclease consists of SEQ ID NO:15.

9. The genetic construct of claim 1, wherein the genetic construct comprises the sequence of SEQ ID NO:17, SEQ ID NO:18, SEQ ID NO:19, or SEQ ID NO:20.

10. A composition encoding a Cas9 nuclease/gRNA ribonucleoprotein comprising a first AAV vector comprising a sequence encoding for a Cas9 nuclease and a second AAV vector comprising a sequence encoding a gRNA specific to amyloid precursor protein (APP), wherein the encoded Cas9 nuclease/gRNA ribonucleoprotein directs cleavage of an APP gene to provide C-terminal truncated APP having a length of 659, 670, 676, or 686 amino acids relative to a human APP amino acid sequence identified in SEQ ID NO:12 or a mouse APP amino acid sequence identified in SEQ ID NO:14.

11. The composition of claim 10, further comprising a nanocarrier delivery vehicle.

12. The composition of claim 11, for delivery intravenously or intrathecally.

* * * * *